US012655145B2

(12) United States Patent
Chauret et al.

(10) Patent No.: US 12,655,145 B2
(45) Date of Patent: Jun. 16, 2026

(54) P2X3 MODULATORS

(71) Applicant: GlaxoSmithKline Intellectual Property (No. 3) Limited, Stevenage (GB)

(72) Inventors: Nathalie Chauret, Laval (CA); Karine Villeneuve, Laval (CA); Jeremy Green, Waltham, MA (US)

(73) Assignee: GlaxoSmithKline Intellectual Property (No.3) Limited, Stevenage (GB)

( * ) Notice: Subject to any disclaimer, the term of this patent is extended or adjusted under 35 U.S.C. 154(b) by 862 days.

(21) Appl. No.: 17/929,035

(22) PCT Filed: Feb. 12, 2021

(86) PCT No.: PCT/IB2021/000091

§ 371 (c)(1),
(2) Date: Aug. 10, 2022

(87) PCT Pub. No.: WO2021/161105

PCT Pub. Date: Aug. 19, 2021

(65) Prior Publication Data

US 2023/0312557 A1 Oct. 5, 2023

Related U.S. Application Data

(60) Provisional application No. 62/977,008, filed on Feb. 14, 2020.

(51) Int. Cl.
*C07D 471/04* (2006.01)

(52) U.S. Cl.
CPC .................................. *C07D 471/04* (2013.01)

(58) Field of Classification Search
CPC .. C07D 471/04; C07D 487/04; C07D 413/06; A61P 11/00; A61P 13/00; A61P 29/00; A61P 1/04; A61P 11/04; A61P 11/06; A61P 11/14; A61P 31/04; A61P 31/06; A61P 31/12; A61P 35/00; A61P 13/02; A61P 15/02; A61P 17/06; A61K 45/06; A61K 31/5377; A61K 31/55; A61K 31/553; A61K 2300/00
See application file for complete search history.

(56) References Cited

U.S. PATENT DOCUMENTS

| | | | |
|---|---|---|---|
| 9,598,409 | B2 | 3/2017 | Buon et al. |
| 10,111,883 | B1 | 10/2018 | Garceau et al. |
| 2017/0326141 | A1 | 11/2017 | Trower |
| 2023/0068538 | A1 | 3/2023 | Lou et al. |

FOREIGN PATENT DOCUMENTS

| | | | | |
|---|---|---|---|---|
| CN | 105246888 A | 1/2016 | | |
| CN | 111377917 A | 7/2020 | | |
| CN | 112409331 A | 2/2021 | | |
| CN | 113164490 A | 7/2021 | | |
| CN | 113727716 A | 11/2021 | | |
| EP | 4169921 A1 | 4/2023 | | |
| JP | 2013511517 A | 4/2013 | | |
| JP | 2016506935 A | 3/2016 | | |
| WO | 2014117274 A1 | 8/2014 | | |
| WO | WO-2019064079 A2 * | 4/2019 | .......... | A61K 31/437 |
| WO | 2020074962 A1 | 4/2020 | | |
| WO | 2020135771 A1 | 7/2020 | | |
| WO | 2020174283 A1 | 9/2020 | | |
| WO | 2021244634 A1 | 12/2021 | | |
| WO | 2022001820 A1 | 1/2022 | | |
| WO | 2022156783 A1 | 7/2022 | | |
| WO | 2022156784 A1 | 7/2022 | | |

OTHER PUBLICATIONS

Bavaskar, Ashish T., et al., "N-Fused Imidazoles As Novel Anticancer Agents That Inhibit Catalytic Activity of Topoisomerase lla and Induce Apoptosis in GI/S Phase", J. Med. Chem. 2011, 54, 14, 5013-5030.
Extended European Search Report for European Application No. 21754440.2, mailed Apr. 3, 2024, 12 Pages.
Partial Supplementary European Search Report for European Application No. 21754440, mailed Dec. 19, 2023, 10 Pages.

* cited by examiner

*Primary Examiner* — Kamal A Saeed
*Assistant Examiner* — Meghan C Heasley
(74) *Attorney, Agent, or Firm* — William B. Stauffer

(57) ABSTRACT

Provided herein are P2X3 modulators and methods of utilizing P2X3 modulators in the treatment of diseases, disorders, or conditions. Also described herein are pharmaceutical compositions containing such compounds.

20 Claims, No Drawings

P2X3 MODULATORS

CROSS-REFERENCE

This application claims the benefit of U.S. Provisional Application No. 62/977,008, filed on Feb. 14, 2020, which is herein incorporated by reference in its entirety.

BACKGROUND

P2X purinoreceptors are a family of ion channels that are activated by extracellular adenosine triphosphate (ATP). Purinoreceptors have been implicated in a variety of biological functions. The P2X3 receptor subunit is a member of this family. It was originally cloned from rat dorsal root ganglia. Chen et al., Nature, vol. 377, pp. 428-431 (1995). The nucleotide and amino acid sequences of both rat and human P2X3 are now known. Lewis, et al., Nature, vol. 377, pp. 432-435 (1995); and Garcia-Guzman, et al., Brain Res. Mol. Brain Res., vol. 47, pp. 59-66 (1997).

In view of the foregoing, there is a need for new P2X3 receptor modulators for treating various disorders related to the P2X3 receptor.

BRIEF SUMMARY OF THE INVENTION

This disclosure provides, for example, compounds and compositions which are P2X3 modulators, and their use as medicinal agents, processes for their preparation, and pharmaceutical compositions that include disclosed compounds as at least one active ingredient. The disclosure also provides for the use of disclosed compounds as medicaments and/or in the manufacture of medicaments for P2X3 modulation in warm-blooded animals such as humans. In some embodiments, the P2X3 modulator is a P2X3 antagonist.

In one aspect is a P2X3 modulator compound of Formula (I), or a pharmaceutically acceptable salt or solvate thereof:

Formula (I)

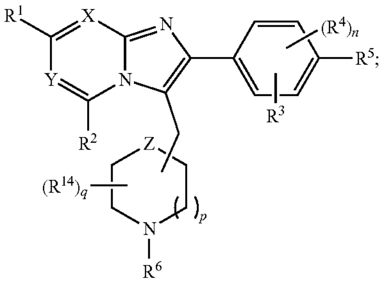

wherein:

X is $C(R^2)$ or N;

Y is $C(R^2)$ or N;

Z is a bond, $CH_2$, or O;

$R^1$ is selected from hydrogen, deuterium, $C_3$-$C_6$alkyl, $C_2$-$C_6$alkenyl, $C_2$-$C_6$alkynyl, $C_1$-$C_6$haloalkyl, $C_3$-$C_6$cycloalkyl, $—OR^7$, $—N(R^7)_2$, $—C(=O)R^8$, $—C(=O)OR^7$, $—C(=O)N(R^7)_2$, $—NR^7C(=O)R^8$, $—NR^{10}S(=O)_2R^8$, $—S(=O)_2R^8$, and $—S(=O)_2N(R^7)_2$;

each $R^2$ is independently selected from hydrogen, deuterium, halogen, —CN, $C_1$-$C_6$alkyl, $C_2$-$C_6$alkenyl, $C_2$-$C_6$alkynyl, $C_1$-$C_6$haloalkyl, $C_1$-$C_6$alkoxy, and $C_3$-$C_6$cycloalkyl;

$R^3$ is selected from hydrogen, deuterium, halogen, —CN, $C_1$-$C_6$alkyl, $C_2$-$C_6$alkenyl, $C_2$-$C_6$alkynyl, $C_1$-$C_6$haloalkyl, $C_3$-$C_6$cycloalkyl, $—OR^7$, $—N(R^7)_2$, $—C(=O)R^8$, $—C(=O)OR^7$, $—C(=O)N(R^7)_2$, $—NR^7C(=O)R^8$, $—NR^{10}S(=O)_2R^8$, $—S(=O)_2R^8$, and $—S(=O)_2N(R^7)_2$;

each $R^4$ is independently selected from deuterium, halogen, —CN, $C_1$-$C_6$alkyl, $C_2$-$C_6$alkenyl, $C_2$-$C_6$alkynyl, $C_1$-$C_6$haloalkyl, $C_1$-$C_6$alkoxy, and $C_3$-$C_6$cycloalkyl; or two $R^4$ are combined to form a bridged heterocycloalkyl ring;

$R^5$ is $—C(=O)N(R^9)(R^{10})$, $—C(=O)OR^9$, $—S(=O)R^{15}$, $—S(=O)_2R^{15}$, $—S(=O)(=NH)R^{15}$, $—C_2$-$C_9$heterocycloalkyl-$N(R^9)(R^{10})$, or $—C_1$-$C_6$haloalkyl-$N(R^9)(R^{10})$;

$R^6$ is selected from $—C(=O)OR^{11}$, $—C(=O)R^{11}$, and $—C(=O)N(R^{12})(R^{13})$;

each $R^7$ is independently selected from hydrogen, deuterium, $C_1$-$C_6$alkyl, and $C_1$-$C_6$haloalkyl;

each $R^8$ is independently selected from $C_1$-$C_6$alkyl;

$R^9$, $R^{10}$, $R^{12}$, and $R^{13}$ are independently selected from hydrogen, deuterium, and $C_1$-$C_6$alkyl;

$R^{11}$ is $C_1$-$C_6$alkyl or $—C_1$-$C_6$alkyl-O—$C_1$-$C_6$alkyl;

$R^{14}$ is $C_1$-$C_6$alkyl;

$R^{15}$ is $C_1$-$C_6$alkyl;

n is 0, 1, 2, or 3;

p is 1, 2, or 3; and q is 0, 1, 2, 3, or 4.

In some embodiments is a compound of Formula (I), or a pharmaceutically acceptable salt or solvate thereof, wherein $R^1$ is $C_1$-$C_6$haloalkyl. In some embodiments is a compound of Formula (I), or a pharmaceutically acceptable salt or solvate thereof, wherein $R^1$ is $—OR^7$. In some embodiments is a compound of Formula (I), or a pharmaceutically acceptable salt or solvate thereof, wherein $R^7$ is $C_1$-$C_6$alkyl. In some embodiments is a compound of Formula (I), or a pharmaceutically acceptable salt or solvate thereof, wherein $R^3$ is halogen. In some embodiments is a compound of Formula (I), or a pharmaceutically acceptable salt or solvate thereof, wherein $R^3$ is $C_1$-$C_6$alkyl. In some embodiments is a compound of Formula (I), or a pharmaceutically acceptable salt or solvate thereof, wherein each $R^4$ is independently selected from halogen, $C_1$-$C_6$alkyl, and $C_1$-$C_6$alkoxy.

In some embodiments is a compound of Formula (I), or a pharmaceutically acceptable salt or solvate thereof, having the structure of Formula (Ia):

Formula (Ia)

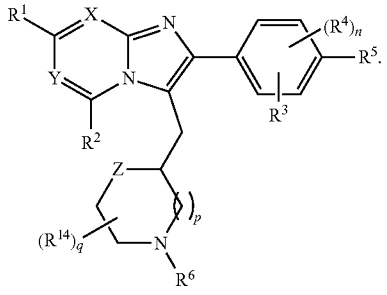

In some embodiments is a compound of Formula (I), or a pharmaceutically acceptable salt or solvate thereof, having the structure of Formula (Ia'):

Formula (Ia')

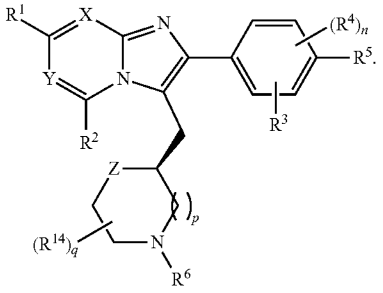

In some embodiments is a compound of Formula (I), or a pharmaceutically acceptable salt or solvate thereof, having the structure of Formula (Ia"):

Formula (Ia'')

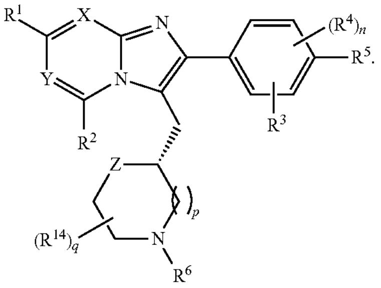

In another aspect is a P2X3 modulator compound of Formula (II), or a pharmaceutically acceptable salt or solvate thereof.

Formula (II)

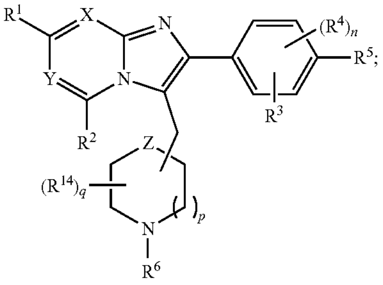

wherein:

X is $C(R^2)$ or N;

Y is $C(R^2)$ or N;

Z is a bond, $CH_2$, or O;

$R^1$ is selected from hydrogen, deuterium, halogen, $C_1$-$C_6$alkyl, $C_2$-$C_6$alkenyl, $C_2$-$C_6$alkynyl, $C_1$-$C_6$haloalkyl, $C_3$-$C_6$cycloalkyl, $—OR^7$, $—N(R^7)_2$, —CN, $—C(=O)R^8$, $—C(=O)OR^7$, $—C(=O)N(R^7)_2$, $—NR^7C(=O)R^8$, $—NR^{10}S(=O)_2R^8$, $—S(=O)_2R^8$, and $—S(=O)_2N(R^7)_2$;

each $R^2$ is independently selected from hydrogen, deuterium, halogen, —CN, $C_1$-$C_6$alkyl, $C_2$-$C_6$alkenyl, $C_2$-$C_6$alkynyl, $C_1$-$C_6$haloalkyl, $C_1$-$C_6$alkoxy, and $C_3$-$C_6$cycloalkyl;

$R^3$ is selected from deuterium, $C_3$-$C_6$alkyl, $C_2$-$C_6$alkenyl, $C_2$-$C_6$alkynyl, $C_1$-$C_6$haloalkyl, $C_3$-$C_6$cycloalkyl, $—N(R^7)_2$, —CN, $—C(=O)R^8$, $—C(=O)OR^7$, $—C(=O)N(R^7)_2$, $—NR^7C(=O)R^8$, $—NR^{10}S(=O)_2R^8$, $—S(=O)_2R^8$, and $—S(=O)_2N(R^7)_2$;

each $R^4$ is independently selected from deuterium, halogen, —CN, $C_1$-$C_6$alkyl, $C_2$-$C_6$alkenyl, $C_2$-$C_6$alkynyl, $C_1$-$C_6$haloalkyl, $C_1$-$C_6$alkoxy, and $C_3$-$C_6$cycloalkyl; or two $R^4$ are combined to form a bridged heterocycloalkyl ring;

$R^5$ is $—C(=O)N(R^9)(R^{10})$, $—C(=O)OR^9$, $—S(=O)R^{15}$, $—S(=O)_2R^{15}$, $—S(=O)(=NH)R^{15}$, $—C_2$-$C_9$heterocycloalkyl-$N(R^9)(R^{10})$, or $—C_1$-$C_6$haloalkyl-$N(R^9)(R^{10})$;

$R^6$ is selected from $—C(=O)OR^{11}$, $—C(=O)R^{11}$, and $—C(=O)N(R^{12})(R^{13})$ each $R^7$ is independently selected from hydrogen, deuterium, $C_1$-$C_6$alkyl, and $C_1$-$C_6$haloalkyl;

each $R^8$ is independently selected from $C_1$-$C_6$alkyl;

$R^9$, $R^{10}$, $R^{12}$, and $R^{13}$ are independently selected from hydrogen, deuterium, and $C_1$-$C_6$alkyl;

$R^{11}$ is $C_1$-$C_6$alkyl or $—C_1$-$C_6$alkyl-O—$C_1$-$C_6$alkyl;

$R^{14}$ is $C_1$-$C_6$alkyl;

$R^{15}$ is $C_1$-$C_6$alkyl;

n is 0, 1, 2, or 3;

p is 1, 2, or 3; and q is 0, 1, 2, 3, or 4.

In some embodiments is a compound of Formula (II), or a pharmaceutically acceptable salt or solvate thereof, having the structure of Formula (IIa):

Formula (IIa)

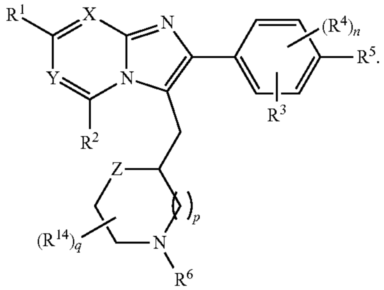

In some embodiments is a compound of Formula (II), or a pharmaceutically acceptable salt or solvate thereof, having the structure of Formula (IIa'):

Formula (IIa')

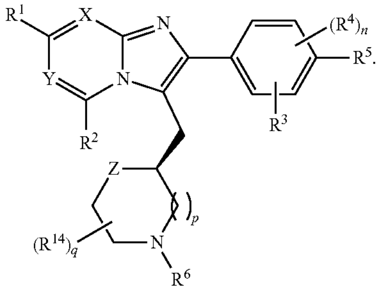

In some embodiments is a compound of Formula (II), or a pharmaceutically acceptable salt or solvate thereof, having the structure of Formula (IIa"):

Formula (IIa″)

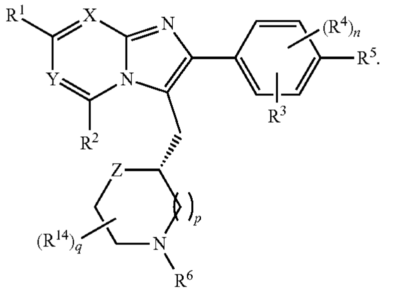

In another aspect is a P2X3 modulator compound of Formula (III), or a pharmaceutically acceptable salt or solvate thereof.

Formula (III)

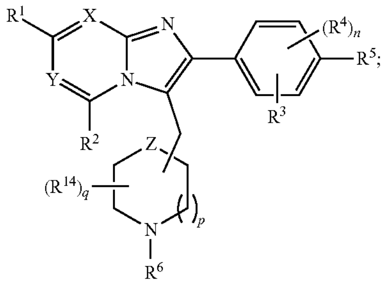

wherein:

X is $C(R^2)$ or N;

Y is $C(R^2)$ or N;

Z is $CH_2$ or O;

$R^1$ is selected from hydrogen, deuterium, halogen, $C_1$-$C_6$alkyl, $C_2$-$C_6$alkenyl, $C_2$-$C_6$alkynyl, $C_1$-$C_6$haloalkyl, $C_3$-$C_6$cycloalkyl, —$OR^7$, —$N(R^7)_2$, —CN, —C(═O)$R^8$, —C(═O)$OR^7$, —C(═O)$N(R^7)_2$, —$NR^7$C(═O)$R^8$, —$NR^{10}$S(═O)$_2R^8$, —S(═O)$_2R^8$, and —S(═O)$_2N(R^7)_2$;

each $R^2$ is independently selected from hydrogen, deuterium, halogen, —CN, $C_1$-$C_6$alkyl, $C_2$-$C_6$alkenyl, $C_2$-$C_6$alkynyl, $C_1$-$C_6$haloalkyl, $C_1$-$C_6$alkoxy, and $C_3$-$C_6$cycloalkyl;

$R^3$ is selected from hydrogen, deuterium, halogen, —CN, $C_1$-$C_6$alkyl, $C_2$-$C_6$alkenyl, $C_2$-$C_6$alkynyl, $C_1$-$C_6$haloalkyl, $C_3$-$C_6$cycloalkyl, —$OR^7$, —$N(R^7)_2$, —C(═O)$R^8$, —C(═O)$OR^7$, —C(═O)$N(R^7)_2$, —$NR^7$C(═O)$R^8$, —$NR^{10}$S(═O)$_2R^8$, —S(═O)$_2R^8$, and —S(═O)$_2N(R^7)_2$;

each $R^4$ is independently selected from deuterium, halogen, —CN, $C_1$-$C_6$alkyl, $C_2$-$C_6$alkenyl, $C_2$-$C_6$alkynyl, $C_1$-$C_6$haloalkyl, $C_1$-$C_6$alkoxy, and $C_3$-$C_6$cycloalkyl; or two $R^4$ are combined to form a bridged heterocycloalkyl ring;

$R^5$ is —C(═O)$N(R^9)(R^{10})$, —C(═O)$OR^9$, —S(═O)$R^{15}$, —S(═O)$_2R^{15}$, —S(═O)(═NH)$R^{15}$, —$C_2$-$C_9$heterocycloalkyl-$N(R^9)(R^{10})$, or —$C_1$-$C_6$haloalkyl-$N(R^9)(R^{10})$;

$R^6$ is selected from —C(═O)$OR^{11}$, —C(═O)$R^{11}$, and —C(═O)$N(R^{12})(R^{13})$;

each $R^7$ is independently selected from hydrogen, deuterium, $C_1$-$C_6$alkyl, and $C_1$-$C_6$haloalkyl;

each $R^8$ is independently selected from $C_1$-$C_6$alkyl;

$R^9$ and $R^{10}$ are independently selected from $C_1$-$C_6$alkyl; or $R^9$ and $R^{10}$ are combined to form a 5- or 6-membered heterocycloalkyl ring optionally substituted with 1, 2, 3, or 4 groups selected from halogen, $C_1$-$C_6$alkyl, $C_1$-$C_6$haloalkyl, hydroxy, and $C_1$-$C_6$alkoxy;

$R^{12}$ and $R^{13}$ are independently selected from hydrogen, deuterium, and $C_1$-$C_6$alkyl;

$R^{11}$ is $C_1$-$C_6$alkyl or —$C_1$-$C_6$alkyl-O—$C_1$-$C_6$alkyl;

$R^{14}$ is $C_1$-$C_6$alkyl;

$R^{15}$ is $C_1$-$C_6$alkyl;

n is 0, 1, 2, or 3;

p is 1, 2, or 3; and q is 0, 1, 2, 3, or 4.

In some embodiments is a compound of Formula (III), or a pharmaceutically acceptable salt or solvate thereof, having the structure of Formula (IIIa):

Formula (IIIa)

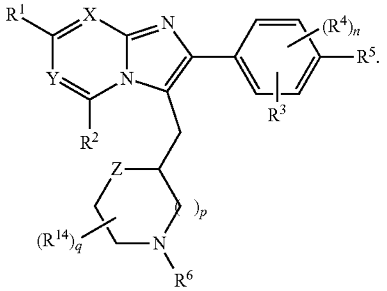

In some embodiments is a compound of Formula (III), or a pharmaceutically acceptable salt or solvate thereof, having the structure of Formula (IIIa'):

Formula (IIIa′)

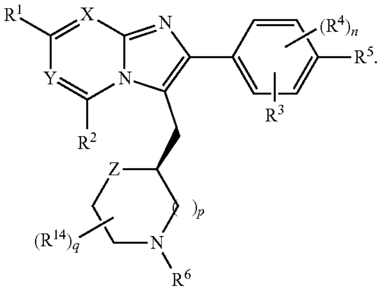

In some embodiments is a compound of Formula (III), or a pharmaceutically acceptable salt or solvate thereof, having the structure of Formula (IIIa"):

Formula (IIIa″)

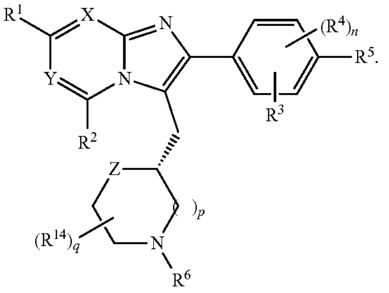

In some embodiments is a compound of Formula (III), (IIIa), (IIIa'), or (IIIa"), or a pharmaceutically acceptable salt or solvate thereof, wherein $R^5$ is —C(O)N($R^9$)($R^{10}$). In some embodiments is a compound of Formula (III), (IIIa), (IIIa'), or (IIIa"), or a pharmaceutically acceptable salt or solvate thereof, wherein $R^9$ and $R^{10}$ are independently selected from $C_1$-$C_6$alkyl. In some embodiments is a compound of Formula (III), (IIIa), (IIIa'), or (IIIa"), or a pharmaceutically acceptable salt or solvate thereof, wherein $R^9$ and $R^{10}$ are combined to form a 5- or 6-membered heterocycloalkyl ring optionally substituted with 1, 2, 3, or 4 groups selected from halogen, $C_1$-$C_6$alkyl, $C_1$-$C_6$haloalkyl, hydroxy, and $C_1$-$C_6$alkoxy. In some embodiments is a compound of Formula (III), (IIIa), (IIIa'), or (IIIa"), or a pharmaceutically acceptable salt or solvate thereof, wherein $R^5$ is —C(═O)OR$^9$. In some embodiments is a compound of Formula (III), (IIIa), (IIIa'), or (IIIa"), or a pharmaceutically acceptable salt or solvate thereof, wherein $R^3$ is $C_1$-$C_6$alkyl. In some embodiments is a compound of Formula (III), (IIIa), (IIIa'), or (IIIa"), or a pharmaceutically acceptable salt or solvate thereof, wherein $R^3$ is halogen. In some embodiments is a compound of Formula (II), (IIa), (IIa'), or (IIa"), (III), (IIIa), (IIIa'), or (IIIa"), or a pharmaceutically acceptable salt or solvate thereof, wherein each $R^4$ is independently selected from halogen, $C_1$-$C_6$alkyl, and $C_1$-$C_6$alkoxy.

In another aspect is a P2X3 modulator compound of Formula (IV), or a pharmaceutically acceptable salt or solvate thereof.

Formula (IV)

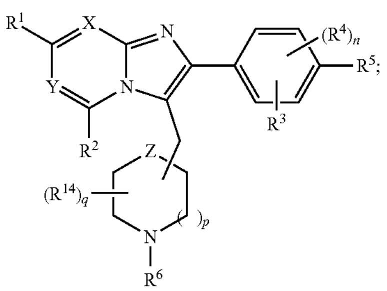

wherein:

X is C($R^2$) or N;

Y is C($R^2$) or N;

Z is $CH_2$ or O;

$R^1$ is selected from hydrogen, deuterium, halogen, $C_1$-$C_6$alkyl, $C_2$-$C_6$alkenyl, $C_2$-$C_6$alkynyl, $C_1$-$C_6$haloalkyl, $C_3$-$C_6$cycloalkyl, —OR$^7$, —N($R^7$)$_2$, —CN, —C(═O)R$^8$, —C(═O)OR$^7$, —C(═O)N($R^7$)$_2$, —NR$^7$C(═O)R$^8$, —NR$^{10}$S(═O)$_2$R$^8$, —S(═O)$_2$R$^8$, and —S(═O)$_2$N($R^7$)$_2$;

each $R^2$ is independently selected from hydrogen, deuterium, halogen, —CN, $C_1$-$C_6$alkyl, $C_2$-$C_6$alkenyl, $C_2$-$C_6$alkynyl, $C_1$-$C_6$haloalkyl, $C_1$-$C_6$alkoxy, and $C_3$-$C_6$cycloalkyl;

$R^3$ is selected from halogen, —CN, $C_2$-$C_6$alkenyl, $C_2$-$C_6$alkynyl, $C_1$-$C_6$haloalkyl, $C_3$-$C_6$cycloalkyl, —OR$^7$, —N($R^7$)$_2$, —C(═O)R$^8$, —C(═O)OR$^7$, —C(═O)N($R^7$)$_2$, —NR$^7$C(═O)R$^8$, —NR$^{10}$S(═O)$_2$R$^8$, —S(═O)$_2$R$^8$, and —S(═O)$_2$N($R^7$)$_2$;

each $R^4$ is independently selected from deuterium, —CN, $C_2$-$C_6$alkenyl, $C_2$-$C_6$alkynyl, $C_1$-$C_6$haloalkyl, $C_1$-$C_6$alkoxy, and $C_3$-$C_6$cycloalkyl; or two $R^4$ are combined to form a bridged heterocycloalkyl ring;

$R^5$ is —C(═O)N($R^9$)($R^{10}$), —C(═O)OR$^9$, —S(═O)R$^{15}$, —S(═O)$_2$R$^{15}$, —S(═O)(═NH)R$^{15}$, —$C_2$-$C_9$heterocycloalkyl-N($R^9$)($R^{10}$), or —$C_1$-$C_6$haloalkyl-N($R^9$)($R^{10}$);

$R^6$ is selected from —C(═O)R$^{11}$;

each $R^7$ is independently selected from hydrogen, deuterium, $C_1$-$C_6$alkyl, and $C_1$-$C_6$haloalkyl;

each $R^8$ is independently selected from $C_1$-$C_6$alkyl;

$R^9$, $R^{10}$, $R^{12}$, and $R^{13}$ are independently selected from hydrogen, deuterium, and $C_1$-$C_6$alkyl;

$R^{11}$ is $C_1$-$C_6$alkyl or —$C_1$-$C_6$alkyl-O—$C_1$-$C_6$alkyl;

$R^{14}$ is $C_1$-$C_6$alkyl;

$R^{15}$ is $C_1$-$C_6$alkyl;

n is 0, 1, 2, or 3;

p is 1, 2, or 3; and q is 0, 1, 2, 3, or 4.

In some embodiments is a compound of Formula (IV), or a pharmaceutically acceptable salt or solvate thereof, having the structure of Formula (IVa):

Formula (IVa)

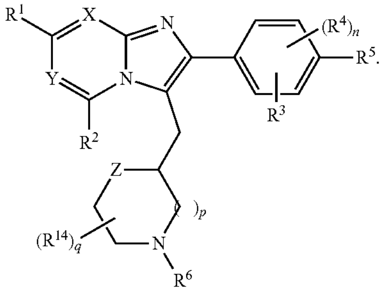

In some embodiments is a compound of Formula (IV), or a pharmaceutically acceptable salt or solvate thereof, having the structure of Formula (IVa'):

Formula (IVa')

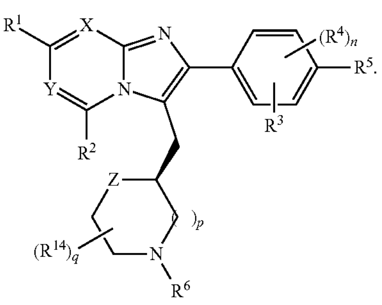

In some embodiments is a compound of Formula (IV), or a pharmaceutically acceptable salt or solvate thereof, having the structure of Formula (IVa"):

Formula (IVa")

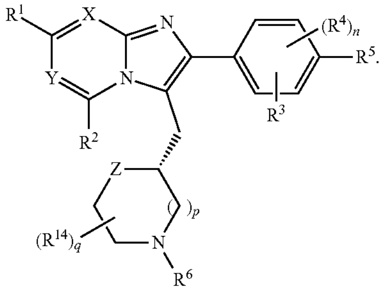

In another aspect is a P2X3 modulator compound of Formula (V), or a pharmaceutically acceptable salt or solvate thereof.

Formula (V)

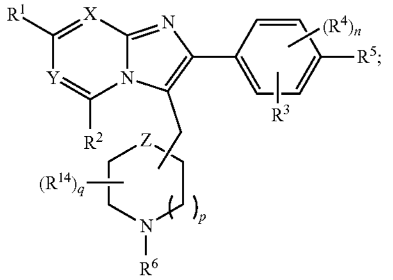

wherein:

X is $C(R^2)$ or N;

Y is $C(R^2)$ or N;

Z is $CH_2$ or O;

$R^1$ is selected from hydrogen, deuterium, halogen, $C_1$-$C_6$alkyl, $C_2$-$C_6$alkenyl, $C_2$-$C_6$alkynyl, $C_1$-$C_6$haloalkyl, $C_3$-$C_6$cycloalkyl, —$OR^7$, —$N(R^7)_2$, —CN, —C(=O)$R^8$, —C(=O)$OR^7$, —C(=O)$N(R^7)_2$, —$NR^7$C(=O)$R^8$, —$NR^{10}S(=O)_2R^8$, —$S(=O)_2R^8$, and —$S(=O)_2N(R^7)_2$;

each $R^2$ is independently selected from hydrogen, deuterium, halogen, —CN, $C_1$-$C_6$alkyl, $C_2$-$C_6$alkenyl, $C_2$-$C_6$alkynyl, $C_1$-$C_6$haloalkyl, $C_1$-$C_6$alkoxy, and $C_3$-$C_6$cycloalkyl;

$R^3$ is selected from hydrogen, deuterium, halogen, —CN, $C_1$-$C_6$alkyl, $C_2$-$C_6$alkenyl, $C_2$-$C_6$alkynyl, $C_1$-$C_6$haloalkyl, $C_3$-$C_6$cycloalkyl, —$OR^7$, —$N(R^7)_2$, —C(=O)$R^8$, —C(=O)$OR^7$, —C(=O)$N(R^7)_2$, —$NR^7$C(=O)$R^8$, —$NR^{10}S(=O)_2R^8$, —$S(=O)_2R^8$, and —$S(=O)_2N(R^7)_2$;

each $R^4$ is independently selected from deuterium, halogen, —CN, $C_1$-$C_6$alkyl, $C_2$-$C_6$alkenyl, $C_2$-$C_6$alkynyl, $C_1$-$C_6$haloalkyl, $C_1$-$C_6$alkoxy, and $C_3$-$C_6$cycloalkyl; or two $R^4$ are combined to form a bridged heterocycloalkyl ring;

$R^5$ is —C(=O)$N(R^9)(R^{10})$, —C(=O)$OR^9$, —S(=O)$R^{15}$, —$S(=O)_2R^{15}$, —S(=O)(=NH)$R^{15}$, —$C_2$-$C_9$heterocycloalkyl-$N(R^9)(R^{10})$, or —$C_1$-$C_6$haloalkyl-$N(R^9)(R^{10})$;

$R^6$ is selected from —C(=O)$OR^{11}$, —C(=O)$R^{11}$, and —C(=O)$N(R^{12})(R^{13})$ each $R^7$ is independently selected from hydrogen, deuterium, $C_1$-$C_6$alkyl, and $C_1$-$C_6$haloalkyl;

each $R^8$ is independently selected from $C_1$-$C_6$alkyl;

$R^9$, $R^{10}$, $R^{12}$, and $R^{13}$ are independently selected from hydrogen, deuterium, and $C_1$-$C_6$alkyl;

$R^{11}$ is $C_1$-$C_6$alkyl or —$C_1$-$C_6$alkyl-O—$C_1$-$C_6$alkyl;

$R^{14}$ is $C_1$-$C_6$alkyl;

$R^{15}$ is $C_1$-$C_6$alkyl;

n is 0, 1, 2, or 3;

p is 2 or 3; and q is 0, 1, 2, 3, or 4.

In some embodiments is a compound of Formula (V), or a pharmaceutically acceptable salt or solvate thereof, having the structure of Formula (Va):

Formula (Va)

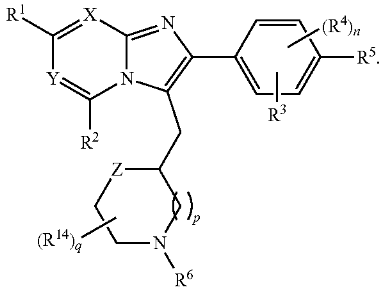

In some embodiments is a compound of Formula (V), or a pharmaceutically acceptable salt or solvate thereof, having the structure of Formula (Va'):

Formula (Va')

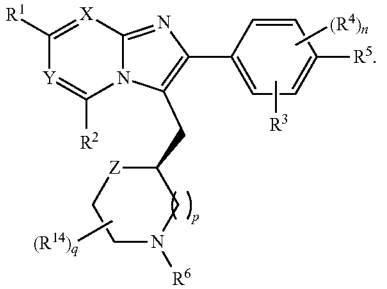

In some embodiments is a compound of Formula (V), or a pharmaceutically acceptable salt or solvate thereof, having the structure of Formula (Va"):

Formula (Va")

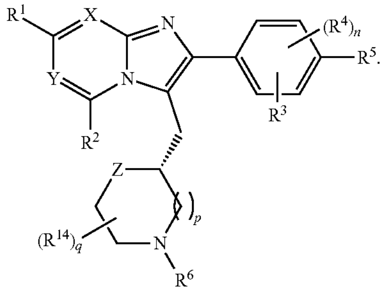

In some embodiments is a compound of Formula (I), (Ia), (Ia'), (Ia"), (II), (IIa), (IIa'), (IIa"), (III), (IIIa), (IIIa'), (IIIa"), (IV), (IVa), (IVa'), or (IVa"), or a pharmaceutically acceptable salt or solvate thereof, wherein Z is O and p is 1. In some embodiments is a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), or a pharmaceutically acceptable salt or solvate thereof, wherein Z is O and p is 2. In some embodiments is a compound of Formula (I), (Ia), (Ia'), (Ia"), (II), (IIa), (IIa'), (IIa"), (III), (IIIa), (IIIa'), (IIIa"), (IV), (IVa), (IVa'), or (IVa"), or a pharmaceutically acceptable salt or solvate thereof, wherein Z is $CH_2$ and p is 1. In some embodiments is a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), or a pharmaceutically acceptable salt or solvate thereof, wherein Z is $CH_2$ and p is 2. In some embodiments is a compound of Formula (IV), (IVa), (IVa'), (IVa"), (V), (Va), (Va'), or (Va"), or a pharmaceutically acceptable salt or solvate thereof, wherein $R^3$ is halogen. In some embodiments is a compound of Formula (II), (IIa), (IIa'), (IIa"), (III), (IIIa), (IIIa'), (IIIa"), (IV), (IVa), (IVa'), (IVa"), (V), (Va), (Va'), or (Va"), or a pharmaceutically acceptable salt or solvate thereof, wherein $R^1$ is $C_1$-$C_6$alkyl. In some embodiments is a compound of Formula (II), (IIa), (IIa'), (IIa"), (III), (IIIa), (IIIa'), (IIIa"), (IV), (IVa), (IVa'), (IVa"), (V), (Va), (Va'), or (Va"), or a pharmaceutically acceptable salt or solvate thereof, wherein $R^1$ is halogen. In some embodiments is a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), or a pharmaceutically acceptable salt or solvate thereof, wherein X is $C(R^2)$ and Y is N. In some embodiments is a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), or a pharmaceutically acceptable salt or solvate thereof, wherein X is N and Y is $C(R^2)$. In some embodiments is a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), or a pharmaceutically acceptable salt or solvate thereof, wherein X is $C(R^2)$ and Y is $C(R^2)$. In some embodiments is a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), or a pharmaceutically acceptable salt or solvate thereof, wherein each $R^2$ is hydrogen. In some embodiments is a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), or a pharmaceutically acceptable salt or solvate thereof, wherein n is 1. In some embodiments is a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), or a pharmaceutically acceptable salt or solvate thereof, wherein n is 2. In some embodiments is a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), or a pharmaceutically acceptable salt or solvate thereof, wherein n is 0. In some embodiments is a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), or a pharmaceutically acceptable salt or solvate thereof, wherein q is 0. In some embodiments is a compound of Formula (I), (Ia), (Ia'), (Ia"), (II), (IIa), (IIa'), (IIa"), (IV), (IVa), (IVa'), (IVa"), (V), (Va), (Va'), or (Va"), or a pharmaceutically acceptable salt or solvate thereof, wherein $R^5$ is $—C(O)N(R^9)(R^{10})$. In some embodiments is a compound of Formula (I), (Ia), (Ia'), (Ia"), (II), (IIa), (IIa'), (IIa"), (IV), (IVa), (IVa'), (IVa"), (V), (Va), (Va'), or (Va"), or a pharmaceutically acceptable salt or solvate thereof, wherein $R^{10}$ is hydrogen. In some embodiments is a compound of Formula (I), (Ia), (Ia'), (Ia"), (II), (IIa), (IIa'), (IIa"), (IV), (IVa), (IVa'), (IVa"), (V), (Va), (Va'), or (Va"), or a pharmaceutically acceptable salt or solvate thereof, wherein $R^5$ is $—C(O)OR^9$. In some embodiments is a compound of Formula (I), (Ia), (Ia'), (Ia"), (II), (IIa), (IIa'), (IIa"), (IV), (IVa), (IVa'), (IVa"), (V), (Va), (Va'), or (Va"), or a pharmaceutically acceptable salt or solvate thereof, wherein $R^9$ is $C_1$-$C_6$alkyl. In some embodiments is a compound of Formula (I), (Ia), (Ia'), (Ia"), (II), (IIa), (IIa'), (IIa"), (IV), (IVa), (IVa'), (IVa"), (V), (Va), (Va'), or (Va"), or a pharmaceutically acceptable salt or solvate thereof, wherein $R^9$ is hydrogen. In some embodiments is a compound of Formula (I), (Ia), (Ia'), (Ia"), (II), (IIa), (IIa'), (IIa"), (III), (IIIa), (IIIa'), (IIIa"), (V), (Va), (Va'), or (Va"), or a pharmaceutically acceptable salt or solvate thereof, wherein $R^6$ is selected from $—C(O)OR^{11}$. In some embodiments is a compound of Formula (I), (Ia), (Ia'), (Ia"), (II), (IIa), (IIa'), (IIa"), (III), (IIIa), (IIIa'), (IIIa"), (V), (Va), (Va'), or (Va"), or a pharmaceutically acceptable salt or solvate thereof, wherein $R^6$ is $—C(O)R^{11}$. In some embodiments is a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), or a pharmaceutically acceptable salt or solvate thereof, wherein $R^{11}$ is $C_1$-$C_6$alkyl. In some embodiments is a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), or a pharmaceutically acceptable salt or solvate thereof, wherein $R^{11}$ is $—CH_3$.

In another aspect is a pharmaceutical composition comprising a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), or a pharmaceutically acceptable salt or solvate thereof, and at least one inactive ingredient selected from pharmaceutically acceptable carriers, diluents, and excipients. In some embodiments, the pharmaceutical composition is formulated for administration to a mammal by intravenous administration, subcutaneous administration, oral administration, inhalation, nasal administration, topical administration, or ophthalmic administration. In some embodiments, the pharmaceutical composition is in the form of a tablet, a pill, a capsule, a liquid, a suspension, a gel, a dispersion, a solution, an emulsion, an ointment, or a lotion.

In another aspect is a method for treating a disorder associated with P2X3 activity in a mammal in need thereof, comprising administering to the mammal in need thereof a therapeutically effective amount of a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), or a pharmaceutically acceptable salt or solvate thereof.

In another aspect is a method for treating pain in a mammal in need thereof, comprising administering to the mammal in need thereof a therapeutically effective amount of a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), or a pharmaceutically acceptable salt or solvate thereof.

In another aspect is a method for treating urinary tract disorder in a mammal in need thereof, comprising administering to the mammal in need thereof a therapeutically effective amount of a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), or a pharmaceutically acceptable salt or solvate thereof. In some embodiments, the urinary tract disorder comprises neurogenic overactive bladder, non-neurogenic overactive bladder, interstitial cystitis, prostatitis, prostadynia, and benign prostatic hyperplasia.

In another aspect is a method of reducing or preventing uncontrolled loss of urine in a mammal in need thereof, comprising administering to the mammal in need thereof a therapeutically effective amount of a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), or a pharmaceutically acceptable salt or solvate thereof. In some embodiments, the uncontrolled loss of urine is associated with urge incontinence, cough incontinence, stress incontinence, overflow incontinence, functional incontinence, neurogenic incontinence, post-prostatectomy incontinence, urinary urgency, nocturia, and enuresis.

In another aspect is a method for treating cough in a mammal in need thereof, comprising administering to the mammal in need thereof a therapeutically effective amount of a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), or a pharmaceutically acceptable salt or solvate thereof. In some embodiments, the cough is an acute cough or a chronic cough. In some embodiments, the cough is associated with a disease, disorder, or condition selected from chronic obstructive pulmonary disease, asthma, tuberculosis, bronchitis, bronchiectasis, suppurative pulmonary disease, respiratory malignancies, allergy, cystic fibrosis, pulmonary fibrosis, respiratory tract inflammation, emphysema, pneumonia, lung cancer, lung neoplasia, sore throat, common cold, influenza, respiratory tract infection, bronchoconstriction, sarcoidosis, viral or bacterial infection of the upper airways, angiotension converting enzyme (ACE) inhibitor therapy, smoker's cough, chronic non-productive cough, neoplastic cough, cough due to gastroesophageal reflux, and inhalation of irritants, smoke, smog, dust, or air pollution.

In another aspect is a method for treating pruritus in a mammal in need thereof, comprising administering to the mammal in need thereof a therapeutically effective amount of a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), or a pharmaceutically acceptable salt or solvate thereof. In some embodiments, the pruritus is associated with an inflammatory skin disease, an infectious skin disease, an autoimmune skin disease, or a pregnancy-related skin disease. In some embodiments, the pruritus is associated with an inflammatory skin disease selected from the group consisting of atopic dermatitis, allergic, irritant contact dermatitis, exsiccation dermatitis, nummular and dyshidrotic dermatitis, lichen planus, lichen sclerosus et atrophicus, polymorphous light eruption psoriasis, Grover's disease, mucinosis, mastocytosis, and urticaria. In some embodiments, the pruritus is associated with an infectious skin disease selected from the group consisting of mycoses, bacterial and viral infections, scabies, pediculosis, insect bites, and folliculitides. In some embodiments, the pruritus is associated with an autoimmune skin disease selected from the group consisting of dermatitis herpetiformis (Duhring's disease), bullous pemphigoid; genodermatoses, Darier's disease, and Hailey-Hailey disease. In some embodiments, the pruritus is associated with a pregnancy-related skin disease selected from the group consisting of polymorphic eruption of pregnancy (PEP), atopic eruption of pregnancy, pemphigoid gestationis, neoplasias, and cutaneous T-cell lymphoma. In some embodiments, the pruritus is associated with prurigo nodularis. In some embodiments, the pruritus is associated with a kidney disease or a therapeutic procedure to treat a kidney disease. In some embodiments, the pruritus is associated with a chronic kidney disease. In some embodiments, the pruritus is associated with a therapeutic procedure to treat a kidney disease, wherein the therapeutic procedure to treat the kidney disease is selected from the group consisting of hemodialysis and peritoneal dialysis. In some embodiments, the pruritus is associated with a medical procedure or treatment. In some embodiments, the pruritus is associated with a medical treatment with a drug selected from the group consisting of opioids, anti-malarial drugs, anti-cancer therapies, and epidermal growth factor receptor inhibitors.

In another aspect is a method for treating endometriosis, endometriosis-associated pain, and endometriosis-associated symptoms in a mammal in need thereof, comprising administering to the mammal in need thereof a therapeutically effective amount of a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), or a pharmaceutically acceptable salt or solvate thereof. In some embodiments is a method for treating endometriosis in a mammal in need thereof, comprising administering to the mammal in need thereof a therapeutically effective amount of a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), or a pharmaceutically acceptable salt or solvate thereof. In some embodiments is a method for treating endometriosis-associated pain in a mammal in need thereof, comprising administering to the mammal in need thereof a therapeutically effective amount of a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), or a pharmaceutically acceptable salt or solvate thereof. In some embodiments is a method for treating endometriosis-associated symptoms in a mammal in need thereof, comprising administering to the mammal in need thereof a therapeutically effective amount of a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), or a pharmaceutically acceptable salt or solvate thereof. In some embodiments, the endometriosis-associated symptoms are selected from dysmenorrhea, dyspareunia, dysuria, and dyschezia.

In some embodiments of the methods described herein, the mammal is a human. In some embodiments of the methods described herein, the method further comprises the administration of a second therapeutic agent. In some embodiments, the second therapeutic agent is a NK-1 antagonist. In some embodiments, the NK-1 antagonist is selected from the group consisting of serlopitant, aprepitant, casopitant, dapitant, ezlopitant, fosaprepitant, lanepitant, maropitant, netupitant, nolpitant, orvepitant, rolapitant, vestipitant, vofopitant, AV-818, BIIF 1149CL, CP122,721, DNK-333, GSK-424887, L-733060, L-759274, LY-686017, M516102, and TA-5538. In some embodiments, the second therapeutic agent is selected from a hormonal contraceptive, a non-steroidal anti-inflammatory agent (NSAID), a prostaglandin E synthase (PTGES) inhibitor, an interleukin-1 receptor-associated kinase 4 (IRAK4) inhibitor, a prostanoid EP4 receptor antagonist, an aldo-keto reductase 1C3 (AKR1C3) inhibitor, and a prolactin receptor (PRLR) antagonist.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

As used herein and in the appended claims, the singular forms "a," "an," and "the" include plural referents unless the context clearly dictates otherwise. Thus, for example, reference to "an agent" includes a plurality of such agents, and reference to "the cell" includes reference to one or more cells (or to a plurality of cells) and equivalents thereof. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range varies between 1% and 15% of the stated number or numerical range. The term "comprising" (and related terms such as "comprise" or "comprises" or "having" or "including") is not intended to exclude that which in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

As used herein, $C_1$-$C_x$ includes $C_1$-$C_2$, $C_1$-$C_3$ . . . $C_1$-$C_x$. $C_1$-$C_x$ refers to the number of carbon atoms that make up the moiety to which it designates (excluding optional substituents).

"Amino" refers to the —$NH_2$ radical.

"Cyano" refers to the —CN radical.

"Nitro" refers to the —$NO_2$ radical.

"Oxa" refers to the —O— radical.

"Oxo" refers to the =O radical.

"Thioxo" refers to the =S radical.

"Imino" refers to the =N—H radical.

"Oximo" refers to the =N—OH radical.

"Alkyl" or "alkylene" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to six carbon atoms (e.g., $C_1$-$C_6$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), and 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —$OC(O)R^a$, —$N(R^a)_2$, —$C(O)R^a$, —$C(O)OR^a$, —$C(O)N(R^a)_2$, —$N(R^a)C(O)OR^f$, —OC(O)—$NR^aR^f$, —$N(R^a)C(O)R^f$, —$N(R^a)S(O)_tR^f$ (where t is 1 or 2), —$S(O)_tOR^a$ (where t is 1 or 2), —$S(O)_tR^f$ (where t is 1 or 2) and —$S(O)_tN(R^a)_2$ (where t is 1 or 2) where each $R^a$ is independently hydrogen, alkyl, fluoroalkyl, cycloalkyl, aryl, aralkyl, heterocycloalkyl, heteroaryl or heteroarylalkyl, and each $R^f$ is independently alkyl, fluoroalkyl, cycloalkyl, aryl, aralkyl, heterocycloalkyl, heteroaryl or heteroarylalkyl.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —OC(O)—$R^f$, —$N(R^a)_2$, —$C(O)R^a$, —$C(O)OR^a$, —$C(O)N(R^a)_2$, —$N(R^a)C(O)OR^f$, —OC(O)—$NR^aR^f$, —$N(R^a)C(O)R^f$, —$N(R^a)S(O)_tR^f$ (where t is 1 or 2), —$S(O)_tOR^a$ (where t is 1 or 2), —$S(O)_tR$ (where t is 1 or 2) and —$S(O)_tN(R^a)_2$ (where t is 1 or 2) where each $R^a$ is independently hydrogen, alkyl, fluoroalkyl, cycloalkyl, aryl, aralkyl, heterocycloalkyl, heteroaryl or heteroarylalkyl, and each $R^f$ is independently alkyl, fluoroalkyl, cycloalkyl, aryl, aralkyl, heterocycloalkyl, heteroaryl or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —$OR^a$, —$SR^a$, —$OC(O)R^a$, —$N(R^a)_2$, —$C(O)R^a$, —$C(O)OR^a$, —$C(O)N(R^a)_2$, —$N(R^a)C(O)OR^f$, —OC(O)—$NR^aR^f$, —$N(R^a)C(O)R^f$, —$N(R^a)S(O)_tR^f$ (where t is 1 or 2), —$S(O)_tOR^a$ (where t is 1 or 2), —$S(O)_tR^f$ (where t is 1 or 2) and —$S(O)_tN(R^a)_2$ (where t is 1 or 2) where each $R^a$ is independently hydrogen, alkyl, fluoroalkyl, cycloalkyl, aryl, aralkyl, heterocycloalkyl, heteroaryl or heteroarylalkyl, and each R is independently alkyl, fluoroalkyl, cycloalkyl, aryl, aralkyl, heterocycloalkyl, heteroaryl or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—C(O)$R^a$, —$R^b$—C(O)$OR^a$, —$R^b$—C(O)$N(R^a)_2$, —$R^b$—O—$R^c$—C(O)$N(R^a)_2$, —$R^b$—$N(R^a)$C(O)$OR^a$, —$R^b$—$N(R^a)$C(O)$R^a$, —$R^b$—$N(R^a)S(O)_tR^a$ (where t is 1 or 2), —$R^b$—$S(O)_tOR^a$ (where t is 1 or 2), —$R^b$—$S(O)_tR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl (optionally substituted with one or more halo groups), aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

"Aryloxy" refers to a radical bonded through an oxygen atom of the formula —O-aryl, where aryl is as defined above.

"Aralkyl" refers to a radical of the formula —$R^c$-aryl where R is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkyloxy" refers to a radical bonded through an oxygen atom of the formula —O— aralkyl, where aralkyl is as defined above.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Cycloalkyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a cycloalkyl comprises three to ten carbon atoms. In other embodiments, a cycloalkyl comprises five to seven carbon atoms. The cycloalkyl is attached to the rest of the molecule by a single bond. Cycloalkyls are saturated, (i.e., containing single C—C bonds only) or partially unsaturated (i.e., containing one or more double bonds or triple bonds.) Examples of monocyclic cycloalkyls include, e.g., cyclopropyl, cyclobutyl, cyclopentyl, cyclohexyl, cycloheptyl, and cyclooctyl. In certain embodiments, a cycloalkyl comprises three to eight carbon atoms (e.g., $C_3$-$C_8$ cycloalkyl). In other embodiments, a cycloalkyl comprises three to seven carbon atoms (e.g., $C_3$-$C_7$ cycloalkyl). In other embodiments, a cycloalkyl comprises three to six carbon atoms (e.g., $C_3$-$C_6$ cycloalkyl). In other embodiments, a cycloalkyl comprises three to five carbon atoms (e.g., $C_3$-$C_5$ cycloalkyl). In other embodiments, a cycloalkyl comprises three to four carbon atoms (e.g., $C_3$-$C_4$ cycloalkyl). A partially unsaturated cycloalkyl is also referred to as "cycloalkenyl." Examples of monocyclic cycloalkenyls include, e.g., cyclopentenyl, cyclohexenyl, cycloheptenyl, and cyclooctenyl. Polycyclic cycloalkyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "cycloalkyl" is meant to include cycloalkyl radicals optionally substituted by one or more substituents independently selected from alkyl, alkenyl, alkynyl, halo, fluoroalkyl, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—C(O)$R^a$, —$R^b$—C(O)$OR^a$, —$R^b$—C(O)$N(R^a)_2$, —$R^b$—O—$R^c$—C(O)$N(R^a)_2$, —$R^b$—$N(R^a)$C(O)$OR^a$, —$R^b$—$N(R^a)$C(O)$R^a$, —$R^b$—$N(R^a)S(O)_tR^a$ (where t is 1 or 2), —$R^b$—$S(O)_tOR^a$ (where t is 1 or 2), —$R^b$—$S(O)_tR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl (optionally substituted with one or more halo groups), aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

"Halo" or "halogen" refers to bromo, chloro, fluoro or iodo substituents.

"Haloalkyl" refers to an alkyl radical, as defined above, that is substituted by one or more halo radicals, as defined above.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical are optionally substituted as defined above for an alkyl group.

"Haloalkoxy" refers to an alkoxy radical, as defined above, that is substituted by one or more halo radicals, as defined above.

"Heterocycloalkyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocycloalkyl radical is a monocyclic, bicyclic, tricyclic or tetracyclic ring system, which include fused, spiro, or bridged ring systems. The heteroatoms in the heterocycloalkyl radical are optionally oxidized. One or more nitrogen atoms, if present, are optionally quaternized. The heterocycloalkyl radical is partially or fully saturated. In some embodiments, the heterocycloalkyl is attached to the rest of the molecule through any atom of the ring(s). Examples of such heterocycloalkyl radicals include, but are not limited to, dioxolanyl, thienyl[1,3]

dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocycloalkyl" is meant to include heterocycloalkyl radicals as defined above that are optionally substituted by one or more substituents selected from alkyl, alkenyl, alkynyl, halo, fluoroalkyl, oxo, thioxo, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—O—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2), —$R^b$—$S(O)_tR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

"Heteroaryl" refers to a radical derived from a 5- to 18-membered aromatic ring radical that comprises one to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Unless stated otherwise specifically in the specification, the term "heteroaryl" is meant to include heteroaryl radicals as defined above that are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—O—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2), —$R^b$—$S(O)_tR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroaryloxy" refers to radical bonded through an oxygen atom of the formula —O— heteroaryl, where heteroaryl is as defined above.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

In some embodiments, the compounds disclosed herein contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. In certain embodiments, the compounds presented herein exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

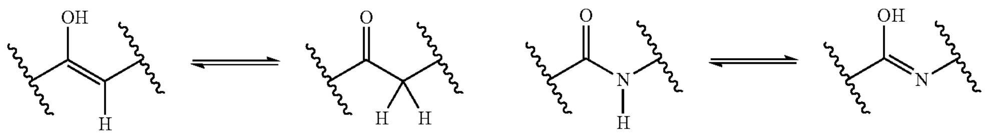

-continued

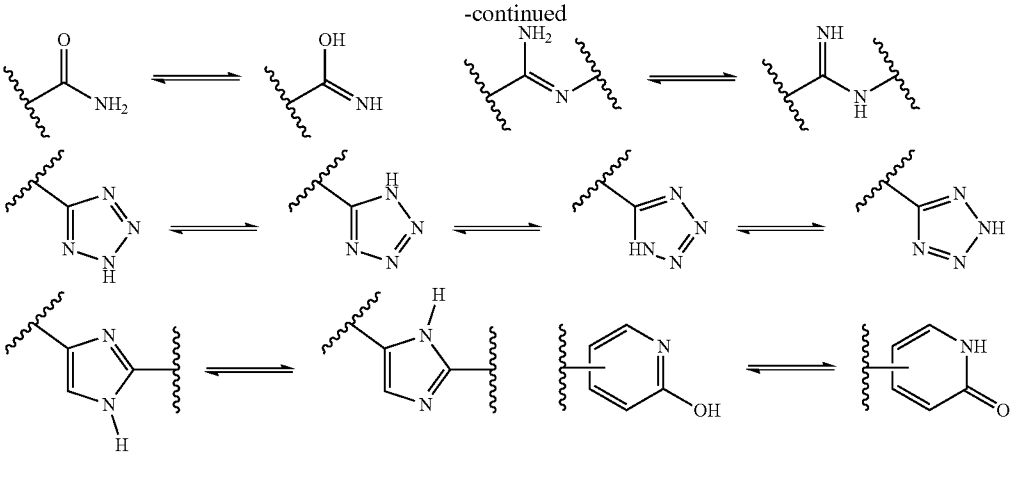

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Prodrugs", includes compounds that, after administration, are metabolized into a pharmacologically active drug (R. B. Silverman, 1992, "The Organic Chemistry of Drug Design and Drug Action," Academic Press, Chp. 8). A prodrug may be used to improve how a compound is absorbed, distributed, metabolized, and excreted.

"Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997)). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

The term "mammal" refers to a human, a non-human primate, canine, feline, bovine, ovine, porcine, murine, or other veterinary or laboratory mammal. Those skilled in the art recognize that a therapy which reduces the severity of a pathology in one species of mammal is predictive of the effect of the therapy on another species of mammal.

As used herein, "treatment" or "treating" or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are administered to a patient at risk of developing a particular disease, or to a patient reporting one or more of the physiological symptoms of a disease, even though a diagnosis of this disease has not been made.

Compounds

The compounds of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va") described herein are P2X3 modulators. In some embodiments, the compounds of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va") described herein are P2X3 antagonists. In some embodiments, the compounds of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va") described herein, and compositions comprising these compounds, are useful for treating pain, a urinary tract disorder, cough, pruritus, endometriosis, endometriosis-associated pain, or endometriosis-associated symptoms.

In some embodiments is a compound of Formula (I):

Formula (I)

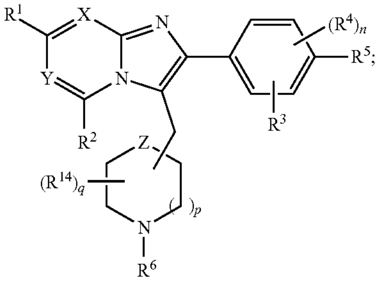

wherein:

X is $C(R^2)$ or N;

Y is $C(R^2)$ or N;

Z is a bond, $CH_2$, or O;

$R^1$ is selected from hydrogen, deuterium, $C_3$-$C_6$alkyl, $C_2$-$C_6$alkenyl, $C_2$-$C_6$alkynyl, $C_1$-$C_6$haloalkyl, $C_3$-$C_6$cycloalkyl, —$OR^7$, —$N(R^7)_2$, —C(═O)$R^8$, —C(═O)$OR^7$, —C(═O)$N(R^7)_2$, —$NR^7$C(═O)$R^8$, —$NR^{10}$S(═O)$_2R^8$, —S(═O)$_2R^8$, and —S(═O)$_2$N$(R^7)_2$;

each $R^2$ is independently selected from hydrogen, deuterium, halogen, —CN, $C_1$-$C_6$alkyl, $C_2$-$C_6$alkenyl, $C_2$-$C_6$alkynyl, $C_1$-$C_6$haloalkyl, $C_1$-$C_6$alkoxy, and $C_3$-$C_6$cycloalkyl;

$R^3$ is selected from hydrogen, deuterium, halogen, —CN, $C_1$-$C_6$alkyl, $C_2$-$C_6$alkenyl, $C_2$-$C_6$alkynyl, $C_1$-$C_6$haloalkyl, $C_3$-$C_6$cycloalkyl, —$OR^7$, —$N(R^7)_2$, —C(═O)$R^8$, —C(═O)$OR^7$, —C(═O)$N(R^7)_2$, —$NR^7$C(═O)$R^8$, —$NR^{10}$S(═O)$_2R^8$, —S(═O)$_2R^8$, and —S(═O)$_2N(R^7)_2$;

each $R^4$ is independently selected from deuterium, halogen, —CN, $C_1$-$C_6$alkyl, $C_2$-$C_6$alkenyl, $C_2$-$C_6$alkynyl, $C_1$-$C_6$haloalkyl, $C_1$-$C_6$alkoxy, and $C_3$-$C_6$cycloalkyl; or two $R^4$ are combined to form a bridged heterocycloalkyl ring;

$R^5$ is —C(═O)$N(R^9)(R^{10})$, —C(═O)$OR^9$, —S(═O)$R^{15}$, —S(═O)$_2R^{15}$, —S(═O)(═NH)$R^{15}$, —$C_2$-$C_9$heterocycloalkyl-$N(R^9)(R^{10})$, or —$C_1$-$C_6$haloalkyl-$N(R^9)(R^{10})$;

$R^6$ is selected from —C(═O)$OR^{11}$, —C(═O)$R^{11}$, and —C(═O)$N(R^{12})(R^{13})$;

each $R^7$ is independently selected from hydrogen, deuterium, $C_1$-$C_6$alkyl, and $C_1$-$C_6$haloalkyl;

each $R^8$ is independently selected from $C_1$-$C_6$alkyl;

$R^9$, $R^{10}$, $R^{12}$, and $R^{13}$ are independently selected from hydrogen, deuterium, and $C_1$-$C_6$alkyl;

$R^{11}$ is $C_1$-$C_6$alkyl or —$C_1$-$C_6$alkyl-O—$C_1$-$C_6$alkyl;

$R^{14}$ is $C_1$-$C_6$alkyl;

$R^{15}$ is $C_1$-$C_6$alkyl;

n is 0, 1, 2, or 3;

p is 1, 2, or 3; and q is 0, 1, 2, 3, or 4;

or a pharmaceutically acceptable salt or solvate thereof.

In some embodiments is a compound of Formula (I), or a pharmaceutically acceptable salt or solvate thereof, having the structure of Formula (Ia):

Formula (Ia)

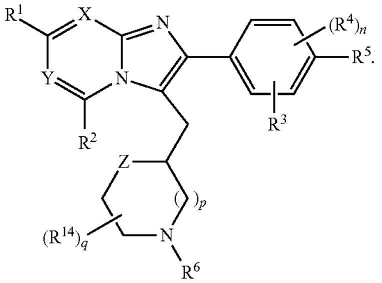

In some embodiments is a compound of Formula (I), or a pharmaceutically acceptable salt or solvate thereof, having the structure of Formula (Ia'):

Formula (Ia')

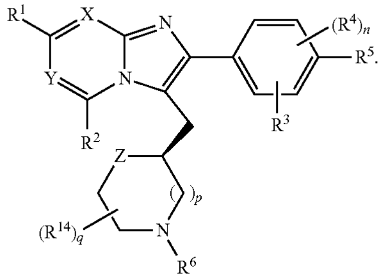

In some embodiments is a compound of Formula (I), or a pharmaceutically acceptable salt or solvate thereof, having the structure of Formula (Ia"):

Formula (Ia")

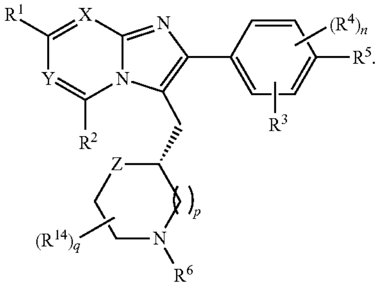

In some embodiments is a compound of Formula (I), (Ia), (Ia'), or (Ia"), or a pharmaceutically acceptable salt or solvate thereof, wherein X is $C(R^2)$. In some embodiments is a compound of Formula (I), (Ia), (Ia'), or (Ia"), or a pharmaceutically acceptable salt or solvate thereof, wherein X is C(H). In some embodiments is a compound of Formula (I), (Ia), (Ia'), or (Ia"), or a pharmaceutically acceptable salt or solvate thereof, wherein X is N.

In some embodiments is a compound of Formula (I), (Ia), (Ia'), or (Ia"), or a pharmaceutically acceptable salt or solvate thereof, wherein Y is $C(R^2)$. In some embodiments is a compound of Formula (I), (Ia), (Ia'), or (Ia"), or a pharmaceutically acceptable salt or solvate thereof, wherein Y is C(H). In some embodiments is a compound of Formula (I), (Ia), (Ia'), or (Ia"), or a pharmaceutically acceptable salt or solvate thereof, wherein Y is N.

In some embodiments is a compound of Formula (I), (Ia), (Ia'), or (Ia"), or a pharmaceutically acceptable salt or solvate thereof, wherein Z is O. In some embodiments is a compound of Formula (I), (Ia), (Ia'), or (Ia"), or a pharmaceutically acceptable salt or solvate thereof, wherein Z is $CH_2$. In some embodiments is a compound of Formula (I), (Ia), (Ia'), or (Ia"), or a pharmaceutically acceptable salt or solvate thereof, wherein Z is a bond.

In some embodiments is a compound of Formula (I), (Ia), (Ia'), or (Ia"), or a pharmaceutically acceptable salt or solvate thereof, wherein each $R^2$ is hydrogen.

In some embodiments is a compound of Formula (I), (Ia), (Ia'), or (Ia"), or a pharmaceutically acceptable salt or solvate thereof, wherein q is 0. In some embodiments is a compound of Formula (I), (Ia), (Ia'), or (Ia"), or a pharmaceutically acceptable salt or solvate thereof, wherein q is 1. In some embodiments is a compound of Formula (I), (Ia), (Ia'), or (Ia"), or a pharmaceutically acceptable salt or solvate thereof, wherein q is 2.

In some embodiments is a compound of Formula (I), (Ia), (Ia'), or (Ia"), or a pharmaceutically acceptable salt or solvate thereof, wherein $R^6$ is $—C(=O)OR^{11}$. In some embodiments is a compound of Formula (I), (Ia), (Ia'), or (Ia"), or a pharmaceutically acceptable salt or solvate thereof, wherein $R^6$ is $—C(=O)OCH_3$. In some embodiments is a compound of Formula (I), (Ia), (Ia'), or (Ia"), or a pharmaceutically acceptable salt or solvate thereof, wherein $R^6$ is $—C(=O)OCH_2CH_3$. In some embodiments is a compound of Formula (I), (Ia), (Ia'), or (Ia"), or a pharmaceutically acceptable salt or solvate thereof, wherein $R^6$ is $—C(=O)R^{11}$. In some embodiments is a compound of Formula (I), (Ia), (Ia'), or (Ia"), or a pharmaceutically acceptable salt or solvate thereof, wherein $R^6$ is $—C(=O)CH_3$. In some embodiments is a compound of Formula (I), (Ia), (Ia'), or (Ia"), or a pharmaceutically acceptable salt or solvate thereof, wherein $R^6$ is $—C(=O)CH_2CH_3$. In some embodiments is a compound of Formula (I), (Ia), (Ia'), or (Ia"), or a pharmaceutically acceptable salt or solvate thereof, wherein $R^6$ is $—C(=O)N(R^{12})(R^{13})$. In some embodiments is a compound of Formula (I), (Ia), (Ia'), or (Ia"), or a pharmaceutically acceptable salt or solvate thereof, wherein $R^6$ is $—C(=O)N(H)(CH_3)$.

In some embodiments is a compound of Formula (I), (Ia), (Ia'), or (Ia"), or a pharmaceutically acceptable salt or solvate thereof, wherein $R^5$ is $—C(=O)N(R^9)(R^{10})$. In some embodiments is a compound of Formula (I), (Ia), (Ia'), or (Ia"), or a pharmaceutically acceptable salt or solvate thereof, wherein $R^5$ is $—C(=O)N(H)(CH_3)$. In some embodiments is a compound of Formula (I), (Ia), (Ia'), or (Ia"), or a pharmaceutically acceptable salt or solvate thereof, wherein $R^5$ is $—C(=O)NH_2$. In some embodiments is a compound of Formula (I), (Ia), (Ia'), or (Ia"), or a pharmaceutically acceptable salt or solvate thereof, wherein $R^5$ is $—C(=O)N(CH_3)_2$. In some embodiments is a compound of Formula (I), (Ia), (Ia'), or (Ia"), or a pharmaceutically acceptable salt or solvate thereof, wherein $R^5$ is $—C(=O)OR^9$. In some embodiments is a compound of Formula (I), (Ia), (Ia'), or (Ia"), or a pharmaceutically acceptable salt or solvate thereof, wherein $R^5$ is $—C(=O)OCH_3$. In some embodiments is a compound of Formula (I), (Ia), (Ia'), or (Ia"), or a pharmaceutically acceptable salt or solvate thereof, wherein $R^5$ is $—C(=O)OCH_2CH_3$.

In some embodiments is a compound of Formula (I), (Ia), (Ia'), or (Ia"), or a pharmaceutically acceptable salt or solvate thereof, wherein $R^1$ is $C_1$-$C_6$haloalkyl. In some embodiments is a compound of Formula (I), (Ia), (Ia'), or (Ia"), or a pharmaceutically acceptable salt or solvate thereof, wherein $R^1$ is $—CF_3$. In some embodiments is a compound of Formula (I), (Ia), (Ia'), or (Ia"), or a pharmaceutically acceptable salt or solvate thereof, wherein $R^1$ is $—CHF_2$. In some embodiments is a compound of Formula (I), (Ia), (Ia'), or (Ia"), or a pharmaceutically acceptable salt or solvate thereof, wherein $R^1$ is $—OR^7$. In some embodiments is a compound of Formula (I), (Ia), (Ia'), or (Ia"), or a pharmaceutically acceptable salt or solvate thereof, wherein $R^1$ is $—OR^7$ and $R^7$ is $C_1$-$C_6$alkyl. In some embodiments is a compound of Formula (I), (Ia), (Ia'), or (Ia"), or a pharmaceutically acceptable salt or solvate thereof, wherein $R^1$ is $—OR^7$ and $R^7$ is $C_1$-$C_6$haloalkyl. In some embodiments is a compound of Formula (I), (Ia), (Ia'), or (Ia"), or a pharmaceutically acceptable salt or solvate thereof, wherein $R^1$ is hydrogen. In some embodiments is a compound of Formula (I), (Ia), (Ia'), or (Ia"), or a pharmaceutically acceptable salt or solvate thereof, wherein $R^1$ is deuterium. In some embodiments is a compound of Formula (I), (Ia), (Ia'), or (Ia"), or a pharmaceutically acceptable salt or solvate thereof, wherein $R^1$ is $C_3$-$C_6$alkyl.

In some embodiments is a compound of Formula (I), (Ia), (Ia'), or (Ia"), or a pharmaceutically acceptable salt or solvate thereof, wherein $R^3$ is selected from hydrogen, deuterium, halogen, $C_1$-$C_6$alkyl, and $—OR^7$. In some embodiments is a compound of Formula (I), (Ia), (Ia'), or (Ia"), or a pharmaceutically acceptable salt or solvate thereof, wherein $R^3$ is halogen. In some embodiments is a compound of Formula (I), (Ia), (Ia'), or (Ia"), or a pharmaceutically acceptable salt or solvate thereof, wherein $R^3$ is $C_1$-$C_6$alkyl. In some embodiments is a compound of Formula (I), (Ia), (Ia'), or (Ia"), or a pharmaceutically acceptable salt or solvate thereof, wherein $R^3$ is $—CH_3$. In some embodiments is a compound of Formula (I), (Ia), (Ia'), or (Ia"), or a pharmaceutically acceptable salt or solvate thereof, wherein $R^3$ is $—OR^7$. In some embodiments is a compound of Formula (I), (Ia), (Ia'), or (Ia"), or a pharmaceutically acceptable salt or solvate thereof, wherein $R^3$ is $—OCH_3$. In some embodiments is a compound of Formula (I), (Ia), (Ia'), or (Ia"), or a pharmaceutically acceptable salt or solvate thereof, wherein $R^3$ is hydrogen. In some embodiments is a compound of Formula (I), (Ia), (Ia'), or (Ia"), or a pharmaceutically acceptable salt or solvate thereof, wherein $R^3$ is deuterium.

In some embodiments is a compound of Formula (I), (Ia), (Ia'), or (Ia"), or a pharmaceutically acceptable salt or solvate thereof, wherein n is 1. In some embodiments is a compound of Formula (I), (Ia), (Ia'), or (Ia"), or a pharmaceutically acceptable salt or solvate thereof, wherein n is 2. In some embodiments is a compound of Formula (I), (Ia), (Ia'), or (Ia"), or a pharmaceutically acceptable salt or solvate thereof, wherein n is 0.

In some embodiments is a compound of Formula (I), (Ia), (Ia'), or (Ia"), or a pharmaceutically acceptable salt or solvate thereof, wherein each $R^4$ is independently selected from deuterium, halogen, $C_1$-$C_6$alkyl, $C_1$-$C_6$haloalkyl, and $C_1$-$C_6$alkoxy. In some embodiments is a compound of Formula (I), (Ia), (Ia'), or (Ia"), or a pharmaceutically acceptable salt or solvate thereof, wherein each $R^4$ is independently selected from halogen, $C_1$-$C_6$alkyl, and $C_1$-$C_6$alkoxy. In some embodiments is a compound of Formula (I), (Ia), (Ia'), or (Ia"), or a pharmaceutically acceptable salt or solvate thereof, wherein each $R^4$ is halogen.

In some embodiments is a compound of Formula (I), (Ia), (Ia'), or (Ia"), or a pharmaceutically acceptable salt or solvate thereof, wherein n is 1 or 2 and each $R^4$ is independently selected from deuterium, halogen, $C_1$-$C_6$alkyl, $C_1$-$C_6$haloalkyl, and $C_1$-$C_6$alkoxy. In some embodiments is a compound of Formula (I), (Ia), (Ia'), or (Ia"), or a pharmaceutically acceptable salt or solvate thereof, wherein n is 1 or 2 and each $R^4$ is independently selected from halogen, $C_1$-$C_6$alkyl, and $C_1$-$C_6$alkoxy. In some embodiments is a compound of Formula (I), (Ia), (Ia'), or (Ia"), or a pharmaceutically acceptable salt or solvate thereof, wherein n is 1 or 2 and each $R^4$ is halogen.

In some embodiments is a compound of Formula (I), (Ia), (Ia'), or (Ia"), or a pharmaceutically acceptable salt or solvate thereof, wherein p is 1. In some embodiments is a compound of Formula (I), (Ia), (Ia'), or (Ia"), or a pharmaceutically acceptable salt or solvate thereof, wherein p is 2. In some embodiments is a compound of Formula (I), (Ia), (Ia'), or (Ia"), or a pharmaceutically acceptable salt or solvate thereof, wherein p is 3.

In some embodiments is a compound of Formula (II):

Formula (II)

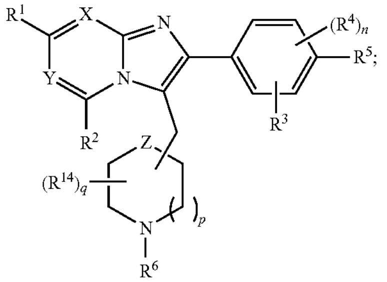

wherein:

X is $C(R^2)$ or N;

Y is $C(R^2)$ or N;

Z is a bond, $CH_2$, or O;

$R^1$ is selected from hydrogen, deuterium, halogen, $C_1$-$C_6$alkyl, $C_2$-$C_6$alkenyl, $C_2$-$C_6$alkynyl, $C_1$-$C_6$haloalkyl, $C_3$-$C_6$cycloalkyl, $—OR^7$, $—N(R^7)_2$, —CN, $—C(=O)R^8$, $—C(=O)OR^7$, $—C(=O)N(R^7)_2$, $—NR^7C(=O)R^8$, $—NR^{10}S(=O)_2R^8$, $—S(=O)_2R^8$, and $—S(=O)_2N(R^7)_2$;

each $R^2$ is independently selected from hydrogen, deuterium, halogen, —CN, $C_1$-$C_6$alkyl, $C_2$-$C_6$alkenyl, $C_2$-$C_6$alkynyl, $C_1$-$C_6$haloalkyl, $C_1$-$C_6$alkoxy, and $C_3$-$C_6$cycloalkyl;

$R^3$ is selected from deuterium, $C_3$-$C_6$alkyl, $C_2$-$C_6$alkenyl, $C_2$-$C_6$alkynyl, $C_1$-$C_6$haloalkyl, $C_3$-$C_6$cycloalkyl, $—N(R^7)_2$, —CN, $—C(=O)R^8$, $—C(=O)OR^7$, $—C(=O)N(R^7)_2$, $—NR^7C(=O)R^8$, $—NR^{10}S(=O)_2R^8$, $—S(=O)_2R^8$, and $—S(=O)_2N(R^7)_2$;

each $R^4$ is independently selected from deuterium, halogen, —CN, $C_1$-$C_6$alkyl, $C_2$-$C_6$alkenyl, $C_2$-$C_6$alkynyl, $C_1$-$C_6$haloalkyl, $C_1$-$C_6$alkoxy, and $C_3$-$C_6$cycloalkyl; or two $R^4$ are combined to form a bridged heterocycloalkyl ring;

$R^5$ is $—C(=O)N(R^9)(R^{10})$, $—C(=O)OR^9$, $—S(=O)R^{15}$, $—S(=O)_2R^{15}$, $—S(=O)(=NH)R^{15}$, $—C_2$-$C_9$heterocycloalkyl-$N(R^9)(R^{10})$, or $—C_1$-$C_6$haloalkyl-$N(R^9)(R^{10})$;

$R^6$ is selected from $—C(=O)OR^{11}$, $—C(=O)R^{11}$, and $—C(=O)N(R^{12})(R^{13})$;

each $R^7$ is independently selected from hydrogen, deuterium, $C_1$-$C_6$alkyl, and $C_1$-$C_6$haloalkyl;

each $R^8$ is independently selected from $C_1$-$C_6$alkyl;

$R^9$, $R^{10}$, $R^{12}$, and $R^{13}$ are independently selected from hydrogen, deuterium, and $C_1$-$C_6$alkyl;

$R^{11}$ is $C_1$-$C_6$alkyl or $—C_1$-$C_6$alkyl-O—$C_1$-$C_6$alkyl;

$R^{14}$ is $C_1$-$C_6$alkyl;

$R^{15}$ is $C_1$-$C_6$alkyl;

n is 0, 1, 2, or 3;

p is 1, 2, or 3; and q is 0, 1, 2, 3, or 4;

or a pharmaceutically acceptable salt or solvate thereof.

In some embodiments is a compound of Formula (II), or a pharmaceutically acceptable salt or solvate thereof, having the structure of Formula (IIa):

Formula (IIa)

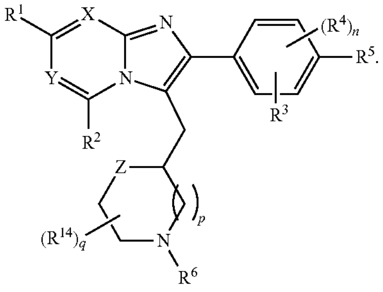

In some embodiments is a compound of Formula (II), or a pharmaceutically acceptable salt or solvate thereof, having the structure of Formula (IIa'):

Formula (IIa')

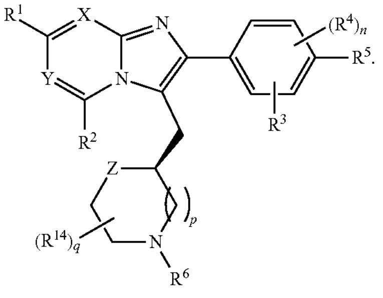

In some embodiments is a compound of Formula (II), or a pharmaceutically acceptable salt or solvate thereof, having the structure of Formula (IIa"):

Formula (IIa'')

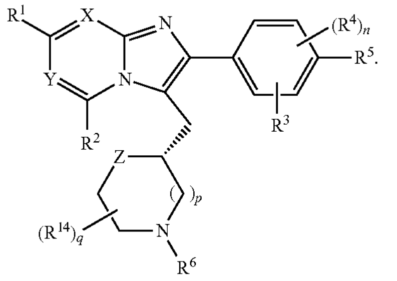

In some embodiments is a compound of Formula (II), (IIa), (IIa'), or (IIa"), or a pharmaceutically acceptable salt or solvate thereof, wherein X is $C(R^2)$. In some embodiments is a compound of Formula (II), (IIa), (IIa'), or (IIa"), or a pharmaceutically acceptable salt or solvate thereof, wherein X is C(H). In some embodiments is a compound of Formula (II), (IIa), (IIa'), or (IIa"), or a pharmaceutically acceptable salt or solvate thereof, wherein X is N.

In some embodiments is a compound of Formula (II), (IIa), (IIa'), or (IIa"), or a pharmaceutically acceptable salt or solvate thereof, wherein Y is $C(R^2)$. In some embodiments is a compound of Formula (II), (IIa), (IIa'), or (IIa"), or a pharmaceutically acceptable salt or solvate thereof, wherein Y is C(H). In some embodiments is a compound of Formula (II), (IIa), (IIa'), or (IIa"), or a pharmaceutically acceptable salt or solvate thereof, wherein Y is N.

In some embodiments is a compound of Formula (II), (IIa), (IIa'), or (IIa"), or a pharmaceutically acceptable salt or solvate thereof, wherein Z is O. In some embodiments is a compound of Formula (II), (IIa), (IIa'), or (IIa"), or a pharmaceutically acceptable salt or solvate thereof, wherein Z is $CH_2$. In some embodiments is a compound of Formula (II), (IIa), (IIa'), or (IIa"), or a pharmaceutically acceptable salt or solvate thereof, wherein Z is a bond.

In some embodiments is a compound of Formula (II), (IIa), (IIa'), or (IIa"), or a pharmaceutically acceptable salt or solvate thereof, wherein each $R^2$ is hydrogen.

In some embodiments is a compound of Formula (II), (IIa), (IIa'), or (IIa"), or a pharmaceutically acceptable salt or solvate thereof, wherein q is 0. In some embodiments is a compound of Formula (II), (IIa), (IIa'), or (IIa"), or a pharmaceutically acceptable salt or solvate thereof, wherein q is 1. In some embodiments is a compound of Formula (II), (IIa), (IIa'), or (IIa"), or a pharmaceutically acceptable salt or solvate thereof, wherein q is 2.

In some embodiments is a compound of Formula (II), (IIa), (IIa'), or (IIa"), or a pharmaceutically acceptable salt or solvate thereof, wherein $R^6$ is $—C(=O)OR^{11}$. In some embodiments is a compound of Formula (II), (IIa), (IIa'), or (IIa"), or a pharmaceutically acceptable salt or solvate thereof, wherein $R^6$ is $—C(=O)OCH_3$. In some embodiments is a compound of Formula (II), (IIa), (IIa'), or (IIa"), or a pharmaceutically acceptable salt or solvate thereof, wherein $R^6$ is $—C(=O)OCH_2CH_3$. In some embodiments is a compound of Formula (II), (IIa), (IIa'), or (IIa"), or a pharmaceutically acceptable salt or solvate thereof, wherein $R^6$ is $—C(=O)R^{11}$. In some embodiments is a compound of Formula (II), (IIa), (IIa'), or (IIa"), or a pharmaceutically acceptable salt or solvate thereof, wherein $R^6$ is $—C(=O)CH_3$. In some embodiments is a compound of Formula (II), (IIa), (IIa'), or (IIa"), or a pharmaceutically acceptable salt or solvate thereof, wherein $R^6$ is $—C(=O)CH_2CH_3$. In some embodiments is a compound of Formula (II), (IIa), (IIa'), or (IIa"), or a pharmaceutically acceptable salt or solvate thereof, wherein $R^6$ is $—C(=O)N(R^{12})(R^{13})$. In some embodiments is a compound of Formula (II), (IIa), (IIa'), or (IIa"), or a pharmaceutically acceptable salt or solvate thereof, wherein $R^6$ is $—C(=O)N(H)(CH_3)$.

In some embodiments is a compound of Formula (II), (IIa), (IIa'), or (IIa"), or a pharmaceutically acceptable salt or solvate thereof, wherein $R^5$ is $—C(=O)N(R^9)(R^{10})$. In some embodiments is a compound of Formula (II), (IIa), (IIa'), or (IIa"), or a pharmaceutically acceptable salt or solvate thereof, wherein $R^5$ is $—C(=O)N(H)(CH_3)$. In some embodiments is a compound of Formula (II), (IIa), (IIa'), or (IIa"), or a pharmaceutically acceptable salt or solvate thereof, wherein $R^5$ is $—C(=O)NH_2$. In some embodiments is a compound of Formula (II), (IIa), (IIa'), or (IIa"), or a pharmaceutically acceptable salt or solvate thereof, wherein $R^5$ is $—C(=O)N(CH_3)_2$. In some embodiments is a compound of Formula (II), (IIa), (IIa'), or (IIa"), or a pharmaceutically acceptable salt or solvate thereof, wherein $R^5$ is $—C(=O)OR^9$. In some embodiments is a compound of Formula (II), (IIa), (IIa'), or (IIa"), or a pharmaceutically acceptable salt or solvate thereof, wherein $R^5$ is $—C(=O)OCH_3$. In some embodiments is a compound of Formula (II), (IIa), (IIa'), or (IIa"), or a pharmaceutically acceptable salt or solvate thereof, wherein $R^5$ is $—C(=O)OCH_2CH_3$.

In some embodiments is a compound of Formula (II), (IIa), (IIa'), or (IIa"), or a pharmaceutically acceptable salt or solvate thereof, wherein $R^1$ is $C_1$-$C_6$alkyl. In some embodiments is a compound of Formula (II), (IIa), (IIa'), or (IIa"), or a pharmaceutically acceptable salt or solvate thereof, wherein $R^1$ is $—CH_3$. In some embodiments is a compound of Formula (II), (IIa), (IIa'), or (IIa"), or a pharmaceutically acceptable salt or solvate thereof, wherein $R^1$ is $C_1$-$C_6$haloalkyl. In some embodiments is a compound of Formula (II), (IIa), (IIa'), or (IIa"), or a pharmaceutically acceptable salt or solvate thereof, wherein $R^1$ is $—CF_3$. In some embodiments is a compound of Formula (II), (IIa), (IIa'), or (IIa"), or a pharmaceutically acceptable salt or solvate thereof, wherein $R^1$ is $—CHF_2$. In some embodiments is a compound of Formula (II), (IIa), (IIa'), or (IIa"), or a pharmaceutically acceptable salt or solvate thereof, wherein $R^1$ is $—OR^7$. In some embodiments is a compound of Formula (II), (IIa), (IIa'), or (IIa"), or a pharmaceutically acceptable salt or solvate thereof, wherein $R^1$ is $—OR^7$ and $R^7$ is $C_1$-$C_6$alkyl. In some embodiments is a compound of Formula (II), (IIa), (IIa'), or (IIa"), or a pharmaceutically acceptable salt or solvate thereof, wherein $R^1$ is $—OR^7$ and $R^7$ is $C_1$-$C_6$haloalkyl. In some embodiments is a compound of Formula (II), (IIa), (IIa'), or (IIa"), or a pharmaceutically acceptable salt or solvate thereof, wherein $R^1$ is hydrogen. In some embodiments is a compound of Formula (II), (IIa), (IIa'), or (IIa"), or a pharmaceutically acceptable salt or solvate thereof, wherein $R^1$ is deuterium. In some embodiments is a compound of Formula (II), (IIa), (IIa'), or (IIa"), or a pharmaceutically acceptable salt or solvate thereof, wherein $R^1$ is $C_3$-$C_6$alkyl.

In some embodiments is a compound of Formula (II), (IIa), (IIa'), or (IIa"), or a pharmaceutically acceptable salt or solvate thereof, wherein $R^3$ is selected from deuterium and $C_3$-$C_6$alkyl. In some embodiments is a compound of Formula (II), (IIa), (IIa'), or (IIa"), or a pharmaceutically acceptable salt or solvate thereof, wherein $R^3$ is $C_3$-$C_6$alkyl. In some embodiments is a compound of Formula (II), (IIa), (IIa'), or (IIa"), or a pharmaceutically acceptable salt or solvate thereof, wherein $R^3$ is deuterium.

In some embodiments is a compound of Formula (II), (IIa), (IIa'), or (IIa"), or a pharmaceutically acceptable salt or solvate thereof, wherein n is 1. In some embodiments is a compound of Formula (II), (IIa), (IIa'), or (IIa"), or a pharmaceutically acceptable salt or solvate thereof, wherein n is 2. In some embodiments is a compound of Formula (II), (IIa), (IIa'), or (IIa"), or a pharmaceutically acceptable salt or solvate thereof, wherein n is 0.

In some embodiments is a compound of Formula (II), (IIa), (IIa'), or (IIa"), or a pharmaceutically acceptable salt or solvate thereof, wherein each $R^4$ is independently selected from deuterium, halogen, $C_1$-$C_6$alkyl, $C_1$-$C_6$haloalkyl, and $C_1$-$C_6$alkoxy. In some embodiments is a compound of Formula (II), (IIa), (IIa'), or (IIa"), or a pharmaceutically acceptable salt or solvate thereof, wherein each $R^4$ is independently selected from halogen, $C_1$-$C_6$alkyl, and $C_1$-$C_6$alkoxy. In some embodiments is a compound of Formula (II), (IIa), (IIa'), or (IIa"), or a pharmaceutically acceptable salt or solvate thereof, wherein each $R^4$ is halogen.

In some embodiments is a compound of Formula (II), (IIa), (IIa'), or (IIa"), or a pharmaceutically acceptable salt or solvate thereof, wherein n is 1 or 2 and each $R^4$ is independently selected from deuterium, halogen, $C_1$-$C_6$alkyl, $C_1$-$C_6$haloalkyl, and $C_1$-$C_6$alkoxy. In some embodiments is a compound of Formula (II), (IIa), (IIa'), or (IIa"), or a pharmaceutically acceptable salt or solvate thereof, wherein n is 1 or 2 and each $R^4$ is independently selected from halogen, $C_1$-$C_6$alkyl, and $C_1$-$C_6$alkoxy. In some embodiments is a compound of Formula (II), (IIa), (IIa'), or (IIa"), or a pharmaceutically acceptable salt or solvate thereof, wherein n is 1 or 2 and each $R^4$ is halogen.

In some embodiments is a compound of Formula (II), (IIa), (IIa'), or (IIa"), or a pharmaceutically acceptable salt or solvate thereof, wherein p is 1. In some embodiments is a compound of Formula (II), (IIa), (IIa'), or (IIa"), or a pharmaceutically acceptable salt or solvate thereof, wherein p is 2. In some embodiments is a compound of Formula (II), (IIa), (IIa'), or (IIa"), or a pharmaceutically acceptable salt or solvate thereof, wherein p is 3.

In some embodiments is a compound of Formula (III):

Formula (III)

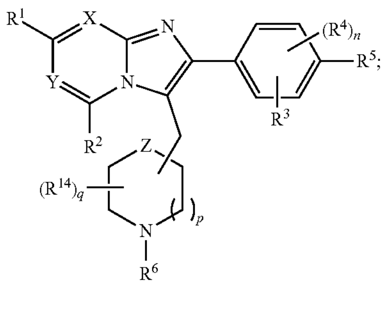

wherein:

X is $C(R^2)$ or N;

Y is $C(R^2)$ or N;

Z is $CH_2$ or O;

$R^1$ is selected from hydrogen, deuterium, halogen, $C_1$-$C_6$alkyl, $C_2$-$C_6$alkenyl, $C_2$-$C_6$alkynyl, $C_1$-$C_6$haloalkyl, $C_3$-$C_6$cycloalkyl, $—OR^7$, $—N(R^7)_2$, —CN, $—C(=O)R^8$, $—C(=O)OR^7$, $—C(=O)N(R^7)_2$, $—NR^7C(=O)R^8$, $—NR^{10}S(=O)_2R^8$, $—S(=O)_2R^8$, and $—S(=O)_2N(R^7)_2$;

each $R^2$ is independently selected from hydrogen, deuterium, halogen, —CN, $C_1$-$C_6$alkyl, $C_2$-$C_6$alkenyl, $C_2$-$C_6$alkynyl, $C_1$-$C_6$haloalkyl, $C_1$-$C_6$alkoxy, and $C_3$-$C_6$cycloalkyl;

$R^3$ is selected from hydrogen, deuterium, halogen, —CN, $C_1$-$C_6$alkyl, $C_2$-$C_6$alkenyl, $C_2$-$C_6$alkynyl, $C_1$-$C_6$haloalkyl, $C_3$-$C_6$cycloalkyl, $—OR^7$, $—N(R^7)_2$, $—C(=O)R^8$, $—C(=O)OR^7$, $—C(=O)N(R^7)_2$, $—NR^7C(=O)R^8$, $—NR^{10}S(=O)_2R^8$, $—S(=O)_2R^8$, and $—S(=O)_2N(R^7)_2$;

each $R^4$ is independently selected from deuterium, halogen, —CN, $C_1$-$C_6$alkyl, $C_2$-$C_6$alkenyl, $C_2$-$C_6$alkynyl, $C_1$-$C_6$haloalkyl, $C_1$-$C_6$alkoxy, and $C_3$-$C_6$cycloalkyl; or two $R^4$ are combined to form a bridged heterocycloalkyl ring;

$R^5$ is $—C(=O)N(R^9)(R^{10})$, $—C(=O)OR^9$, $—S(=O)R^{15}$, $—S(=O)_2R^{15}$, $—S(=O)(=NH)R^{15}$, $—C_2$-$C_9$heterocycloalkyl-$N(R^9)(R^{10})$, or $—C_1$-$C_6$haloalkyl-$N(R^9)(R^{10})$;

$R^6$ is selected from $—C(=O)OR^{11}$, $—C(=O)R^{11}$, and $—C(=O)N(R^{12})(R^{13})$;

each $R^7$ is independently selected from hydrogen, deuterium, $C_1$-$C_6$alkyl, and $C_1$-$C_6$haloalkyl;

each $R^8$ is independently selected from $C_1$-$C_6$alkyl;

$R^9$ and $R^{10}$ are independently selected from $C_1$-$C_6$alkyl; or $R^9$ and $R^{10}$ are combined to form a 5- or 6-membered heterocycloalkyl ring optionally substituted with 1, 2, 3, or 4 groups selected from halogen, $C_1$-$C_6$alkyl, $C_1$-$C_6$haloalkyl, hydroxy, and $C_1$-$C_6$alkoxy;

$R^{12}$ and $R^{13}$ are independently selected from hydrogen, deuterium, and $C_1$-$C_6$alkyl;

$R^{11}$ is $C_1$-$C_6$alkyl or $—C_1$-$C_6$alkyl-O—$C_1$-$C_6$alkyl;

$R^{14}$ is $C_1$-$C_6$alkyl;

$R^{15}$ is $C_1$-$C_6$alkyl;

n is 0, 1, 2, or 3;

p is 1, 2, or 3; and q is 0, 1, 2, 3, or 4;

or a pharmaceutically acceptable salt or solvate thereof.

In some embodiments is a compound of Formula (III), or a pharmaceutically acceptable salt or solvate thereof, having the structure of Formula (IIIa):

Formula (IIIa)

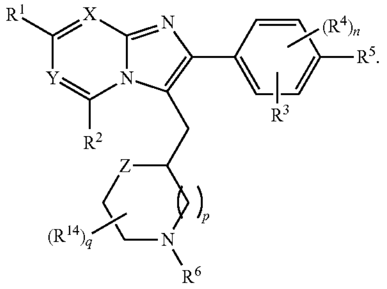

In some embodiments is a compound of Formula (III), or a pharmaceutically acceptable salt or solvate thereof, having the structure of Formula (IIIa'):

Formula (IIIa')

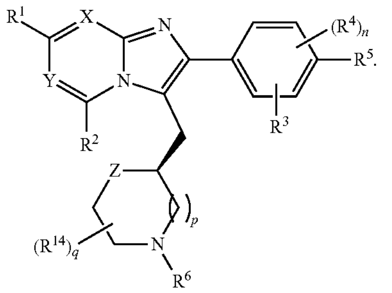

In some embodiments is a compound of Formula (III), or a pharmaceutically acceptable salt or solvate thereof, having the structure of Formula (IIIa"):

Formula (IIIa")

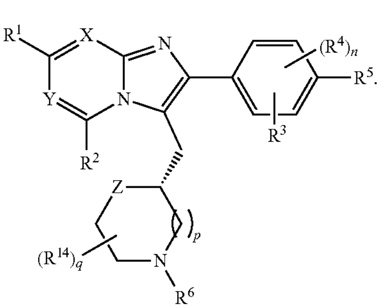

In some embodiments is a compound of Formula (III), (IIIa), (IIIa'), or (IIIa"), or a pharmaceutically acceptable salt or solvate thereof, wherein X is $C(R^2)$. In some embodiments is a compound of Formula (III), (IIIa), (IIIa'), or (IIIa"), or a pharmaceutically acceptable salt or solvate thereof, wherein X is C(H). In some embodiments is a compound of Formula (III), (IIIa), (IIIa'), or (IIIa"), or a pharmaceutically acceptable salt or solvate thereof, wherein X is N.

In some embodiments is a compound of Formula (III), (IIIa), (IIIa'), or (IIIa"), or a pharmaceutically acceptable salt or solvate thereof, wherein Y is $C(R^2)$. In some embodiments is a compound of Formula (III), (IIIa), (IIIa'), or (IIIa"), or a pharmaceutically acceptable salt or solvate thereof, wherein Y is C(H). In some embodiments is a compound of Formula (III), (IIIa), (IIIa'), or (IIIa"), or a pharmaceutically acceptable salt or solvate thereof, wherein Y is N.

In some embodiments is a compound of Formula (III), (IIIa), (IIIa'), or (IIIa"), or a pharmaceutically acceptable salt or solvate thereof, wherein Z is O. In some embodiments is a compound of Formula (III), (IIIa), (IIIa'), or (IIIa"), or a pharmaceutically acceptable salt or solvate thereof, wherein Z is $CH_2$.

In some embodiments is a compound of Formula (III), (IIIa), (IIIa'), or (IIIa"), or a pharmaceutically acceptable salt or solvate thereof, wherein each $R^2$ is hydrogen.

In some embodiments is a compound of Formula (III), (IIIa), (IIIa'), or (IIIa"), or a pharmaceutically acceptable salt or solvate thereof, wherein q is 0. In some embodiments is a compound of Formula (III), (IIIa), (IIIa'), or (IIIa"), or a pharmaceutically acceptable salt or solvate thereof, wherein q is 1. In some embodiments is a compound of Formula (III), (IIIa), (IIIa'), or (IIIa"), or a pharmaceutically acceptable salt or solvate thereof, wherein q is 2.

In some embodiments is a compound of Formula (III), (IIIa), (IIIa'), or (IIIa"), or a pharmaceutically acceptable salt or solvate thereof, wherein $R^6$ is $—C(=O)OR^{11}$. In some embodiments is a compound of Formula (III), (IIIa), (IIIa'), or (IIIa"), or a pharmaceutically acceptable salt or solvate thereof, wherein $R^6$ is $—C(=O)OCH_3$. In some embodiments is a compound of Formula (III), (IIIa), (IIIa'), or (IIIa"), or a pharmaceutically acceptable salt or solvate thereof, wherein $R^6$ is $—C(=O)OCH_2CH_3$. In some embodiments is a compound of Formula (III), (IIIa), (IIIa'), or (IIIa"), or a pharmaceutically acceptable salt or solvate thereof, wherein $R^6$ is $—C(=O)R^{11}$. In some embodiments is a compound of Formula (III), (IIIa), (IIIa'), or (IIIa"), or a pharmaceutically acceptable salt or solvate thereof, wherein $R^6$ is $—C(=O)CH_3$. In some embodiments is a compound of Formula (III), (IIIa), (IIIa'), or (IIIa"), or a pharmaceutically acceptable salt or solvate thereof, wherein $R^6$ is $—C(=O)CH_2CH_3$. In some embodiments is a compound of Formula (III), (IIIa), (IIIa'), or (IIIa"), or a pharmaceutically acceptable salt or solvate thereof, wherein $R^6$ is $—C(=O)N(R^{12})(R^{13})$. In some embodiments is a compound of Formula (III), (IIIa), (IIIa'), or (IIIa"), or a pharmaceutically acceptable salt or solvate thereof, wherein $R^6$ is $—C(=O)N(H)(CH_3)$.

In some embodiments is a compound of Formula (III), (IIIa), (IIIa'), or (IIIa"), or a pharmaceutically acceptable salt or solvate thereof, wherein $R^5$ is $—C(=O)N(R^9)(R^{10})$. In some embodiments is a compound of Formula (III), (IIIa), (IIIa'), or (IIIa"), or a pharmaceutically acceptable salt or solvate thereof, wherein $R^5$ is $—C(=O)N(R^9)(R^{10})$ and $R^9$ and $R^{10}$ are independently selected from $C_1$-$C_6$alkyl. In some embodiments is a compound of Formula (III), (IIIa), (IIIa'), or (IIIa"), or a pharmaceutically acceptable salt or solvate thereof, wherein $R^5$ is $—C(=O)N(CH_3)_2$. In some embodiments is a compound of Formula (III), (IIIa), (IIIa'), or (IIIa"), or a pharmaceutically acceptable salt or solvate thereof, wherein $R^5$ is $—C(=O)N(R^9)(R^{10})$ and $R^9$ and $R^{10}$ are combined to form a 5- or 6-membered heterocycloalkyl ring optionally substituted with 1, 2, 3, or 4 groups selected from halogen, $C_1$-$C_6$alkyl, $C_1$-$C_6$haloalkyl, hydroxy, and $C_1$-$C_6$alkoxy. In some embodiments is a compound of Formula (III), (IIIa), (IIIa'), or (IIIa"), or a pharmaceutically acceptable salt or solvate thereof, wherein $R^5$ is $—C(=O)OR^9$. In some embodiments is a compound of Formula (III), (IIIa), (IIIa'), or (IIIa"), or a pharmaceutically acceptable salt or solvate thereof, wherein $R^5$ is $—C(=O)OCH_3$. In some embodiments is a compound of Formula (III), (IIIa), (IIIa'), or (IIIa"), or a pharmaceutically acceptable salt or solvate thereof, wherein $R^5$ is $—C(=O)OCH_2CH_3$.

In some embodiments is a compound of Formula (III), (IIIa), (IIIa'), or (IIIa"), or a pharmaceutically acceptable salt or solvate thereof, wherein $R^1$ is $C_1$-$C_6$alkyl. In some embodiments is a compound of Formula (III), (IIIa), (IIIa'), or (IIIa"), or a pharmaceutically acceptable salt or solvate thereof, wherein $R^1$ is $—CH_3$. In some embodiments is a compound of Formula (III), (IIIa), (IIIa'), or (IIIa"), or a pharmaceutically acceptable salt or solvate thereof, wherein $R^1$ is halogen. In some embodiments is a compound of Formula (III), (IIIa), (IIIa'), or (IIIa"), or a pharmaceutically acceptable salt or solvate thereof, wherein $R^1$ is $C_1$-$C_6$haloalkyl. In some embodiments is a compound of Formula (III), (IIIa), (IIIa'), or (IIIa"), or a pharmaceutically acceptable salt or solvate thereof, wherein $R^1$ is $—CF_3$. In some embodiments is a compound of Formula (III), (IIIa), (IIIa'), or (IIIa"), or a pharmaceutically acceptable salt or solvate thereof, wherein $R^1$ is —$CHF_2$. In some embodiments is a compound of Formula (III), (IIIa), (IIIa'), or (IIIa"), or a pharmaceutically acceptable salt or solvate thereof, wherein $R^1$ is —$OR^7$. In some embodiments is a compound of Formula (III), (IIIa), (IIIa'), or (IIIa"), or a pharmaceutically acceptable salt or solvate thereof, wherein $R^1$ is —$OR^7$ and $R^7$ is $C_1$-$C_6$alkyl. In some embodiments is a compound of Formula (III), (IIIa), (IIIa'), or (IIIa"), or a pharmaceutically acceptable salt or solvate thereof, wherein $R^1$ is —$OR^7$ and $R^7$ is $C_1$-$C_6$haloalkyl. In some embodiments is a compound of Formula (III), (IIIa), (IIIa'), or (IIIa"), or a pharmaceutically acceptable salt or solvate thereof, wherein $R^1$ is hydrogen. In some embodiments is a compound of Formula (III), (IIIa), (IIIa'), or (IIIa"), or a pharmaceutically acceptable salt or solvate thereof, wherein $R^1$ is deuterium. In some embodiments is a compound of Formula (III), (IIIa), (IIIa'), or (IIIa"), or a pharmaceutically acceptable salt or solvate thereof, wherein $R^1$ is $C_3$-$C_6$alkyl.

In some embodiments is a compound of Formula (III), (IIIa), (IIIa'), or (IIIa"), or a pharmaceutically acceptable salt or solvate thereof, wherein $R^3$ is selected from hydrogen, deuterium, halogen, $C_1$-$C_6$alkyl, and —$OR^7$. In some embodiments is a compound of Formula (III), (IIIa), (IIIa'), or (IIIa"), or a pharmaceutically acceptable salt or solvate thereof, wherein $R^3$ is halogen. In some embodiments is a compound of Formula (III), (IIIa), (IIIa'), or (IIIa"), or a pharmaceutically acceptable salt or solvate thereof, wherein $R^3$ is $C_1$-$C_6$alkyl. In some embodiments is a compound of Formula (III), (IIIa), (IIIa'), or (IIIa"), or a pharmaceutically acceptable salt or solvate thereof, wherein $R^3$ is —$CH_3$. In some embodiments is a compound of Formula (III), (IIIa), (IIIa'), or (IIIa"), or a pharmaceutically acceptable salt or solvate thereof, wherein $R^3$ is —$OR^7$. In some embodiments is a compound of Formula (III), (IIIa), (IIIa'), or (IIIa"), or a pharmaceutically acceptable salt or solvate thereof, wherein $R^3$ is —$OCH_3$. In some embodiments is a compound of Formula (III), (IIIa), (IIIa'), or (IIIa"), or a pharmaceutically acceptable salt or solvate thereof, wherein $R^3$ is hydrogen. In some embodiments is a compound of Formula (III), (IIIa), (IIIa'), or (IIIa"), or a pharmaceutically acceptable salt or solvate thereof, wherein $R^3$ is deuterium.

In some embodiments is a compound of Formula (III), (IIIa), (IIIa'), or (IIIa"), or a pharmaceutically acceptable salt or solvate thereof, wherein n is 1. In some embodiments is a compound of Formula (III), (IIIa), (IIIa'), or (IIIa"), or a pharmaceutically acceptable salt or solvate thereof, wherein n is 2. In some embodiments is a compound of Formula (III), (IIIa), (IIIa'), or (IIIa"), or a pharmaceutically acceptable salt or solvate thereof, wherein n is 0.

In some embodiments is a compound of Formula (III), (IIIa), (IIIa'), or (IIIa"), or a pharmaceutically acceptable salt or solvate thereof, wherein each $R^4$ is independently selected from deuterium, halogen, $C_1$-$C_6$alkyl, $C_1$-$C_6$haloalkyl, and $C_1$-$C_6$alkoxy. In some embodiments is a compound of Formula (III), (IIIa), (IIIa'), or (IIIa"), or a pharmaceutically acceptable salt or solvate thereof, wherein each $R^4$ is independently selected from halogen, $C_1$-$C_6$alkyl, and $C_1$-$C_6$alkoxy. In some embodiments is a compound of Formula (III), (IIIa), (IIIa'), or (IIIa"), or a pharmaceutically acceptable salt or solvate thereof, wherein each $R^4$ is halogen.

In some embodiments is a compound of Formula (III), (IIIa), (IIIa'), or (IIIa"), or a pharmaceutically acceptable salt or solvate thereof, wherein n is 1 or 2 and each $R^4$ is independently selected from deuterium, halogen, $C_1$-$C_6$alkyl, $C_1$-$C_6$haloalkyl, and $C_1$-$C_6$alkoxy. In some embodiments is a compound of Formula (III), (IIIa), (IIIa'), or (IIIa"), or a pharmaceutically acceptable salt or solvate thereof, wherein n is 1 or 2 and each $R^4$ is independently selected from halogen, $C_1$-$C_6$alkyl, and $C_1$-$C_6$alkoxy. In some embodiments is a compound of Formula (III), (IIIa), (IIIa'), or (IIIa"), or a pharmaceutically acceptable salt or solvate thereof, wherein n is 1 or 2 and each $R^4$ is halogen.

In some embodiments is a compound of Formula (III), (IIIa), (IIIa'), or (IIIa"), or a pharmaceutically acceptable salt or solvate thereof, wherein p is 1. In some embodiments is a compound of Formula (III), (IIIa), (IIIa'), or (IIIa"), or a pharmaceutically acceptable salt or solvate thereof, wherein p is 2.

In some embodiments is a compound of Formula (IV):

Formula (IV)

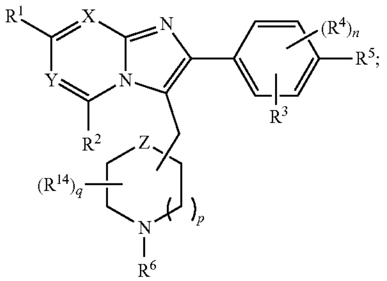

wherein:

X is $C(R^2)$ or N;

Y is $C(R^2)$ or N;

Z is $CH_2$ or O;

$R^1$ is selected from hydrogen, deuterium, halogen, $C_1$-$C_6$alkyl, $C_2$-$C_6$alkenyl, $C_2$-$C_6$alkynyl, $C_1$-$C_6$haloalkyl, $C_3$-$C_6$cycloalkyl, —$OR^7$, —$N(R^7)_2$, —CN, —$C(=O)R^8$, —$C(=O)OR^7$, —$C(=O)N(R^7)_2$, —$NR^7C(=O)R^8$, —$NR^{10}S(=O)_2R^8$, —$S(=O)_2R^8$, and —$S(=O)_2N(R^7)_2$;

each $R^2$ is independently selected from hydrogen, deuterium, halogen, —CN, $C_1$-$C_6$alkyl, $C_2$-$C_6$alkenyl, $C_2$-$C_6$alkynyl, $C_1$-$C_6$haloalkyl, $C_1$-$C_6$alkoxy, and $C_3$-$C_6$cycloalkyl;

$R^3$ is selected from halogen, —CN, $C_2$-$C_6$alkenyl, $C_2$-$C_6$alkynyl, $C_1$-$C_6$haloalkyl, $C_3$-$C_6$cycloalkyl, —$OR^7$, —$N(R^7)_2$, —$C(=O)R^8$, —$C(=O)OR^7$, —$C(=O)N(R^7)_2$, —$NR^7C(=O)R^8$, —$NR^{10}S(=O)_2R^8$, —$S(=O)_2R^8$, and —$S(=O)_2N(R^7)_2$;

each $R^4$ is independently selected from deuterium, —CN, $C_2$-$C_6$alkenyl, $C_2$-$C_6$alkynyl, $C_1$-$C_6$haloalkyl, $C_1$-$C_6$alkoxy, and $C_3$-$C_6$cycloalkyl; or two $R^4$ are combined to form a bridged heterocycloalkyl ring;

$R^5$ is —$C(=O)N(R^9)(R^{10})$, —$C(=O)OR^9$, —$S(=O)R^{15}$, —$S(=O)_2R^{15}$, —$S(=O)(=NH)R^{15}$, —$C_2$-$C_9$heterocycloalkyl-$N(R^9)(R^{10})$, or —$C_1$-$C_6$haloalkyl-$N(R^9)(R^{10})$;

$R^6$ is selected from —$C(=O)R^1$;

each $R^7$ is independently selected from hydrogen, deuterium, $C_1$-$C_6$alkyl, and $C_1$-$C_6$haloalkyl;

each $R^8$ is independently selected from $C_1$-$C_6$alkyl;

$R^9$, $R^{10}$, $R^{12}$, and $R^{13}$ are independently selected from hydrogen, deuterium, and $C_1$-$C_6$alkyl;

$R^{11}$ is $C_1$-$C_6$alkyl or —$C_1$-$C_6$alkyl-O—$C_1$-$C_6$alkyl;

$R^{14}$ is $C_1$-$C_6$alkyl;

$R^{15}$ is $C_1$-$C_6$alkyl;

n is 0, 1, 2, or 3;

p is 1, 2, or 3; and q is 0, 1, 2, 3, or 4;

or a pharmaceutically acceptable salt or solvate thereof.

In some embodiments is a compound of Formula (IV), or a pharmaceutically acceptable salt or solvate thereof, having the structure of Formula (IVa):

Formula (IVa)

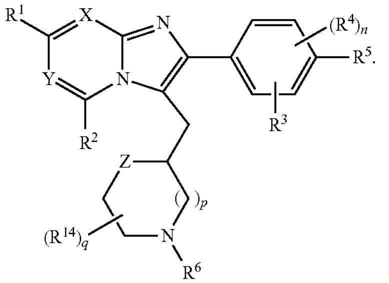

In some embodiments is a compound of Formula (IV), or a pharmaceutically acceptable salt or solvate thereof, having the structure of Formula (IVa'):

Formula (IVa')

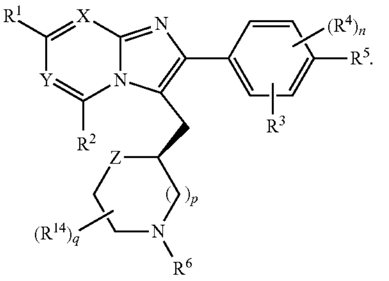

In some embodiments is a compound of Formula (IV), or a pharmaceutically acceptable salt or solvate thereof, having the structure of Formula (IVa"):

Formula (IVa")

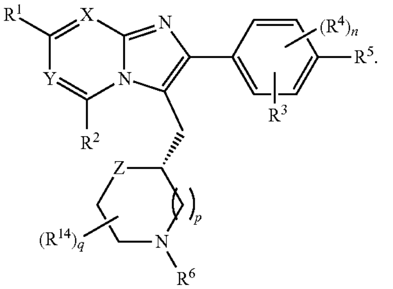

In some embodiments is a compound of Formula (IV), (IVa), (IVa'), or (IVa"), or a pharmaceutically acceptable salt or solvate thereof, wherein X is $C(R^2)$. In some embodiments is a compound of Formula (IV), (IVa), (IVa'), or (IVa"), or a pharmaceutically acceptable salt or solvate thereof, wherein X is C(H). In some embodiments is a compound of Formula (IV), (IVa), (IVa'), or (IVa"), or a pharmaceutically acceptable salt or solvate thereof, wherein X is N.

In some embodiments is a compound of Formula (IV), (IVa), (IVa'), or (IVa"), or a pharmaceutically acceptable salt or solvate thereof, wherein Y is $C(R^2)$. In some embodiments is a compound of Formula (IV), (IVa), (IVa'), or (IVa"), or a pharmaceutically acceptable salt or solvate thereof, wherein Y is C(H). In some embodiments is a compound of Formula (IV), (IVa), (IVa'), or (IVa"), or a pharmaceutically acceptable salt or solvate thereof, wherein Y is N.

In some embodiments is a compound of Formula (IV), (IVa), (IVa'), or (IVa"), or a pharmaceutically acceptable salt or solvate thereof, wherein Z is O. In some embodiments is a compound of Formula (IV), (IVa), (IVa'), or (IVa"), or a pharmaceutically acceptable salt or solvate thereof, wherein Z is $CH_2$.

In some embodiments is a compound of Formula (IV), (IVa), (IVa'), or (IVa"), or a pharmaceutically acceptable salt or solvate thereof, wherein each $R^2$ is hydrogen.

In some embodiments is a compound of Formula (IV), (IVa), (IVa'), or (IVa"), or a pharmaceutically acceptable salt or solvate thereof, wherein q is 0. In some embodiments is a compound of Formula (IV), (IVa), (IVa'), or (IVa"), or a pharmaceutically acceptable salt or solvate thereof, wherein q is 1. In some embodiments is a compound of Formula (IV), (IVa), (IVa'), or (IVa"), or a pharmaceutically acceptable salt or solvate thereof, wherein q is 2.

In some embodiments is a compound of Formula (IV), (IVa), (IVa'), or (IVa"), or a pharmaceutically acceptable salt or solvate thereof, wherein $R^6$ is $—C(=O)CH_3$. In some embodiments is a compound of Formula (IV), (IVa), (IVa'), or (IVa"), or a pharmaceutically acceptable salt or solvate thereof, wherein $R^6$ is $—C(=O)CH_2CH_3$.

In some embodiments is a compound of Formula (IV), (IVa), (IVa'), or (IVa"), or a pharmaceutically acceptable salt or solvate thereof, wherein $R^5$ is $—C(=O)N(R^9)(R^{10})$. In some embodiments is a compound of Formula (IV), (IVa), (IVa'), or (IVa"), or a pharmaceutically acceptable salt or solvate thereof, wherein $R^5$ is $—C(=O)N(H)(CH_3)$. In some embodiments is a compound of Formula (IV), (IVa), (IVa'), or (IVa"), or a pharmaceutically acceptable salt or solvate thereof, wherein $R^5$ is $—C(=O)NH_2$. In some embodiments is a compound of Formula (IV), (IVa), (IVa'), or (IVa"), or a pharmaceutically acceptable salt or solvate thereof, wherein $R^5$ is $—C(=O)N(CH_3)_2$. In some embodiments is a compound of Formula (IV), (IVa), (IVa'), or (IVa"), or a pharmaceutically acceptable salt or solvate thereof, wherein $R^5$ is $—C(=O)OR^9$. In some embodiments is a compound of Formula (IV), (IVa), (IVa'), or (IVa"), or a pharmaceutically acceptable salt or solvate thereof, wherein $R^5$ is $—C(=O)OCH_3$. In some embodiments is a compound of Formula (IV), (IVa), (IVa'), or (IVa"), or a pharmaceutically acceptable salt or solvate thereof, wherein $R^5$ is $—C(=O)OCH_2CH_3$.

In some embodiments is a compound of Formula (IV), (IVa), (IVa'), or (IVa"), or a pharmaceutically acceptable salt or solvate thereof, wherein $R^1$ is $C_1$-$C_6$alkyl. In some embodiments is a compound of Formula (IV), (IVa), (IVa'), or (IVa"), or a pharmaceutically acceptable salt or solvate thereof, wherein $R^1$ is $—CH_3$. In some embodiments is a compound of Formula (IV), (IVa), (IVa'), or (IVa"), or a pharmaceutically acceptable salt or solvate thereof, wherein $R^1$ is halogen. In some embodiments is a compound of Formula (IV), (IVa), (IVa'), or (IVa"), or a pharmaceutically acceptable salt or solvate thereof, wherein $R^1$ is $C_1$-$C_6$haloalkyl. In some embodiments is a compound of Formula (IV), (IVa), (IVa'), or (IVa"), or a pharmaceutically acceptable salt or solvate thereof, wherein $R^1$ is $—CF_3$. In some embodiments is a compound of Formula (IV), (IVa), (IVa'), or (IVa"), or a pharmaceutically acceptable salt or solvate thereof, wherein $R^1$ is $—CHF_2$. In some embodiments is a compound of Formula (IV), (IVa), (IVa'), or (IVa''), or a pharmaceutically acceptable salt or solvate thereof, wherein $R^1$ is —$OR^7$. In some embodiments is a compound of Formula (IV), (IVa), (IVa'), or (IVa''), or a pharmaceutically acceptable salt or solvate thereof, wherein $R^1$ is —$OR^7$ and $R^7$ is $C_1$-$C_6$alkyl. In some embodiments is a compound of Formula (IV), (IVa), (IVa'), or (IVa''), or a pharmaceutically acceptable salt or solvate thereof, wherein $R^1$ is —$OR^7$ and $R^7$ is $C_1$-$C_6$haloalkyl. In some embodiments is a compound of Formula (IV), (IVa), (IVa'), or (IVa''), or a pharmaceutically acceptable salt or solvate thereof, wherein $R^1$ is hydrogen. In some embodiments is a compound of Formula (IV), (IVa), (IVa'), or (IVa''), or a pharmaceutically acceptable salt or solvate thereof, wherein $R^1$ is deuterium. In some embodiments is a compound of Formula (IV), (IVa), (IVa'), or (IVa''), or a pharmaceutically acceptable salt or solvate thereof, wherein $R^1$ is $C_3$-$C_6$alkyl.

In some embodiments is a compound of Formula (IV), (IVa), (IVa'), or (IVa''), or a pharmaceutically acceptable salt or solvate thereof, wherein $R^3$ is selected from halogen and —$OR^7$. In some embodiments is a compound of Formula (IV), (IVa), (IVa'), or (IVa''), or a pharmaceutically acceptable salt or solvate thereof, wherein $R^3$ is halogen. In some embodiments is a compound of Formula (IV), (IVa), (IVa'), or (IVa''), or a pharmaceutically acceptable salt or solvate thereof, wherein $R^3$ is —$OR^7$. In some embodiments is a compound of Formula (IV), (IVa), (IVa'), or (IVa''), or a pharmaceutically acceptable salt or solvate thereof, wherein $R^3$ is —$OCH_3$.

In some embodiments is a compound of Formula (IV), (IVa), (IVa'), or (IVa''), or a pharmaceutically acceptable salt or solvate thereof, wherein n is 1. In some embodiments is a compound of Formula (IV), (IVa), (IVa'), or (IVa''), or a pharmaceutically acceptable salt or solvate thereof, wherein n is 2. In some embodiments is a compound of Formula (IV), (IVa), (IVa'), or (IVa''), or a pharmaceutically acceptable salt or solvate thereof, wherein n is 0.

In some embodiments is a compound of Formula (IV), (IVa), (IVa'), or (IVa''), or a pharmaceutically acceptable salt or solvate thereof, wherein each $R^4$ is independently selected from deuterium, $C_1$-$C_6$haloalkyl, and $C_1$-$C_6$alkoxy. In some embodiments is a compound of Formula (IV), (IVa), (IVa'), or (IVa''), or a pharmaceutically acceptable salt or solvate thereof, wherein each $R^4$ is $C_1$-$C_6$alkoxy.

In some embodiments is a compound of Formula (IV), (IVa), (IVa'), or (IVa''), or a pharmaceutically acceptable salt or solvate thereof, wherein n is 1 or 2 and each $R^4$ is independently selected from deuterium, $C_1$-$C_6$haloalkyl, and $C_1$-$C_6$alkoxy. In some embodiments is a compound of Formula (IV), (IVa), (IVa'), or (IVa''), or a pharmaceutically acceptable salt or solvate thereof, wherein n is 1 or 2 and each $R^4$ is $C_1$-$C_6$alkoxy. In some embodiments is a compound of Formula (IV), (IVa), (IVa'), or (IVa''), or a pharmaceutically acceptable salt or solvate thereof, wherein n is 1 or 2 and each $R^4$ is $C_1$-$C_6$haloalkyl.

In some embodiments is a compound of Formula (IV), (IVa), (IVa'), or (IVa''), or a pharmaceutically acceptable salt or solvate thereof, wherein p is 1. In some embodiments is a compound of Formula (IV), (IVa), (IVa'), or (IVa''), or a pharmaceutically acceptable salt or solvate thereof, wherein p is 2.

In some embodiments is a compound of Formula (V):

Formula (V)

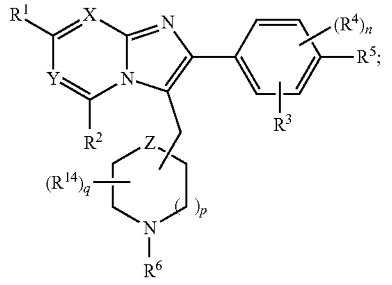

wherein:

X is $C(R^2)$ or N;

Y is $C(R^2)$ or N;

Z is $CH_2$ or O;

$R^1$ is selected from hydrogen, deuterium, halogen, $C_1$-$C_6$alkyl, $C_2$-$C_6$alkenyl, $C_2$-$C_6$alkynyl, $C_1$-$C_6$haloalkyl, $C_3$-$C_6$cycloalkyl, —$OR^7$, —$N(R^7)_2$, —CN, —$C(=O)R^8$, —$C(=O)OR^7$, —$C(=O)N(R^7)_2$, —$NR^7C(=O)R^8$, —$NR^{10}S(=O)_2R^8$, —$S(=O)_2R^8$, and —$S(=O)_2N(R^7)_2$;

each $R^2$ is independently selected from hydrogen, deuterium, halogen, —CN, $C_1$-$C_6$alkyl, $C_2$-$C_6$alkenyl, $C_2$-$C_6$alkynyl, $C_1$-$C_6$haloalkyl, $C_1$-$C_6$alkoxy, and $C_3$-$C_6$cycloalkyl;

$R^3$ is selected from hydrogen, deuterium, halogen, —CN, $C_1$-$C_6$alkyl, $C_2$-$C_6$alkenyl, $C_2$-$C_6$alkynyl, $C_1$-$C_6$haloalkyl, $C_3$-$C_6$cycloalkyl, —$OR^7$, —$N(R^7)_2$, —$C(=O)R^8$, —$C(=O)OR^7$, —$C(=O)N(R^7)_2$, —$NR^7C(=O)R^8$, —$NR^{10}S(=O)_2R^8$, —$S(=O)_2R^8$, and —$S(=O)_2N(R^7)_2$;

each $R^4$ is independently selected from deuterium, halogen, —CN, $C_1$-$C_6$alkyl, $C_2$-$C_6$alkenyl, $C_2$-$C_6$alkynyl, $C_1$-$C_6$haloalkyl, $C_1$-$C_6$alkoxy, and $C_3$-$C_6$cycloalkyl; or two $R^4$ are combined to form a bridged heterocycloalkyl ring;

$R^5$ is —$C(=O)N(R^9)(R^{10})$, —$C(=O)OR^9$, —$S(=O)R^{15}$, —$S(=O)_2R^{15}$, —$S(=O)(=NH)R^{15}$, —$C_2$-$C_9$heterocycloalkyl-$N(R^9)(R^{10})$, or —$C_1$-$C_6$haloalkyl-$N(R^9)(R^{10})$;

$R^6$ is selected from —$C(=O)OR^{11}$, —$C(=O)R^{11}$, and —$C(=O)N(R^{12})(R^{13})$;

each $R^7$ is independently selected from hydrogen, deuterium, $C_1$-$C_6$alkyl, and $C_1$-$C_6$haloalkyl;

each $R^8$ is independently selected from $C_1$-$C_6$alkyl;

$R^9$, $R^{10}$, $R^{12}$, and $R^{13}$ are independently selected from hydrogen, deuterium, and $C_1$-$C_6$alkyl;

$R^{11}$ is $C_1$-$C_6$alkyl or —$C_1$-$C_6$alkyl-O—$C_1$-$C_6$alkyl;

$R^{14}$ is $C_1$-$C_6$alkyl;

$R^{15}$ is $C_1$-$C_6$alkyl;

n is 0, 1, 2, or 3;

p is 2 or 3; and q is 0, 1, 2, 3, or 4;

or a pharmaceutically acceptable salt or solvate thereof.

In some embodiments is a compound of Formula (V), or a pharmaceutically acceptable salt or solvate thereof, having the structure of Formula (Va):

Formula (Va)

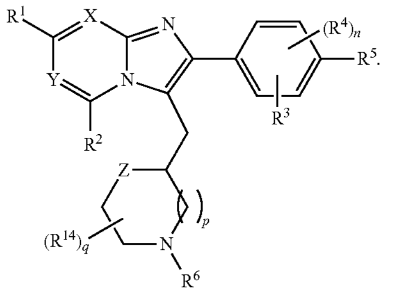

In some embodiments is a compound of Formula (V), or a pharmaceutically acceptable salt or solvate thereof, having the structure of Formula (Va'):

Formula (Va')

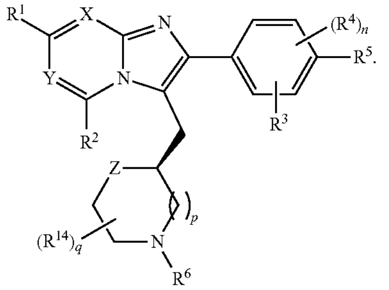

In some embodiments is a compound of Formula (V), or a pharmaceutically acceptable salt or solvate thereof, having the structure of Formula (Va"):

Formula (Va")

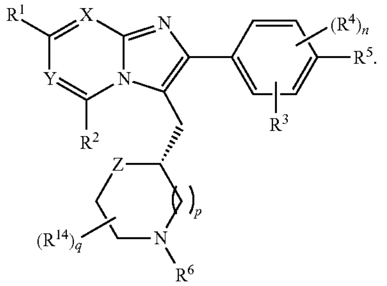

In some embodiments is a compound of Formula (V), (Va), (Va'), or (Va"), or a pharmaceutically acceptable salt or solvate thereof, wherein X is $C(R^2)$. In some embodiments is a compound of Formula (V), (Va), (Va'), or (Va"), or a pharmaceutically acceptable salt or solvate thereof, wherein X is C(H). In some embodiments is a compound of Formula (V), (Va), (Va'), or (Va"), or a pharmaceutically acceptable salt or solvate thereof, wherein X is N.

In some embodiments is a compound of Formula (V), (Va), (Va'), or (Va"), or a pharmaceutically acceptable salt or solvate thereof, wherein Y is $C(R^2)$. In some embodiments is a compound of Formula (V), (Va), (Va'), or (Va"), or a pharmaceutically acceptable salt or solvate thereof, wherein Y is C(H). In some embodiments is a compound of Formula (V), (Va), (Va'), or (Va"), or a pharmaceutically acceptable salt or solvate thereof, wherein Y is N.

In some embodiments is a compound of Formula (V), (Va), (Va'), or (Va"), or a pharmaceutically acceptable salt or solvate thereof, wherein Z is O. In some embodiments is a compound of Formula (V), (Va), (Va'), or (Va"), or a pharmaceutically acceptable salt or solvate thereof, wherein Z is $CH_2$.

In some embodiments is a compound of Formula (V), (Va), (Va'), or (Va"), or a pharmaceutically acceptable salt or solvate thereof, wherein each $R^2$ is hydrogen.

In some embodiments is a compound of Formula (V), (Va), (Va'), or (Va"), or a pharmaceutically acceptable salt or solvate thereof, wherein q is 0. In some embodiments is a compound of Formula (V), (Va), (Va'), or (Va"), or a pharmaceutically acceptable salt or solvate thereof, wherein q is 1. In some embodiments is a compound of Formula (V), (Va), (Va'), or (Va"), or a pharmaceutically acceptable salt or solvate thereof, wherein q is 2.

In some embodiments is a compound of Formula (V), (Va), (Va'), or (Va"), or a pharmaceutically acceptable salt or solvate thereof, wherein $R^6$ is $-C(=O)OR^{11}$. In some embodiments is a compound of Formula (V), (Va), (Va'), or (Va"), or a pharmaceutically acceptable salt or solvate thereof, wherein $R^6$ is $-C(=O)OCH_3$. In some embodiments is a compound of Formula (V), (Va), (Va'), or (Va"), or a pharmaceutically acceptable salt or solvate thereof, wherein $R^6$ is $-C(=O)OCH_2CH_3$. In some embodiments is a compound of Formula (V), (Va), (Va'), or (Va"), or a pharmaceutically acceptable salt or solvate thereof, wherein $R^6$ is $-C(=O)R^{11}$. In some embodiments is a compound of Formula (V), (Va), (Va'), or (Va"), or a pharmaceutically acceptable salt or solvate thereof, wherein $R^6$ is $-C(=O)CH_3$. In some embodiments is a compound of Formula (V), (Va), (Va'), or (Va"), or a pharmaceutically acceptable salt or solvate thereof, wherein $R^6$ is $-C(=O)CH_2CH_3$. In some embodiments is a compound of Formula (V), (Va), (Va'), or (Va"), or a pharmaceutically acceptable salt or solvate thereof, wherein $R^6$ is $-C(=O)N(R^{12})(R^{13})$. In some embodiments is a compound of Formula (V), (Va), (Va'), or (Va"), or a pharmaceutically acceptable salt or solvate thereof, wherein $R^6$ is $-C(=O)N(H)(CH_3)$.

In some embodiments is a compound of Formula (V), (Va), (Va'), or (Va"), or a pharmaceutically acceptable salt or solvate thereof, wherein $R^5$ is $-C(=O)N(R^9)(R^{10})$. In some embodiments is a compound of Formula (V), (Va), (Va'), or (Va"), or a pharmaceutically acceptable salt or solvate thereof, wherein $R^5$ is $-C(=O)N(H)(CH_3)$. In some embodiments is a compound of Formula (V), (Va), (Va'), or (Va"), or a pharmaceutically acceptable salt or solvate thereof, wherein $R^5$ is $-C(=O)NH_2$. In some embodiments is a compound of Formula (V), (Va), (Va'), or (Va"), or a pharmaceutically acceptable salt or solvate thereof, wherein $R^5$ is $-C(=O)N(CH_3)_2$. In some embodiments is a compound of Formula (V), (Va), (Va'), or (Va"), or a pharmaceutically acceptable salt or solvate thereof, wherein $R^5$ is $-C(=O)OR^9$. In some embodiments is a compound of Formula (V), (Va), (Va'), or (Va"), or a pharmaceutically acceptable salt or solvate thereof, wherein $R^5$ is $-C(=O)OCH_3$. In some embodiments is a compound of Formula (V), (Va), (Va'), or (Va"), or a pharmaceutically acceptable salt or solvate thereof, wherein $R^5$ is $-C(=O)OCH_2CH_3$.

In some embodiments is a compound of Formula (V), (Va), (Va'), or (Va"), or a pharmaceutically acceptable salt or solvate thereof, wherein $R^1$ is $C_1$-$C_6$alkyl. In some embodiments is a compound of Formula (V), (Va), (Va'), or (Va"), or a pharmaceutically acceptable salt or solvate thereof, wherein $R^1$ is —$CH_3$. In some embodiments is a compound of Formula (V), (Va), (Va'), or (Va"), or a pharmaceutically acceptable salt or solvate thereof, wherein $R^1$ is halogen. In some embodiments is a compound of Formula (V), (Va), (Va'), or (Va"), or a pharmaceutically acceptable salt or solvate thereof, wherein $R^1$ is $C_1$-$C_6$haloalkyl. In some embodiments is a compound of Formula (V), (Va), (Va'), or (Va"), or a pharmaceutically acceptable salt or solvate thereof, wherein $R^1$ is —$CF_3$. In some embodiments is a compound of Formula (V), (Va), (Va'), or (Va"), or a pharmaceutically acceptable salt or solvate thereof, wherein $R^1$ is —$CHF_2$. In some embodiments is a compound of Formula (V), (Va), (Va'), or (Va"), or a pharmaceutically acceptable salt or solvate thereof, wherein $R^1$ is —$OR^7$. In some embodiments is a compound of Formula (V), (Va), (Va'), or (Va"), or a pharmaceutically acceptable salt or solvate thereof, wherein $R^1$ is —$OR^7$ and $R^7$ is $C_1$-$C_6$alkyl. In some embodiments is a compound of Formula (V), (Va), (Va'), or (Va"), or a pharmaceutically acceptable salt or solvate thereof, wherein $R^1$ is —$OR^7$ and $R^7$ is $C_1$-$C_6$haloalkyl. In some embodiments is a compound of Formula (V), (Va), (Va'), or (Va"), or a pharmaceutically acceptable salt or solvate thereof, wherein $R^1$ is hydrogen. In some embodiments is a compound of Formula (V), (Va), (Va'), or (Va"), or a pharmaceutically acceptable salt or solvate thereof, wherein $R^1$ is deuterium. In some embodiments is a compound of Formula (V), (Va), (Va'), or (Va"), or a pharmaceutically acceptable salt or solvate thereof, wherein $R^1$ is $C_3$-$C_6$alkyl.

In some embodiments is a compound of Formula (V), (Va), (Va'), or (Va"), or a pharmaceutically acceptable salt or solvate thereof, wherein $R^3$ is selected from hydrogen, deuterium, halogen, $C_1$-$C_6$alkyl, and —$OR^7$. In some embodiments is a compound of Formula (V), (Va), (Va'), or (Va"), or a pharmaceutically acceptable salt or solvate thereof, wherein $R^3$ is halogen. In some embodiments is a compound of Formula (V), (Va), (Va'), or (Va"), or a pharmaceutically acceptable salt or solvate thereof, wherein $R^3$ is $C_1$-$C_6$alkyl. In some embodiments is a compound of Formula (V), (Va), (Va'), or (Va"), or a pharmaceutically acceptable salt or solvate thereof, wherein $R^3$ is —$CH_3$. In some embodiments is a compound of Formula (V), (Va), (Va'), or (Va"), or a pharmaceutically acceptable salt or solvate thereof, wherein $R^3$ is —$OR^7$. In some embodiments is a compound of Formula (V), (Va), (Va'), or (Va"), or a pharmaceutically acceptable salt or solvate thereof, wherein $R^3$ is —$OCH_3$. In some embodiments is a compound of Formula (V), (Va), (Va'), or (Va"), or a pharmaceutically acceptable salt or solvate thereof, wherein $R^3$ is hydrogen. In some embodiments is a compound of Formula (V), (Va), (Va'), or (Va"), or a pharmaceutically acceptable salt or solvate thereof, wherein $R^3$ is deuterium.

In some embodiments is a compound of Formula (V), (Va), (Va'), or (Va"), or a pharmaceutically acceptable salt or solvate thereof, wherein n is 1. In some embodiments is a compound of Formula (V), (Va), (Va'), or (Va"), or a pharmaceutically acceptable salt or solvate thereof, wherein n is 2. In some embodiments is a compound of Formula (V), (Va), (Va'), or (Va"), or a pharmaceutically acceptable salt or solvate thereof, wherein n is 0.

In some embodiments is a compound of Formula (V), (Va), (Va'), or (Va"), or a pharmaceutically acceptable salt or solvate thereof, wherein each $R^4$ is independently selected from deuterium, halogen, $C_1$-$C_6$alkyl, $C_1$-$C_6$haloalkyl, and $C_1$-$C_6$alkoxy. In some embodiments is a compound of Formula (V), (Va), (Va'), or (Va"), or a pharmaceutically acceptable salt or solvate thereof, wherein each $R^4$ is independently selected from halogen, $C_1$-$C_6$alkyl, and $C_1$-$C_6$alkoxy. In some embodiments is a compound of Formula (V), (Va), (Va'), or (Va"), or a pharmaceutically acceptable salt or solvate thereof, wherein each $R^4$ is halogen.

In some embodiments is a compound of Formula (V), (Va), (Va'), or (Va"), or a pharmaceutically acceptable salt or solvate thereof, wherein n is 1 or 2 and each $R^4$ is independently selected from deuterium, halogen, $C_1$-$C_6$alkyl, $C_1$-$C_6$haloalkyl, and $C_1$-$C_6$alkoxy. In some embodiments is a compound of Formula (V), (Va), (Va'), or (Va"), or a pharmaceutically acceptable salt or solvate thereof, wherein n is 1 or 2 and each $R^4$ is independently selected from halogen, $C_1$-$C_6$alkyl, and $C_1$-$C_6$alkoxy. In some embodiments is a compound of Formula (V), (Va), (Va'), or (Va"), or a pharmaceutically acceptable salt or solvate thereof, wherein n is 1 or 2 and each $R^4$ is halogen.

In some embodiments is a compound of Formula (V), (Va), (Va'), or (Va"), or a pharmaceutically acceptable salt or solvate thereof, wherein p is 2. In some embodiments is a compound of Formula (V), (Va), (Va'), or (Va"), or a pharmaceutically acceptable salt or solvate thereof, wherein p is 3.

In some embodiments described herein, the P2X3 modulator is selected from:

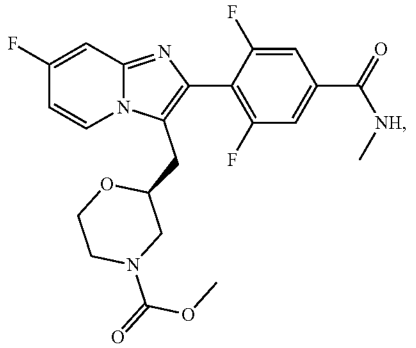

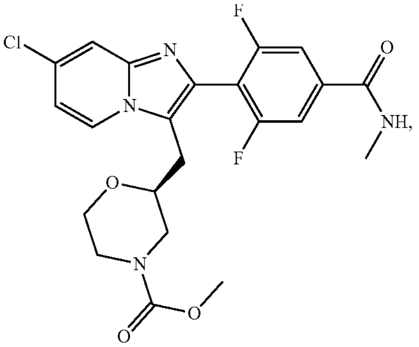

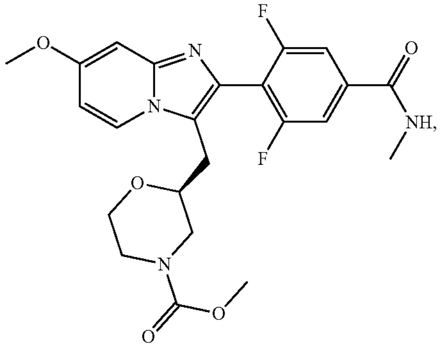

-continued
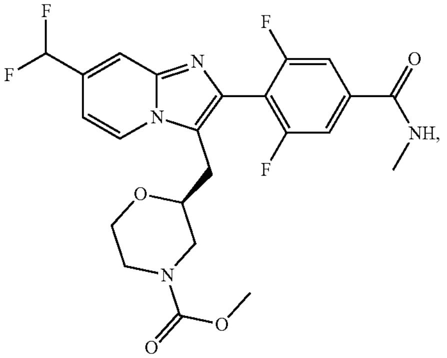
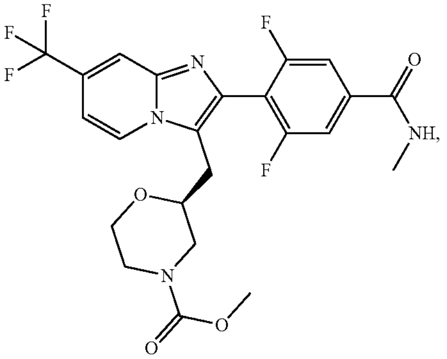
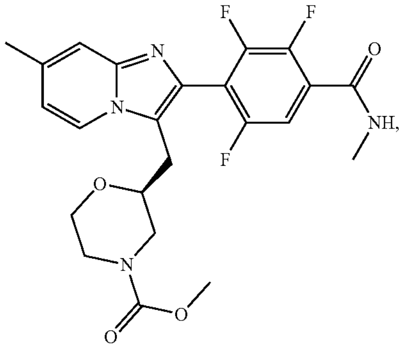
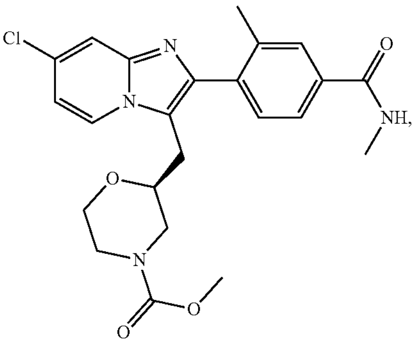
-continued
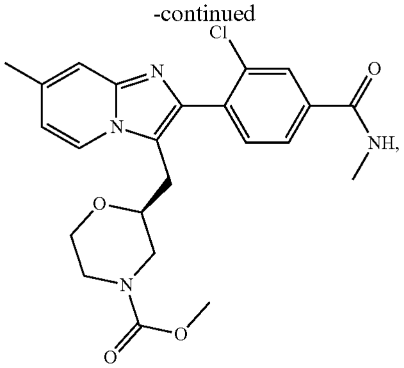
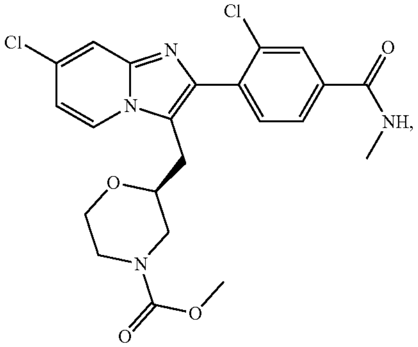
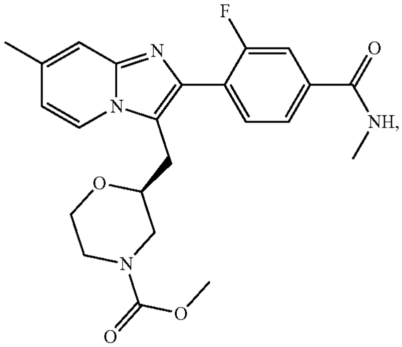
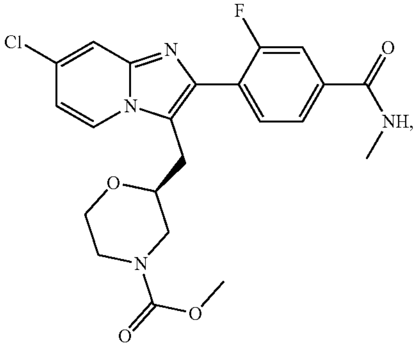
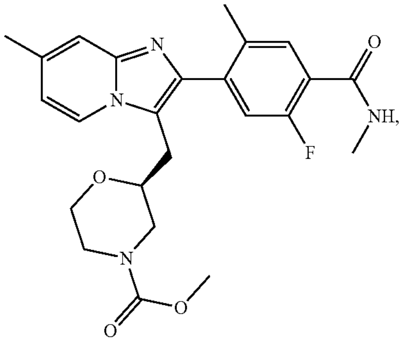

-continued
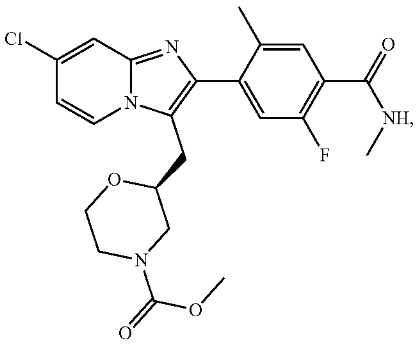
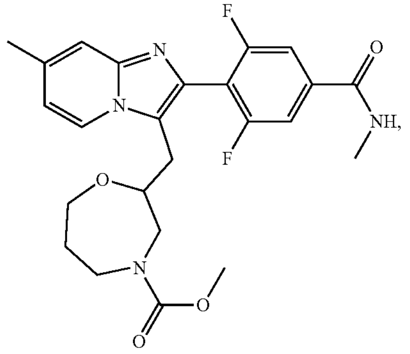
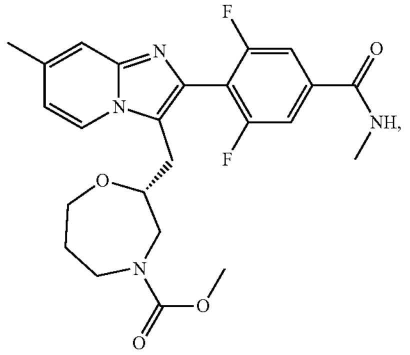
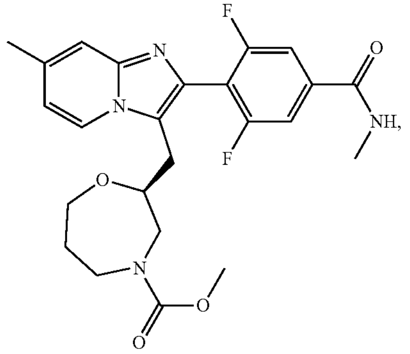
-continued
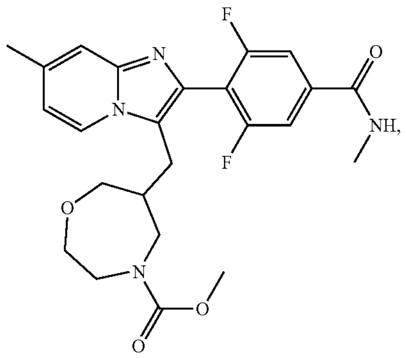
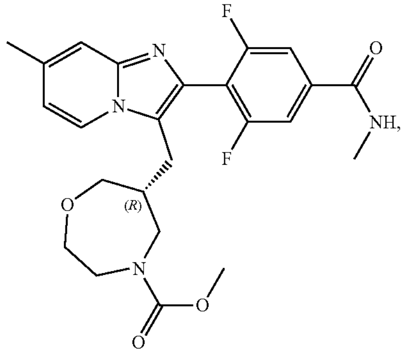
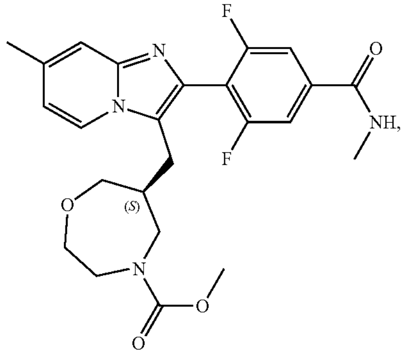
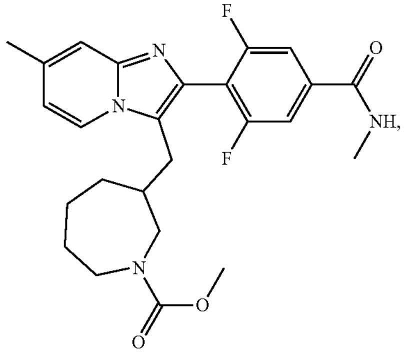

-continued
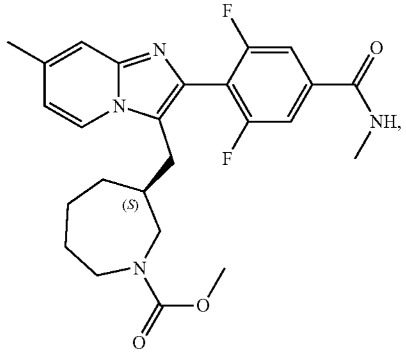
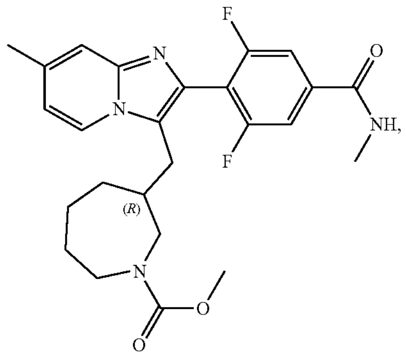
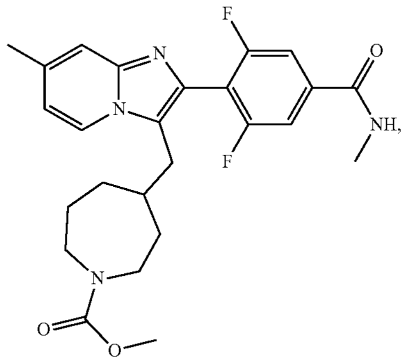
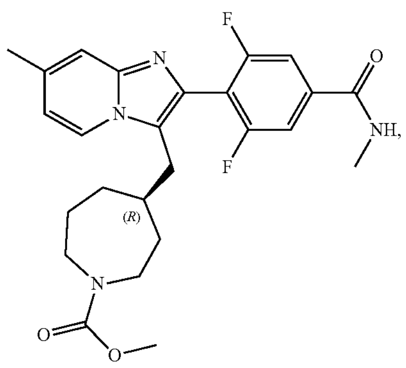
-continued
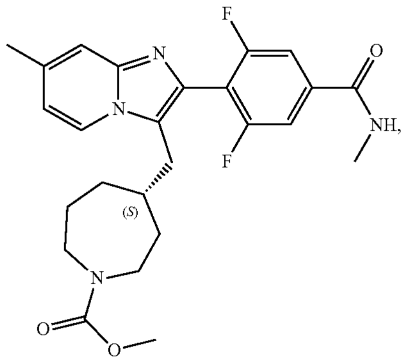
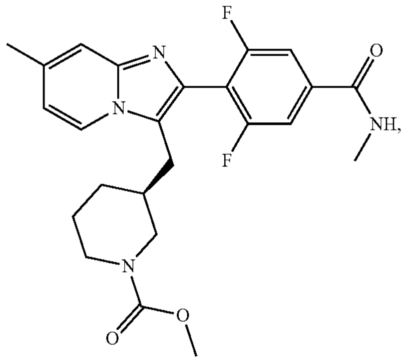
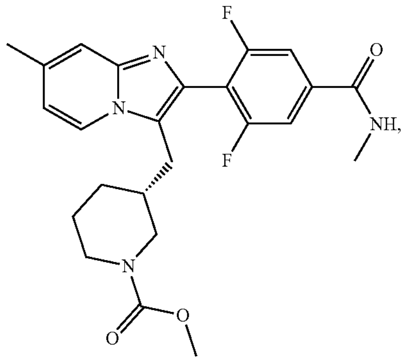
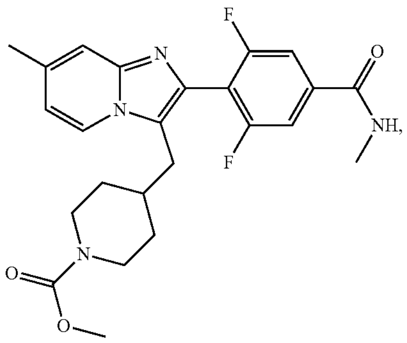

-continued
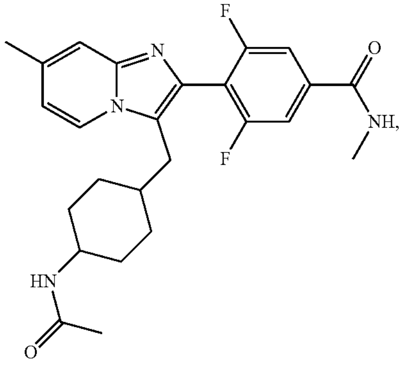
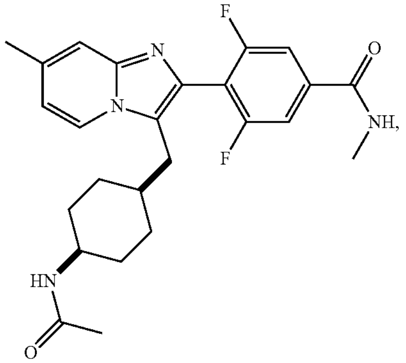
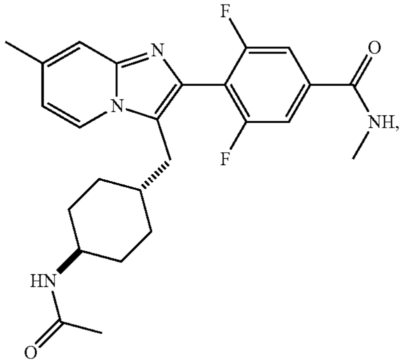
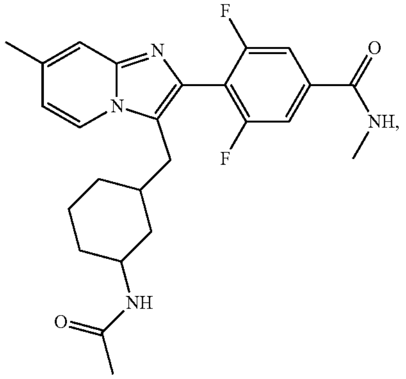
-continued
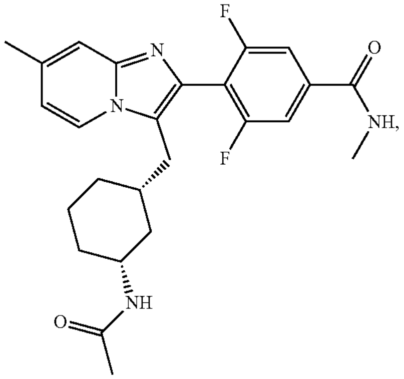
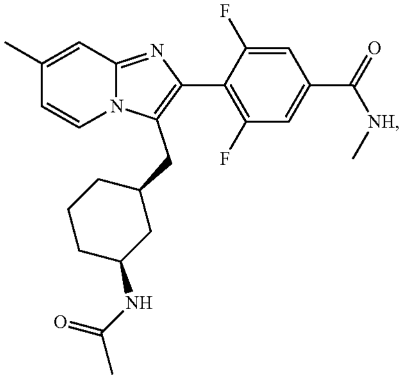
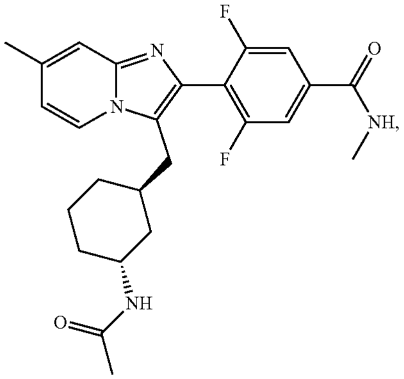
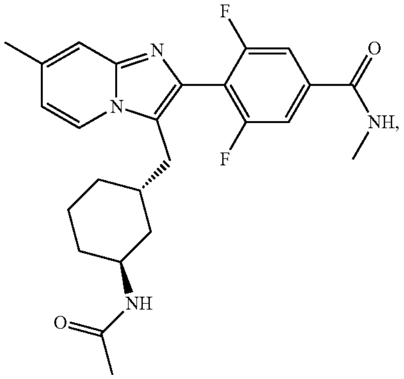

-continued
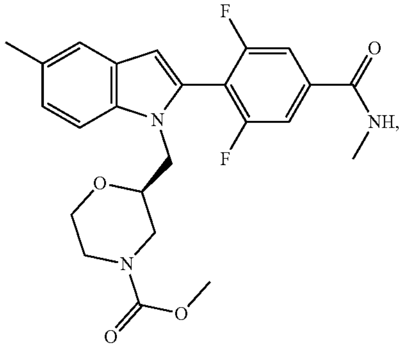
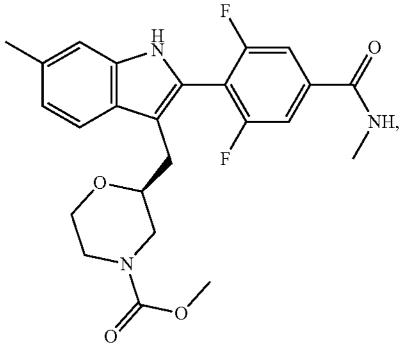
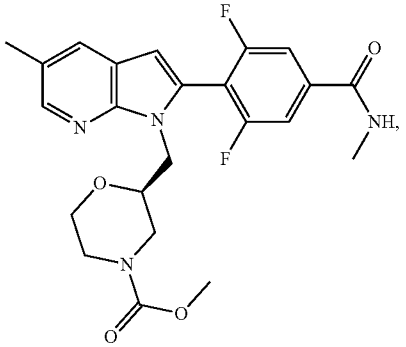
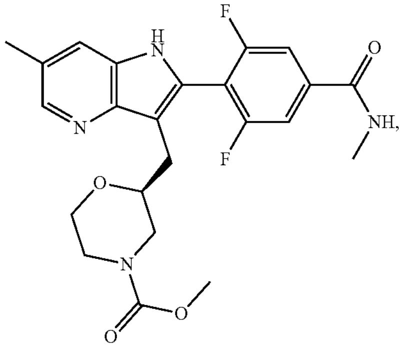
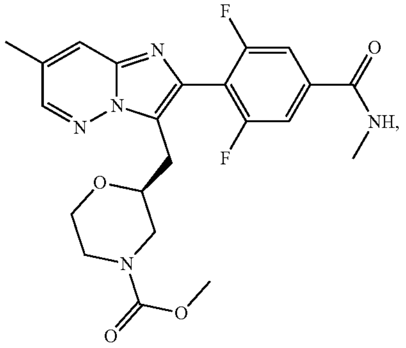
-continued
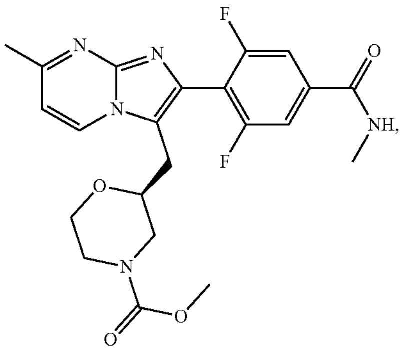
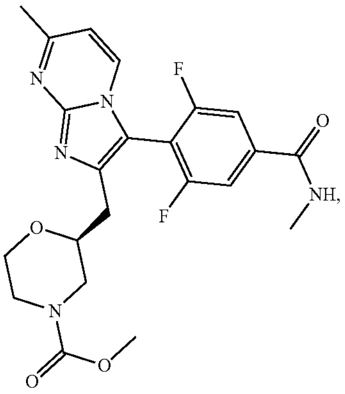
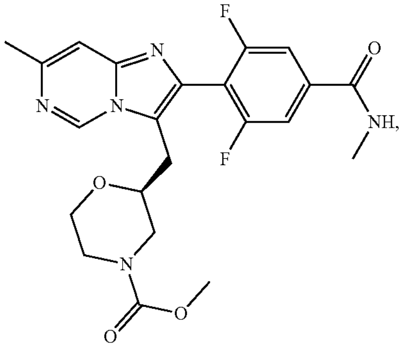
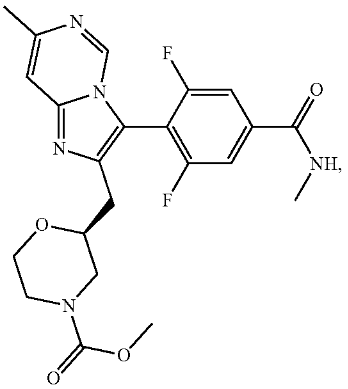

-continued
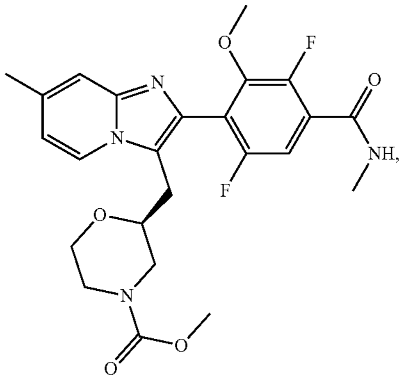
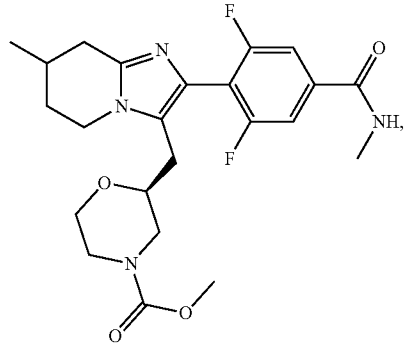
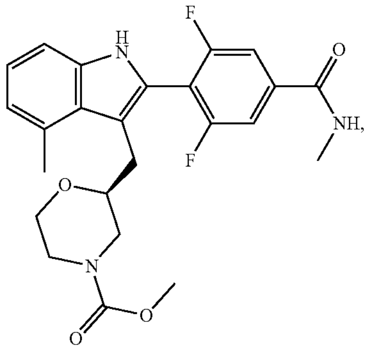
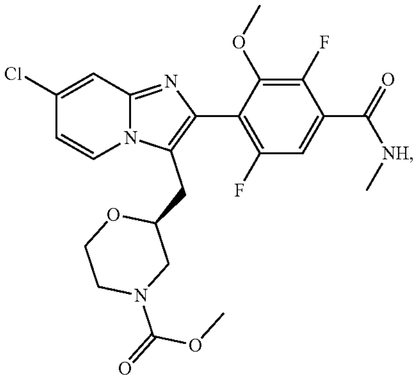
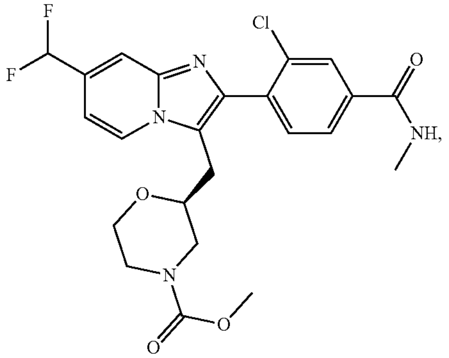
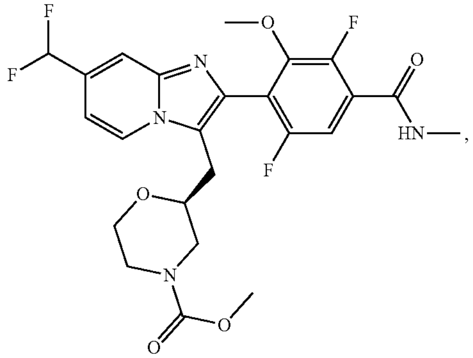
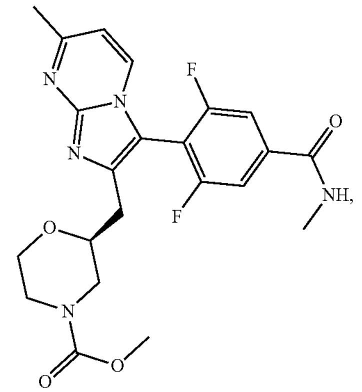
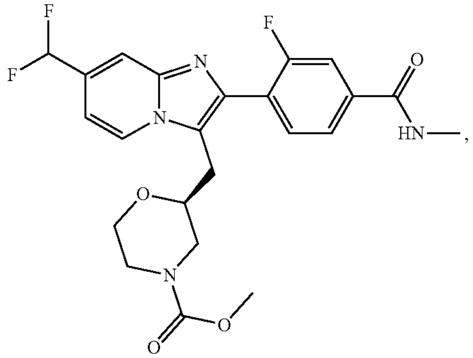

-continued
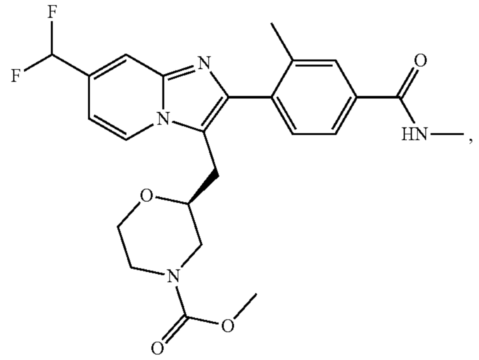
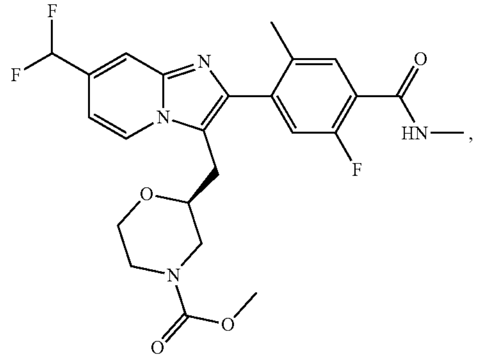
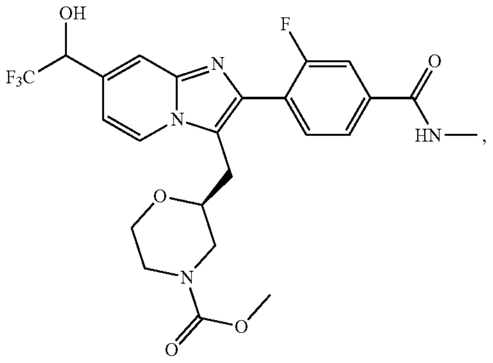
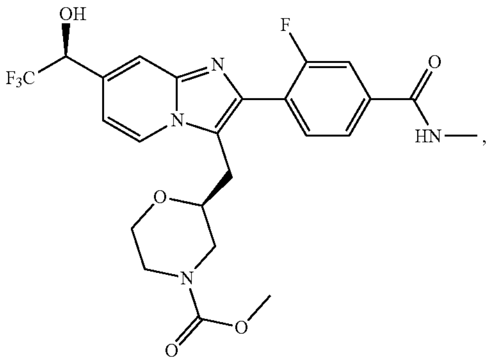
-continued
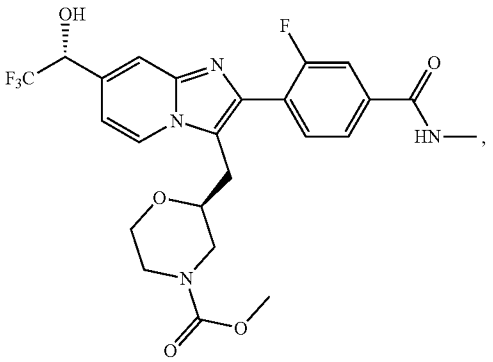
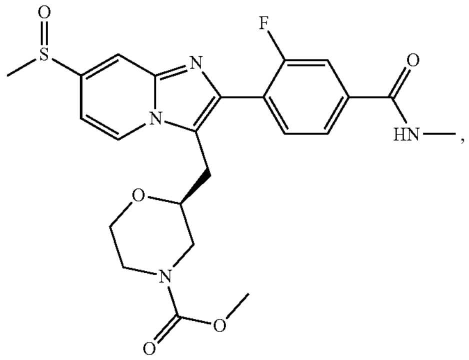
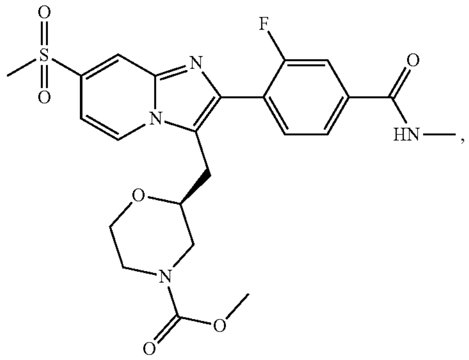
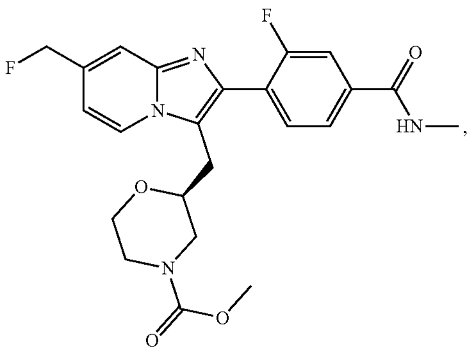

-continued
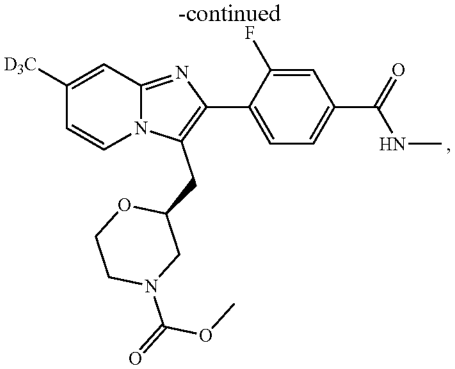
,
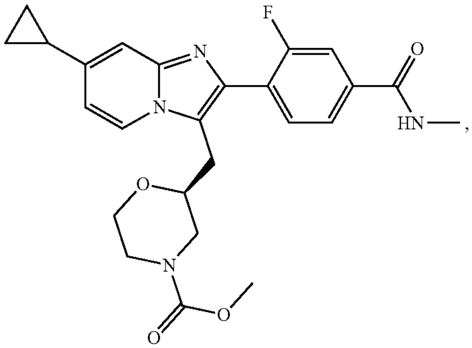
,
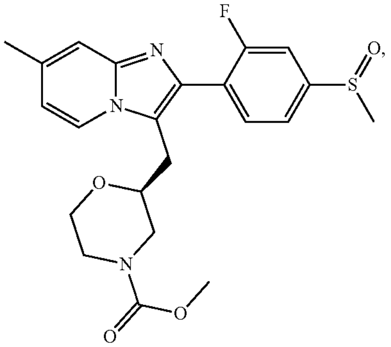
,
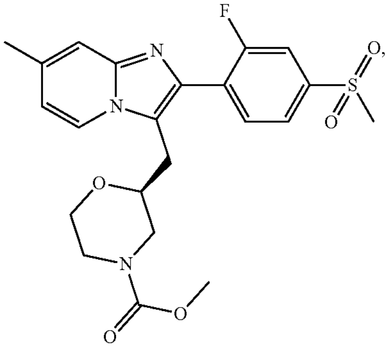
,
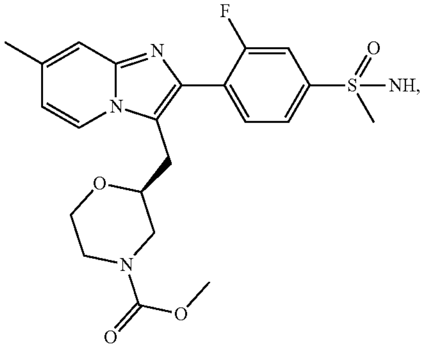
,
-continued
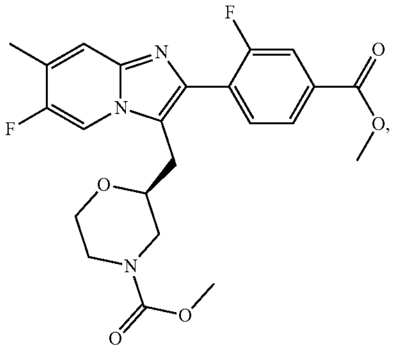
,
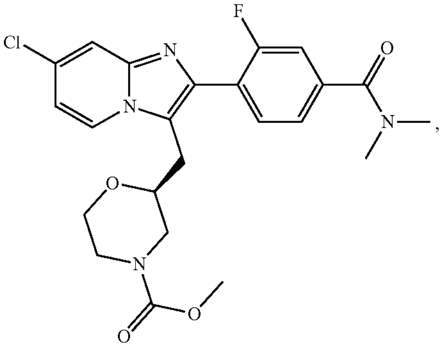
,
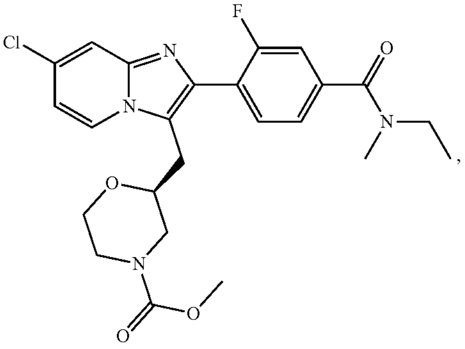
,
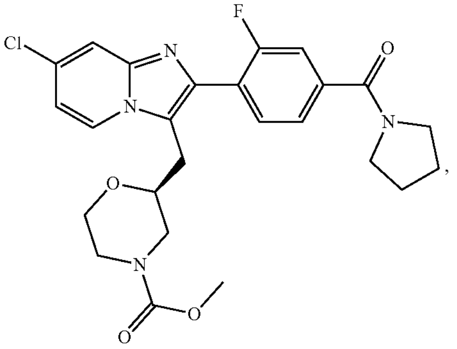
, -continued

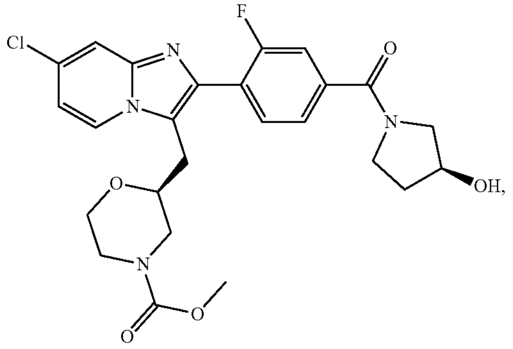

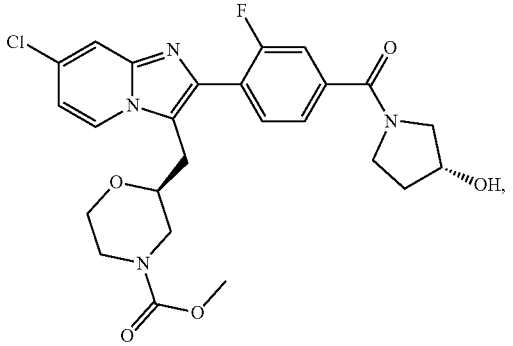

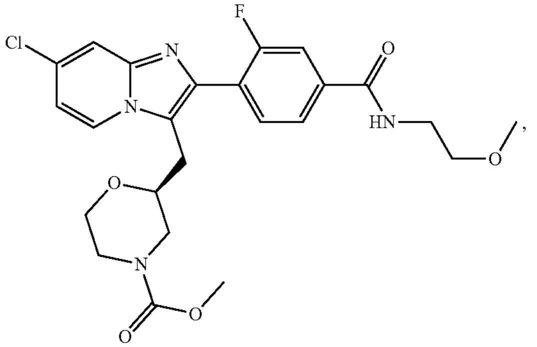

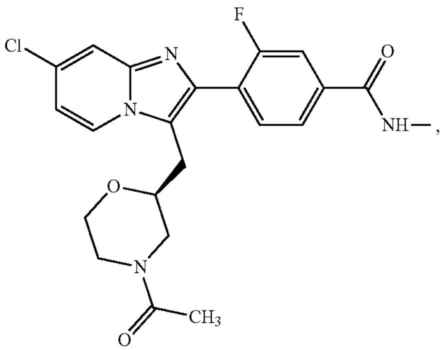

-continued

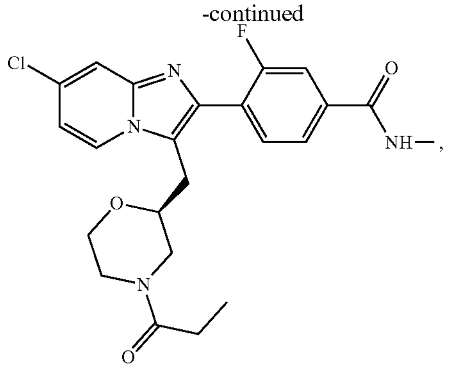

and

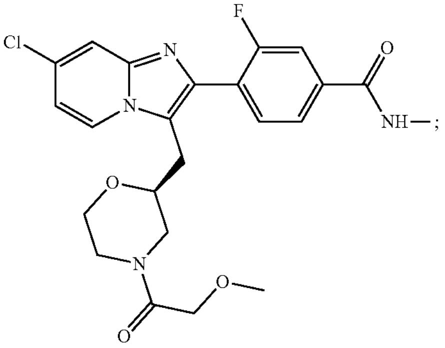

or a pharmaceutically acceptable salt or solvate thereof.

In certain embodiments, a disclosed compound utilized by one or more of the foregoing methods is one of the generic, subgeneric, or specific compounds described herein, such as a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), described herein.

Preparation of the Compounds

The compounds used in the methods described herein are made according to procedures disclosed in U.S. Pat. No. 9,598,409, which is herein incorporated by reference in its entirety, or by known organic synthesis techniques, starting from commercially available chemicals and/or from compounds described in the chemical literature. Commercially available chemicals are obtained from standard commercial sources including Acros Organics (Geel, Belgium), Aldrich Chemical (Milwaukee, WI, including Sigma Chemical and Fluka), Apin Chemicals Ltd. (Milton Park, UK), Ark Pharm, Inc. (Libertyville, IL), Avocado Research (Lancashire, U.K.), BDH Inc. (Toronto, Canada), Bionet (Cornwall, U.K.), Chemservice Inc. (West Chester, PA), Combi-blocks (San Diego, CA), Crescent Chemical Co. (Hauppauge, NY), eMolecules (San Diego, CA), Fisher Scientific Co. (Pittsburgh, PA), Fisons Chemicals (Leicestershire, UK), Frontier Scientific (Logan, UT), ICN Biomedicals, Inc. (Costa Mesa, CA), Key Organics (Cornwall, U.K.), Lancaster Synthesis (Windham, NH), Matrix Scientific, (Columbia, SC), Maybridge Chemical Co. Ltd. (Cornwall, U.K.), Parish Chemical Co. (Orem, UT), Pfaltz & Bauer, Inc. (Waterbury, CN), Polyorganix (Houston, TX), Pierce Chemical Co. (Rockford, IL), Riedel de Haen AG (Hanover, Germany), Ryan Scientific, Inc. (Mount Pleasant, SC), Spectrum Chemicals (Gardena, CA), Sundia Meditech, (Shanghai, China), TCI America (Portland, OR), Trans World Chemicals, Inc. (Rockville, MD), and WuXi (Shanghai, China).

Suitable reference books and treatises that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatises that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are also identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

Further Forms of Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds of the invention include isotopes of hydrogen, carbon, nitrogen, oxygen, phosphorous, sulfur, fluorine and chloride, such as $^{2}H$, $^{3}H$, $^{13}C$, $^{14}C$, $^{15}N$, $^{16}O$, $^{17}O$, $^{31}P$, $^{32}P$, $^{35}S$, $^{18}F$, and $^{36}Cl$, respectively. Compounds described herein, and the pharmaceutically acceptable salts, esters, solvate, hydrates or derivatives thereof which contain the aforementioned isotopes and/or other isotopes of other atoms are within the scope of this invention. Certain isotopically-labeled compounds, for example those into which radioactive isotopes such as $^{3}H$ and $^{14}C$ are incorporated, are useful in drug and/or substrate tissue distribution assays. Tritiated, i. e., $^{3}H$ and carbon-14, i. e., $^{14}C$, isotopes are particularly preferred for their ease of preparation and detectability. Further, substitution with heavy isotopes such as deuterium, i.e., $^{2}H$, produces certain therapeutic advantages resulting from greater metabolic stability, for example increased in vivo half-life or reduced dosage requirements. In some embodiments, the isotopically labeled compounds, pharmaceutically acceptable salt, ester, solvate, hydrate or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the invention, or by separately reacting a purified compound in its free form with a suitable acid or base, and isolating the salt thus formed.

Prodrugs

In some embodiments, the compounds described herein are formulated as agents which are converted in vivo to active forms in order to alter the biodistribution or the pharmacokinetics for a particular agent. For example, a carboxylic acid group can be esterified, e.g., with a methyl group or an ethyl group to yield an ester. When the ester is administered to a subject, the ester is cleaved, enzymatically or non enzymatically, reductively, oxidatively, or hydrolytically, to reveal the anionic group. An anionic group can be esterified with moieties (e.g., acyloxymethyl esters) which are cleaved to reveal an intermediate agent which subsequently decomposes to yield the active agent. The prodrug moieties may be metabolized in vivo by esterases or by other mechanisms to carboxylic acids. Alternatively, other functional groups may be modified into a prodrug form. For instance, an amine group may be converted into a carbamate or amide which would be cleavable in vivo.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran or methanol. In addition, the compounds provided herein exist in unsolvated as well as solvated forms. In general, the solvated forms are considered equivalent to the unsolvated forms for the purposes of the compounds and methods provided herein.

Pharmaceutical Compositions

In certain embodiments, the compounds described herein are administered as a pure chemical. In other embodiments, the compounds described herein are combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, $21^{st}$ Ed. Mack Pub. Co., Easton, PA (2005)).

Accordingly, provided herein is a pharmaceutical composition comprising at least one compound described herein, or a pharmaceutically acceptable salt, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable carrier and a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), or a pharmaceutically acceptable salt thereof.

Another embodiment provides a pharmaceutical composition consisting essentially of a pharmaceutically acceptable carrier and a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), or a pharmaceutically acceptable salt thereof.

In certain embodiments, the compound as described herein is substantially pure, in that it contains less than about 5%, or less than about 1%, or less than about 0.1%, of other organic small molecules, such as contaminating intermediates or by-products that are created, for example, in one or more of the steps of a synthesis method.

These formulations include those suitable for oral, topical, buccal, parenteral (e.g., subcutaneous, intramuscular, intradermal, or intravenous), or aerosol administration.

Exemplary pharmaceutical compositions are used in the form of a pharmaceutical preparation, for example, in solid, semisolid or liquid form, which includes one or more of a disclosed compound, as an active ingredient, in a mixture with an organic or inorganic carrier or excipient suitable for external, enteral or parenteral applications. In some embodiments, the active ingredient is compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

In some embodiments, a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), described herein are administered to subjects in a biologically compatible form suitable for topical administration to treat or prevent dermal diseases, disorders or conditions. By “biologically compatible form suitable for topical administration” is meant a form of the compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), to be administered in which any toxic effects are outweighed by the therapeutic effects of the inhibitor. Administration of a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), as described herein can be in any pharmacological form including a therapeutically effective amount of a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), alone or in combination with a pharmaceutically acceptable carrier.

Topical administration of a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), may be presented in the form of an aerosol, a semi-solid pharmaceutical composition, a powder, or a solution. By the term "a semi-solid composition" is meant an ointment, cream, salve, jelly, or other pharmaceutical composition of substantially similar consistency suitable for application to the skin. Examples of semi-solid compositions are given in Chapter 17 of The Theory and Practice of Industrial Pharmacy, Lachman, Lieberman and Kanig, published by Lea and Febiger (1970) and in Chapter 67 of Remington's Pharmaceutical Sciences, 15th Edition (1975) published by Mack Publishing Company.

Dermal or skin patches are another method for transdermal delivery of the therapeutic or pharmaceutical compositions described herein. Patches can provide an absorption enhancer such as DMSO to increase the absorption of the compounds. Patches can include those that control the rate of drug delivery to the skin. Patches may provide a variety of dosing systems including a reservoir system or a monolithic system, respectively. The reservoir design may, for example, have four layers: the adhesive layer that directly contacts the skin, the control membrane, which controls the diffusion of drug molecules, the reservoir of drug molecules, and a water-resistant backing. Such a design delivers uniform amounts of the drug over a specified time period, the rate of delivery has to be less than the saturation limit of different types of skin. The monolithic design, for example, typically has only three layers: the adhesive layer, a polymer matrix containing the compound, and a water-proof backing. This design brings a saturating amount of drug to the skin. Thereby, delivery is controlled by the skin. As the drug amount decreases in the patch to below the saturating level, the delivery rate falls.

In one embodiment, the topical composition may, for example, take the form of hydrogel based on polyacrylic acid or polyacrylamide; as an ointment, for example with polyethylene glycol (PEG) as the carrier, like the standard ointment DAB 8 (50% PEG 300, 50% PEG 1500); or as an emulsion, especially a microemulsion based on water-in-oil or oil-in-water, optionally with added liposomes. Suitable permeation accelerators (entraining agents) include sulfoxide derivatives such as dimethylsulfoxide (DMSO) or decylmethylsulfoxide (decyl-MSO) and transcutol (diethyleneglycolmonoethylether) or cyclodextrin; as well as pyrrolidones, for example 2-pyrrolidone, N-methyl-2-pyrrolidone, 2-pyrrolidone-5-carboxylic acid, or the biodegradable N-(2-hydroxyethyl)-2-pyrrolidone and the fatty acid esters thereof; urea derivatives such as dodecylurea, 1,3-didodecylurea, and 1,3-diphenylurea; terpenes, for example D-limonene, menthone, a-terpinol, carvol, limonene oxide, or 1,8-cineol.

Ointments, pastes, creams and gels also can contain excipients, such as starch, tragacanth, cellulose derivatives, polyethylene glycols, silicones, bentonites, silicic acid, and talc, or mixtures thereof. Powders and sprays also can contain excipients such as lactose, talc, silicic acid, aluminum hydroxide, calcium silicates and polyamide powder, or mixtures of these substances. Solutions of nanocrystalline antimicrobial metals can be converted into aerosols or sprays by any of the known means routinely used for making aerosol pharmaceuticals. In general, such methods comprise pressurizing or providing a means for pressurizing a container of the solution, usually with an inert carrier gas, and passing the pressurized gas through a small orifice. Sprays can additionally contain customary propellants, such a chlorofluorohydrocarbons and volatile unsubstituted hydrocarbons, such as butane and propane.

In some embodiments for preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition is readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, cellulose, microcrystalline cellulose, silicified microcrystalline cellulose, lactose, sucrose, glucose, mannitol, and/or silicic acid; (2) binders, such as, for example, carboxymethylcellulose, hypromellose, alginates, gelatin, polyvinyl pyrrolidone, sucrose and/or acacia; (3) humectants, such as glycerol; (4) disintegrating agents, such as crospovidone, croscarmellose sodium, sodium starch glycolate, agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, docusate sodium, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, in some embodiments, the compositions comprise buffering agents. In some embodiments, solid compositions of a similar type are also employed as fillers in soft and hard-filled gelatin capsules using such excipients as lactose or milk sugars, as well as high molecular weight polyethylene glycols and the like.

In some embodiments, a tablet is made by compression or molding, optionally with one or more accessory ingredients. In some embodiments, compressed tablets are prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. In some embodiments, molded tablets are made by molding in a suitable machine a mixture of the subject composition moistened with an inert liquid diluent. In some embodiments, tablets, and other solid dosage forms, such as dragees, capsules, pills and granules, are scored or prepared with coatings and shells, such as enteric coatings and other coatings.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, in some embodiments, the liquid dosage forms contain inert diluents, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

In some embodiments, suspensions, in addition to the subject composition, contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

In some embodiments, powders and sprays contain, in addition to a subject composition, excipients such as lactose, talc, silicic acid, aluminum hydroxide, calcium silicates and polyamide powder, or mixtures of these substances. In some embodiments, sprays additionally contain customary propellants, such as chlorofluorohydrocarbons and volatile unsubstituted hydrocarbons, such as butane and propane.

Compositions and compounds disclosed herein alternatively are administered by aerosol. This is accomplished by preparing an aqueous aerosol, liposomal preparation or solid particles containing the compound. In some embodiments, a non-aqueous (e.g., fluorocarbon propellant) suspension is used. In some embodiments, sonic nebulizers are used because they minimize exposing the agent to shear, which results in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which are reconstituted into sterile injectable solutions or dispersions just prior to use, which, in some embodiments, contain antioxidants, buffers, bacteriostats, solutes which render the formulation isotonic with the blood of the intended recipient or suspending or thickening agents.

Examples of suitable aqueous and non-aqueous carriers which are employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity is maintained, for example, by the use of coating materials, such as lecithin, by the maintenance of the required particle size in the case of dispersions, and by the use of surfactants.

The dose of the composition comprising at least one compound described herein differs, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity). Optimal doses are generally determined using experimental models and/or clinical trials. In some embodiments, the optimal dose depends upon the body mass, weight, or blood volume of the patient.

Oral doses typically range from about 1.0 mg to about 1000 mg, one to four times, or more, per day.

Methods

Pain

P2X3 is selectively expressed on nociceptive, small diameter sensory neurons (i.e., neurons that are stimulated by pain or injury), which is consistent with a role in pain sensitivity. And blocking P2X3 receptors has been reported to be analgesic in animal models of chronic inflammatory and neuropathic pain. Jarvis, et al., PNAS, 99, 17179-17184 (2002). It is, therefore, believed that a method for reducing the P2X3 level or activity would be useful for modulating pain sensation in a subject suffering from pain.

In some embodiments is a method for treating pain in a mammal in need thereof, comprising administering to the mammal in need thereof a therapeutically effective amount of a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), or a pharmaceutically acceptable salt or solvate thereof. In some embodiments, the pain is inflammatory and pain. In some embodiments, the pain is neuropathic pain. In some embodiments, the pain is chronic pain.

Urinary Tract Disorder

P2X3 is reportedly involved in afferent pathways controlling urinary bladder volume reflexes. Consequently, inhibiting P2X3 may have therapeutic potential for treating disorders of urine storage and voiding, such as overactive bladder. Cockayne, et al., Nature, vol. 407, pp. 1011-1015 (2000). Results from recent studies also suggest that P2X2/3 is predominantly expressed (over P2X3) in bladder sensory neurons, and are likely to play a role in sensing of urinary bladder filling and nociception. Zhong, et al., Neuroscience, vol. 120, pp. 667-675 (2003).

In some embodiments is a method for treating urinary tract disorder in a mammal in need thereof, comprising administering to the mammal in need thereof a therapeutically effective amount of a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), or a pharmaceutically acceptable salt or solvate thereof. In some embodiments, the urinary tract disorder comprises neurogenic overactive bladder, non-neurogenic overactive bladder, interstitial cystitis, prostatitis, prostadynia, and benign prostatic hyperplasia.

In some embodiments is a method of reducing or preventing uncontrolled loss of urine in a mammal in need thereof, comprising administering to the mammal in need thereof a therapeutically effective amount of a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), or a pharmaceutically acceptable salt or solvate thereof. In some embodiments, the uncontrolled loss of urine is associated with urge incontinence, cough incontinence, stress incontinence, overflow incontinence, functional incontinence, neurogenic incontinence, post-prostatectomy incontinence, urinary urgency, nocturia, and enuresis.

Cough

The majority of stimuli triggering cough are affecting the upper airways (e.g. strong odor/smoke, cold air, post-nasal drips, aspiration of gastroesophageal reflux, speaking). Furthermore, the greatest concentration of cough receptors is in the larynx, carina and bifurcation of the medium to large-sized bronchi. These observations indicate that the upper airways play a major role in cough. Therefore, given that upper airways are innervated by jugular C-fibres that express primarily P2X3 channels, it suggests that P2X3 homotrimeric receptors are responsible for the increase in cough reflex sensitivity.

In some embodiments is a method for treating cough in a mammal in need thereof, comprising administering to the mammal in need thereof a therapeutically effective amount of a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), or a pharmaceutically acceptable salt or solvate thereof. In some embodiments, the cough is an acute cough or a chronic cough. In some embodiments, the cough is associated with a disease, disorder, or condition selected from chronic obstructive pulmonary disease, asthma, tuberculosis, bronchitis, bronchiectasis, suppurative pulmonary disease, respiratory malignancies, allergy, cystic fibrosis, pulmonary fibrosis, respiratory tract inflammation, emphysema, pneumonia, lung cancer, lung neoplasia, sore throat, common cold, influenza, respiratory tract infection, bronchoconstriction, sarcoidosis, viral or bacterial infection of the upper airways, angiotension converting enzyme (ACE) inhibitor therapy, smoker's cough, chronic non-productive cough, neoplastic cough, cough due to gastroesophageal reflux, and inhalation of irritants, smoke, smog, dust, or air pollution.

Pruritus

Pruritogenic stimuli can be induced by mechanical, thermal and chemical means, which are sensed by afferent neurons innervating the skin and transmitted to the thalamus for processing and reflex initiation. Stimuli and afferent transmission acts through a wide variety of afferent neurons (pruriceptive neurons), which are a population partially overlapping in molecular phenotype with pain-sensing neurons in the skin. Pruriceptive neurons can respond to a wide variety of stimuli, but pathological itch is induced primarily by endogenous chemical agents (e.g. histamine, substance P, gastrin-release peptide, interleukins, nerve growth factors) acting at neuron terminals in the skin. These pruritogenic agents are released in the context of disorders with excessive inflammation (e.g. atopic dermatitis, psoriasis), systemic disease (e.g. chronic liver and kidney disease) neuropathic disorders (e.g. post-herpetic itch), or psychogenic conditions (e.g. obsessive compulsive disorder, substance abuse) (Yosipovitch et al., N. Engl. J. Med., 2013, 1625-1634).

Pruriceptive afferent neurons are characterized as c- or aδ-fibers of the dorsal root ganglions that innervate skin tissues and form synapses with the spinal cord. C- and aδ-fibers terminals in the skin express receptors responding to pruritogenic chemical agents to initiate action potentials that are transmitted to the CNS. These neurons also express P2X3 cation channels that regulate neuronal sensitivity to excitation by a pruritogenic stimuli. Notably, P2X3 channels are co-expressed on the cell membrane of MgprA3+ neurons, the major pruriceptive neuron phenotype innervating the skin, and the number of these neurons is increased in mouse models of chronic itch (Han et al., Nat. Neurosci., 2013, 174-182; Zhao et al., J. Clin. Invest., 2013, 4769-4780).

P2X3 channels are neuronal excitability regulators that are activated by local release of ATP, a neurotransmitter and extracellular messenger with pro-inflammatory properties. ATP is well established as an important chemical messenger released in excess by neuronal and non-neuronal cell types in multiple pathological conditions (Burnstock, Front. Pharmacol., 2017, 661; Burnstock, Biochem. Pharmacol., 2017, doi:10.1016/j.bcp.2017.07.016). Accordingly, the increased release of ATP can lead to hyperexcitability of afferent pruriceptive neurons and heightened sensitivity to any pruritogenic agent released pathologically in the skin. Overall, P2X3 channels acting through pathological ATP release may be potentially relevant targets to modulate the sensitivity of afferent neurons to itch sensations. Their inhibition could offer an approach to dampen peripheral hypersensitivity to itch in various diseases, with a broad mechanism independent of the pathological stimuli acting at itch receptors.

In some embodiments is a method for treating pruritus in a mammal in need thereof, comprising administering to the mammal in need thereof a therapeutically effective amount of a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), or a pharmaceutically acceptable salt or solvate thereof. In some embodiments, the pruritus is associated with an inflammatory skin disease, an infectious skin disease, an autoimmune skin disease, or a pregnancy-related skin disease. In some embodiments, the pruritus is associated with an inflammatory skin disease selected from the group consisting of atopic dermatitis, allergic, irritant contact dermatitis, exsiccation dermatitis, nummular and dyshidrotic dermatitis, lichen planus, lichen sclerosus et atrophicus, polymorphous light eruption psoriasis, Grover's disease, mucinosis, mastocytosis, and urticaria. In some embodiments, the pruritus is associated with an infectious skin disease selected from the group consisting of mycoses, bacterial and viral infections, scabies, pediculosis, insect bites, and folliculitides. In some embodiments, the pruritus is associated with an autoimmune skin disease selected from the group consisting of dermatitis herpetiformis (Duhring's disease), bullous pemphigoid; genodermatoses, Darier's disease, and Hailey-Hailey disease. In some embodiments, the pruritus is associated with a pregnancy-related skin disease selected from the group consisting of polymorphic eruption of pregnancy (PEP), atopic eruption of pregnancy, pemphigoid gestationis, neoplasias, and cutaneous T-cell lymphoma. In some embodiments, the pruritus is associated with prurigo nodularis. In some embodiments, the pruritus is associated with a kidney disease or a therapeutic procedure to treat a kidney disease. In some embodiments, the pruritus is associated with a chronic kidney disease. In some embodiments, the pruritus is associated with a therapeutic procedure to treat a kidney disease, wherein the therapeutic procedure to treat the kidney disease is selected from the group consisting of hemodialysis and peritoneal dialysis. In some embodiments, the pruritus is associated with a medical procedure or treatment. In some embodiments, the pruritus is associated with a medical treatment with a drug selected from the group consisting of opioids, anti-malarial drugs, anti-cancer therapies, and epidermal growth factor receptor inhibitors.

Endometriosis

The pain associated with endometriosis is attributed to functional endometriotic lesions, embedded with nerve fibers, on the outside of the uterine cavity. Afferent sensory fibers and pro-inflammatory mediators are correlated with endometriosis-associated pain. In particular, women with endometriosis have elevated levels of pro-inflammatory cytokines, such as interleukin (IL)-1β, IL-6, prostaglandins (PGs), tumor necrosis factor (TNF)-α, and nerve growth factor (NGF) in peritoneal fluid and endometriotic lesions. Inflammatory mediators in the endometriotic peritoneal inflammatory microenvironment activate nociceptive receptors on afferent neurons by stimulating sensory nerve fibers (including C- or Aδ-fibers) innervated within endometriotic lesions, providing the sensitization of sensory neurons and ultimately triggering a pain signal cascade. In some cases, anti-inflammatory agents provide pain relief. However, these agents often provide minimal relief of pain symptoms, and recurrence and serious side-effects can occur (Ding et al., PloS one, 2017, 12(9), 1-17; Yuan et al., Int. J. Nanomed., 2017, 8171-8183).

Afferent neurons found in endometriotic lesions on the outside of the uterine cavity consist of C- or Aδ-fibers of the dorsal root ganglions and form synapses with the spinal cord. C- and Aδ-fiber terminals express receptors that respond to pro-inflammatory mediators to initiate action potentials that are transmitted to the CNS. Important transducers of this signaling pathway expressed by these neurons are P2X3 cation channels. Notably, P2X3 channels are co-expressed on the cell membrane of small- and medium-diameter sensory neurons, which are critical pain transducers of noxious stimuli. Additionally, P2X3 expression in endometriosis endometrium and endometriotic lesions are significantly higher than normal endometrial tissue, and both are positively linked to endometriosis-associated pain. (Han et al., Nat. Neurosci., 2013, 174-182; Vilotti et al., PloS one, 2013, 8(11):e81138; Ding et al., PloS one, 2017, 12(9), 1-17).

Under pathophysiological conditions, the increased release of ATP modulated by inflammatory mediators can lead to activation of P2X3, leading to hyperexcitability of afferent neurons located in the endometrium outside the uterine cavity and heightened sensitivity to endometriosis-associated pain. Overall, P2X3 channels acting through pathological ATP release may be potentially relevant targets to modulate the sensitivity of afferent neurons coupled to endometriosis-associated pain. Their inhibition offers an approach to alleviate pain resulting from endometriosis and endometriosis-like symptoms (Yuan et al., Int. J. Nanomed., 2017, 8171-8183).

In some embodiments is a method for treating endometriosis, endometriosis-associated pain, and endometriosis-associated symptoms in a mammal in need thereof, comprising administering to the mammal in need thereof a therapeutically effective amount of a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), or a pharmaceutically acceptable salt or solvate thereof. In some embodiments is a method for treating endometriosis in a mammal in need thereof, comprising administering to the mammal in need thereof a therapeutically effective amount of a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), or a pharmaceutically acceptable salt or solvate thereof. In some embodiments is a method for treating endometriosis-associated pain in a mammal in need thereof, comprising administering to the mammal in need thereof a therapeutically effective amount of a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), or a pharmaceutically acceptable salt or solvate thereof. In some embodiments is a method for treating endometriosis-associated symptoms in a mammal in need thereof, comprising administering to the mammal in need thereof a therapeutically effective amount of a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), or a pharmaceutically acceptable salt or solvate thereof. In some embodiments, the endometriosis-associated symptoms are selected from dysmenorrhea, dyspareunia, dysuria, and dyschezia.

Pharmaceutical Combinations

Also contemplated herein are combination therapies, for example, co-administering a disclosed compound and an additional active agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration is accomplished, for example, by administering to the subject a single formulation or composition, (e.g., a tablet or capsule having a fixed ratio of each therapeutic agent or in multiple, single formulations (e.g., capsules) for each of the therapeutic agents. Sequential or substantially simultaneous administration of each therapeutic agent is effected by any appropriate route including, but not limited to, oral routes, intravenous routes, intramuscular routes, and direct absorption through mucous membrane tissues. The therapeutic agents are administered by the same route or by different routes. For example, a first therapeutic agent of the combination selected is administered by intravenous injection while the other therapeutic agents of the combination are administered orally. Alternatively, for example, all therapeutic agents are administered orally or all therapeutic agents are administered by intravenous injection.

In some embodiments is a method of treating a disorder associated with P2X3 activity in a mammal in need thereof, comprising administering to the mammal in need thereof a therapeutically effective amount of a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), further comprising administering to the mammal one or more additional pharmaceutical agents. In some embodiments is a method of treating pain in a mammal in need thereof, the method comprising administering to the mammal a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), further comprising administering to the mammal one or more additional pharmaceutical agents. In some embodiments is a method of treating a urinary tract disorder in a mammal in need thereof, the method comprising administering to the mammal a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), further comprising administering to the mammal one or more additional pharmaceutical agents. In some embodiments is a method of treating reducing or preventing uncontrolled loss of urine in a mammal in need thereof, the method comprising administering to the mammal a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), further comprising administering to the mammal one or more additional pharmaceutical agents. In some embodiments is a method of treating cough in a mammal in need thereof, the method comprising administering to the mammal a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), further comprising administering to the mammal one or more additional pharmaceutical agents. In some embodiments is a method of treating pruritus in a mammal in need thereof, the method comprising administering to the mammal a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), further comprising administering to the mammal one or more additional pharmaceutical agents. In some embodiments is a method of treating endometriosis, endometriosis-associated pain, and endometriosis-associated symptoms in a mammal in need thereof, the method comprising administering to the mammal a compound of Formula (I), (Ia), (Ia'), (Ia"), (II), (IIa), (IIa'), (IIa"), (III), (IIIa), (IIIa'), (IIIa"), (IV), (IVa), (IVa'), (IVa"), (V), (Va), (Va'), or (Va"), further comprising administering to the mammal one or more additional pharmaceutical agents.

In some embodiments, the additional pharmaceutical agent is a NK-1 antagonist. In some embodiments, the NK-1 antagonist is selected from the group consisting of serlopitant, aprepitant, casopitant, dapitant, ezlopitant, fosaprepitant, lanepitant, maropitant, netupitant, nolpitant, orvepitant, rolapitant, vestipitant, vofopitant, AV-818, BIIF 1149CL, CP122,721, DNK-333, GSK-424887, L-733060, L-759274, LY-686017, M516102, and TA-5538.

In some embodiments, the one or more additional pharmaceutical agents are selected from the group consisting of selected from a hormonal contraceptive, a non-steroidal anti-inflammatory agent (NSAID), a prostaglandin E synthase (PTGES) inhibitor, an interleukin-1 receptor-associated kinase 4 (IRAK4) inhibitor, a prostanoid EP4 receptor antagonist, an aldo-keto reductase 1C3 (AKR1C3) inhibitor, and a prolactin receptor (PRLR) antagonist. In some embodiments, the additional pharmaceutical agent is a hormonal contraceptive. In some embodiments, the additional pharmaceutical agent is a non-steroidal anti-inflammatory agent (NSAID). In some embodiments, the additional pharmaceutical agent is a prostaglandin E synthase (PTGES) inhibitor. In some embodiments, the additional pharmaceutical agent is an interleukin-1 receptor-associated kinase 4 (IRAK4) inhibitor. In some embodiments, the additional pharmaceutical agent is a prostanoid EP4 receptor antagonist. In some embodiments, the additional pharmaceutical agent is an aldo-keto reductase 1C3 (AKR1C3) inhibitor. In some embodiments, the additional pharmaceutical agent is a prolactin receptor (PRLR) antagonist.

Combination therapy also embraces the administration of the therapeutic agents as described above in further combination with other biologically active ingredients and non-drug therapies. Where the combination therapy further comprises a non-drug treatment, the non-drug treatment is conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination are administered to a patient simultaneously or sequentially. It will be appreciated that the components are present in the same pharmaceutically acceptable carrier and, therefore, are administered simultaneously. Alternatively, the active ingredients are present in separate pharmaceutical carriers, such as conventional oral dosage forms, that are administered either simultaneously or sequentially.

EXAMPLES

These examples are provided for illustrative purposes only and not to limit the scope of the claims provided herein.

List of Abbreviations

As used above, and throughout the description of the invention, the following abbreviations, unless otherwise indicated, shall be understood to have the following meanings:

ACN or MeCN acetonitrile

Bn benzyl

BOC or Boc t-butyl carbamate

CDI 1,1'-carbonyldiimidazole

Cy cyclohexyl

DCE dichloroethane ($ClCH_2CH_2Cl$)

DCM dichloromethane ($CH_2Cl_2$)

DIPEA or DIEA diisopropylethylamine

DMAP 4-(N,N-dimethylamino)pyridine

DMF dimethylformamide

DMA N,N-dimethylacetamide

DMSO dimethylsulfoxide equiv equivalent(s)

Et ethyl

EtOH ethanol

EA or EtOAc ethyl acetate

HATU 1-[bis(dimethylamino)methylene]-1H-1,2,3-triazolo[4,5-b]pyridinium 3-oxid hexafluorophosphate HPLC high performance liquid chromatography LAH lithium aluminum hydride Me methyl MeOH methanol MS mass spectroscopy NMM N-methylmorpholine NMR nuclear magnetic resonance PMB para-methoxybenzyl TEA triethylamine TFA trifluoroacetic acid THF tetrahydrofuran TLC thin layer chromatography I. Chemical Synthesis Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants (J) are reported in Hertz. For proton spectra the solvent peak was used as the reference peak.

Example 1: Synthesis of methyl (S)-2-((2-(2,6-difluoro-4-(methylcarbamoyl)phenyl)-7-fluoroimidazo[1,2-a]pyridin-3-yl)methyl)morpholine-4-carboxylate (A1)

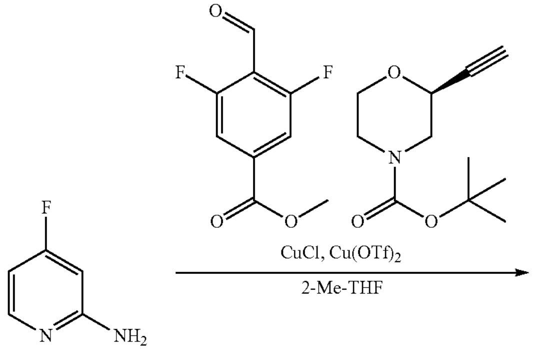

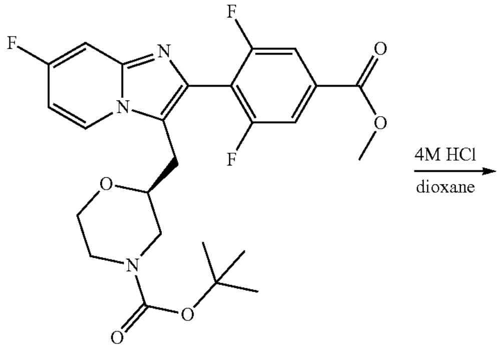

1

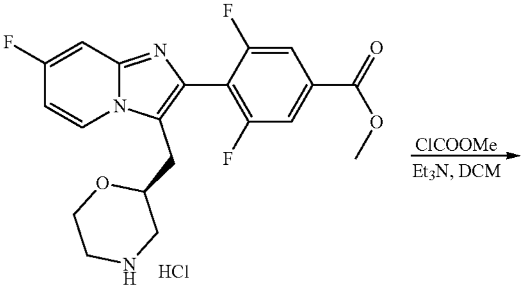

2

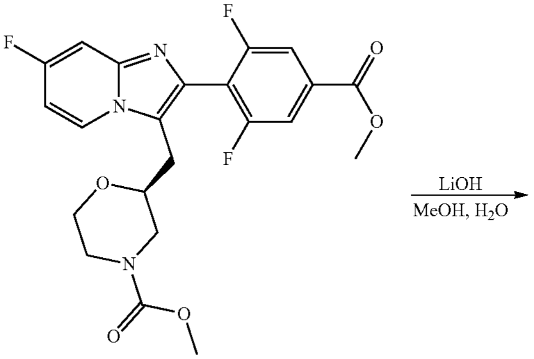

3

-continued

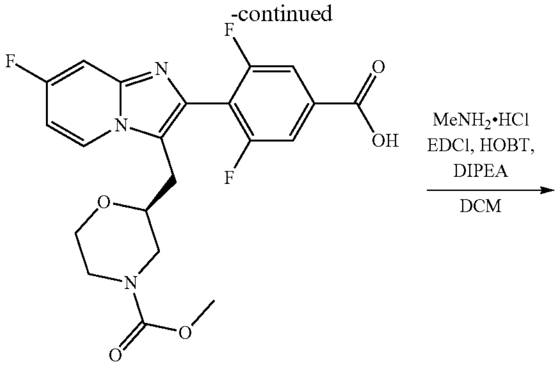

4

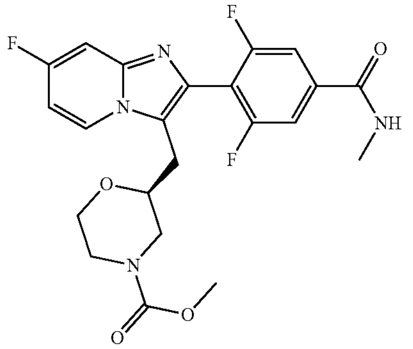

A1

Step 1: To a solution of N-Boc-(S)-2-ethynylmorpholine (989 mg, 4.68 mmol), methyl 3,5-difluoro-4-formylbenzoate (937 mg, 4.68 mmol) and 4-fluoro-2-aminopyridine (500 mg, 4.46 mmol) in 2-Me-THF (10 mL) was added $Cu(OTf)_2$ (242 mg, 669 μmol) and CuCl (66 mg, 669 μmol). The mixture was stirred at 80° C. for 16 h under $N_2$. The mixture was washed with sat. $Na_2CO_3$ (30 mL) and extracted with EA (10 mL×2). The combined organic layers were dried over $Na_2SO_4$, filtered and concentrated. The residue was purified by silica gel chromatography and concentrated to afford compound 1 (200 mg, 9%). LCMS (ESI, m/z): 506.0 $[M+H]^+$. $^1H$ NMR (400 MHz, $CDCl_3$) 8.34-8.32 (m, 1H), 7.75-7.66 (m, 2H), 7.24 (d, J=2.4 Hz, 1H), 6.73-6.71 (m, 1H), 3.97 (s, 3H), 3.78 (s, 2H), 3.62-3.53 (m, 1H), 3.44-3.31 (m, 1H), 3.01-2.95 (m, 2H), 2.89-2.76 (m, 1H), 2.54-2.50 (m, 1H), 1.47 (s, 1H), 1.42 (s, 9H).

Step 2: A solution of compound 1 (320 mg, 633 μmol) in 4M HCl in dioxane (4.0 mL) was stirred at 20° C. for 0.5 h. The mixture was concentrated to afford compound 2 (300 mg) as a yellow oil used in the next step with no further purification. LCMS (ESI, m/z): 406.2 $[M+H]^+$.

Step 3: To a solution of compound 2 (300 mg, 679 umol) in DCM (5.0 mL) was added $Et_3N$ (2.0 mmol, 285 μL) and methyl chloroformate (2.0 mmol, 160 μL at 0° C. The mixture was stirred at 20° C. for 0.5 h. The mixture was diluted with DCM (5 mL) and washed with $H_2O$ (30 mL). The organic layer was dried over $Na_2SO_4$, filtered and concentrated. The residue was purified by silica gel chromatography to afford compound 3 (140 mg, 44%). LCMS (ESI, m/z): 464.2 $[M+H]^+$. $^1H$ NMR (400 MHz, $CDCl_3$) 8.34-8.31 (m, 1H), 7.74-7.64 (m, 2H), 7.26-7.21 (m, 1H), 6.77-6.68 (m, 1H), 3.97 (s, 3H), 3.92-3.73 (m, 3H), 3.68 (s, 3H), 3.58-3.56 (m, 1H), 3.38-3.37 (m, 1H), 3.02-2.82 (m, 3H), 2.64-2.58 (m, 1H).

Step 4: To a solution of compound 3 (140 mg, 302 μmol) in MeOH (2.0 mL) was added $LiOH{\cdot}H_2O$ (25 mg, 600 μmol)

in $H_2O$ (0.6 mL). The mixture was stirred at 20° C. for 0.5 h. The mixture was adjusted to pH=2~3 by addition of 1M aq. HCl, concentrated to remove MeOH, and the aqueous layer was extracted by $CHCl_3$/IPA=3/1 (2×2.0 mL). The combined organic layers were dried over $Na_2SO_4$, filtered and concentrated to afford compound 4 (130 mg, 96%). The product was used into next step directly without further purification. LCMS (ESI, m/z): 450.1 $[M+H]^+$.

Step 5: To a solution of compound 4 (130 mg, 289 μmol) in DCM (2.0 mL) was added EDCI (166 mg, 868 μmol), HOBt (117 mg, 868 μmol), methylamine hydrochloride (98 mg, 1.45 mmol) and DIPEA (1.74 mmol, 300 μL). The mixture was stirred at 20° C. for 16 h. The mixture was washed with $H_2O$ (4.0 mL), and the aqueous washes extracted with DCM (2×2.0 mL). The combined organic layers were dried over $Na_2SO_4$, filtered and concentrated. The crude product was purified by preparative HPLC and the product-containing fraction pooled and lyophilized, to afford compound A1 (38 mg, 28%) as a white solid. LCMS (ESI, m/z): 463.3 $[M+H]^+$. $^1H$ NMR (400 MHz, $CDCl_3$) 8.39-8.26 (m, 1H), 7.49-7.36 (m, 2H), 7.26-7.22 (m, 1H), 7.15-6.94 (m, 1H), 6.75-6.72 (m, 1H), 4.00-3.73 (m, 3H), 3.67 (s, 3H), 3.56 (d, J=2.6 Hz, 1H), 3.37-3.36 (m, 1H), 3.02 (d, J=4.8 Hz, 3H), 2.98-2.79 (m, 3H), 2.63-2.60 (m, 1H).

Example 2: Synthesis of methyl (S)-2-((7-chloro-2-(2,6-difluoro-4-(methyl-carb-amoyl)-phenyl)-imidazo[1,2-a]pyridin-3-yl)methyl)morpholine-4-carboxylate (A2)

A2

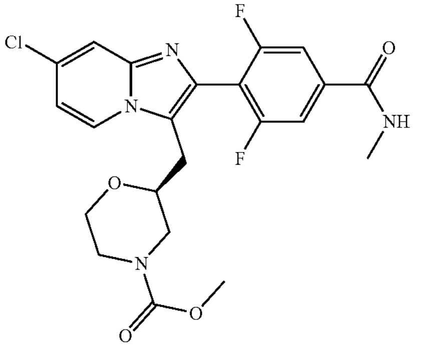

Compound A2 was prepared starting from 4-chloro-2-aminopyridine by the procedures described in Example 1, steps 1-5. LCMS (ESI, m/z): 479.2 $[M+H]^+$. $^1H$ NMR (400 MHz, $CDCl_3$) 8.29 (d, J=7.6 Hz, 1H), 7.61 (d, J=1.6 Hz, 1H), 7.46-7.38 (m, 2H), 6.91 (s, 1H), 6.84-6.82 (m, 1H), 3.98-3.72 (m, 3H), 3.67 (s, 3H), 3.63-3.51 (m, 1H), 3.44-3.30 (m, 1H), 3.03 (d, J=4.8 Hz, 3H), 2.98-2.81 (m, 3H), 2.69-2.54 (m, 1H).

Example 3: Synthesis of methyl (S)-2-((2-(2,6-difluoro-4-(methylcarbamoyl)phenyl)-7-methoxyimidazo[1,2-a]pyridin-3-yl)methyl)morpholine-4-carboxylate (A3)

A3

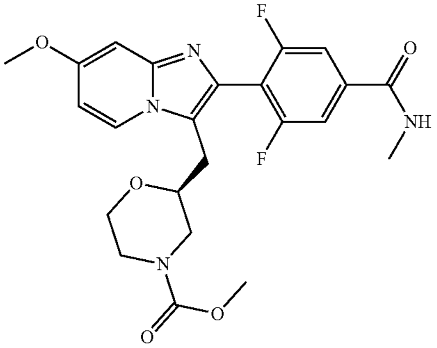

Compound A3 was prepared from 4-methoxy-2-aminopyridine by the procedures described in Example 1, steps 1-5. LCMS (ESI, m/z): 475.1 $[M+H]^+$. $^1H$ NMR (400 MHz, $CDCl_3$) 8.15 (d, J=7.6 Hz, 1H), 7.42 (d, J=7.6 Hz, 2H), 7.23-7.00 (m, 1H), 6.87 (d, J=2.4 Hz, 1H), 6.58-6.55 (m, 1H), 3.88-3.78 (m, 6H), 3.67 (s, 3H), 3.55 (br d, J=2.0 Hz, 1H), 3.40-3.35 (m, 1H), 3.02 (d, J=4.8 Hz, 3H), 2.99-2.88 (m, 3H), 2.61-2.58 (m, 1H).

Example 4: Synthesis of methyl (S)-2-((2-(2,6-difluoro-4-(methylcarbamoyl)phenyl)-7-(di-fluoromethyl)imidazo[1,2-a]pyridin-3-yl)methyl)morpholine-4-carboxylate (A4)

A4

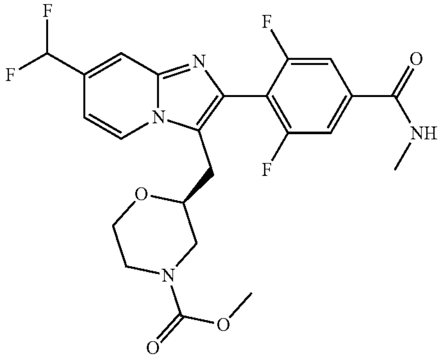

Compound A4 was prepared from 4-difluoromethyl-2-aminopyridine by the procedures described in Example 1, steps 1-5. LCMS (ESI, m/z): 495.3 $[M+H]^+$. $^1H$ NMR (400 MHz, $CDCl_3$) 8.45 (br d, J=7.2 Hz, 1H), 7.75 (s, 1H), 7.44 (d, J=7.6 Hz, 2H), 7.00 (br d, J=7.2 Hz, 1H), 6.84-6.56 (m, 2H), 3.86-3.79 (m, 3H), 3.68 (s, 3H), 3.58 (br d, J=2.4 Hz, 1H), 3.40-3.37 (m, 1H), 3.04-3.00 (m, 5H), 2.95-2.87 (m, 1H), 2.65-2.62 (m, 1H).

Example 5: Synthesis of methyl (S)-2-((2-(2,6-difluoro-4-(methylcarbamoyl)phenyl)-7-(trifluoromethyl)imidazo[1,2-a]pyridin-3-yl)methyl)morpholine-4-carboxylate (A5)

A5

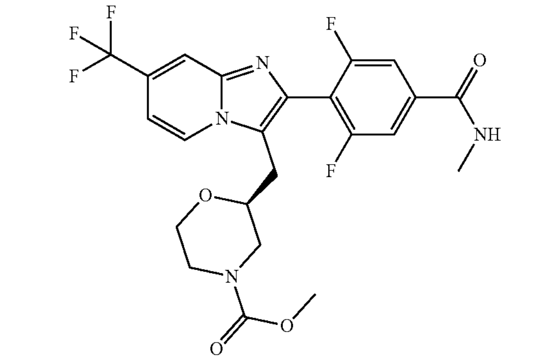

Compound A5 was prepared from 4-trifluoromethyl-2-aminopyridine by the procedures described in Example 1, steps 1-5. LCMS (ESI, m/z): 513.3 $[M+H]^+$. H NMR (400 MHz, $CDCl_3$) 8.49 (d, J=7.2 Hz, 1H), 7.94 (s, 1H), 7.46-7.44 (m, 2H), 7.03-7.01 (m, 2H), 3.86-3.78 (m, 3H), 3.68 (s, 3H), 3.59 (br d, J=2.6 Hz, 1H), 3.40-3.34 (m, 1H), 3.04-2.95 (m, 5H), 2.95-2.82 (m, 1H), 2.65-2.60 (m, 1H).

Example 6: Synthesis of methyl (S)-2-((7-methyl-2-(2,3,6-trifluoro-4-(methylcarbamoyl)-phenyl)imidazo[1,2-a]pyridin-3-yl)methyl)morpholine-4-carboxylate (Aδ)

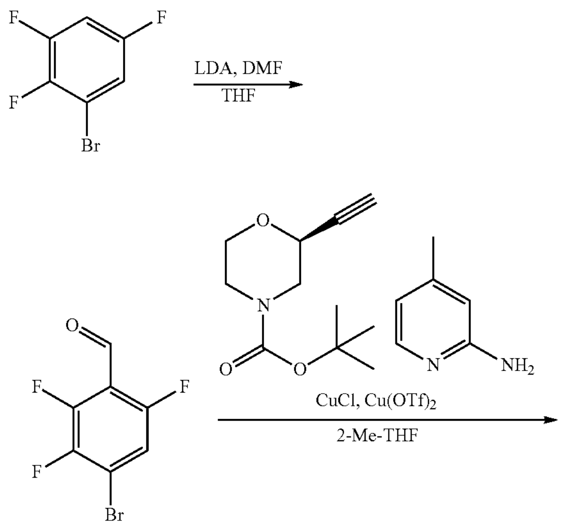

-continued

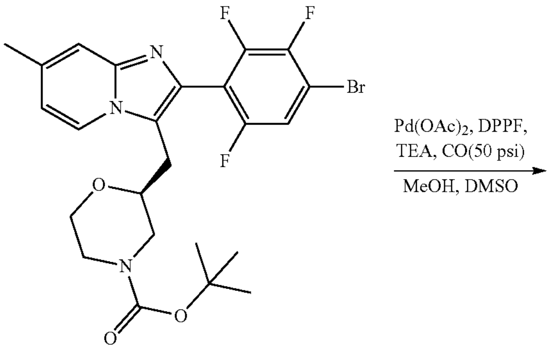

5

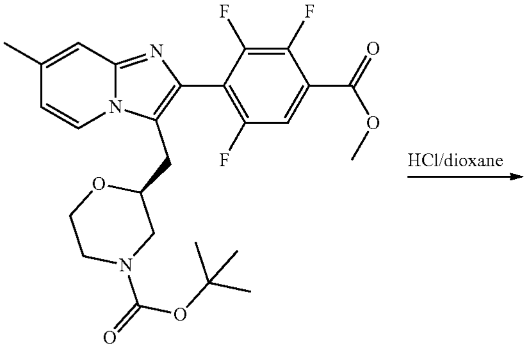

6

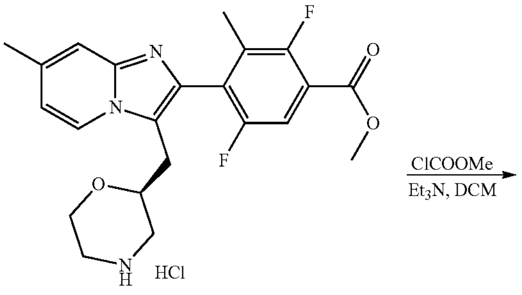

7

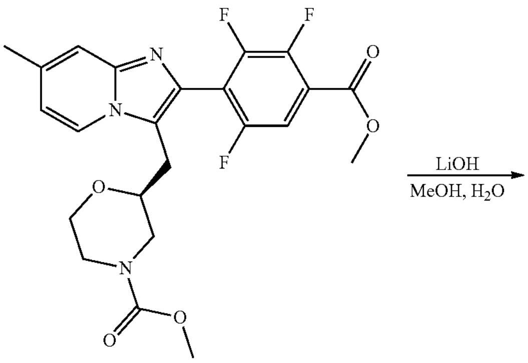

8

-continued

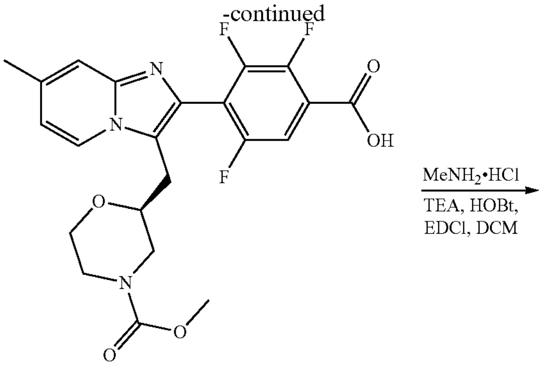

9

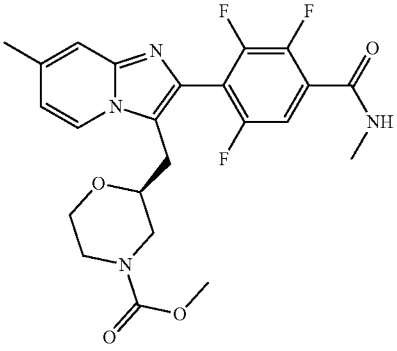

A6

Step 1: To a solution of 2,3,5-trifluorobromobenzene (5.00 g, 23.7 mmol, 2.8 mL) in THF (70 mL) was added 2M LDA (13.0 mL) dropwise at −78° C. under $N_2$. The mixture was stirred at −78° C. for 0.5 h. Then a solution of DMF (26.1 mmol, 2.0 mL) in THF (5 mL) was added to the above reaction mixture. The resulting reaction mixture was stirred at −78° C. for 15 min, then allowed to warm to 20° C. and stirred for 1 h. The mixture was quenched by addition of sat. $NH_4Cl$ (200 mL) and extracted with EA (100 mL×2). The combined extracts were washed with brine (150 mL), dried over $Na_2SO_4$, filtered and concentrated. The residue was purified by silica gel chromatography to afford 2,3,5-trifluoro-4-formyl-bromobenzene (4.50 g, 79%). $^1$H NMR (400 MHz, $CDCl_3$) 10.29 (d, J=0.8 Hz, 1H), 7.29 (td, J=2.3, 4.6 Hz, 1H), 7.26 (d, J=2.4 Hz, 1H).

Step 2: N-Boc-(S)-2-ethynylmorpholine (2.05 g, 9.71 mmol), 2,3,5-trifluoro-4-formyl-bromobenzene (2.32 g, 9.71 mmol) and 4-methyl-2-aminopyridine (1.00 g, 9.25 mmol) were reacted as described in Example 1, step 1, to afford tert-butyl (S)-2-((2-(4-bromo-2,3,6-trifluorophenyl)-7-methylimidazo[1,2-a]pyridin-3-yl)methyl)morpholine-4-carboxylate (5) (440 mg, 8%). LCMS (ESI, m/z): 542.0 $[M+H]^+$. $^1$H NMR (400 MHz, $CDCl_3$) 8.19 (d, J=7.1 Hz, 1H), 7.38 (s, 1H), 7.24 (dt, J=2.5, 5.4 Hz, 1H), 6.69 (br d, J=6.8 Hz, 1H), 3.99-3.71 (m, 3H), 3.60-3.49 (m, 1H), 3.44-3.29 (m, 1H), 3.06-2.91 (m, 2H), 2.83 (br d, J=6.7 Hz, 1H), 2.54 (dd, J=10.7, 13.0 Hz, 1H), 2.42 (s, 3H), 1.43 (s, 9H).

Step 3: To a solution of tert-butyl (S)-2-((2-(4-bromo-2,3,6-trifluorophenyl)-7-methylimidazo[1,2-a]pyridin-3-yl)methyl)morpholine-4-carboxylate (5) (110 mg, 0.20 mmol) in MeOH (2.0 mL) and DMSO (2.0 mL) was added $Pd(OAc)_2$ (5 mg, 0.02 mmol), DPPF (23 mg, 0.04 mol), TEA (0.61 mmol, 85 μL). Then the mixture was stirred at 60° C. for 16 h under CO (50 psi). The mixture was diluted with water (30 mL) and extracted with EA (15 mL×2). The combined extracts were washed with brine (30 mL), dried over $Na_2SO_4$, filtered and concentrated. The residue was purified by silica gel chromatography to afford tert-butyl (S)-2-((7-methyl-2-(2,3,6-trifluoro-4-(methoxycarbonyl)phenyl)imidazo[1,2-a]pyridin-3-yl)methyl)-morpholine-4-carboxylate (6) (80 mg, 66%). LCMS (ESI, m/z): 520.3 $[M+H]^+$. $^1$H NMR (400 MHz, $CDCl_3$) 8.19 (br d, J=7.1 Hz, 1H), 7.57 (ddd, J=2.1, 5.2, 9.2 Hz, 1H), 7.39 (s, 1H), 6.75-6.64 (m, 1H), 4.00 (s, 3H), 3.91-3.66 (m, 3H), 3.61-3.50 (m, 1H), 3.45-3.31 (m, 1H), 3.09-2.92 (m, 2H), 2.89-2.77 (m, 1H), 2.54 (dd, J=10.8, 13.0 Hz, 1H), 2.43 (s, 3H), 1.43 (s, 9H).

Steps 4-7: Compound A6 was prepared starting from tert-butyl (S)-2-((7-methyl-2-(2,3,6-trifluoro-4-(methoxycarbonyl)phenyl)imidazo[1,2-a]pyridin-3-yl)methyl)morpholine-4-carboxylate (6) by the procedures described in Example 1, steps 2-5. LCMS (ESI, m/z): 477.3 $[M+H]^+$. $^1$H NMR (400 MHz, $CDCl_3$) 8.18 (d, J=7.0 Hz, 1H), 7.73 (ddd, J=2.1, 5.6, 9.6 Hz, 1H), 7.39 (s, 1H), 6.78-6.66 (m, 2H), 4.03-3.72 (m, 3H), 3.68 (s, 3H), 3.56 (br dd, J=3.7, 6.9 Hz, 1H), 3.44-3.32 (m, 1H), 3.09 (d, J=4.4 Hz, 3H), 3.06-2.96 (m, 2H), 2.95-2.83 (m, 1H), 2.61 (dd, J=11.0, 12.6 Hz, 1H), 2.43 (s, 3H).

Example 7: Synthesis of methyl (S)-2-((7-chloro-2-(2-methyl-4-(methylcarbamoyl)phenyl)-imidazo[1,2-a]pyridin-3-yl)methyl)morpholine-4-carboxylate (A7)

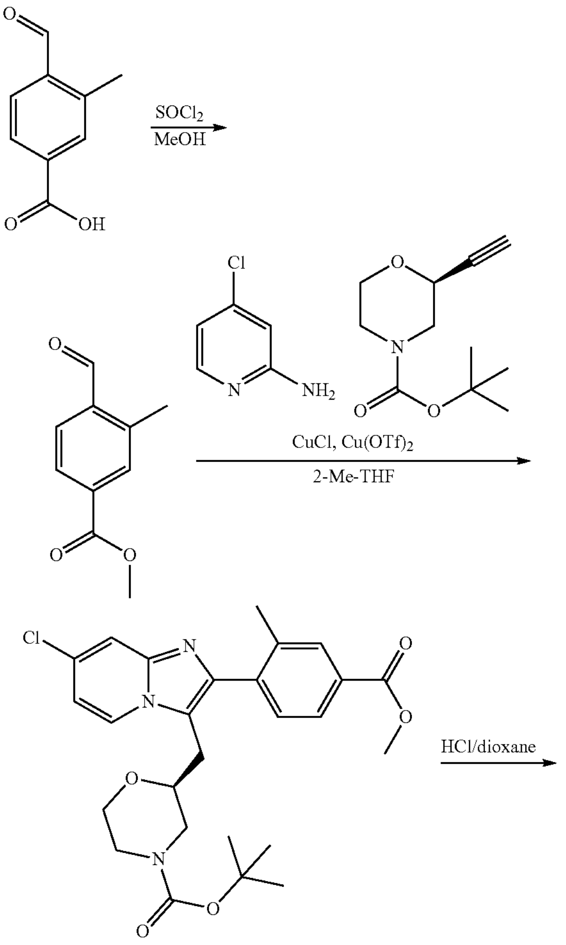

10

-continued

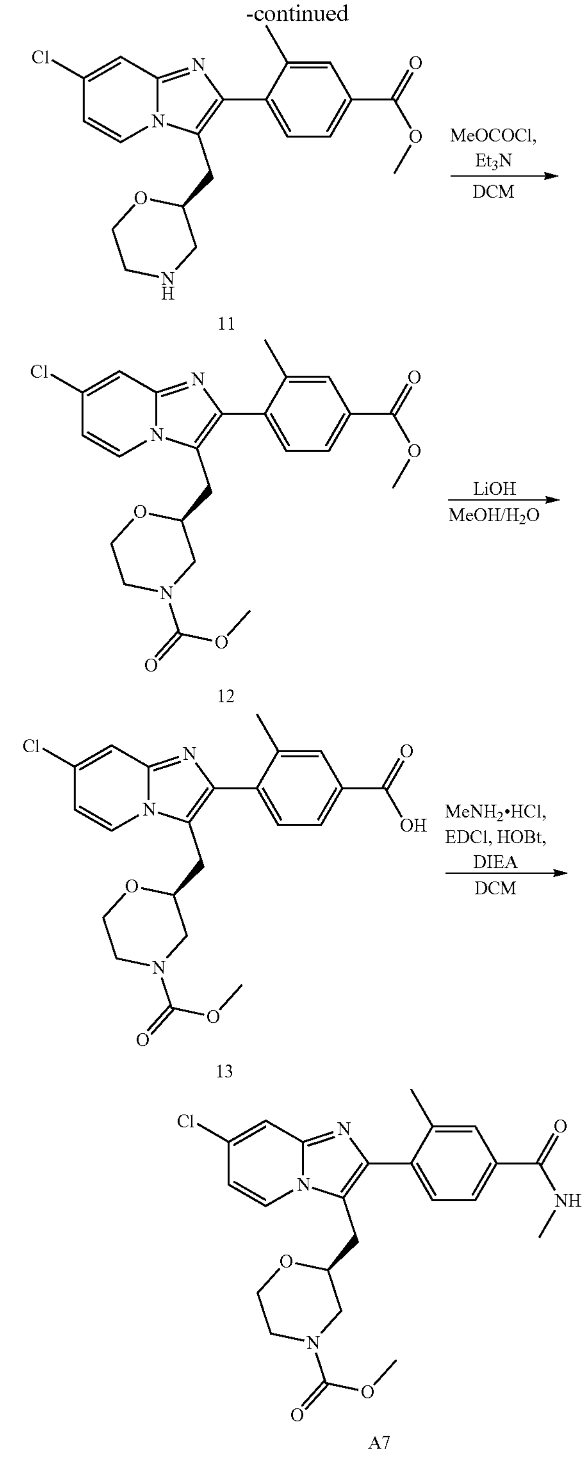

11

12

13

A7

Step 1: To a solution of 4-formyl-3-methyl-benzoic acid (900 mg, 5.48 mmol) in MeOH (10 mL) was added $SOCl_2$ (0.8 mL, 11.0 mmol) dropwise at 0° C. The mixture was stirred at 30° C. for 10 h. The mixture was concentrated, and the residue was purified by column chromatography to obtain methyl 4-formyl-3-methylbenzoate (510 mg, 52%) as a white solid. $^1H$ NMR (400 MHz, $CDCl_3$) 10.35 (s, 1H), 8.00 (d, J=7.9 Hz, 1H), 7.95 (s, 1H), 7.87 (d, J=7.9 Hz, 1H), 3.96 (s, 3H), 2.72 (s, 3H).

Steps 2-6: Compound A7 was prepared starting from N-Boc-(S)-2-ethynylmorpholine, methyl 4-formyl-3-methylbenzoate, and 4-chloro-2-aminopyridine by the procedures described in Example 1, steps 1-5. LCMS (ESI, m/z): 457.1 $[M+H]^+$. $^1H$ NMR (400 MHz, $CDCl_3$) 8.20 (br d, J=7.3 Hz, 1H), 7.71 (d, J=0.7 Hz, 1H), 7.66-7.57 (m, 2H), 7.31 (d, J=7.9 Hz, 1H), 6.82 (dd, J=2.1, 7.3 Hz, 1H), 6.46 (br d, J=3.9 Hz, 1H), 4.03-3.70 (m, 3H), 3.66 (s, 3H), 3.48 (br d, J=3.5 Hz, 1H), 3.36 (br t, J=11.6 Hz, 1H), 3.03 (d, J=4.9 Hz, 3H), 2.99-2.92 (m, 2H), 2.92-2.80 (m, 1H), 2.52 (br t, J=11.6 Hz, 1H), 2.29 (s, 3H).

Example 8: Synthesis of methyl (S)-2-((2-(2-chloro-4-(methylcarbamoyl)phenyl)-7-methyl-imidazo[1,2-a]pyridin-3-yl)methyl)morpholine-4-carboxylate (A8)

A8

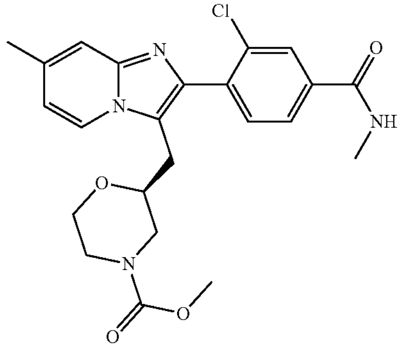

Compound A8 was prepared from N-Boc-(S)-2-ethynylmorpholine, methyl 4-formyl-3-chlorobenzoate, and 4-methyl-2-aminopyridine by the procedures described in Example 1, steps 1-5. LCMS (ESI, m/z): 457.3 $[M+H]^+$. $^1H$ NMR (400 MHz, $CDCl_3$) 8.12 (br d, J=7.1 Hz, 1H), 7.91 (d, J=1.7 Hz, 1H), 7.70 (dd, J=1.7, 7.9 Hz, 1H), 7.55 (d, J=7.9 Hz, 1H), 7.38 (s, 1H), 6.69 (dd, J=1.4, 7.0 Hz, 1H), 6.41 (br s, 1H), 3.96-3.70 (m, 3H), 3.66 (s, 3H), 3.51 (br dd, J=2.1, 5.7 Hz, 1H), 3.42-3.31 (m, 1H), 3.05 (d, J=4.9 Hz, 3H), 3.03-2.99 (m, 2H), 2.93-2.81 (m, 1H), 2.52 (br t, J=11.9 Hz, 1H), 2.43 (s, 3H).

Example 9: Synthesis of methyl (S)-2-((2-(2-chloro-4-(methylcarbamoyl)phenyl)-7-chloro-imidazo[1,2-a]pyridin-3-yl)methyl)morpholine-4-carboxylate (A9)

A9

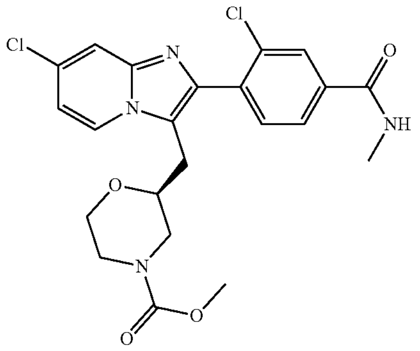

Compound A9 was prepared from N-Boc-(S)-2-ethynylmorpholine, methyl 4-formyl-3-chlorobenzoate, and 4-chloro-2-aminopyridine by the procedures described in Example 1, steps 1-5. LCMS (ESI, m/z): 477.2 [M+H]$^+$. $^1$H NMR (400 MHz, $CDCl_3$) 8.24 (br d, J=7.4 Hz, 1H), 7.92 (d, J=1.5 Hz, 1H), 7.71 (dd, J=1.6, 7.9 Hz, 1H), 7.62 (d, J=2.0 Hz, 1H), 7.52 (d, J=8.0 Hz, 1H), 6.84 (dd, J=2.0, 7.4 Hz, 1H), 6.39 (br d, J=3.8 Hz, 1H), 3.97-3.72 (m, 3H), 3.67 (s, 3H), 3.58-3.47 (m, 1H), 3.44-3.30 (m, 1H), 3.05 (d, J=4.8 Hz, 3H), 3.00 (br d, J=5.8 Hz, 2H), 2.88 (br s, 1H), 2.63-2.49 (m, 1H).

Example 10: Synthesis of methyl (S)-2-((2-(2-fluoro-4-(methylcarbamoyl)phenyl)-7-methylimidazo[1,2-a]pyridin-3-yl)methyl)morpholine-4-carboxylate (A10)

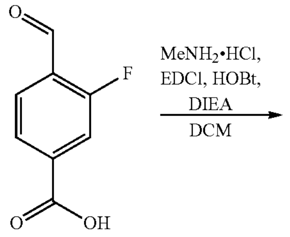

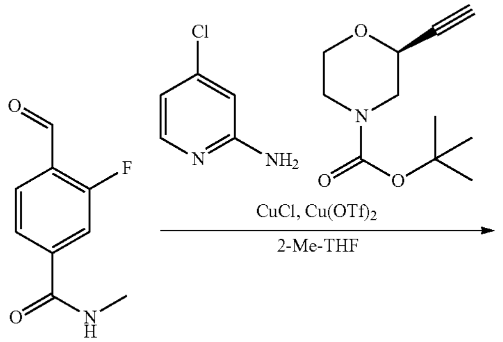

14

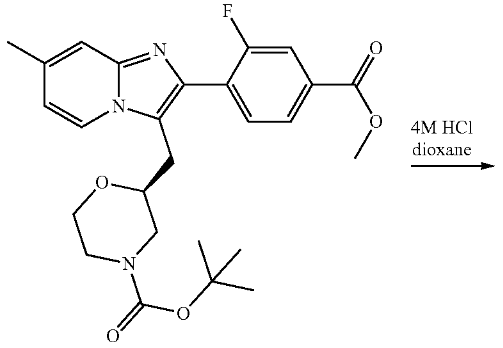

15

-continued

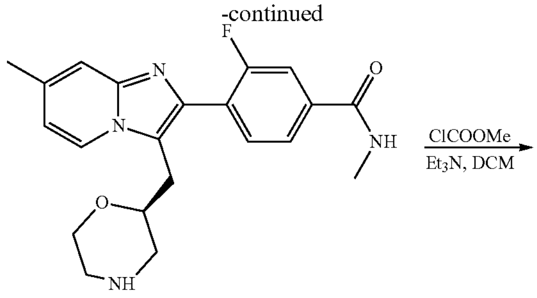

16

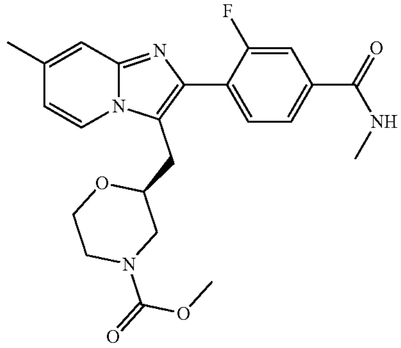

A10

Step 1: To a solution of 3-fluoro-4-formylbenzoic acid (400 mg, 2.38 mmol), methylamine hydrochloride (321 mg, 4.76 mmol) and HOBt (482 mg, 3.57 mmol) in DMF (8 mL) at 0° C. was added TEA (11.9 mmol, 1.7 mL, 5.0 eq) and EDCI (684 mg, 3.57 mmol). The mixture was warmed to 20° C. and stirred at 20° C. for 16 h. The mixture was filtered and the filter cake was washed with EA (20 mL). The combined filtrate was washed with brine (30 mL), the organic layer was dried over $Na_2SO_4$, filtered and concentrated. The residue was purified by silica gel chromatography to afford 3-fluoro-4-formyl-N-methylbenzamide (400 mg, 93%) as a white solid. $^1$H NMR (400 MHz, DMSO-$d_6$) 10.24 (s, 1H), 8.72 (d, J=3.6 Hz, 1H), 7.92 (d, J=7.4 Hz, 1H), 7.83-7.75 (m, 2H), 2.81 (d, J=4.6 Hz, 3H).

Steps 2-4: Compound A10 was prepared starting from N-Boc-(S)-2-ethynylmorpholine, 3-fluoro-4-formyl-N-methylbenzamide, and 4-methyl-2-aminopyridine by the procedures described in Example 1, steps 1-3. LCMS (ESI, m/z): 441.2 [M+H]$^+$. $^1$H NMR (400 MHz, $CDCl_3$) 8.26 (s, 1H), 7.74-7.57 (m, 3H), 7.44 (s, 1H), 6.78-6.64 (m, 2H), 4.01-3.76 (m, 3H), 3.68 (s, 3H), 3.65-3.57 (m, 1H), 3.37-3.34 (m, 1H), 3.03 (d, J=4.8 Hz, 5H), 2.97-2.83 (m, 1H), 2.64-2.59 (m, 1H), 2.44 (s, 3H).

Example 11: Synthesis of methyl (S)-2-((2-(2-fluoro-4-(methylcarbamoyl)phenyl)-7-chloroimidazo[1,2-a]pyridin-3-yl)methyl)morpholine-4-carboxylate (A11)

A11

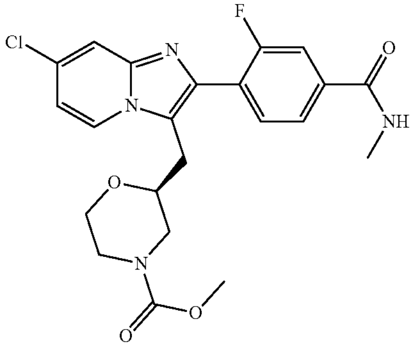

Compound A11 was prepared from N-Boc-(S)-2-ethynylmorpholine, methyl 4-formyl-3-fluorobenzoate, and 4-chloro-2-aminopyridine by the procedures described in Example 1, steps 1-5. LCMS (ESI, m/z): 461.1 $[M+H]^+$. $^1H$ NMR (400 MHz, $CDCl_3$) 8.33 (d, J=7.2 Hz, 1H), 7.77-7.73 (m, 1H), 7.69-7.59 (m, 3H), 6.84-6.82 (m, 1H), 6.45 (d, J=4.6 Hz, 1H), 4.06-3.78 (m, 3H), 3.71 (s, 3H), 3.66 (d, J=2.8 Hz, 1H), 3.41-3.40 (m, 1H), 3.13-3.03 (m, 5H), 2.99-2.87 (m, 1H), 2.67 (s, 1H).

Example 12: Synthesis of methyl (S)-2-((2-(5-fluoro-2-methyl-4-(methylcarbamoyl)phenyl)-7-methylimidazo[1,2-a]pyridin-3-yl)methyl)morpholine-4-carboxylate (A12)

A12

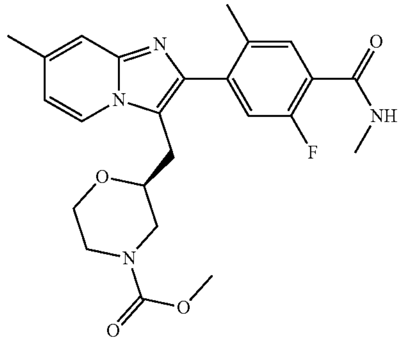

Compound A12 was prepared from N-Boc-(S)-2-ethynylmorpholine, methyl 2-fluoro-4-formyl-5-methylbenzoate, and 4-methyl-2-aminopyridine by the procedures described in Example 1, steps 1-5. LCMS (ESI, m/z): 454.9 $[M+H]^+$. $^1H$ NMR (400 MHz, $CDCl_3$) 8.07 (br d, J=6.8 Hz, 1H), 8.02 (d, J=8.0 Hz, 1H), 7.36 (s, 1H), 7.12 (d, J=12.4 Hz, 1H), 6.87-6.75 (m, 1H), 6.70 (dd, J=1.4, 7.0 Hz, 1H), 4.00-3.73 (m, 3H), 3.67 (s, 3H), 3.56-3.45 (m, 1H), 3.37 (br t, J=9.8 Hz, 1H), 3.11-3.04 (m, 3H), 3.04-2.83 (m, 3H), 2.51 (dd, J=10.6, 13.1 Hz, 1H), 2.43 (s, 3H), 2.28 (s, 3H).

Example 13: Synthesis of methyl (S)-2-((7-chloro-2-(5-fluoro-2-methyl-4-(methylcarbamoyl)phenyl)imidazo[1,2-a]pyridin-3-yl)methyl)morpholine-4-carboxylate (A13)

A13

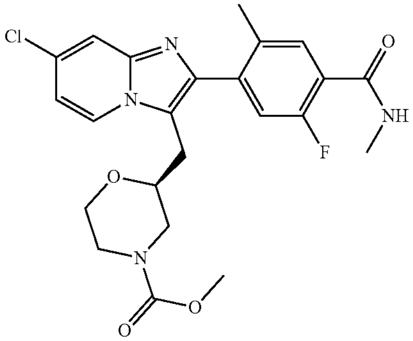

Compound A13 was prepared from N-Boc-(S)-2-ethynylmorpholine, methyl 2-fluoro-4-formyl-5-methylbenzoate, and 4-chloro-2-aminopyridine by the procedures described in Example 1, steps 1-5. LCMS (ESI, m/z): 475.2 $[M+H]^+$. $^1H$ NMR (400 MHz, $CDCl_3$) 8.18 (br d, J=7.2 Hz, 1H), 8.03 (d, J=8.1 Hz, 1H), 7.61 (d, J=1.5 Hz, 1H), 7.10 (d, J=12.2 Hz, 1H), 6.85 (dd, J=2.1, 7.3 Hz, 1H), 6.78 (br dd, J=4.5, 12.0 Hz, 1H), 6.24 (s, 1H), 3.97-3.77 (m, 3H), 3.68 (s, 3H), 3.55-3.45 (m, 1H), 3.38 (br t, J=10.9 Hz, 1H), 3.07 (d, J=4.2 Hz, 3H), 3.03-2.94 (m, 2H), 2.93-2.83 (m, 1H), 2.60-2.51 (m, 1H), 2.27 (s, 3H).

Example 14: Synthesis of methyl 2-((2-(2,6-difluoro-4-(methylcarbamoyl)phenyl)-7-methylimidazo[1,2-a]pyridin-3-yl)methyl)-1,4-oxazepane-4-carboxylate (A14)

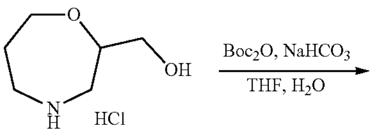

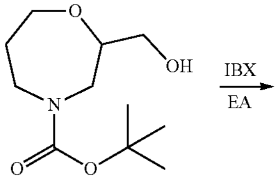

17

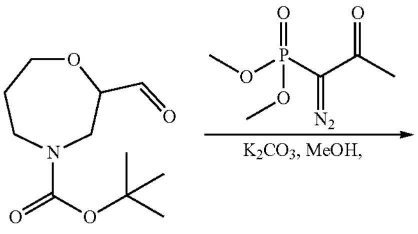

18

-continued
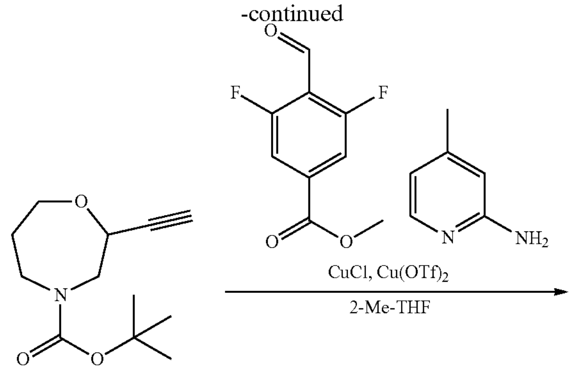
19
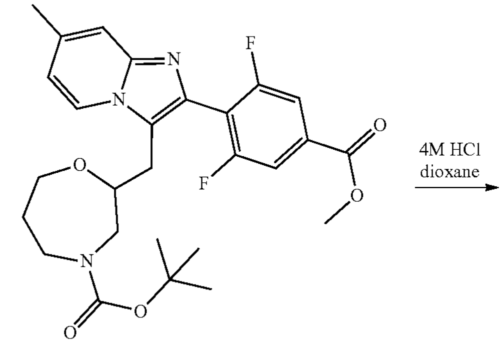
20
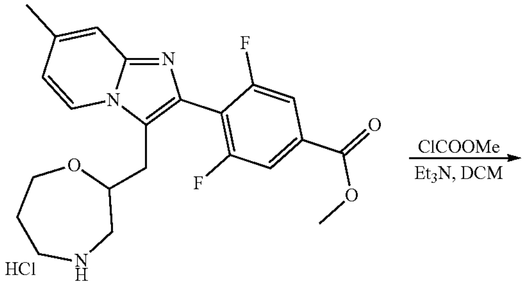
21
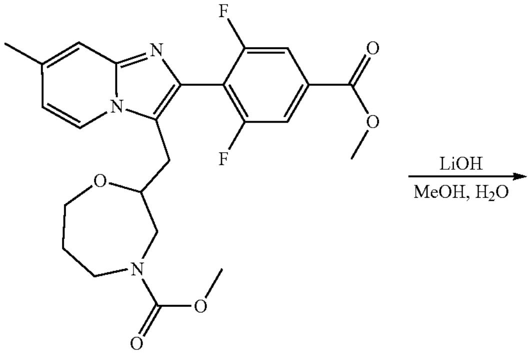
22
-continued
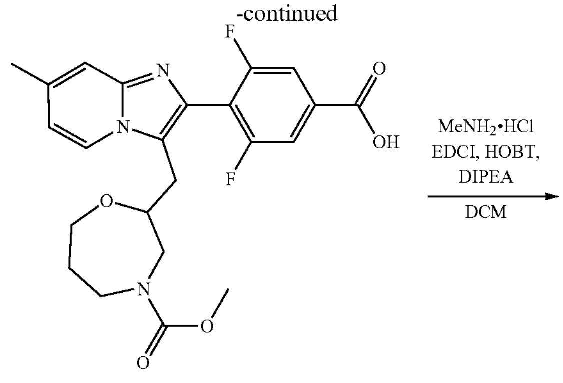
23
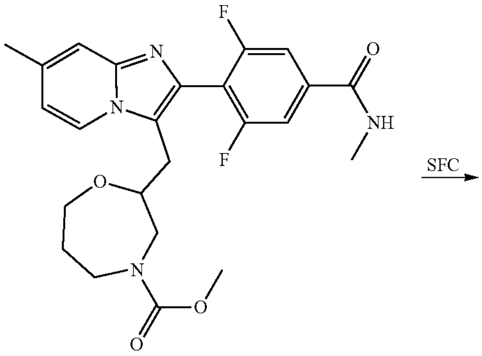
A14
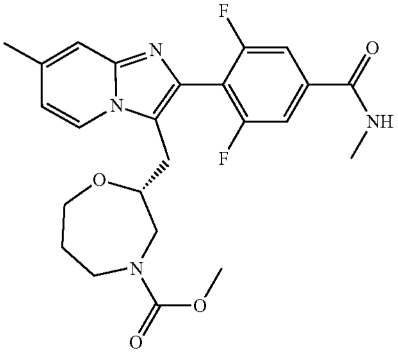
(R)-A14
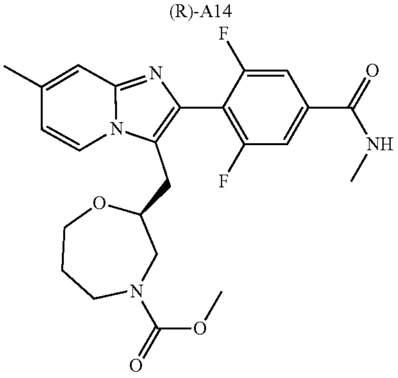
(S)-A14
Step 1: To a solution of (1,4-oxazepan-2-yl)methanol (4.0 g, 23.9 mmol) and $Boc_2O$ (7.8 g, 35.8 mmol) in THF (80 mL) was added $NaHCO_3$ (6.0 g, 71.6 mmol) in $H_2O$ (20 mL). The mixture was stirred at 20° C. for 16 h, then diluted with $H_2O$ (40 mL), extracted with EA (40 mL×2). The combined organic layers were dried over $Na_2SO_4$, filtered and concentrated. The residue was purified by silica gel chromatography and concentrated to obtain compound 17 (5 g, 90%). LCMS (ESI, m/z): 132.3 $[M-100]^+$. $^1H$ NMR (400 MHz, DMSO-$d_6$) 4.69-4.66 (m, 1H), 3.94-3.93 (m, 1H), 3.70-3.69 (m, 1H), 3.59-3.35 (m, 4H), 3.31-3.20 (m, 2H), 3.08-2.89 (m, 1H), 1.81-1.69 (m, 2H), 1.40 (s, 9H).

Step 2: To a solution of compound 17 (1.5 g, 6.49 mmol) in EA (20 mL) was added 2-iodoxybenzoic acid (3.6 g, 13 mmol). The mixture was stirred at 80° C. for 1 h. The mixture was filtered, the filtrate was concentrated to afford product compound 18 (1.4 g, 94%) as a colorless oil, which was used in the next step with no further purification. $^1H$ NMR (400 MHz, $CDCl_3$) 9.64 (d, J=13.4 Hz, 1H), 4.16-4.03 (m, 2H), 4.00-3.90 (m, 1H), 3.67-3.55 (m, 2H), 3.47-3.41 (m, 2H), 2.00-1.85 (m, 2H), 1.44 (s, 9H).

Step 3: To a solution of compound 18 (1.4 g, 6.1 mmol) in MeOH (10 mL) was added $K_2CO_3$ (2.1 g, 15.3 mmol) and the mixture was stirred at 20° C. for 10 min, then a solution of 1-diazo-1-dimethoxyphosphoryl-propan-2-one (1.2 g, 6.11 mmol) in MeOH (5 mL) was added dropwise. The mixture was stirred at 20° C. for 1 h. The mixture was diluted with $H_2O$ until the solid dissolved, extracted with EA (5 mL×2). The combined organic extracts were dried over $Na_2SO_4$, filtered and concentrated, and the residue purified by silica gel chromatography to obtain compound 19 (500 mg, 36%). $^1H$ NMR (400 MHz, $CDCl_3$) 4.40-4.39 (m, 1H), 4.14-3.77 (m, 3H), 3.60-3.58 (m, 1H), 3.33-3.03 (m, 2H), 2.48 (d, J=3.0 Hz, 1H), 2.01-1.78 (m, 2H), 1.45 (s, 9H).

Steps 4-8: Compound A14 was prepared starting from N-Boc-2-ethynyl-1,4-oxazepane (14), methyl 3,5-difluoro-4-formylbenzoate, and 4-methylpyridin-2-amine by the procedures described in Example 1, steps 1-5. LCMS (ESI, m/z): 473.0 $[M+H]^+$. $^1H$ NMR (400 MHz, $CDCl_3$) 8.29-8.16 (m, 1H), 7.44-7.26 (m, 4H), 6.69-6.66 (m, 1H), 3.91-3.80 (m, 1H), 3.69-3.57 (m, 5H), 3.35-3.14 (m, 2H), 3.01 (d, J=4.6 Hz, 3H), 2.98-2.82 (m, 3H), 2.42 (d, J=2.4 Hz, 3H), 1.91-1.79 (m, 3H).

Step 9: Compound A14 was resolved into R and S-isomers by supercritical fluid chromatography. Racemic A14 (40 mg) was separated by chiral SFC on a Daicel Chiralpak AD-H column (250×30 mm. 5-micron particle size) eluted with 30% IPA (containing 0.1% aq. $NH_3$) in supercritical $CO_2$, Flow Rate: 60 g/min to afford the two enantiomers, A14 (PEAK 1) and A14. The samples were dissolved by MeCN (1.0 mL) and $H_2O$ (5.0 mL) and lyophilized (15 mg each). Individual A14 enantiomers were isolated, but absolute stereochemistry was not determined.

LCMS (SFC peak 1): M+H=473.0.

LCMS (SFC peak 2): M+H=473.2.

$^1H$ NMR (400 MHz, $CDCl_3$) (SFC peak 1): 8.22-8.20 (m, 1H), 7.48-7.33 (m, 3H), 7.23-6.98 (m, 1H), 6.68-6.65 (m, 1H), 3.97-3.57 (m, 7H), 3.34-3.14 (m, 2H), 3.02 (d, J=4.6 Hz, 3H), 2.99-2.83 (m, 3H), 2.42 (d, J=1.6 Hz, 3H), 1.88-1.77 (m, 2H).

$^1H$ NMR (400 MHz, $CDCl_3$) (SFC peak 2): 8.29-8.17 (m, 1H), 7.69-7.30 (m, 4H), 6.69-6.66 (m, 1H), 3.97-3.53 (m, 7H), 3.36-3.16 (m, 2H), 3.08-2.82 (m, 6H), 2.42 (d, J=1.6 Hz, 3H), 1.80-1.67 (m, 2H).

Example 15: Synthesis of methyl 6-((2-(2,6-difluoro-4-(methylcarbamoyl)phenyl)-7-meth-ylimidazo[1,2-a]pyridin-3-yl)methyl)-1,4-oxazepane-4-carboxylate (A16)

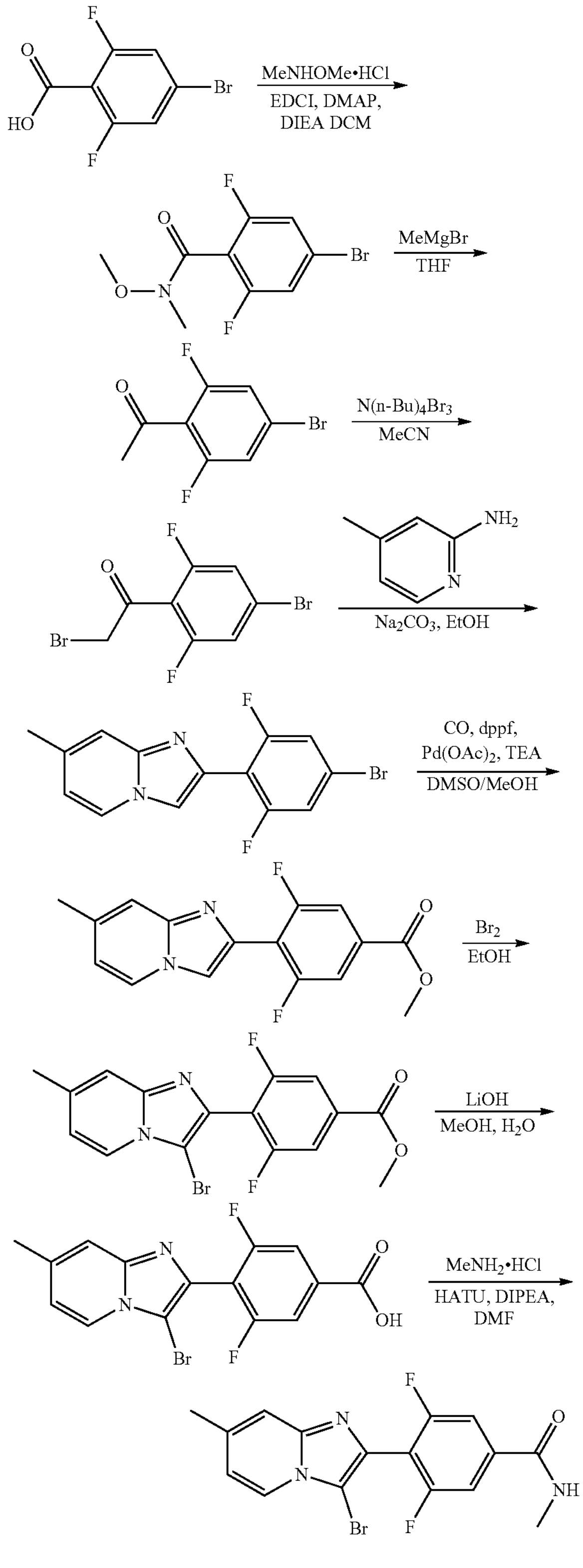

To a solution of 4-bromo-2,6-difluorobenzoic acid (50 g, 211 mmol), N,O-dimethylhydroxylamine hydrochloride (22.6 g, 232.1 mmol), DMAP (2.6 g, 21.1 mmol), DIEA (316 mmol, 55 mL) in DCM (600 mL) was added EDCI (50.5 g, 264 mmol) at 0° C. The mixture was stirred at 20° C. for 16 h and was concentrated to remove DCM, washed with $H_2O$ (400 mL), extracted with EA (150 mL×2). The combined organic layers were dried over $Na_2SO_4$, filtered and concentrated and the residue was purified by column chromatography to obtain 4-bromo-2,6-difluoro-N-methoxy-N-methylbenzamide (39 g, 66%) as a white solid. $^1H$ NMR (400 MHz, $CDCl_3$) 7.14 (d, J=6.6 Hz, 2H), 3.54 (s, 3H), 3.38 (s, 3H).

To a solution of 4-bromo-2,6-difluoro-N-methoxy-N-methylbenzamide (35 g, 125 mmol) in THE (100 mL) under $N_2$ at 0° C. was added methylmagnesium bromide dropwise (3 M, 54 mL). The mixture was stirred at 25° C. for 0.5 then poured into sat. $NH_4Cl$ solution (300 mL), extracted with EA (150 mL×2). The combined organic layers were dried over $Na_2SO_4$, filtered and concentrated. The residue was purified by silica gel chromatography. The eluent was concentrated to obtain 1-(4-bromo-2,6-difluorophenyl)ethan-1-one (28 g) as a colorless oil. $^1H$ NMR (400 MHz, $CDCl_3$) 7.22-7.08 (m, 2H), 2.65-2.50 (m, 3H).

To a solution of 1-(4-bromo-2,6-difluorophenyl)ethan-1-one (28 g, 119 mmol) in MeCN (350 mL) was added tetrabutylammonium tribromide (63.2 g, 131.1 mmol). The mixture was stirred at 25° C. for 2 h. The mixture was diluted with brine (500 mL), extracted with EA (200 mL×2). The combined organic layers were dried over $Na_2SO_4$, filtered and concentrated and the residue was purified by column chromatography to obtain 2-bromo-1-(4-bromo-2,6-difluorophenyl)ethan-1-one (35 g, 94%) as a colorless oil. $^1H$ NMR (400 MHz, $CDCl_3$) 7.71-7.67 (m, 2H), 4.73 (d, J=1.0 Hz, 2H).

To a solution of 2-bromo-1-(4-bromo-2,6-difluorophenyl) ethan-1-one (24 g, 76.5 mmol) and 4-methyl-2-aminopyridine (9.9 g, 91.7 mmol) in EtOH (250 mL) was added $Na_2CO_3$ (16.2 g, 153 mmol). The mixture was heated to 120° C. for 2 h under $N_2$. The mixture was combined with a second reaction batch and the mixture was concentrated to remove EtOH. The residue was washed with $H_2O$ (200 mL), extracted with EA (100 mL×2). The combined organic layers were dried over $Na_2SO_4$, filtered and concentrated and the residue was purified by column chromatography to obtain 2-(4-bromo-2,6-difluorophenyl)-7-methylimidazo[1,2-a]pyridine (20 g) as a brown solid. LCMS (ESI, m/z): 322.9 $[M+H]^+$. $^1H$ NMR (400 MHz, $CDCl_3$) 8.01 (d, J=7.0 Hz, 1H), 7.83 (s, 1H), 7.43 (s, 1H), 7.24-7.09 (m, 2H), 6.64 (d, J=6.8 Hz, 1H), 2.39 (s, 3H).

To a solution of 2-(4-bromo-2,6-difluorophenyl)-7-methylimidazo[1,2-a]pyridine (20 g, 61.9 mmol), TEA (187 mmol, 26 mL), DPPF (6.9 g, 12.4 mmol) in MeOH (300 mL) and DMSO (300 mL) was added $Pd(OAc)_2$ (1.4 g, 6.2 mmol) under $N_2$. The suspension was degassed under vacuum and purged with CO several times. The mixture was stirred under CO (50 psi) at 80° C. for 6 h. The mixture was filtered, and the filtrate was concentrated to remove MeOH. Then the residue was washed with $H_2O$ (2.0 L), extracted with EA (300 mL×3). The combined organic layers were dried over $Na_2SO_4$, filtered and concentrated to remove EA, then the precipitated solid was filtered and concentrated. The concentrated filtrate was purified by silica gel chromatography, and the product combined with the precipitated solid to afford methyl 3,5-difluoro-4-(7-methylimidazo[1,2-a]pyridin-2-yl)benzoate (15 g, 80%) as a yellow solid. LCMS (ESI, m/z): 303.1 $[M+H]^+$. $^1H$ NMR (400 MHz, $CDCl_3$) 8.03 (d, J=6.8 Hz, 1H), 7.94 (s, 1H), 7.73-7.62 (m, 2H), 7.45 (s, 1H), 6.67-6.65 (m, 1H), 3.94 (s, 3H), 2.40 (s, 3H).

To a stirred suspension of methyl 3,5-difluoro-4-(7-methylimidazo[1,2-a]pyridin-2-yl)benzoate (14 g, 46.3 mmol) in EtOH (280 mL) at 0° C. was added $Br_2$ (69.5 mmol, 3.6 mL). The mixture was stirred at 20° C. for 0.5 h, then concentrated to obtain methyl 4-(3-bromo-7-methylimidazo[1,2-a]pyridin-2-yl)-3,5-difluorobenzoate (25 g) as yellow solid which was used in the next step directly without further purification. LCMS (ESI, m/z): 383.2 $[M+H]^+$. $^1H$ NMR (400 MHz, $CDCl_3$) 8.73 (d, J=6.6 Hz, 1H), 7.99-7.76 (m, 3H), 7.56 (d, J=5.4 Hz, 1H), 4.00 (s, 3H), 2.68 (s, 3H).

To a solution of methyl 4-(3-bromo-7-methylimidazo[1,2-a]pyridin-2-yl)-3,5-difluorobenzoate (19 g, 49.9 mmol) in MeOH (240 mL) was added $LiOH{\cdot}H_2O$ (8.4 g, 200 mmol) in $H_2O$ (80 mL). The mixture was stirred at 20° C. for 0.5 h. then concentrated to remove MeOH, and the residue adjusted to pH=2 by aq. HCl (1M). The white solid precipitate was filtered to afford 4-(3-bromo-7-methylimidazo[1,2-a]pyridin-2-yl)-3,5-difluorobenzoic acid (14 g). LCMS (ESI, m/z): 369.0 $[M+H]^+$. $^1H$ NMR (400 MHz, $CDCl_3$) 14.55-12.79 (m, 1H), 8.33 (d, J=7.0 Hz, 1H), 7.73 (d, J=7.8 Hz, 2H), 7.50 (s, 1H), 7.03-7.01 (m, 1H), 2.42 (s, 3H).

To a solution of 4-(3-bromo-7-methylimidazo[1,2-a]pyridin-2-yl)-3,5-difluorobenzoic acid (14 g, 38.1 mmol) in DMF (150 mL) was added DIEA (190.7 mmol, 33.2 mL) and HATU (43.5 g, 114.4 mmol), then methylamine hydrochloride (7.7 g, 114.40 mmol) was added. The mixture was stirred at 25° C. for 1 h. The mixture was added to $H_2O$ (1 L) and the solid precipitate was filtered. The solid was triturated with EA (30 mL) at 25° C. for 10 min and filtered. The filter cake was concentrated to afford 4-(3-bromo-7-methylimidazo[1,2-a]pyridin-2-yl)-3,5-difluoro-N-methylbenzamide (10 g, 69%) as a yellow solid. LCMS (ESI, m/z): 380.2 $[M+H]^+$. $^1H$ NMR (400 MHz, $CDCl_3$) 8.73 (d, J=4.4 Hz, 1H), 8.32 (d, J=7.0 Hz, 1H), 7.69 (d, J=8.3 Hz, 2H), 7.49 (s, 1H), 7.02-7.00 (m, 1H), 2.83 (d, J=4.6 Hz, 3H), 2.42 (s, 3H).

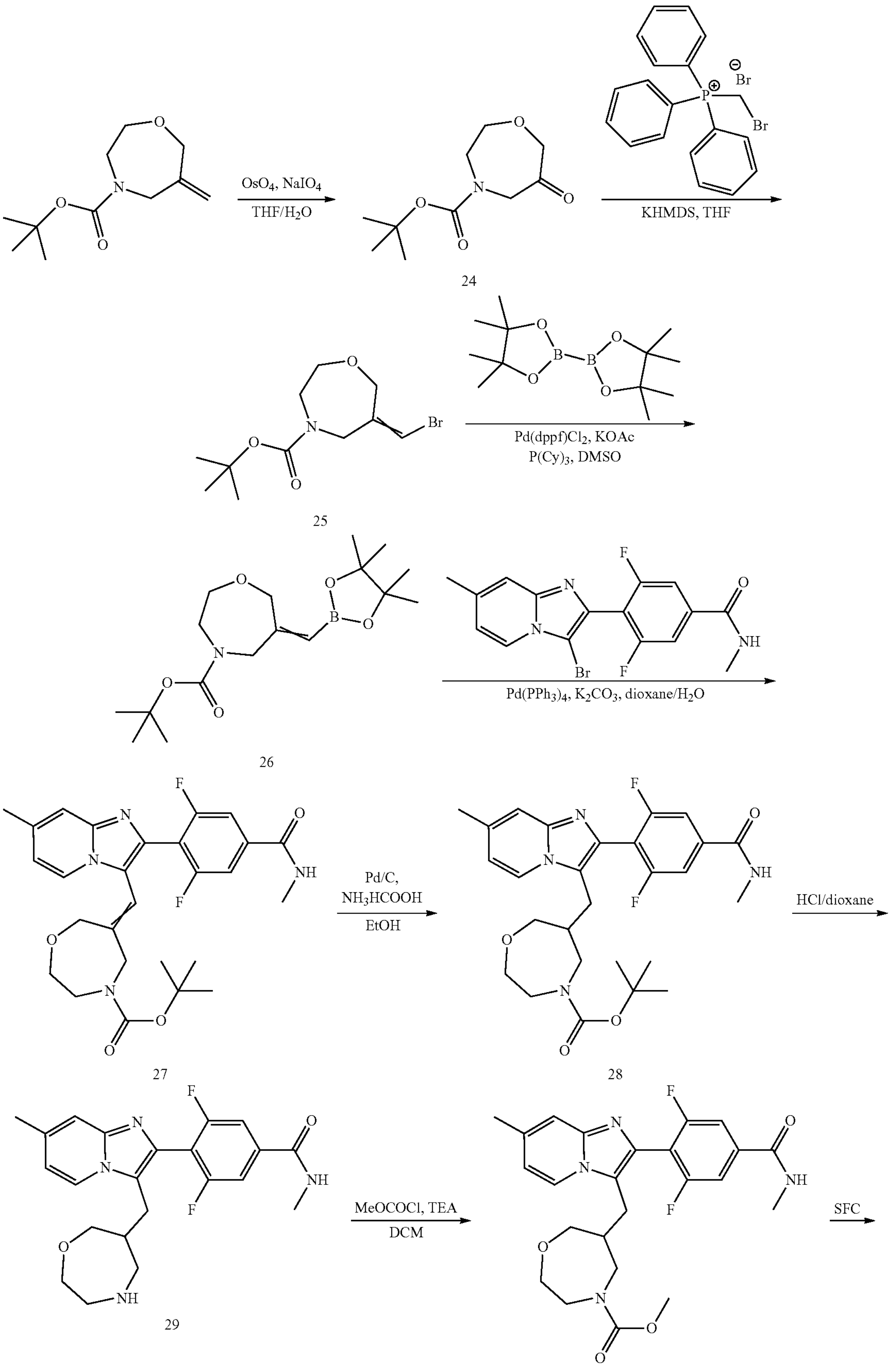
24
25
26
27
28
29
A16

-continued

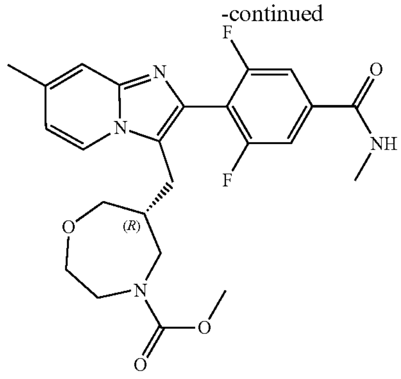

(R)-A16

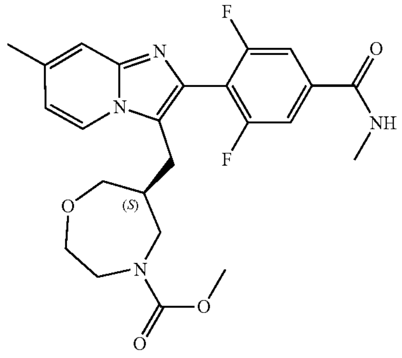

(S)-A16

Step 1: To a mixture of tert-butyl 6-methylene-1,4-oxazepane-4-carboxylate (1.30 g, 6.10 mmol) in THE (13 mL) and $H_2O$ (13 mL) was added $OsO_4$ [11.92 mg, 0.047 mmol, 2.5% wt in t-BuOH (prepared by 0.25 g $OsO_4$ dissolved in 9.75 g t-BuOH)]. The mixture was stirred at 25° C. for 0.5 h then $NaIO_4$ (3.91 g, 18.29 mmol) was added and the mixture was stirred at 25° C. for 16 h. The mixture was diluted with $H_2O$ (50 mL) and extracted with EA (20 mL×3). The combined organic layers were washed with brine, dried over $Na_2SO_4$, filtered and concentrated. The residue was purified by column chromatography and the eluent was concentrated to afford compound 24 (830 mg, 61%) as a colorless oil. LCMS (ESI, m/z): 160.2 $[M-56]^+$.

Step 2: A flask charged with (bromomethyl)triphenylphosphonium bromide (3.36 g, 7.71 mmol) was degassed under vacuum, then cooled to −40° C. under $N_2$. THE (8 mL) was added, followed by KHMDS (1 M, 7.7 mL) under $N_2$. The resulting yellow suspension was stirred at −40° C. for 0.5 h. Then a solution of compound 24 (830 mg, 3.86 mmol) in THE (2 mL) was added. The resulting brown suspension was left to warm to 25° C. and stirred at 25° C. for 0.5 h. The mixture was quenched with sat. $NH_4Cl$ (50 mL) and extracted with EA (30 mL×3). The combined organic layers were washed with brine, dried over $Na_2SO_4$, filtered and concentrated. The residue was purified by column chromatography to afford compound 25 (1 g, 88%). LCMS (ESI, m/z): 192.0 $[M-100]^+$.

Step 3: A mixture of $P(Cy)_3$ (0.21 mmol, 67 μL) and $Pd(dppf)Cl_2$ (75 mg, 0.10 mmol) in DMSO (10.0 mL) was stirred at 25° C. for 10 min under $N_2$. Then a solution of bis(pinacolato)diboron (1.74 g, 6.85 mmol) in DMSO (30 mL), KOAc (1.01 g, 10.3 mmol) and compound 25 (1.00 g, 3.42 mmol) were successively added. The mixture was heated to 80° C. for 12 h under $N_2$. Then cooled and diluted with $H_2O$ (100 mL) and extracted with EA (30 mL×3). The combined organic layers were washed with brine, dried over $Na_2SO_4$, filtered and concentrated. The residue was purified by column chromatography to afford compound 26 (820 mg, 61%). LCMS (ESI, m/z): 284.1 $[M+H]^+$. $^1H$ NMR (400 MHz, $CDCl_3$) 5.48-5.25 (m, 1H), 4.64-4.32 (m, 2H), 4.18-4.08 (m, 2H), 3.80-3.67 (m, 2H), 3.59-3.47 (m, 2H), 1.52-1.42 (m, 9H), 1.32-1.21 (m, 24H).

Step 4: To a mixture of 4-(3-bromo-7-methylimidazo[1,2-a]pyridin-2-yl)-3,5-difluoro-N-methylbenzamide (600 mg, 1.58 mmol), compound 26 (803 mg, 2.37 mmol) and $K_2CO_3$ (436 mg, 3.16 mmol) in $H_2O$ (3 mL) and dioxane (15 mL) was added $Pd(PPh_3)_4$ (182 mg, 0.16 mmol) under $N_2$. The mixture was stirred at 90° C. for 12 h. The mixture was diluted with $H_2O$ (30 mL) and extracted with EA (25 mL×3). The combined organic layers were washed with brine, dried over $Na_2SO_4$, filtered and concentrated. The residue was purified by column chromatography to afford compound 27 (450 mg, 50%). LCMS (ESI, m/z): 513.3 $[M+H]^+$.

Step 5: To a solution of compound 27 (340 mg, 663 μmol) in EtOH (70 mL) was added 10% Pd/C (680 mg) and ammonium formate (418 mg, 6.6 mmol). Then the mixture was stirred at 20° C. for 16 h. The mixture was filtered and concentrated and the residue was purified by prep-HPLC The eluent was extracted with EA (20 mL×2), dried over $Na_2SO_4$, filtered and concentrated to afford compound 28 (270 mg, 77%). LCMS (ESI, m/z): 515.2 $[M+H]^+$. $^1H$ NMR (400 MHz, $CDCl_3$) 8.03-7.89 (m, 1H), 7.40 (br d, J=4.0 Hz, 3H), 7.04-6.92 (m, 1H), 6.74 (br s, 1H), 3.77-3.46 (m, 5H), 3.42-3.15 (m, 3H), 3.03 (d, J=4.8 Hz, 3H), 2.99-2.70 (m, 3H), 2.44 (s, 3H), 2.33-2.15 (m, 1H), 1.44 (s, 5H), 1.32 (s, 5H).

Steps 6 and 7: Compound A16 was prepared starting from compound 28 by the procedures described in Example 1, steps 2 and 3. LCMS (ESI, m/z): 473.2 $[M+H]^+$. $^1H$ NMR (400 MHz, DMSO-$d_6$) 8.70 (br d, J=4.5 Hz, 1H), 8.36 (br t, J=6.4 Hz, 1H), 7.66 (br d, J=7.7 Hz, 2H), 7.37 (s, 1H), 6.87 (d, J=7.0 Hz, 1H), 3.62-3.44 (m, 6H), 3.44-3.36 (m, 2H), 3.26-3.08 (m, 2H), 3.01-2.87 (m, 1H), 2.82 (d, J=4.5 Hz, 3H), 2.80 (br d, J=4.6 Hz, 2H), 2.39 (s, 3H), 2.10 (br s, 1H).

Step 8: Compound A16 was resolved into R and S-isomers by supercritical fluid chromatography as described in Example 14, step 9, to afford the two enantiomers, A16 (Peak 1) and A16 (Peak 2). Individual A16 enantiomers were isolated, but absolute stereochemistry was not determined. LCMS (SFC peak 1): M+H=473.2. LCMS (SFC peak 2): M+H=473.2.

$^1H$ NMR (400 MHz, DMSO-$d_6$) (SFC peak 1): 8.69 (br d, J=4.5 Hz, 1H), 8.37 (br t, J=6.2 Hz, 1H), 7.66 (br d, J=7.6 Hz, 2H), 7.38 (s, 1H), 6.87 (br d, J=6.8 Hz, 1H), 3.60-3.46 (m, 6H), 3.37 (s, 2H), 3.25-3.10 (m, 2H), 2.99-2.88 (m, 1H), 2.84-2.71 (m, 5H), 2.39 (s, 3H), 2.16-2.04 (m, 1H)

$^1H$ NMR (400 MHz, DMSO-$d_6$) (SFC peak 2): 8.70 (br d, J=4.6 Hz, 1H), 8.37 (br t, J=6.5 Hz, 1H), 7.66 (br d, J=7.9 Hz, 2H), 7.38 (br s, 1H), 6.87 (br d, J=7.0 Hz, 1H), 3.62-3.43 (m, 6H), 3.37 (br s, 2H), 3.26-3.08 (m, 2H), 3.01-2.87 (m, 1H), 2.86-2.69 (m, 5H), 2.39 (s, 3H), 2.18-2.02 (m, 1H).

Example 16: Synthesis of methyl 3-((2-(2,6-difluoro-4-(methylcarbamoyl)phenyl)-7-methylimidazo[1,2-a]pyridin-3-yl)methyl)azepane-1-carboxylate (A17)
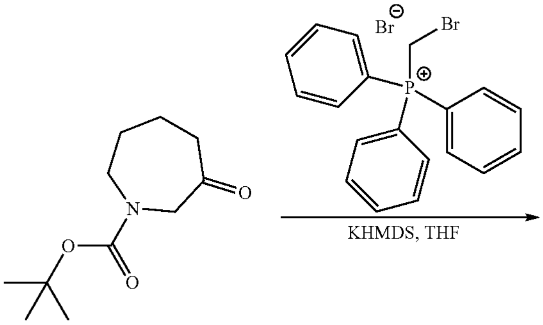
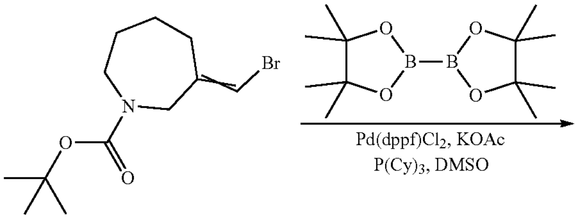
30
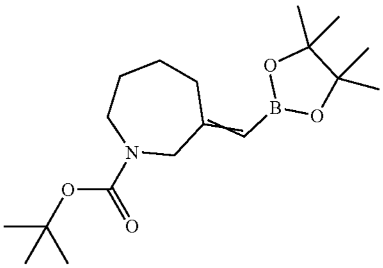
31
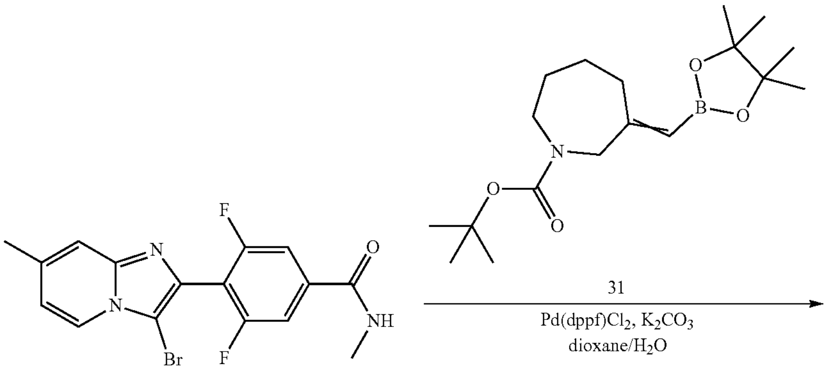

-continued

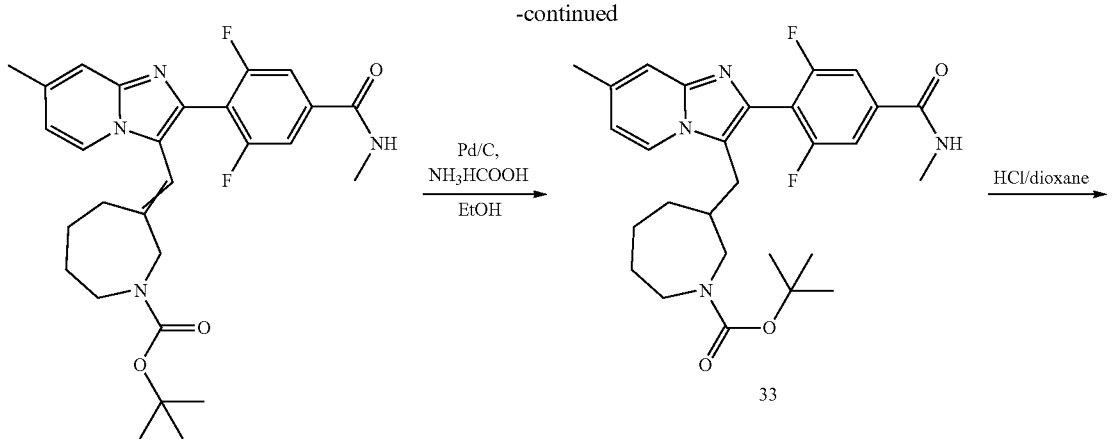

32 33

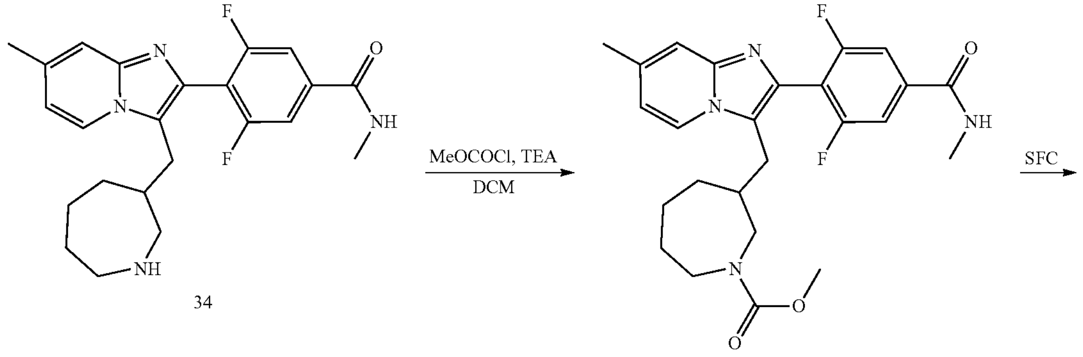

34 A17

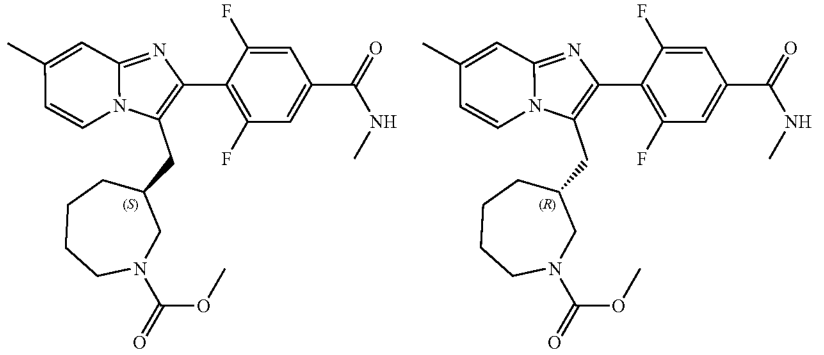

(S)-A17 (R)-A17

Steps 1 and 2: Compound 30 was prepared in 33% yield from tert-butyl 3-oxoazepane-1-carboxylate (4.60 g, 10.6 mmol) using the procedure described in Example 15, step 2, and further transformed using the procedure described in Example 15, step 3, into compound 31 (410 mg, 41%) isolated as a yellow oil. LCMS (ESI, m/z): 338.3 $[M+H]^+$.

Step 3: Compound 31 (404 mg, 1.20 mmol, 1.30 eq) was coupled with 4-(3-bromo-7-methylimidazo[1,2-a]pyridin-2-yl)-3,5-difluoro-N-methylbenzamide (350 mg, 921 μmol, 1.00 eq) using the procedure described in Example 15, step 4, to afford compound 32 (300 mg, 48%). LCMS (ESI, m/z): 511.2 $[M+H]^+$.

Step 4: Compound 32 (280 mg, 548 μmol) was reduced using the procedure described in Example 15, step 5, to afford compound 33 (250 mg, 84%). LCMS (ESI, m/z): 513.3 $[M+H]^+$. $^1$H NMR (400 MHz, DMSO-$d_6$) 8.04-7.81 (m, 1H), 7.42 (br d, J=7.0 Hz, 3H), 7.11-6.90 (m, 1H), 6.75 (dd, J=1.3, 7.1 Hz, 1H), 3.79-3.60 (m, 1H), 3.57-3.42 (m, 1H), 3.05-2.87 (m, 5H), 2.79-2.58 (m, 2H), 2.56-2.46 (m, 1H), 2.44 (d, J=2.4 Hz, 3H), 1.51-1.14 (m, 16H).

Steps 5 and 6: Compound A17 was prepared from compound 33 using the procedures described in Example 1, steps 2 and 3. LCMS (ESI, m/z): 471.2 $[M+H]^+$. $^1$H NMR (400 MHz, DMSO-$d_6$) 8.69 (br d, J=4.5 Hz, 1H), 8.33 (br t, J=6.5 Hz, 1H), 7.66 (br d, J=7.8 Hz, 2H), 7.37 (br s, 1H), 6.86 (br d, J=7.0 Hz, 1H), 3.58-3.46 (m, 2H), 3.30 (s, 3H), 3.13-2.97 (m, 1H), 2.82 (d, J=4.5 Hz, 3H), 2.79-2.64 (m, 3H), 2.38 (s, 3H), 1.98-1.78 (m, 1H), 1.68-1.32 (m, 5H), 1.11-0.89 (m, 3H).

Step 7: Compound A17 (100 mg) was resolved into R and S-isomers by chiral SFC on a Daicel Chiralpak AD-H column (250×30 mm. 5-micron particle size) eluted with 40% MeOH (0.1% aq. $NH_3$) in supercritical $CO_2$, as described in Example 14, step 9, to afford the two enantiomers, A17 (Peak 1) (28 mg) and (S)-A17 (Peak 2) (39 mg). Individual A17 enantiomers were isolated, but absolute stereochemistry was not determined.

LCMS (SFC peak 1): M+H=471.2.

LCMS (SFC peak 2): M+H=471.2.

$^1$H NMR (400 MHz, DMSO-$d_6$) (SFC peak 1): 8.69 (q, J=4.2 Hz, 1H), 8.33 (t, J=6.9 Hz, 1H), 7.66 (br d, J=7.9 Hz, 2H), 7.37 (br s, 1H), 6.91-6.82 (m, 1H), 3.51 (s, 2H), 3.45-3.37 (m, 1H), 3.30 (br s, 3H), 3.11-2.96 (m, 1H), 2.82 (d, J=4.5 Hz, 3H), 2.79-2.65 (m, 3H), 2.39 (s, 3H), 2.01-1.79 (m, 2H), 1.70-1.32 (m, 5H), 1.02-0.91 (m, 2H).

$^1$H NMR (400 MHz, DMSO-$d_6$) (SFC peak 2): 8.69 (br d, J=4.6 Hz, 1H), 8.33 (br t, J=6.6 Hz, 1H), 7.66 (br d, J=7.7 Hz, 2H), 7.37 (br s, 1H), 6.86 (br d, J=7.0 Hz, 1H), 3.62-3.48 (m, 2H), 3.30 (br s, 2H), 3.11-2.96 (m, 1H), 2.82 (d, J=4.4 Hz, 3H), 2.79 (br s, 3H), 2.39 (s, 3H), 2.06-1.79 (m, 2H), 1.72-1.31 (m, 5H), 1.06-0.89 (m, 2H).

Example 17: Synthesis of methyl 4-((2-(2,6-difluoro-4-(methylcarbamoyl)phenyl)-7-methylimidazo[1,2-a]pyridin-3-yl)methyl)azepane-1-carboxylate (A18)

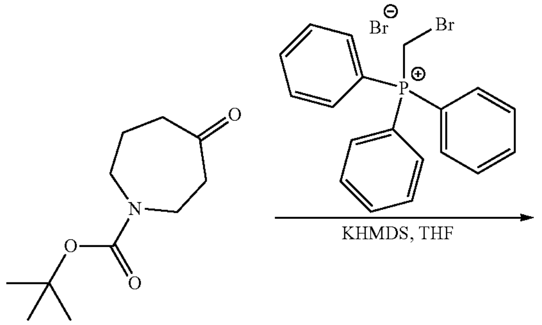

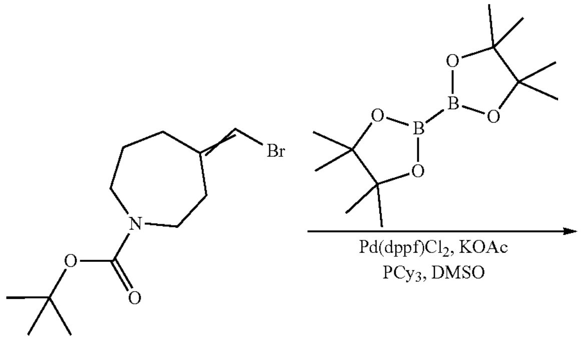

35

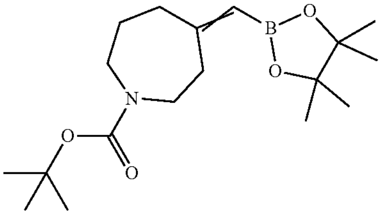

36

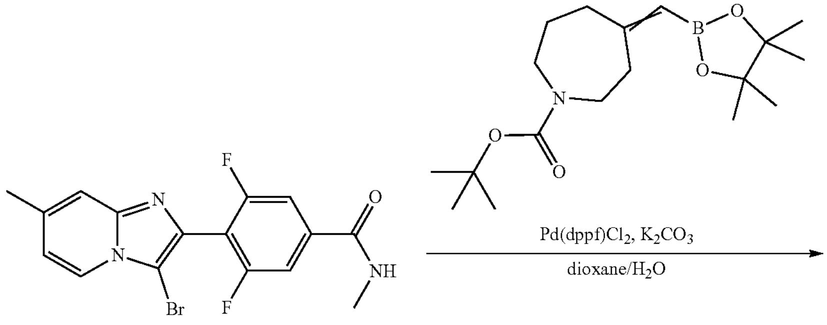

-continued

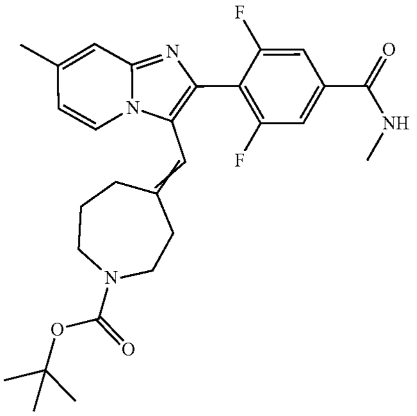

37

Pd/C,
NH3HCOOH
EtOH

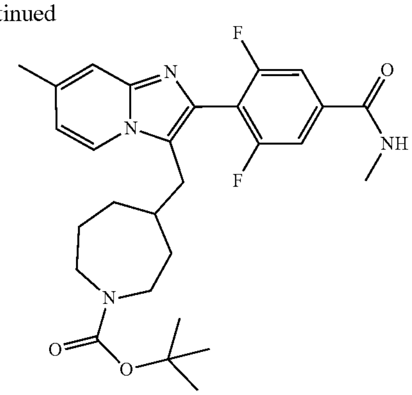

38

HCl/dioxane

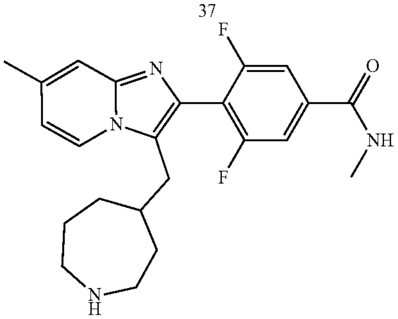

39

MeOCOCl, TEA
DCM

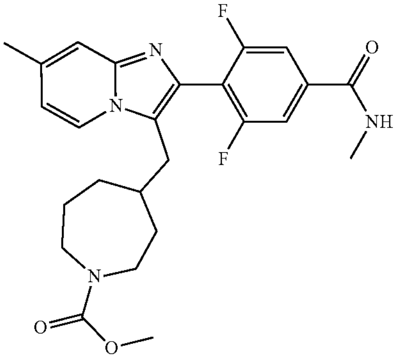

A18

SFC

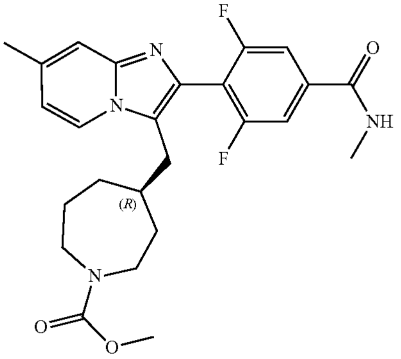

(R)-A18

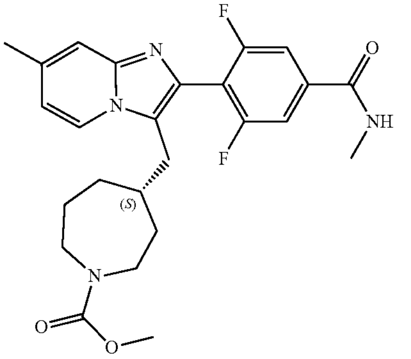

(S)-A18

Steps 1-6: Compound A18 was prepared from tert-butyl 4-oxoazepane-1-carboxylate by the procedures described in Example 16, steps 1-6. LCMS (ESI, m/z): 471.2 $[M+H]^+$. $^1H$ NMR (400 MHz, $CDCl_3$) 7.85 (d, J=7.1 Hz, 1H), 7.46-7.35 (m, 3H), 6.81-6.69 (m, 2H), 3.65 (s, 3H), 3.61-3.18 (m, 3H), 3.04 (d, J=4.8 Hz, 4H), 2.86-2.68 (m, 2H), 2.44 (s, 3H), 1.62-1.53 (m, 2H), 1.44-1.14 (m, 4H), 1.10-0.93 (in, 1H).

Step 7: Compound A18 (35 mg) was separated by chiral HPLC on a Daicel Chiralpak IG column (250×30 mm. 5-micron particle size) eluted with 30% EtOH (0.1% aq. $NH_3$) in heptane, Flow Rate: 70 g/min to afford the two enantiomers, A18 (Peak 1) (11 mg) and A18 (Peak 2) (9 mg). Individual A18 enantiomers were isolated, but absolute stereochemistry was not determined.

LCMS (SFC peak 1): M+H=471.2.

LCMS (SFC peak 2): M+H=471.2.

$^1H$ NMR (400 MHz, MeOD) (SFC peak 1): 8.47 (dd, J=3.7, 7.0 Hz, 1H), 7.71-7.61 (m, 2H), 7.53 (br s, 1H), 7.15 (br t, J=5.3 Hz, 1H), 3.61 (d, J=2.6 Hz, 3H), 3.55-3.44 (m, 1H), 3.42-3.34 (m, 2H), 3.17-3.06 (m, 1H), 2.96 (s, 3H), 2.92 (dd, J=1.8, 7.5 Hz, 2H), 2.54 (s, 3H), 1.87-1.57 (m, 4H), 1.51-1.35 (m, 1H), 1.30-1.16 (m, 1H), 1.14-0.99 (m, 1H).

$^1H$ NMR (400 MHz, MeOD) (SFC peak 2): 8.53 (dd, J=3.5, 7.2 Hz, 1H), 7.71-7.64 (m, 2H), 7.58 (s, 1H), 7.22 (br t, J=5.3 Hz, 1H), 3.61 (d, J=2.2 Hz, 3H), 3.56-3.44 (m, 1H), 3.42-3.32 (m, 2H), 3.18-3.06 (m, 1H), 2.96 (s, 3H), 2.95-2.92 (m, 2H), 2.57 (s, 3H), 1.91-1.56 (m, 4H), 1.50-1.35 (m, 1H), 1.25 (ddd, J=3.6, 6.7, 14.1 Hz, 1H), 1.15-1.00 (m, 1H).

Example 18: Synthesis of methyl (S)-3-((2-(2,6-difluoro-4-(methylcarbamoyl)phenyl)-7-methylimidazo[1,2-a]pyridin-3-yl)methyl)piperidine-1-carboxylate ((S)-A19)

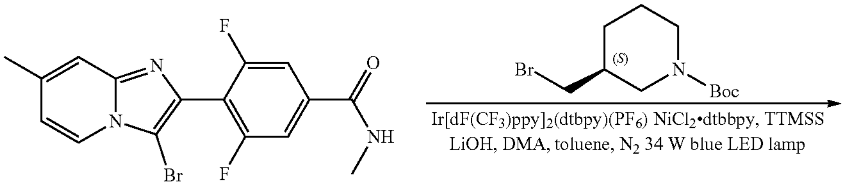

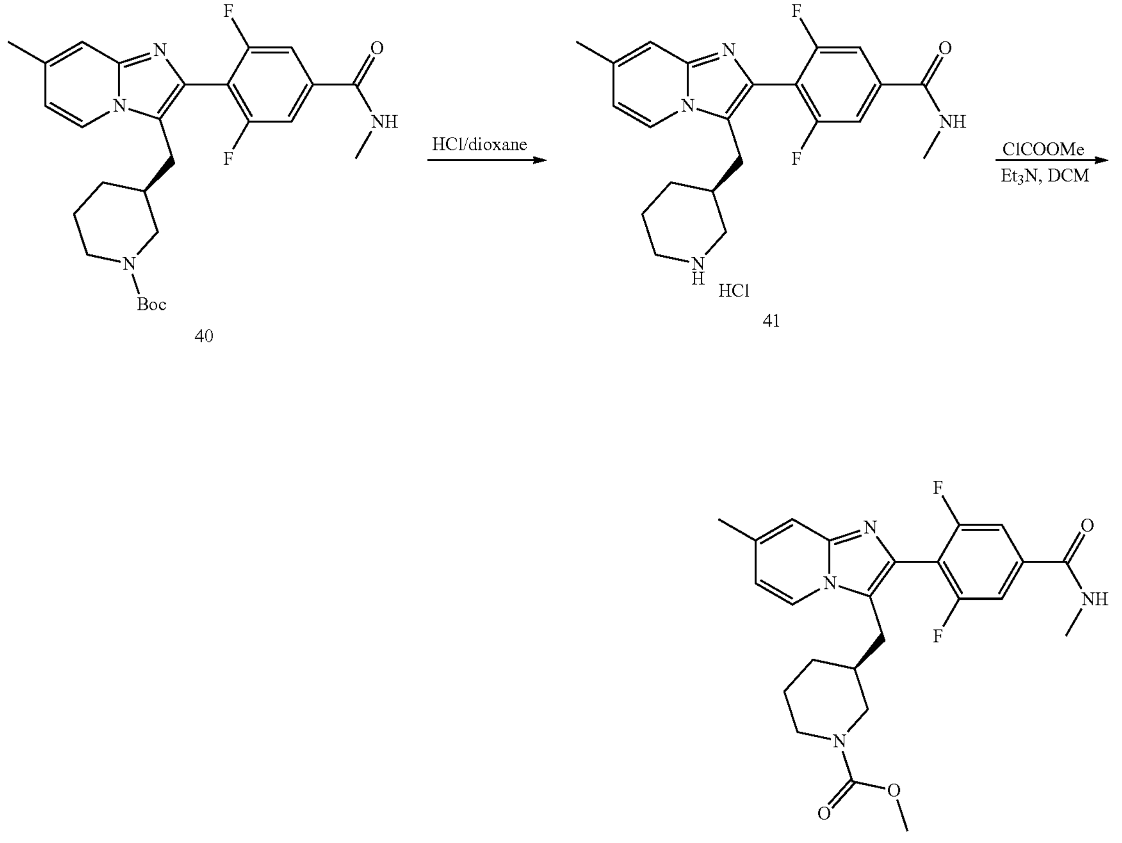

40

41

(S)-A19

Step 1: To an 8 mL vial equipped with a stir bar was added 4-(3-bromo-7-methylimidazo[1,2-a]pyridin-2-yl)-3,5-difluoro-N-methylbenzamide (50 mg, 0.13 mmol), tert-butyl (S)-3-(bromomethyl)piperidine-1-carboxylate (48 mg, 0.17 mmol), Ir[dF($CF_3$)ppy]$_2$-(dtbpy)($PF_6$) (2 mg, 1.32 μmol), $NiCl_2$·dtbbpy (0.3 mg, 0.66 μmol), TTMSS (0.13 mmol, 40 μL), LiOH (32 mg, 1.32 mmol) in DMA (0.75 mL) and toluene (0.75 mL). The vial was sealed under $N_2$ and stirred and irradiated with a 34 W blue LED lamp (7 cm away), with cooling fan to maintain the reaction temperature at 25° C. for 16 h. The crude product was purified by prep-HPLC to afford compound 40 (15 mg, 30%) as a white solid.

Steps 2 and 3: Compound (S)-A19 was prepared starting from compound 40 by the procedures described in Example 1, steps 2 and 3. LCMS (ESI, m/z): 457.2 $[M+H]^+$. $^1$H NMR (400 MHz, DMSO-$d_6$) 7.86 (d, J=7.0 Hz, 1H), 7.40 (d, J=7.4 Hz, 3H), 7.11-6.84 (m, 1H), 6.73-6.71 (m, 1H), 3.88 (d, J=12.8 Hz, 1H), 3.62 (s, 3H), 3.02 (d, J=4.8 Hz, 3H), 2.91-2.75 (m, 1H), 2.72-2.59 (m, 2H), 2.43 (s, 3H), 1.73 (s, 2H), 1.61-1.43 (m, 3H), 1.31-1.17 (m, 1H), 0.92-0.74 (m, 1H).

Example 19: Synthesis of methyl (R)-3-((2-(2,6-difluoro-4-(methylcarbamoyl)phenyl)-7-methylimidazo[1,2-a]pyridin-3-yl)methyl)piperidine-1-carboxylate ((R)-A19)
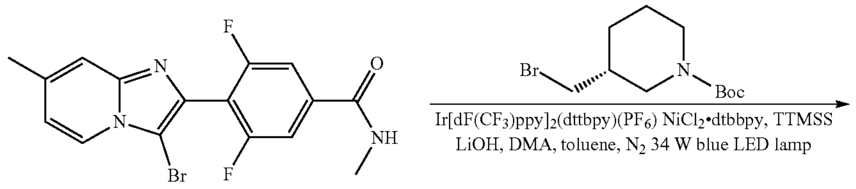
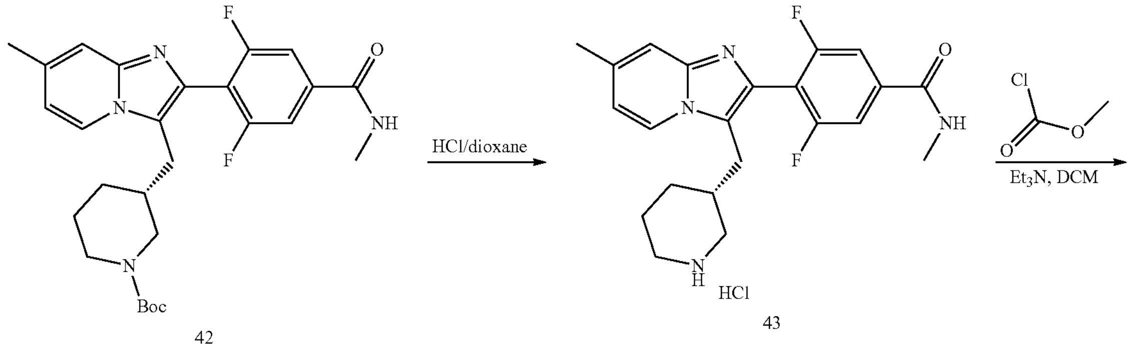
42
43
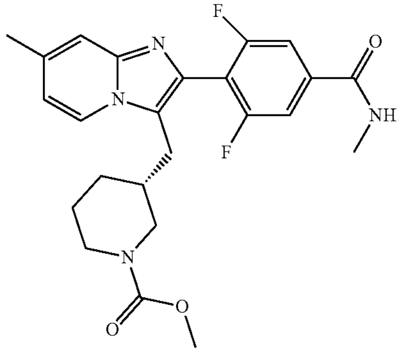
(R)-A19

Compound (R)-A19 was prepared from 4-(3-bromo-7-methylimidazo[1,2-a]pyridin-2-yl)-3,5-difluoro-N-methylbenzamide and tert-butyl (R)-3-(bromomethyl)piperidine-1-carboxylate by the methods described in Example 18, steps 1-3. LCMS (ESI, m/z): 457.2 $[M+H]^+$. $^1H$ NMR (400 MHz, $CDCl_3$) 8.27-7.79 (m, 2H), 7.66-7.47 (m, 3H), 6.89 (d, J=6.8 Hz, 1H), 4.09-3.73 (m, 2H), 3.62 (s, 3H), 3.00 (d, J=4.6 Hz, 3H), 2.94 (d, J=4.2 Hz, 1H), 2.85-2.76 (m, 1H), 2.72-2.61 (m, 2H), 2.48 (s, 3H), 2.42-2.36 (m, 1H), 1.50 (d, J=14.2 Hz, 2H), 1.35-1.15 (m, 1H), 1.01-0.75 (m, 1H).

Example 20: Synthesis of methyl 4-((2-(2,6-difluoro-4-(methylcarbamoyl)phenyl)-7-methylimidazo[1,2-a]pyridin-3-yl)methyl)piperidine-1-carboxylate (A20)

A20

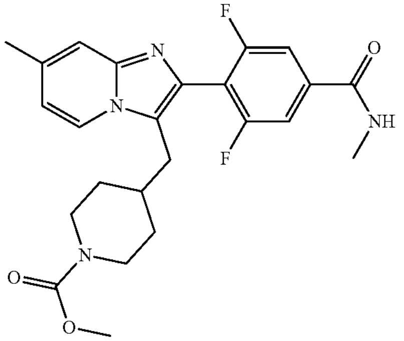

Compound A20 was prepared from N-Boc-4-ethynylpiperidine, methyl 4-formyl-3,5-difluorobenzoate, and 4-methyl-2-aminopyridine by the methods described in Example 1, steps 1-5. LCMS (ESI, m/z): 457.3 $[M+H]^+$. $^1H$ NMR (400 MHz, $CDCl_3$) 7.98 (d, J=7.0 Hz, 1H), 7.68-7.49 (m, 4H), 6.91 (d, J=6.6 Hz, 1H), 4.17-3.91 (m, 2H), 3.63 (s, 3H), 3.01 (d, J=4.8 Hz, 3H), 2.79 (d, J=7.2 Hz, 2H), 2.67-2.51 (m, 3H), 2.49 (s, 3H), 1.56-1.42 (m, 2H), 1.10-0.89 (m, 2H).

Example 21: Synthesis of 4-(3-((4-acetamidocyclohexyl)methyl)-7-methylimidazo[1,2-a]pyridin-2-yl)-3,5-difluoro-N-methylbenzamide (A21)

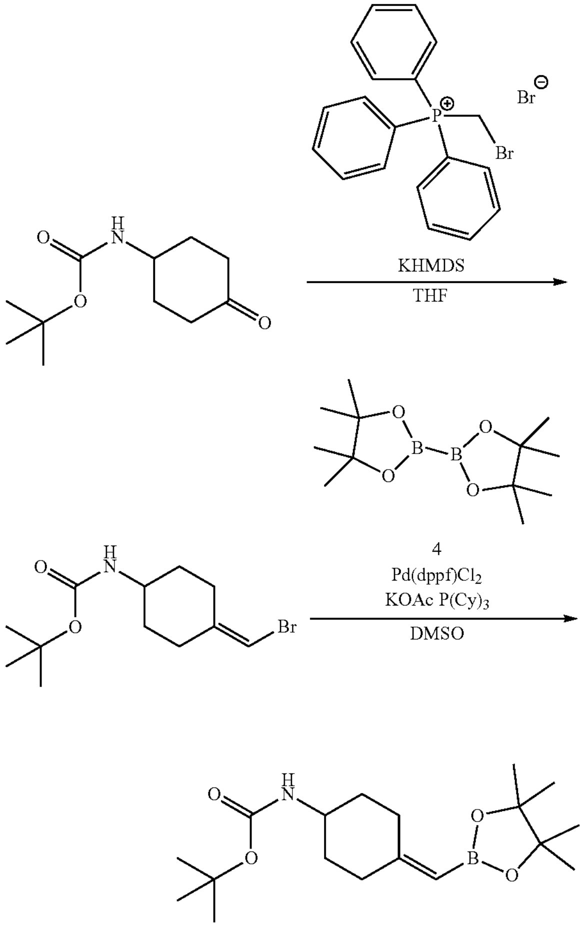

-continued

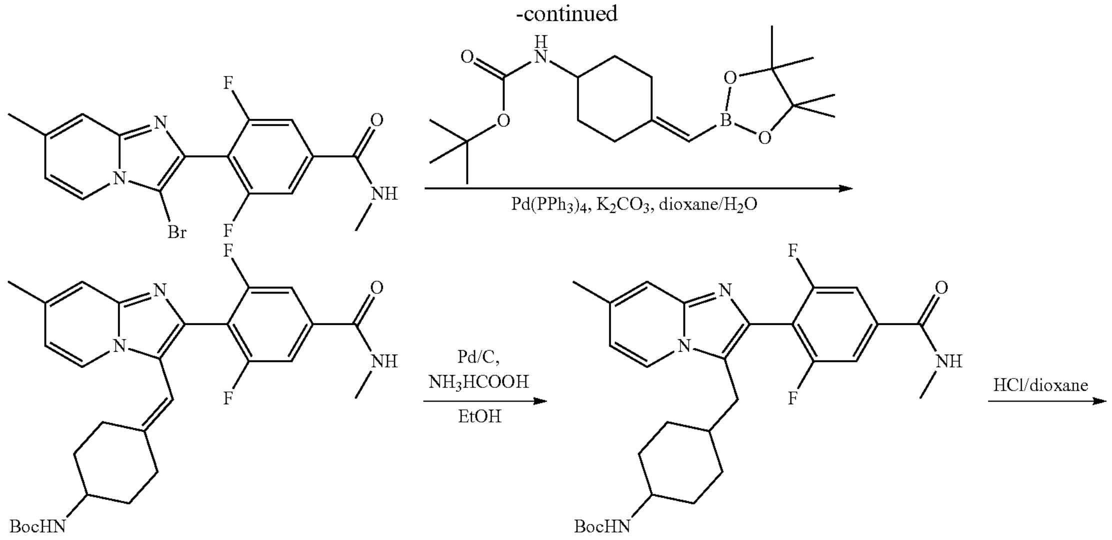

44

45

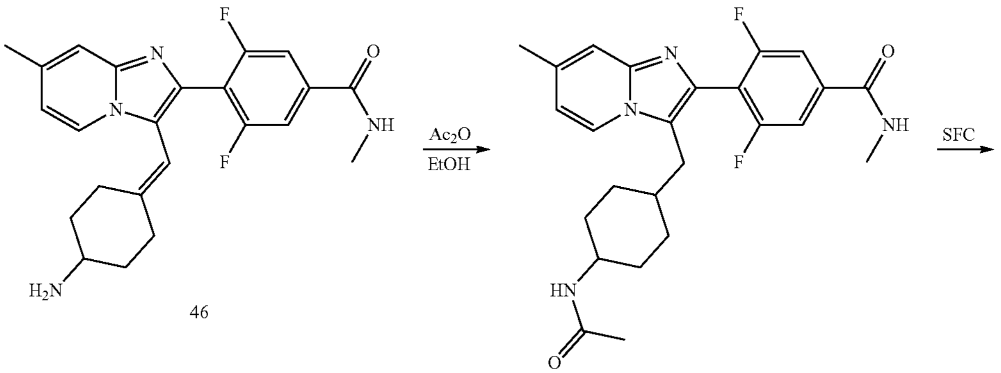

46

A21

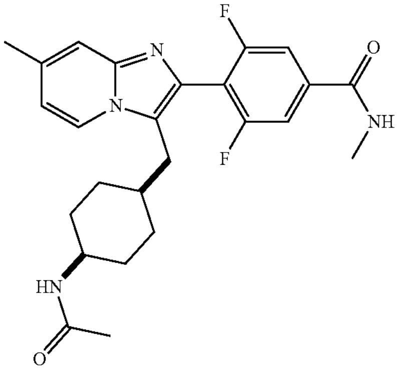

cis-A21

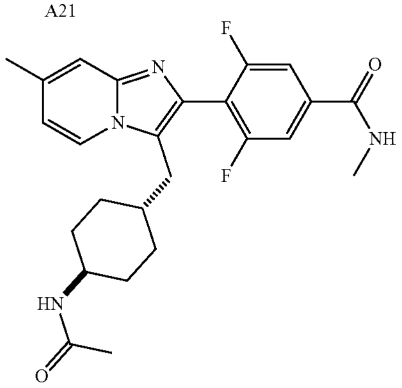

trans-A21

Steps 1 and 2: tert-Butyl (4-((4,4,5,5-tetramethyl-1,3,2-dioxaborolan-2-yl)methylene)cyclohexyl)carbamate (1.4 g) was prepared from tert-butyl (4-oxocyclohexyl)carbamate (2.0 g) according to Example 15, steps 2 and 3. described above. LCMS (ESI, m/z): 238.1 $[M-100]^+$.

Step 3: To a mixture of 4-(3-bromo-7-methylimidazo[1,2-a]pyridin-2-yl)-3,5-difluoro-N-methylbenzamide (1.00 g, 2.63 mmol), tert-butyl (4-((4,4,5,5-tetramethyl-1,3,2-dioxaborolan-2-yl)methylene)cyclohexyl)carbamate (1.33 g, 3.95 mmol) and $K_2CO_3$ (727 mg, 5.26 mmol) in $H_2O$ (4 mL) and dioxane (20 mL) was added $Pd(PPh_3)_4$ (304 mg, 263 μmol) under $N_2$. The mixture was stirred at 90° C. for 12 h. The mixture was diluted with $H_2O$ (30 mL) and extracted with EA (25 mL×3). The combined organic layers were washed with brine, dried over $Na_2SO_4$, filtered and concentrated and the residue purified by column chromatography to obtain compound 44 (1 g, 74%). LCMS (ESI, m/z): 511.2 $[M+H]^+$.

Step 4: Compound 45 (410 mg) was prepared using the procedure described in Example 15, step 5, to afford compound 44 (500 mg). LCMS (ESI, m/z): 513.3 $[M+H]^+$. $^1H$ NMR (400 MHz, DMSO-$d_6$) 7.85 (d, J=7.0 Hz, 1H), 7.43-7.37 (m, 4H), 6.75-6.68 (m, 1H), 4.31 (br s, 1H), 3.31-3.15 (m, 1H), 3.02 (d, J=4.6 Hz, 4H), 2.71 (d, J=7.3 Hz, 2H), 2.43 (s, 4H), 1.88 (br d, J=9.0 Hz, 2H), 1.58 (br d, J=9.6 Hz, 2H), 1.42 (s, 3H), 1.40 (s, 9H), 0.96-0.80 (m, 4H).

Step 5: Compound 46 was prepared from compound 45 (240 mg) using the procedure described in Example 1, step 2. LCMS (ESI, m/z): 413.1 $[M+H]^+$.

Step 6: To a solution of compound 46 (140 mg, 339 μmol) in EtOH (3 mL) was added $Ac_2O$ (680 μmol, 64 μL). Then the reaction was stirred at 80° C. for 3 h. The mixture diluted with water (30 mL) and adjusted to pH=8 with sat. $NaHCO_3$. The mixture was extracted with EA (20 mL×2). The organic layer was washed with brine (30 mL), dried over $Na_2SO_4$, filtered and concentrated. The residue was combined with a second reaction product and purified by prep-HPLC then lyophilized to afford compound A21 (120 mg, 77%) as a white solid. LCMS (ESI, m/z): 455.2 $[M+H]^+$.

Step 7: Compound A21 (100 mg) was separated into cis- and trans-isomers by SFC on a Daicel Chiralpak AD-H column (250×30 mm. 5-micron particle size) eluted with 40% IPA (0.1% aq. $NH_3$) in supercritical $CO_2$, Flow Rate: 70 g/min to afford cis-A21 and trans-A21 as white solids (4.6 mg, 61 mg).

cis-A21

LCMS: 455.2 $[M+H]^+$.

1H NMR (400 MHz, MeOD) 8.23 (d, J=7.0 Hz, 1H), 7.63-7.53 (m, 2H), 7.35 (s, 1H), 6.90 (d, J=7.1 Hz, 1H), 3.76 (br d, J=4.9 Hz, 1H), 2.95 (s, 3H), 2.89 (d, J=7.4 Hz, 2H), 2.46 (s, 3H), 1.87 (s, 3H), 1.81-1.70 (m, 1H), 1.44 (br s, 6H), 1.30-1.14 (m, 2H).

trans-A21

LCMS: 455.2 $[M+H]^+$.

1H NMR (400 MHz, MeOD) 8.24 (d, J=7.0 Hz, 1H), 7.63-7.54 (m, 2H), 7.34 (s, 1H), 6.89 (dd, J=1.5, 7.0 Hz, 1H), 3.44 (tt, J=3.8, 11.4 Hz, 1H), 2.95 (s, 3H), 2.81 (d, J=7.0 Hz, 2H), 2.45 (s, 3H), 1.85 (s, 3H), 1.81-1.74 (m, 2H), 1.66-1.48 (m, 3H), 1.12-1.00 (m, 2H), 0.99-0.85 (m, 2H).

Example 22: Synthesis of 4-(3-((3-acetamidocyclohexyl)methyl)-7-methylimidazo[1,2-a]pyridin-2-yl)-3,5-difluoro-N-methylbenzamide (cis-A22)

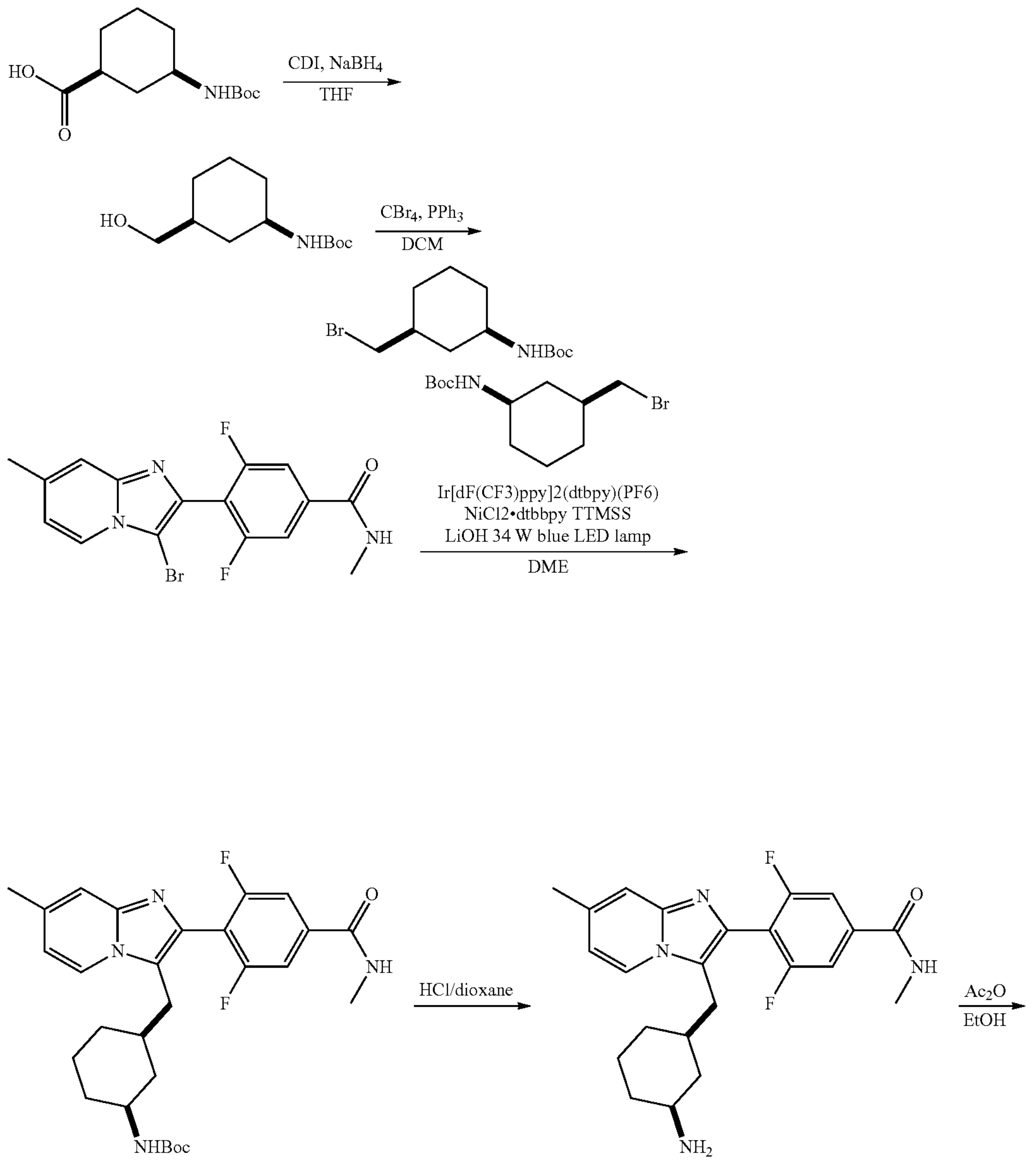

47

48

-continued

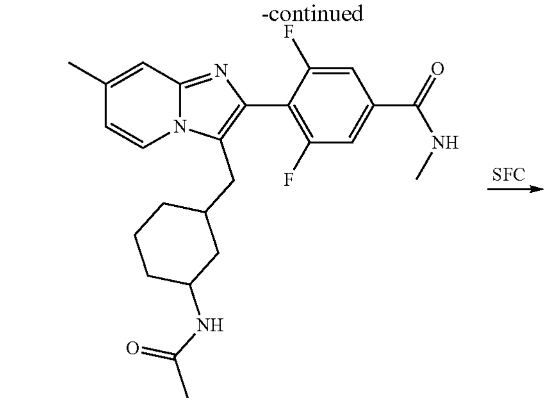

cis-A22

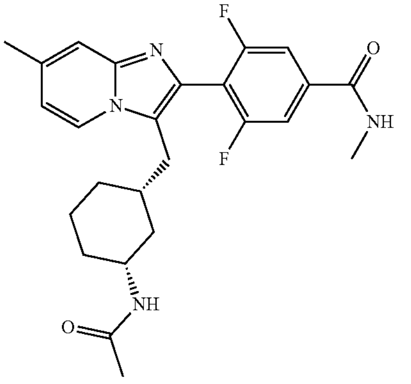

(1S,3R)-A22

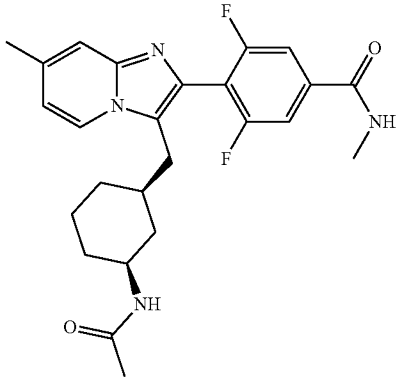

(1R,3S)-A22

Step 1: To a solution of (cis)-3-((tert-butoxycarbonyl) amino)cyclohexane-1-carboxylic acid (2.00 g, 8.22 mmol) in THE (20 mL) was added CDI (2.00 g, 12.3 mmol). The mixture was stirred at 20° C. for 16 h. Then the mixture was added to a solution of $NaBH_4$ (373 mg, 9.86 mmol) in $H_2O$ (2 mL) at 0° C. The resulting reaction mixture was stirred at 20° C. for 1 h. The mixture was quenched by aq. $NH_4Cl$ (50 mL) and extracted with EA (20 mL×3). The combined organic layers were washed with brine (50 mL), dried over $Na_2SO_4$, filtered and concentrated. The residue was purified by silica gel chromatography to afford tert-butyl ((cis)-3-(hydroxymethyl)cyclohexyl)carbamate (1.80 g, 95%) as a white solid. $^1H$ NMR (400 MHz, $CDCl_3$) 4.42 (br s, 1H), 3.47 (br t, J=5.3 Hz, 3H), 2.11-1.93 (m, 2H), 1.85-1.78 (m, 1H), 1.60 (dtt, J=3.1, 6.1, 12.0 Hz, 1H), 1.51 (br s, 1H), 1.44 (s, 9H), 1.39-1.25 (m, 1H), 1.00 (dq, J=3.8, 12.4 Hz, 1H), 0.93-0.82 (m, 1H), 0.81-0.72 (m, 1H).

Step 2: To a solution of tert-butyl ((cis)-3-(hydroxymethyl)cyclohexyl)carbamate (800 mg, 3.49 mmol) and $PPh_3$ (1.37 g, 5.23 mmol) in DCM (16 mL) was added $CBr_4$ (1.74 g, 5.23 mmol) at 0° C. under $N_2$. Then the reaction was stirred at 20° C. for 1 h, then was concentrated. The residue was purified by silica gel chromatography to afford tert-butyl ((cis)-3-(bromo-methyl)cyclohexyl)carbamate (800 mg, 78%) as a white solid. $^1H$ NMR (400 MHz, $CDCl_3$) 4.40 (br d, J=1.2 Hz, 1H), 3.57-3.37 (m, 1H), 3.31 (d, J=5.9 Hz, 2H), 2.14 (br d, J=12.3 Hz, 1H), 1.97 (br d, J=11.4 Hz, 1H), 1.87-1.68 (m, 4H), 1.45 (s, 10H), 1.41-1.32 (m, 1H), 1.03-0.80 (m, 4H).

Step 3: To a 40 mL vial equipped with a stir bar was added 4-(3-bromo-7-methylimidazo[1,2-a]pyridin-2-yl)-3,5-difluoro-N-methylbenzamide (400 mg, 1.05 mmol), tert-butyl ((cis)-3-(bromomethyl)cyclohexyl)carbamate (615 mg, 2.10 mmol), Ir[dF(CF3)ppy]2(dtbpy)(PF6) (12 mg, 10.5 umol), $NiCl_2$·dtbbpy (2 mg, 5.3 μmol), TTMSS (1.05 mmol, 325 μL), LiOH (252 mg, 10.5 mmol) in DME (15 mL). The vial was sealed and placed under nitrogen. The reaction was stirred and irradiated with a 34 W blue LED lamp (7 cm away), with cooling fan to keep the reaction temperature at 25° C. for 14 h. The mixture was diluted with water (50 mL), adjusted to pH=8 with aq. HCl (1 M) and extracted with EA (20 mL×2). The organic layer was washed with brine (30 mL), dried over $Na_2SO_4$, filtered and concentrated. The crude product was purified by prep-HPLC. The pooled fractions were adjusted to pH=8 with sat. $NaHCO_3$ and the mixture extracted with EA (20 mL×2). The organic layer was washed with brine (30 mL), dried over $Na_2SO_4$, filtered and concentrated to afford compound 47 (50 mg). LCMS (ESI, m/z): 513.3 $[M+H]^+$. $^1H$ NMR (400 MHz, $CDCl_3$) 7.85 (d, J=7.0 Hz, 1H), 7.42-7.34 (m, 3H), 6.93 (br d, J=7.9 Hz, 1H), 6.72 (dd, J=1.6, 7.1 Hz, 1H), 4.38-4.24 (m, 1H), 3.34-3.20 (m, 1H), 3.04 (d, J=4.8 Hz, 4H), 2.44 (s, 3H), 1.42 (s, 10H).

Step 4: Compound 48 (33 mg, 97%) was prepared from compound 47 (50 mg) using the procedure described in Example 1, step 2. LCMS (ESI, m/z): 413.1 $[M+H]^+$.

Step 5: To a solution of compound 48 (18.0 mg, 43.6 μmol) in EtOH (1.0 mL) was added $Ac_2O$ (87 μmol, 8 μL). The reaction was stirred at 80° C. for 2 h then diluted with water (20 mL) and adjusted to pH=8 with sat. $NaHCO_3$. The mixture was extracted with EA (10 mL×2). The combined organic layers were washed with brine (20 mL), dried over $Na_2SO_4$, filtered and concentrated. Compound cis-A22 (19 mg) was obtained as a light yellow solid. LCMS (ESI, m/z): 455.3 $[M+H]^+$.

Step 6: Compound cis-A22 (35.0 mg, 77 μmol) was separated by a combination of preparative HPLC and SFC methods to afford the two pure cis-stereoisomers, cis-A22 (Peak 1) (7.9 mg) and cis-A22 (Peak 2) (6.4 mg). Individual cis-A22 stereoisomers were isolated, but absolute stereochemistry was not determined.

Peak 1

LCMS: 455.3 $[M+H]^+$.

1H NMR (400 MHz, $CDCl_3$) 7.87 (d, J=6.9 Hz, 1H), 7.41 (br s, 1H), 7.39 (d, J=7.6 Hz, 2H), 6.95 (br d, J=3.0 Hz, 1H), 6.75 (dd, J=1.5, 7.0 Hz, 1H), 5.25 (br d, J=8.4 Hz, 1H), 3.63 (ttd, J=4.1, 7.9, 11.8 Hz, 1H), 3.04 (d, J=4.8 Hz, 3H), 2.82-2.65 (m, 2H), 2.45 (s, 3H), 1.92 (s, 3H), 1.90-1.82 (m, 2H), 1.49 (br d, J=11.6 Hz, 2H), 1.28-1.11 (m, 2H), 0.89 (dq, J=2.9, 12.2 Hz, 1H), 0.71-0.52 (m, 2H).

Peak 2

LCMS: 455.1 $[M+H]^+$.

1H NMR (400 MHz, $CDCl_3$) 7.86 (d, J=7.0 Hz, 1H), 7.39 (d, J=7.5 Hz, 3H), 6.85 (br d, J=4.8 Hz, 1H), 6.73 (dd, J=1.5, 7.0 Hz, 1H), 5.24 (br d, J=8.3 Hz, 1H), 3.70-3.57 (m, 1H), 3.04 (d, J=4.8 Hz, 3H), 2.81-2.66 (m, 2H), 2.44 (s, 3H), 1.92 (s, 3H), 1.90-1.81 (m, 2H), 1.49 (br d, J=12.8 Hz, 2H), 1.28-1.12 (m, 2H), 0.95-0.83 (m, 1H), 0.70-0.54 (m, 2H).

Example 23: Synthesis of 4-(3-((3-acetamidocyclohexyl)methyl)-7-methylimidazo[1,2-a]pyridin-2-yl)-3,5-difluoro-N-methylbenzamide (trans-A22)

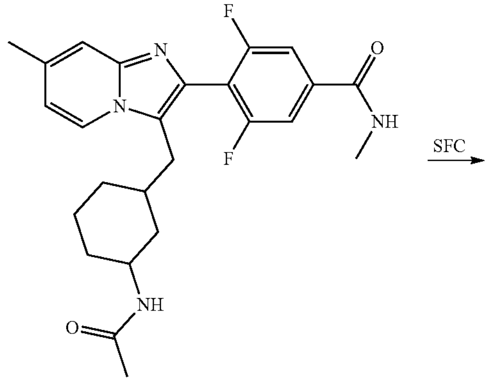

trans-A22

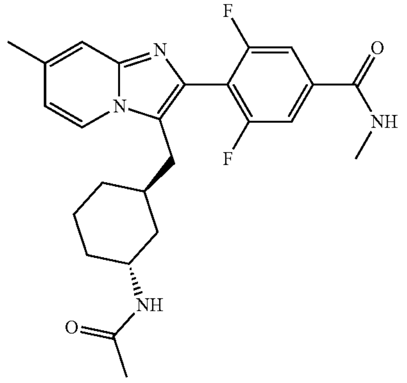

(1R,3R)-A22

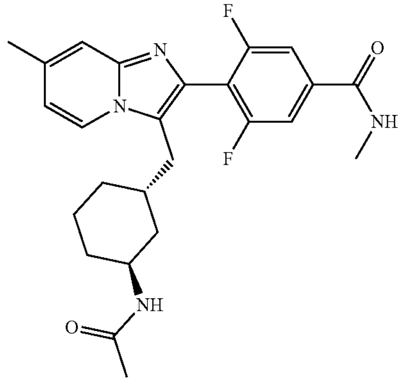

(1S,3S)-A22

The two trans-isomers of A22 were prepared as described above for the cis-isomers of A22, starting from trans-3-((tert-butoxycarbonyl)amino)cyclohexane-1-carboxylic acid. Compound trans-A22 (35.0 mg, 77 μmol) was separated by a combination of preparative HPLC and SFC methods to afford the two pure trans-stereoisomers, trans-A22 (Peak 1) (7.8 mg) and trans-A22 (Peak 2) (9.7 mg). Individual trans-A22 stereoisomers were isolated, but absolute stereochemistry was not determined.

Peak 1

LCMS: 455.2 $[M+H]^+$.

1H NMR (400 MHz, MeOD) 8.24 (d, J=7.0 Hz, 1H), 7.63-7.51 (m, 2H), 7.34 (s, 1H), 6.90 (dd, J=1.4, 7.1 Hz, 1H), 3.82 (br s, 1H), 2.95 (s, 3H), 2.92-2.84 (m, 2H), 2.45 (s, 3H), 2.06-1.92 (m, 1H), 1.87 (s, 3H), 1.60-1.28 (m, 7H), 1.07-0.93 (m, 1H).

Peak 2

LCMS: 455.2 $[M+H]^+$.

1H NMR (400 MHz, MeOD) 8.29-8.16 (m, 1H), 7.63-7.51 (m, 2H), 7.34 (s, 1H), 6.90 (br d, J=7.1 Hz, 1H), 3.82 (br s, 1H), 2.95 (s, 3H), 2.91-2.83 (m, 2H), 2.45 (s, 3H), 2.07-1.92 (m, 1H), 1.87 (s, 3H), 1.56-1.28 (m, 7H), 1.08-0.93 (m, 1H).

Example 24: Synthesis of methyl (S)-2-((2-(2,6-difluoro-4-(methylcarbamoyl)phenyl)-5-methyl-1H-indol-1-yl)methyl)morpholine-4-carboxylate (A23)
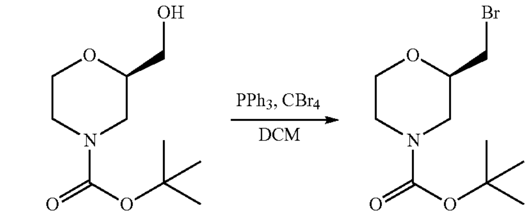
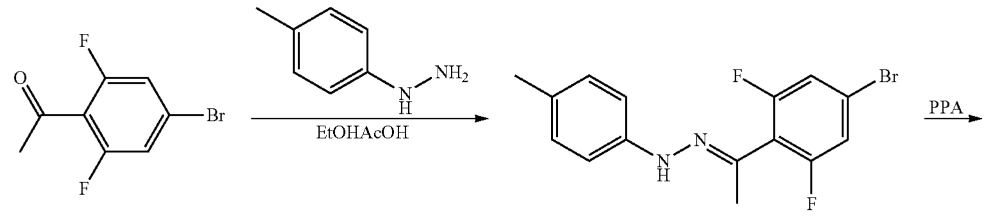
49
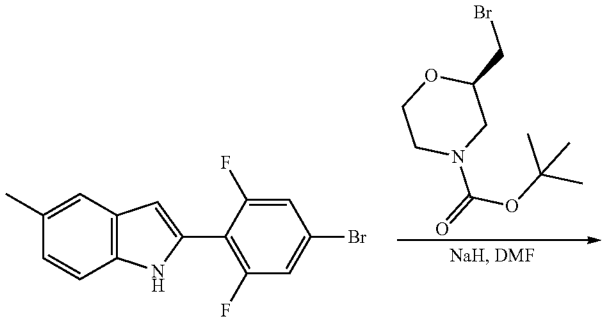
50
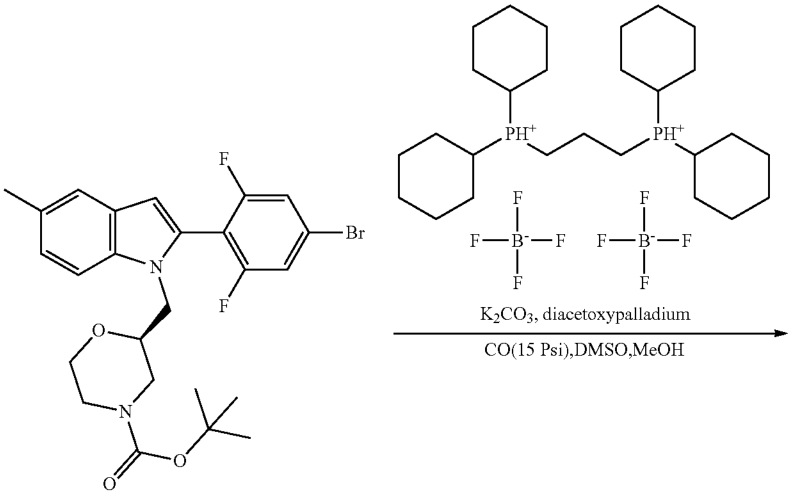
51

-continued

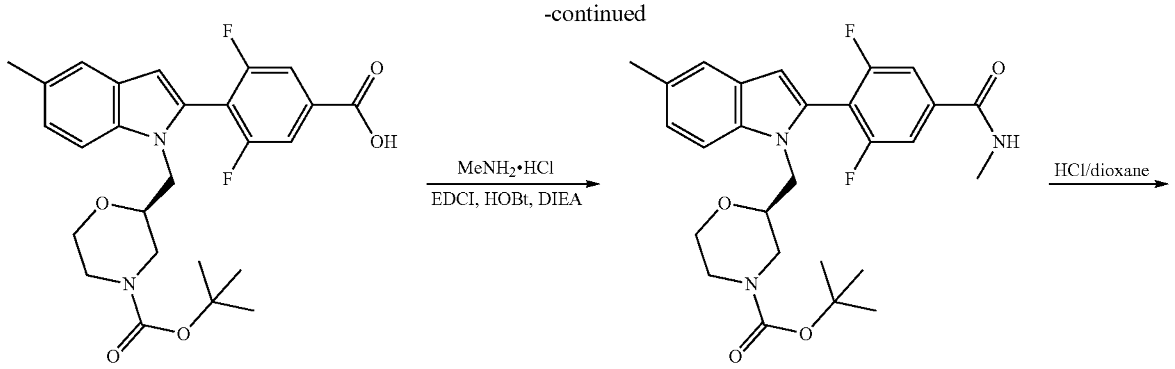

52 53

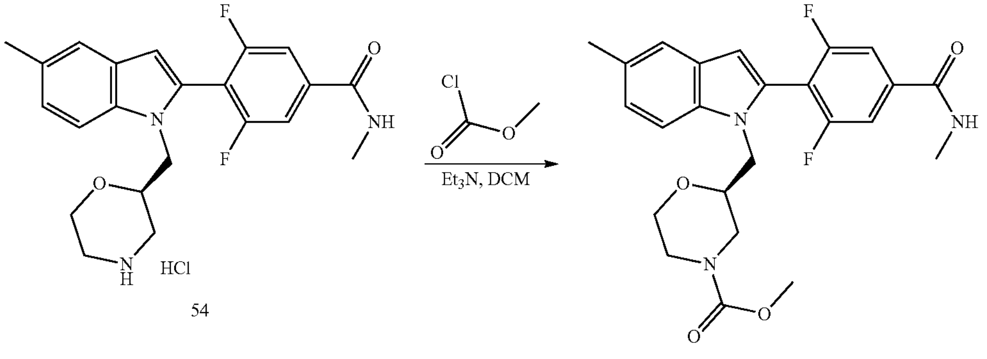

54 A23

Step 1: To a solution of tert-butyl (R)-2-(hydroxymethyl) morpholine-4-carboxylate (5.00 g, 23 mmol) in DCM (100 mL) was added $PPh_3$ (12.1 g, 46 mmol) and $CBr_4$ (15.3 g, 46 mmol) at 0° C. Then the reaction was stirred at 20° C. for 1 hr. The product was purified by silica gel chromatography to afford tert-butyl (R)-2-(bromomethyl)morpholine-4-carboxylate (5.20 g, 81%). $^1$H NMR (400 MHz, $CDCl_3$) 4.19-3.98 (m, 1H), 3.92 (br dd, J=1.8, 11.5 Hz, 1H), 3.83 (br d, J=7.9 Hz, 1H), 3.67-3.50 (m, 2H), 3.43-3.30 (m, 2H), 2.97 (br t, J=11.5 Hz, 1H), 2.75 (br s, 1H), 1.47 (s, 9H).

Step 2: To a solution of 4-bromo-2,6-difluoroacetophenone (2.0 g, 8.51 mmol) in EtOH (20 mL) was added p-tolylhydrazine hydrochloride (1.4 g, 8.94 mmol) and AcOH (50 μL). The mixture was stirred at 80° C. for 4 h. The reaction was concentrated to obtain the product, compound 49 (2.9 g) which was used directly without further purification. LCMS (ESI, m/z): 339.0 $[M+H]^+$.

Step 3: A solution of compound 49 (2.9 g, 8.52 mmol) in PPA (30 mL) was stirred at 120° C. for 12 h. The reaction was diluted with water (200 mL) and sat. $NH_4Cl$ solution (500 mL), extracted with EA (300 mL×3). The combined extracts were dried over $Na_2SO_4$, filtered and concentrated, and the crude product was purified by reversed-phase HPLC. Fractions were concentrated to remove MeCN, and the remaining liquid was extracted with EA (50 mL×3) to obtain compound 50 (1.3 g, 35% yield) as an oil. LCMS (ESI, m/z): 322.0 $[M+H]^+$. $^1$H NMR (400 MHz, $CDCl_3$) 8.84 (br s, 1H), 7.46 (d, J=0.4 Hz, 1H), 7.33-7.31 (m, 1H), 7.24-7.21 (m, 2H), 7.10-7.08 (m, 2H), 2.47 (s, 3H).

Step 4: To a solution of compound 50 (1.1 g, 3.41 mmol) in DMF (11 mL) was added NaH (273 mg, 6.8 mmol, 60% dispersion) and tert-butyl (R)-2-(bromomethyl)morpholine-4-carboxylate (1.9 g, 6.83 mmol). The mixture was stirred at 25° C. for 14 h. The reaction was diluted with water (50 mL), extracted with EA (20 mL×3). The combined extracts were washed with brine, dried over $Na_2SO_4$, filtered and concentrated to get the crude product which was purified by column chromatography to afford compound 51 (1.3 g, 65%). LCMS (ESI, m/z): 523.2 $[M+H]^+$.

Step 5: To a solution of compound 51 (730 mg, 1.40 mmol) in DMSO (8 mL) and MeOH (1.5 mL) was added $K_2CO_3$ (290 mg, 2.10 mmol), diacetoxypalladium (16 mg, 70 μmol) and 1,3-bis(dicyclohexylphosphino)propane bistetrafluoroborate (86 mg, 0.14 mmol). The mixture was stirred at 100° C. for 12 h under CO (15 psi). The reaction was diluted with water (20 mL) and filtered. The filter cake was washed with EA (20 mL), and the filtrate was extracted with EA (10 mL×3). The combined organics were dried over $Na_2SO_4$, filtered and concentrated and the crude product was purified by reversed-phase HPLC and lyophilized to afford compound 52 (450 mg, 59%). LCMS (ESI, m/z): 487.2 $[M+H]^+$. $^1$H NMR (400 MHz, $CDCl_3$) 7.74 (br d, J=7.2 Hz, 2H), 7.46 (s, 1H), 7.37 (d, J=8.4 Hz, 1H), 7.13 (br d, J=42 Hz, 1H), 6.60 (s, 1H), 4.16-4.12 (m, 2H), 3.70-3.55 (m, 4H), 3.32 (br s, 1H), 2.77-2.72 (m, 1H), 2.48 (s, 3H), 2.36-2.30 (m, 1H), 1.40 (s, 9H).

Steps 6-8: Compound A23 (88.4 mg) was prepared from compound 52 (230 mg, 0.46 mmol) using the procedures described in Example 1, steps 5, 2, and 3. $^1$H NMR (400 MHz, $CDCl_3$) 7.74 (br d, J=7.2 Hz, 2H), 7.45-7.41 (m, 3H), 7.32 (d, J=8.4 Hz, 1H), 7.11 (br d, J=8.4 Hz, 1H), 6.56 (s, 1H), 6.28 (br d, J=2.0 Hz, 1H), 4.10-4.03 (m, 2H), 3.71-3.64 (m, 6H), 3.53-3.50 (m, 1H), 3.29 (br s, 1H), 3.06 (d, J=5.2 Hz, 3H), 2.78 (br s, 1H), 2.47 (s, 3H), 2.40-2.34 (m, 1H).

Example 25: Synthesis of methyl (S)-2-((2-(2,6-difluoro-4-(methylcarbamoyl)phenyl)6-methyl-1H-indol-3-yl)methyl)morpholine-4-carboxylate (A24)

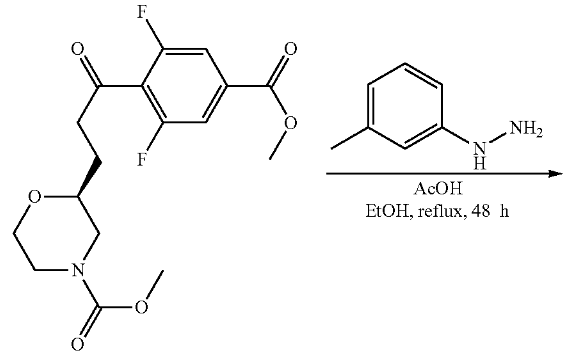

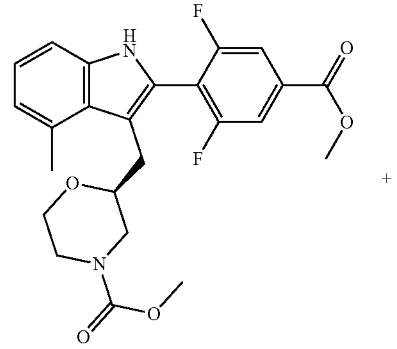

55A

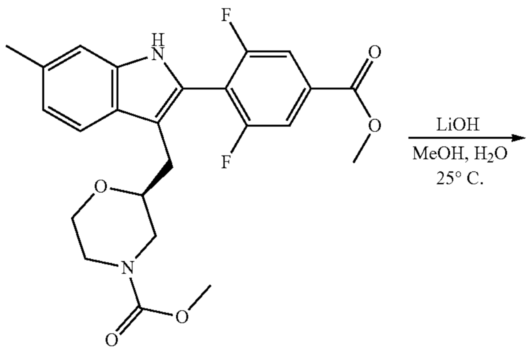

55B

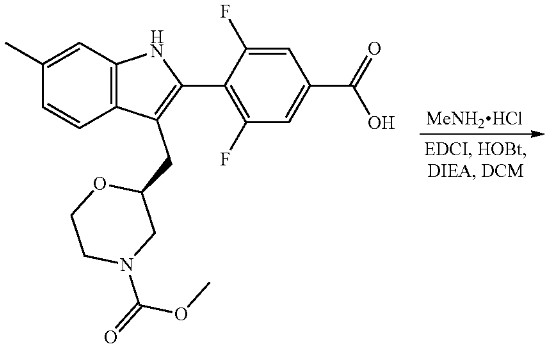

56

-continued

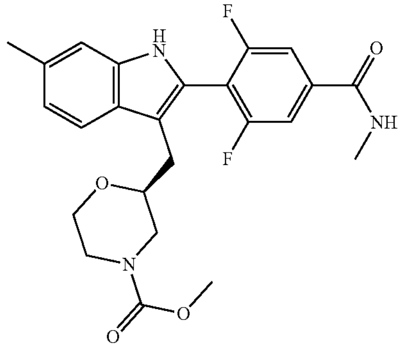

A24

Step 1: To a solution of methyl (S)-2-(3-(2,6-difluoro-4-(methoxycarbonyl)phenyl)-3-oxopropyl)morpholine-4-carboxylate (1 g, 2.69 mmol), m-tolylhydrazine (395 mg, 3.23 mmol) in EtOH (10 mL) was added AcOH (15 μL). The mixture was stirred at 80° C. for 48 hr. The reaction was concentrated and the residue was purified by prep-HPLC to isolate two peaks. Compound 55A (130 mg, 10% yield) and compound 55B (150 mg, 12% yield) were isolated as yellow solids. LCMS (ESI, m/z): 459.2 $[M+H]^+$. $^1H$ NMR (400 MHz, $CDCl_3$) 8.00 (s, 1H), 7.64-7.60 (m, 2H), 7.53 (d, J=8.4 Hz, 1H), 7.12 (s, 1H), 6.93 (br d, J=8.0 Hz, 1H), 3.90 (s, 3H), 3.71-3.67 (m, 3H), 3.54-3.49 (m, 4H), 3.35-3.29 (m, 1H), 2.98-2.94 (m, 1H), 2.74-2.67 (m, 2H), 2.41-2.35 (m, 4H).

Steps 2 and 3: Compound A24 was prepared starting from compound 55B by the procedures described in Example 1, steps 4 and 5. LCMS (ESI, m/z): 458.1 $[M+H]^+$. $^1H$ NMR (400 MHz, $CDCl_3$) 8.30 (s, 1H), 7.60 (d, J=8.4 Hz, 1H), 7.41 (br d, J=7.6 Hz, 2H), 7.19 (s, 1H), 7.01 (br d, J=8.0 Hz, 1H), 6.43 (br s, 1H), 3.78 (br d, J=11.2 Hz, 3H), 3.61-3.56 (m, 4H), 3.43-3.37 (br t, J=10.9 Hz, 1H), 3.04-3.01 (m, 4H), 2.93-2.85 (m, 1H), 2.78-2.75 (m, 1H), 2.48-2.42 (m, 4H).

Example 26: Synthesis of methyl (S)-2-((2-(2,6-difluoro-4-(methylcarbamoyl)phenyl)-5-methyl-1H-pyrrolo[2,3-b]pyridin-1-yl)methyl)morpholine-4-carboxylate (A25)

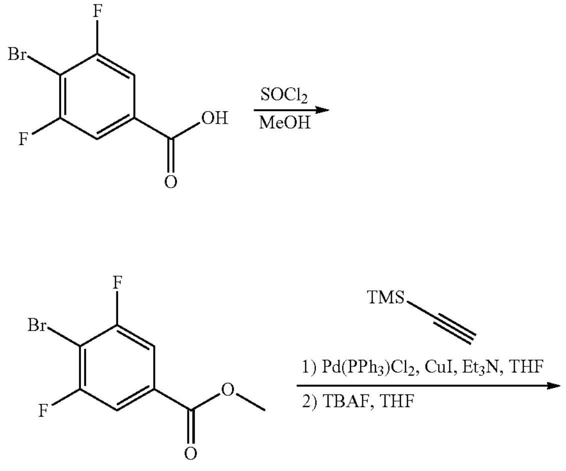

-continued

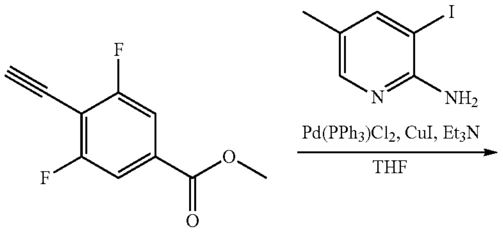

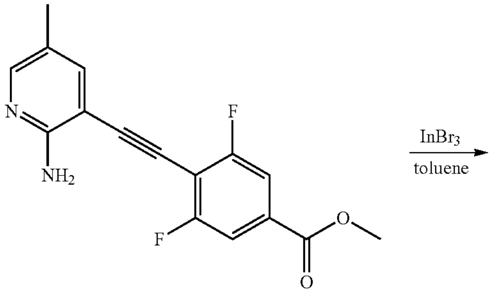

57

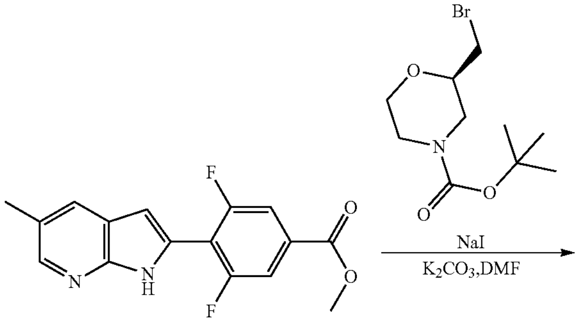

58

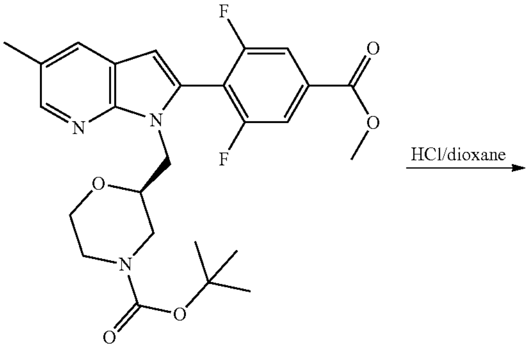

59

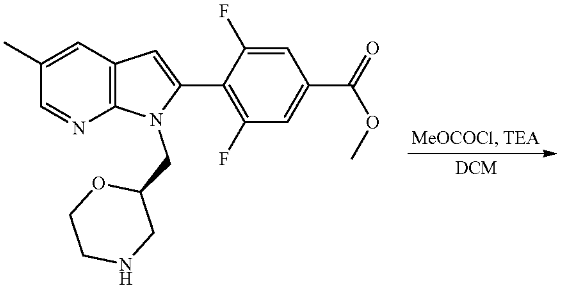

60

-continued

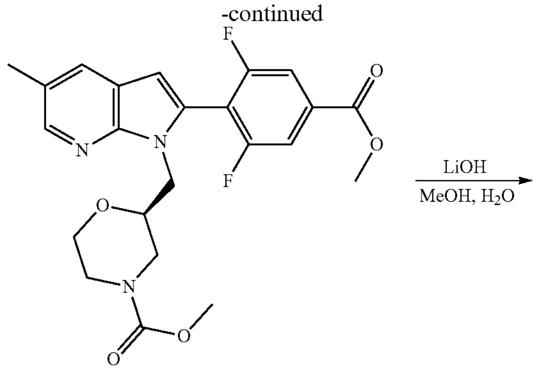

61

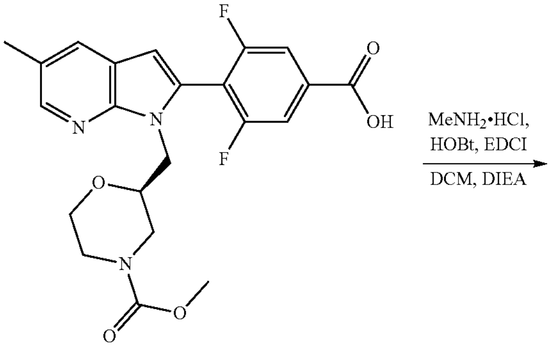

62

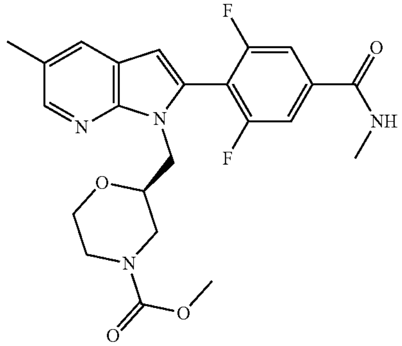

A25

Step 1: To a solution of 4-bromo-3,5-difluorobenzoic acid (5.00 g, 21.1 mmol) in MeOH (60 mL) was added $SOCl_2$ (138 mmol, 10 mL). Then the mixture was stirred at 80° C. for 2 hr. The mixture was concentrated and the product methyl 4-bromo-3,5-difluorobenzoate (5.00 g, 93%) was used into next step without further purification. $^1$H NMR (400 MHz, $CDCl_3$) 7.62 (d, J=6.6 Hz, 2H), 3.95 (s, 3H).

Step 2: To a solution of methyl 4-bromo-3,5-difluorobenzoate (2.50 g, 9.96 mmol) in THE (30 mL) was added trimethylsilylacetylene (10 mmol, 1.4 mL), CuI (94.8 mg, 500 μmol), TEA (39.8 mmol, 5.5 mL) and $Pd(PPh_3)_2Cl_2$ (349 mg, 500 μmol). Then the reaction was stirred at 60° C. for 3 hrs. The mixture was diluted with water (100 mL) and extracted with EA (50 mL×2). The organic layer was washed with brine (100 mL), dried over $Na_2SO_4$, filtered and concentrated. The residue was purified by silica gel chromatography and the residue (2.00 g) dissolved in THE (20 mL). TBAF (1 M, 9 mL) was added at 0° C. and the reaction was stirred at 20° C. for 1 hr. The mixture was diluted with water (100 mL) and extracted with EA (30 mL×3). The organic layer was washed with brine (90 mL), dried over $Na_2SO_4$, filtered and concentrated. The residue was purified by silica gel chromatography to afford methyl 4-ethynyl-3,5-difluorobenzoate (600 mg, 39%) as a light yellow solid. $^1$H NMR (400 MHz, $CDCl_3$) 7.59-7.53 (m, 2H), 3.94 (s, 3H), 0.30 (s, 9H).

Step 3: To a solution of methyl 4-ethynyl-3,5-difluorobenzoate (599 mg, 3.06 mmol) and 3-iodo-5-methylpyridin-2-amine (715 mg, 3.06 mmol) in THE (10 mL) and TEA (10 mL) was added CuI (29.1 mg, 153 μmol) and $Pd(PPh_3)_2Cl_2$ (107 mg, 153 μmol). The mixture was stirred at 60° C. for 2 h under $N_2$. The mixture was diluted with water (100 mL) and extracted with EA (30 mL×3). The organic layer was washed with brine (100 mL), dried over $Na_2SO_4$, filtered and concentrated. The residue was purified by silica gel chromatography to afford compound 57 (700 mg, 73%). LCMS (ESI, m/z): 303.0 $[M+H]^+$. $^1$H NMR (400 MHz, $CDCl_3$) 7.95 (d, J=1.7 Hz, 1H), 7.67-7.59 (m, 2H), 7.51 (d, J=2.0 Hz, 1H), 5.02 (br s, 2H), 3.96 (s, 3H), 2.21 (s, 3H).

Step 4: To a solution of compound 57 (550 mg, 1.82 mmol) in toluene (35 mL) was added indium tribromide (129 mg, 364 μmol). Then the mixture was stirred at 125° C. for 72 h under $N_2$. The mixture was diluted with water (150 mL) and adjusted to pH=8 with aq. $NaHCO_3$. The mixture was extracted with EA (50 mL×3). The organic layer was washed with brine (100 mL), dried over $Na_2SO_4$, filtered and concentrated. The residue was dissolved in MeOH (45 mL) and adjusted to pH=4 with aq. HCl (1 M). Then 30 mL of water was added. The solid was precipitated and filtered. The filter cake was washed with PE (10 mL). Compound 58 (250 mg, 41%) was obtained as a light yellow solid. LCMS (ESI, m/z): 303.1 $[M+H]^+$. $^1$H NMR (400 MHz, $CDCl_3$) 9.68-9.45 (m, 1H), 8.24 (s, 1H), 7.79 (s, 1H), 7.75-7.69 (m, 2H), 7.16 (d, J=1.3 Hz, 1H), 3.97 (s, 3H), 2.46 (s, 3H).

Step 5: To a solution of compound 58 (110 mg, 364 μmol) in DMF (3.5 mL) was added tert-butyl (R)-2-(bromomethyl) morpholine-4-carboxylate (204 mg, 728 μmol), $Cs_2CO_3$ (296 mg, 910 umol) and NaI (27.3 mg, 182 umol). Then the mixture was stirred at 60° C. for 16 h. The mixture was diluted with water (20 mL) and extracted with EA (10 mL×3). The organic layer was washed with brine (20 mL), dried over $Na_2SO_4$, filtered and concentrated. The residue was purified by silica gel chromatography to afford compound 59 (130 mg, 69%). LCMS (ESI, m/z): 502.1 $[M+H]^+$. $^1$H NMR (400 MHz, $CDCl_3$) 8.23 (s, 1H), 7.75 (s, 1H), 7.70 (br d, J=7.7 Hz, 2H), 6.53 (s, 1H), 4.38-4.23 (m, 2H), 3.99 (s, 3H), 3.89-3.62 (m, 2H), 3.61-3.50 (m, 2H), 3.24 (br t, J=11.5 Hz, 1H), 2.77-2.64 (m, 1H), 2.46 (s, 3H), 2.38-2.26 (m, 1H), 1.39 (s, 9H).

Steps 6-9: Compound A25 (46 mg) was prepared from compound 59 (130 mg, 259 μmol) using the procedures described in Example 1, steps 2-5. LCMS (ESI, m/z): 459.2 $[M+H]^+$. $^1$H NMR (400 MHz, $CDCl_3$) 8.22 (d, J=1.6 Hz, 1H), 7.75 (s, 1H), 7.47-7.39 (m, 2H), 6.52 (s, 1H), 6.27-6.15 (m, 1H), 4.30 (br s, 2H), 3.92-3.69 (m, 2H), 3.64 (s, 3H), 3.63-3.52 (m, 2H), 3.30-3.19 (m, 1H), 3.07 (d, J=4.9 Hz, 3H), 2.84-2.70 (m, 1H), 2.46 (s, 3H), 2.43-2.34 (m, 1H).

Example 27: Synthesis of methyl (S)-2-((2-(2,6-difluoro-4-(methylcarbamoyl)phenyl)-6-methyl-1H-pyrrolo[3,2-b]pyridin-3-yl)methyl)morpholine-4-carboxylate (A26)

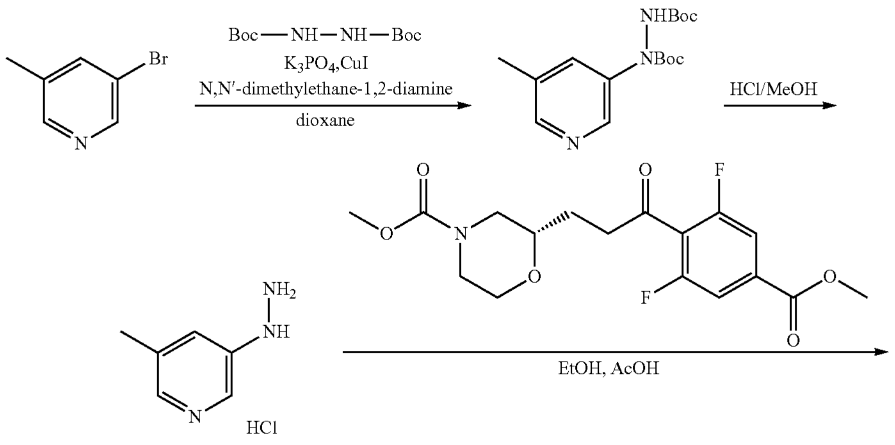

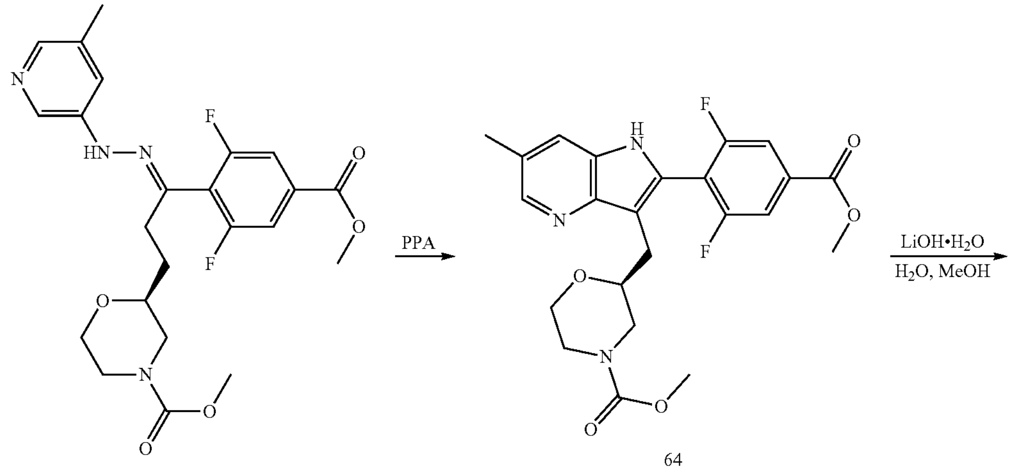

63 64

-continued

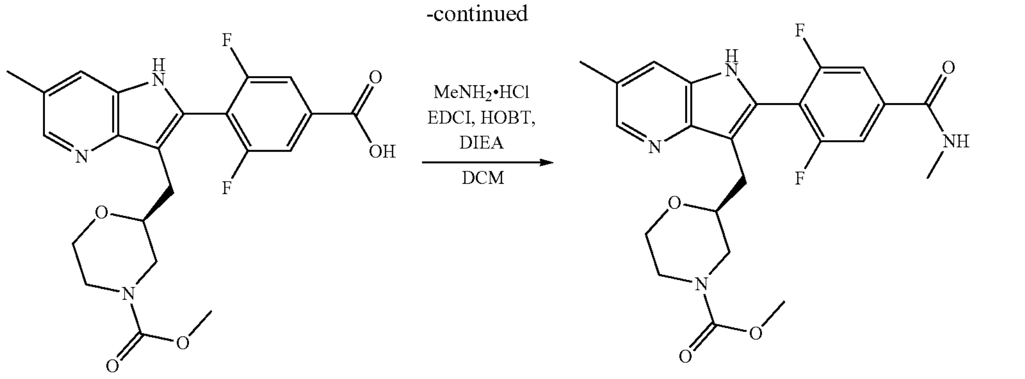

65 A26

Step 1: To a solution of 3-bromo-5-methylpyridine (8 g, 46.5 mmol) and di-tert-butyl hydrazine-1,2-dicarboxylate (10.8 g, 46.5 mmol) in dioxane (80 mL) was added CuI (1.77 g, 9.3 mmol) and $K_3PO_4$ (29.6 g, 140 mmol) and N,N'-dimethylethane-1,2-diamine (1.64 g, 2.00 mL). The mixture was stirred at 100° C. for 3 hr. The reaction was diluted with water (300 mL) and extracted with EA (100 mL×3). The combined organic layers were dried over $Na_2SO_4$, filtered and concentrated. The residue was purified by column chromatography and the product was concentrated to afford di-tert-butyl 1-(5-methylpyridin-3-yl)hydrazine-1,2-dicarboxylate (9 g, 60%) as a white solid.

Step 2: A solution of di-tert-butyl 1-(5-methylpyridin-3-yl)hydrazine-1,2-dicarboxylate (3 g, 9.28 mmol) in 4M HCl in MeOH (30 mL) was stirred at 30° C. for 0.5 hr. The reaction mixture was concentrated to afford 3-hydrazineyl-5-methylpyridine hydrochloride (1.48 g) which was used without further purification. LCMS (ESI, m/z): 124.1 $[M+H]^+$. $^1H$ NMR (400 MHz, $CDCl_3$) 8.39 (s, 1H), 8.36 (d, J=2.4 Hz, 1H), 8.00 (m, 1H), 2.58 (s, 3H).

Step 3: To a solution of methyl (S)-2-(3-(2,6-difluoro-4-(methoxycarbonyl)phenyl)-3-oxopropyl)morpholine-4-carboxylate (1.2 g, 3.23 mmol) and 3-hydrazinyl-5-methylpyridine hydrochloride (1.44 g, 9.05 mmol) in EtOH (13 mL) was added AcOH (18.5 μL). The mixture was stirred at 80° C. for 15 h. The reaction mixture was concentrated, and the product compound 63 was used directly without further purification. LCMS (ESI, m/z): 477.1 $[M+H]^+$.

Step 4: A mixture of compound 63 (1.54 g, 3.23 mmol) in PPA (20 mL) was stirred at 110° C. for 1 hr. The reaction mixture was added to sat. $Na_2CO_3$ (1.5 L) and then extracted with EA (500 mL×3). The combined organic layers were dried over $Na_2SO_4$, filtered and concentrated and the residue was purified by reverse phase chromatography to afford compound 64 (300 mg, 20%). LCMS (ESI, m/z): 460.1 $[M+H]^+$. $^1H$ NMR (400 MHz, $CDCl_3$) 8.32-8.28 (m, 3H), 7.73-7.66 (m, 2H), 3.99-3.97 (m, 3H), 3.94-3.69 (m, 4H), 3.64 (s, 3H), 3.41-3.27 (m, 1H), 3.04-2.79 (m, 3H), 2.61-2.55 (m, 1H), 2.44 (s, 3H).

Steps 5 and 6: Compound A26 (57 mg) was prepared from compound 64 (140 mg) using the procedures described in Example 1, steps 4 and 5. LCMS (ESI, m/z): 459.1 $[M+H]^+$. $^1H$ NMR (400 MHz, $CDCl_3$) 8.47-8.31 (m, 1H), 7.59 (br s, 1H), 7.46-7.38 (m, 2H), 7.19-7.12 (m, 1H), 3.78-3.66 (m, 4H), 3.62-3.60 (m, 3H), 3.33-3.31 (m, 1H), 3.05 (br s, 2H), 2.99 (br d, J=4.0 Hz, 3H), 2.88-2.84 (m, 2H), 2.45 (br s, 3H).

Example 28: Synthesis of methyl (S)-2-((2-(2,6-difluoro-4-(methylcarbamoyl)phenyl)-7-methylimidazo[1,2-b]pyridazin-3-yl)methyl)morpholine-4-carboxylate (A27)

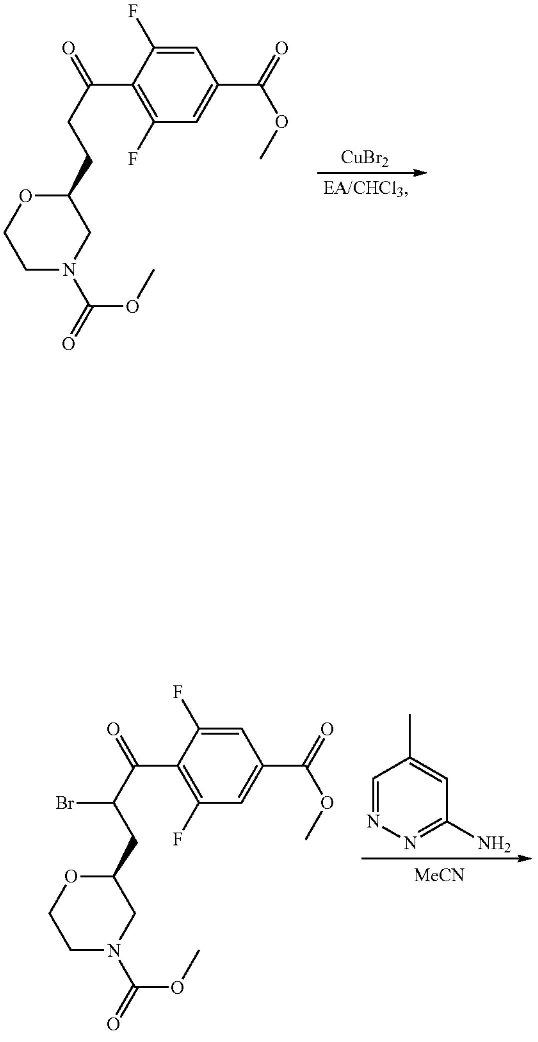

66

-continued

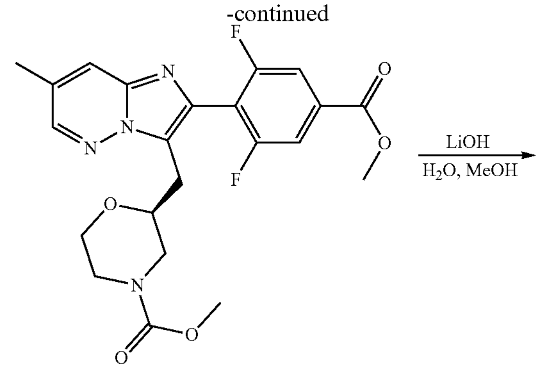

67

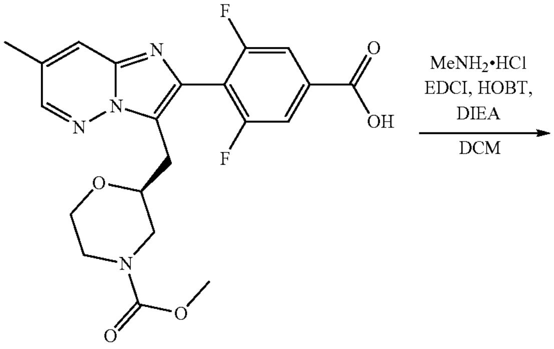

68

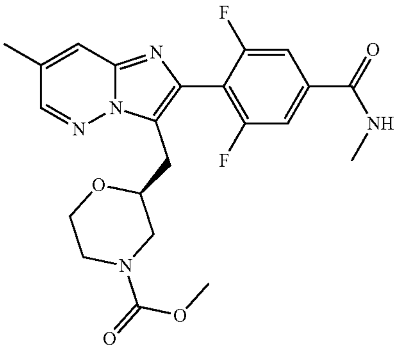

A27

Step 1: To a solution of methyl (S)-2-(3-(2,6-difluoro-4-(methoxycarbonyl)phenyl)-3-oxopropyl)morpholine-4-carboxylate (5 g, 13.5 mmol) in $CHCl_3$ (30 mL) and EtOAc (30 mL) was added $CuBr_2$ (6 g, 26.9 mmol). The mixture was stirred at 85° C. for 3 h. The mixture was filtered and the filtrate concentrated and the residue purified by column chromatography to afford compound 66 (5.6 g, 87%). LCMS (ESI, m/z): 449.1 $[M+H]^+$. $^1H$ NMR (400 MHz, $CDCl_3$) 7.69-7.61 (m, 2H), 5.26-5.10 (m, 1H), 4.04-3.83 (m, 6H), 3.76-3.71 (m, 3H), 3.70-3.42 (m, 2H), 2.98 (br d, J=11.0 Hz, 1H), 2.87-2.25 (m, 2H), 2.24-2.10 (m, 1H).

Step 2: A mixture of compound 66 (1 g, 2.22 mmol) and 3-amino-5-methylpyridazine (727 mg, 6.66 mmol) in MeCN (20 mL) was heated to 80° C. for 3 days. The mixture was diluted with $H_2O$ (50 mL) and extracted with EA (50 mL×3). The combined organic layers were washed with brine, dried over $Na_2SO_4$, filtered and concentrated to obtained residue. The residue was purified by preparative TLC to obtain compound 67 (96 mg, 9%). LCMS (ESI, m/z): 461.2 $[M+H]^+$. $^1H$ NMR (400 MHz, $CDCl_3$) 8.48 (d, J=2.0 Hz, 1H), 7.82 (dd, J=1.2, 1.8 Hz, 1H), 7.79-7.72 (m, 2H), 3.99 (s, 3H), 3.85 (br d, J=12.3 Hz, 1H), 3.78-3.71 (m, 2H), 3.65 (s, 4H), 3.31-3.17 (m, 3H), 2.94-2.80 (m, 1H), 2.66-2.54 (m, 1H), 2.51 (d, J=1.0 Hz, 3H).

Steps 3 and 4: Compound A27 (20 mg) was prepared from compound 67 (90 mg) using the procedures described in Example 1, steps 4 and 5. LCMS (ESI, m/z): 460.0 $[M+H]^+$. $^1H$ NMR (400 MHz, $CDCl_3$) 8.24 (d, J=1.8 Hz, 1H), 7.78-7.63 (m, 1H), 7.42 (br d, J=7.4 Hz, 2H), 7.36 (br d, J=13.1 Hz, 1H), 3.95-3.65 (m, 4H), 3.63 (s, 3H), 3.37-3.19 (m, 2H), 3.16-3.06 (m, 1H), 2.99 (d, J=4.6 Hz, 3H), 2.92-2.78 (m, 1H), 2.54 (br dd, J=10.7, 12.8 Hz, 1H), 2.45 (s, 3H).

Example 29: Synthesis of methyl (S)-2-((2-(2,6-difluoro-4-(methylcarbamoyl)phenyl)-7-methylimidazo[1,2-a]pyrimidin-3-yl)methyl)morpholine-4-carboxylate (A28)

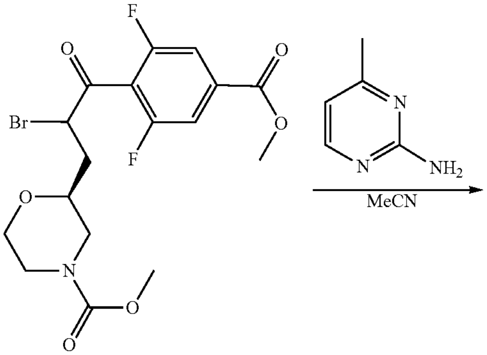

66

-continued

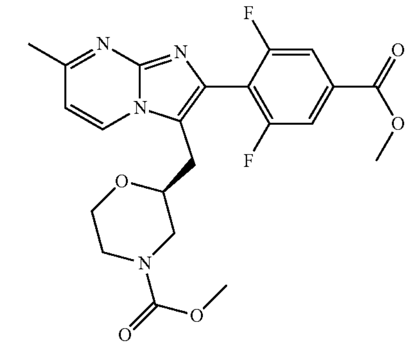

69A

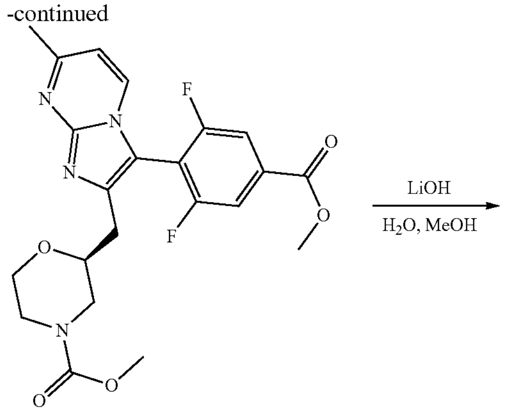

69B

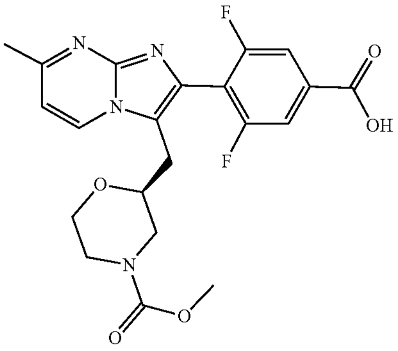

70A

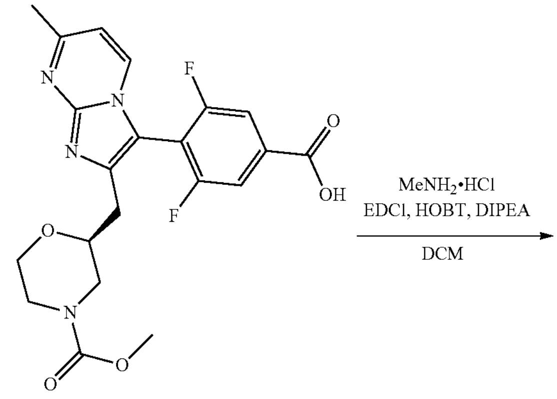

70B

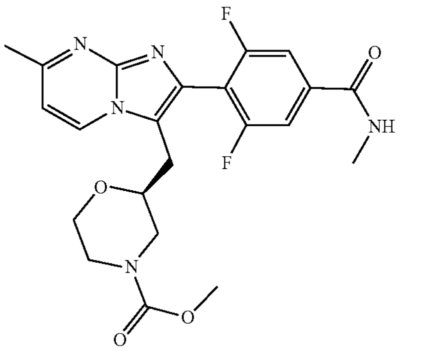

A28

+

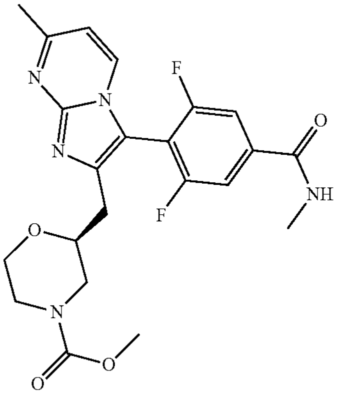

A33

Step 1: To a solution of compound 66 (1 g, 2.22 mmol) in MeCN (10 mL) was added 2-amino-4-methylpyrimidine (727 mg, 6.66 mmol). The mixture was stirred at 80° C. for 3 days. The reaction was concentrated, and the residue was purified by preparative HPLC. Lyophilization of the eluent afforded a mixture of compounds 69A and 69B (350 mg) as a white solid. LCMS (ESI, m/z): 461.1 $[M+H]^+$; 461.0 $[M+H]^+$. $^1H$ NMR (400 MHz, $CDCl_3$) 8.55 (d, J=7.2 Hz, 1H), 7.70-7.68 (d, J=7.7 Hz, 2H), 6.77 (d, J=7.2 Hz, 1H), 3.99 (s, 3H), 3.97-3.86 (m, 1H), 3.84-3.75 (m, 2H), 3.69 (s, 3H), 3.59-3.57 (m, 1H), 3.39 (br t, J=9.7 Hz, 1H), 3.00-2.80 (m, 4H), 2.65 (s, 3H).

Step 2: To a solution of compounds 69A and 69B (270 mg, 0.59 mmol) in MeOH (3.0 mL) and $H_2O$ (0.6 mL) was added $LiOH{\cdot}H_2O$ (49 mg, 1.17 mmol). The mixture was stirred at 25° C. for 1 h. The reaction mixture was diluted with water (10 mL), adjusted to pH=7-8 by aq. HCl (1 M), the solution lyophilized to afford a mixture of compounds 70A and 70B (261 mg, 99.7%) which were used as obtained.

Steps 3 and 4: The mixture of compounds 70A and 70B (260 mg, 0.58 mmol) was treated as described in Example 1, step 5 to afford A28 (151 mg, 56%). LCMS (ESI, m/z): 460.2 $[M+H]^+$. $^1H$ NMR (400 MHz, $CDCl_3$) 8.62-8.57 (m, 2H), 7.43 (br d, J=7.6 Hz, 2H), 6.81 (d, J=6.8 Hz, 1H), 3.78-3.76 (m, 3H), 3.66 (s, 3H), 3.53 (br s, 1H), 3.39-3.34 (m, 1H), 3.03 (br s, 3H), 2.88 (br s, 3H), 2.66-2.57 (m, 4H).

Example 30: Synthesis of methyl (S)-2-((2-(2,6-difluoro-4-(methylcarbamoyl)phenyl)-7-methylimidazo[1,2-c]pyrimidin-3-yl)methyl)morpholine-4-carboxylate (A29)

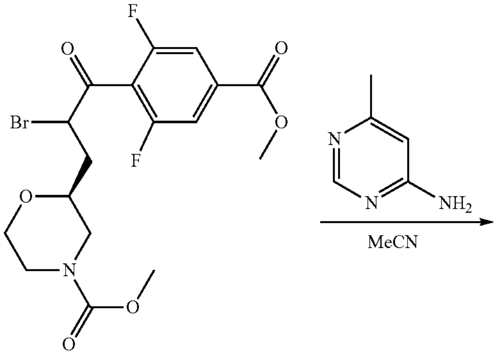

66

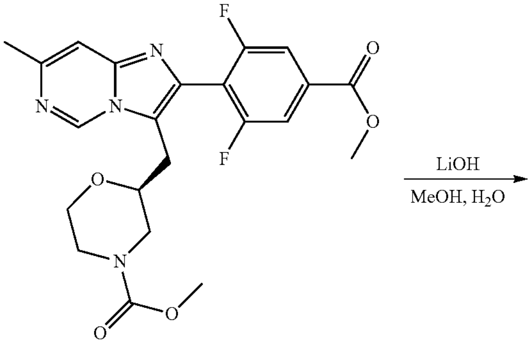

71

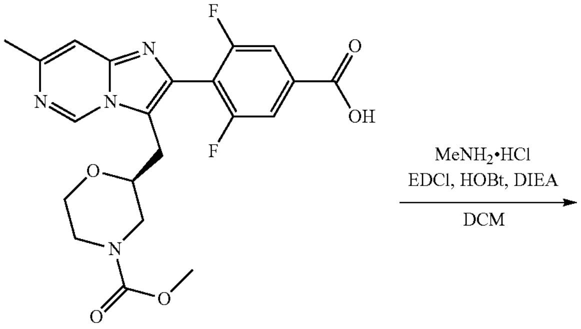

72

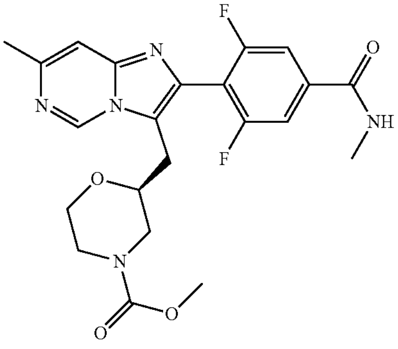

A29

Step 1: To a mixture of compound 66 (900 mg, 2.00 mmol) and 4-amino-6-methylpyrimidine (654 mg, 6.00 mmol) in MeCN (18 mL) was stirred at 80° C. for 3 days. The mixture was diluted with water (50 mL) and extracted with EA (20 mL×3). The organic layer was washed with brine, dried over $Na_2SO_4$, filtered and concentrated. The residue was purified by prep-HPLC to afford compound 71 (100 mg). LCMS (ESI, m/z): 461.1 $[M+H]^+$.

Step 2: Compound 72 (75 mg) was prepared from compound 71 (80 mg) using the procedure described in Example 1, step 4.

Steps 3 and 4: Compound 72 (75 mg, 0.17 mmol) was treated with methylamine hydrochloride (34 mg, 0.50 mmol), EDCI (64 mg, 0.34 mmol), HOBt (45 mg, 0.34 mmol) and DIEA (1.68 mmol, 0.3 mL) in DCM (3 mL) as described in General Method 5 above. The crude product was purified by prep-HPLC and further purified by chiral SFC to obtain A29 (2.6 mg, 3%). In addition, isomeric compound A37 (18 mg, 24%) was also obtained. This isomer was formed in the first step but not isolated; the mixture was used directly and the isomer isolated in the final step. LCMS (ESI, m/z): 460.2 $[M+H]^+$. $^1$H NMR (400 MHz, $CDCl_3$) 8.49 (d, J=1.3 Hz, 1H), 7.52 (dd, J=1.9, 7.8 Hz, 2H), 7.35 (s, 1H), 6.23 (br s, 1H), 4.08-3.93 (m, 1H), 3.91-3.81 (m, 2H), 3.76 (dd, J=2.6, 11.6 Hz, 1H), 3.68 (s, 3H), 3.50-3.42 (m, 1H), 3.08 (d, J=4.9 Hz, 3H), 2.99-2.87 (m, 2H), 2.85-2.77 (m, 1H), 2.71-2.60 (m, 1H), 2.57 (s, 3H).

Compound A37

A37

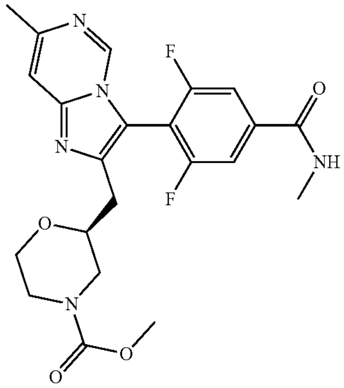

LCMS: 460.1 $[M+H]^+$.

1H NMR (400 MHz, $CDCl_3$) 9.21 (d, J=1.1 Hz, 1H), 7.48-7.41 (m, 2H), 7.31 (s, 1H), 6.35 (br d, J=4.9 Hz, 1H), 4.05-3.78 (m, 3H), 3.70 (s, 3H), 3.62 (dt, J=3.2, 6.6 Hz, 1H), 3.46-3.34 (m, 1H), 3.06 (d, J=4.9 Hz, 3H), 3.03 (br d, J=7.4 Hz, 2H), 2.98-2.84 (m, 1H), 2.73-2.61 (m, 1H), 2.56 (s, 3H).

Example 31: Synthesis of methyl (S)-2-((2-(3,6-difluoro-2-methoxy-4-(methylcarbamoyl)-phenyl)-7-methylimidazo[1,2-a]pyridin-3-yl)methyl)morpholine-4-carboxylate (A30)

A30

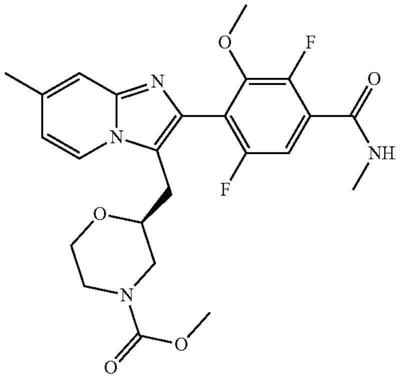

Compound A30 was prepared from 2,3,5-trifluorobromobenzene by the procedures described in Example 1, steps 1-5. LCMS (ESI, m/z): 489.3 $[M+H]^+$. $^1H$ NMR (400 MHz, $CDCl_3$) 8.16 (d, J=7.0 Hz, 1H), 7.61 (dd, J=5.8, 9.5 Hz, 1H), 7.38 (s, 1H), 6.76 (br dd, J=4.6, 10.9 Hz, 1H), 6.68 (dd, J=1.3, 7.1 Hz, 1H), 3.76 (d, J=0.8 Hz, 5H), 3.67 (s, 3H), 3.59-3.49 (m, 1H), 3.44-3.30 (m, 1H), 3.08 (d, J=4.5 Hz, 3H), 3.03-2.93 (m, 2H), 2.92-2.81 (m, 1H), 2.64-2.54 (m, 1H), 2.42 (s, 3H).

Example 32: Synthesis of methyl (S)-2-((2-(2,6-difluoro-4-(methylcarbamoyl)phenyl)-4-methyl-1H-indol-3-yl)methyl)morpholine-4-carboxylate (A31)

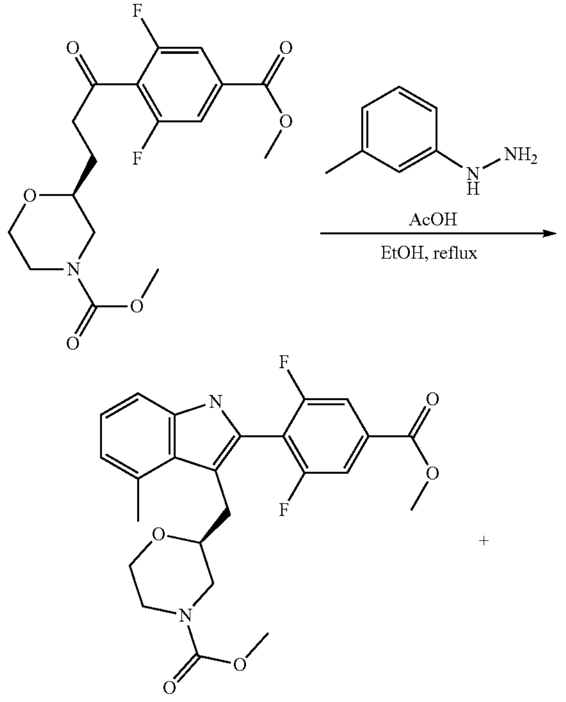

73A

-continued

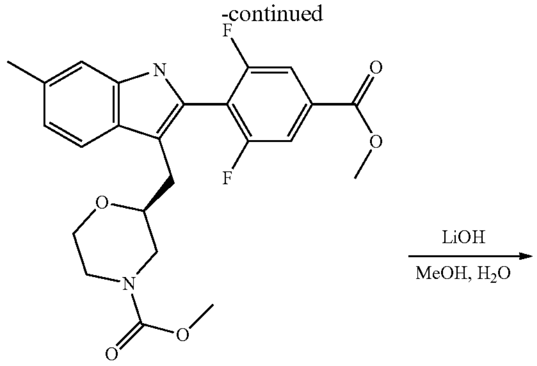

73B

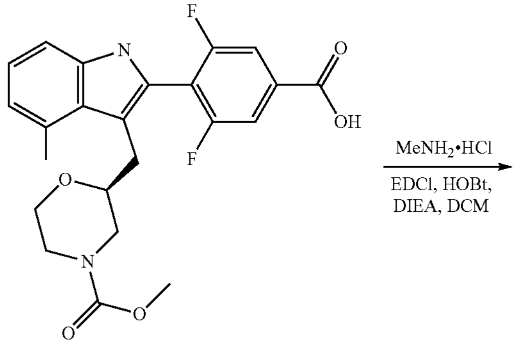

74

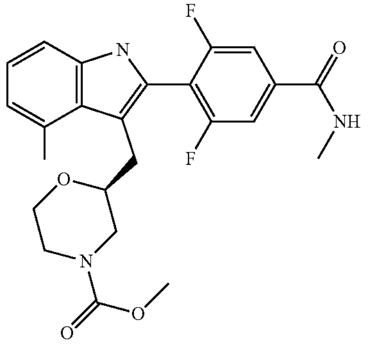

A31

Step 1: To a solution of methyl (S)-2-(3-(2,6-difluoro-4-(methoxycarbonyl)phenyl)-3-oxopropyl)morpholine-4-carboxylate (1 g, 2.69 mmol), m-tolylhydrazine (395 mg, 3.23 mmol) in EtOH (10 mL) was added AcOH (16 μL, 270 μmol). The mixture was stirred at 80° C. for 48 hr. The reaction was concentrated and the residue purified by prep-HPLC to obtain two product peaks, isolated after lyophilization. Compound 73A (130 mg, 10%) and compound 73B (150 mg, 12%) were obtained as yellow solids. LCMS (ESI, m/z): 461.1 $[M+H]^+$.

Compound 73A

LCMS: 459.2 $[M+H]^+$.

1H NMR (400 MHz, $CDCl_3$) 8.14 (s, 1H), 7.71 (d, J=8.0 Hz, 2H), 7.16-7.12 (m, 1H), 6.92 (br d, J=6.8 Hz, 1H), 3.99 (s, 3H), 3.77-3.71 (m, 3H), 3.61 (s, 3H), 3.48-3.23 (m, 3H), 2.83-2.75 (m, 5H), 2.26-2.21 (m, 1H).

Compound 73B

1H NMR (400 MHz, $CDCl_3$) 8.00 (s, 1H), 7.64-7.60 (m, 2H), 7.53 (d, J=8.4 Hz, 1H), 7.12 (s, 1H), 6.93 (br d, J=8.0 Hz, 1H), 3.90 (s, 3H), 3.71-3.67 (m, 3H), 3.54-3.49 (m, 4H), 3.35-3.29 (m, 1H), 2.98-2.94 (m, 1H), 2.74-2.67 (m, 2H), 2.41-2.35 (m, 4H).

Step 2: To a solution of compound 73A (130 mg, 284 μmol) in MeOH (0.2 mL) and $H_2O$ (0.1 mL) was added $LiOH{\cdot}H_2O$ (24 mg, 570 μmol). The mixture was stirred at 25° C. for 2 hr. The reaction was diluted with water (5 mL), adjust pH to 3-4 by aq. HCl (1 M) and extracted by EA (3 mL×3). The combined organic layers were dried over $Na_2SO_4$, filtered and concentrated to afford compound 74 (120 mg, 95%) which was used as obtained in the next step. LCMS (ESI, m/z): 445.1 $[M+H]^+$.

Step 3: Compound 74 (80 mg, 180 μmol) and methylamine hydrochloride (37 mg, 540 μmol) in DCM (2.0 mL) were coupled as described in General Method 5 above to afford A31 (54 mg, 65%). LCMS (ESI, m/z): 458.1 $[M+H]^+$. 1H NMR (400 MHz, $CDCl_3$) 8.48 (br s, 1H), 7.42 (br d, J=7.6 Hz, 2H), 7.24 (s, 1H), 7.15-7.11 (m, 1H), 6.91 (br d, J=6.8 Hz, 1H), 6.41 (br s, 1H), 3.76-3.73 (m, 3H), 3.60 (s, 3H), 3.50-3.48 (m, 1H), 3.41-3.35 (m, 1H), 3.27-3.23 (m, 1H), 3.05 (d, J=4.8 Hz, 3H), 2.82-2.75 (m, 5H), 2.25-2.19 (m, 1H).

Example 33: Synthesis of methyl (S)-2-((2-(2-chloro-4-(methylcarbamoyl)phenyl)-7-(di-fluoromethyl)imidazo[1,2-a]pyridin-3-yl)methyl)morpholine-4-carboxylate (A32)

A32

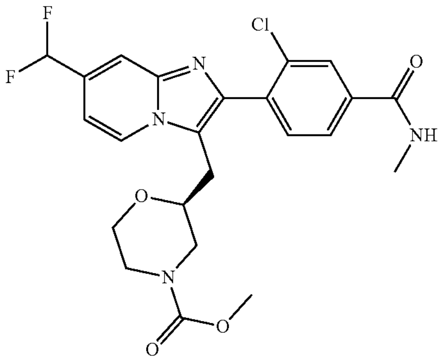

Compound A32 was prepared from N-Boc-(S)-2-ethynylmorpholine, methyl 3-chloro-4-formylbenzoate and 2-amino-4-(difluoromethyl)pyridine by the procedures described in Example 1, steps 1-5. LCMS (ESI, m/z): 493.2 $[M+H]^+$. $^1H$ NMR (400 MHz, $CDCl_3$) 8.38 (d, J=6.8 Hz, 1H), 7.92 (d, J=1.4 Hz, 1H), 7.81-7.66 (m, 2H), 7.52 (d, J=7.8 Hz, 1H), 7.01-6.99 (m, 1H), 6.87-6.55 (m, 1H), 6.45 (d, J=1.4 Hz, 1H), 3.94-3.72 (m, 3H), 3.66 (s, 3H), 3.53-3.52 (m, 1H), 3.35-3.34 (m, 1H), 3.04 (d, J=4.6 Hz, 5H), 2.95-2.75 (m, 1H), 2.56 (s, 1H).

Example 34: Synthesis of methyl (S)-2-((3-(2,6-difluoro-4-(methylcarbamoyl)phenyl)-7-methylimidazo[1,2-a]pyrimidin-2-yl)methyl)morpholine-4-carboxylate (A33)

A33

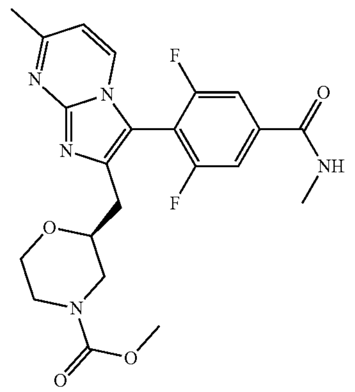

Compound A33 was isolated as from the synthesis of compound A28 (Example 29). LCMS (ESI, m/z): 460.3 $[M+H]^+$. $^1H$ NMR (400 MHz, $CDCl_3$) 7.85 (br d, J=7.2 Hz, 1H), 7.52 (d, J=8.0 Hz, 2H), 6.79 (d, J=7.2 Hz, 1H), 6.45-6.42 (m, 1H), 4.05-4.01 (m, 2H), 3.77-3.73 (m, 2H), 3.66 (s, 3H), 3.48-3.44 (m, 1H), 3.07 (d, J=4.8 Hz, 3H), 2.94-2.84 (m, 4H), 2.66 (s, 3H).

Example 35: Synthesis of methyl (2S)-2-((2-(2,6-difluoro-4-(methylcarbamoyl)phenyl)-7-methyl-5,6,7,8-tetrahydroimidazo[1,2-a]pyridin-3-yl)methyl)morpholine-4-carboxylate (A34)

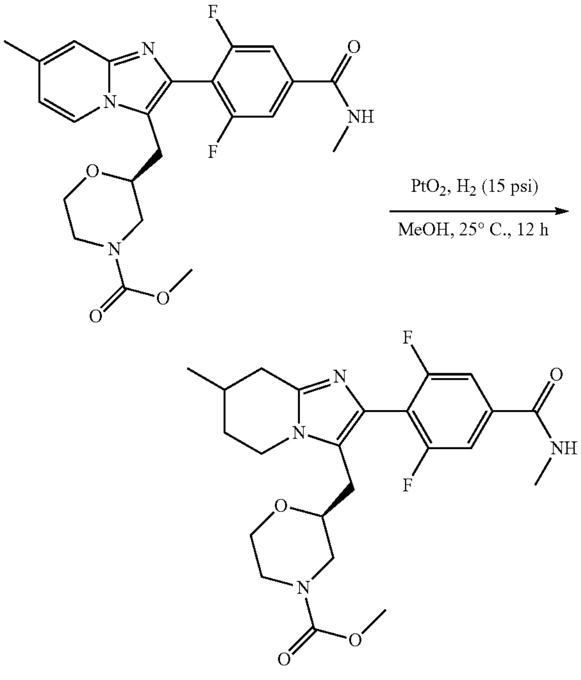

A34

To a solution of methyl (S)-2-((2-(2,6-difluoro-4-(methylcarbamoyl)phenyl)-7-methyl-imidazo[1,2-a]pyridin-3-yl)methyl)morpholine-4-carboxylate (50 mg, 109 μmol) in MeOH (2.5 mL) was added $PtO_2$ (13 mg, 55 μmol) under $N_2$. The suspension was degassed under vacuum and purged with $H_2$ several times. The mixture was stirred under an atmosphere of $H_2$ (15 psi) at 25° C. for 16 h. The mixture was then filtered and concentrated, and the residue was purified by HPLC to afford A34 (16 mg, 30%) as a white solid. LCMS (ESI, m/z): 463.1 $[M+H]^+$. $^1H$ NMR (400 MHz, $CDCl_3$) 7.63 (br s, 1H), 7.39-7.29 (m, 2H), 4.26-3.98 (m, 1H), 3.93-3.68 (m, 4H), 3.65 (s, 3H), 3.33 (br s, 2H), 3.12-3.02 (m, 1H), 2.97 (d, J=4.6 Hz, 3H), 2.91-2.79 (m, 1H), 2.73-2.57 (m, 2H), 2.54-2.39 (m, 2H), 2.07 (br d, J=11.5 Hz, 2H), 1.80-1.61 (m, 1H), 1.17 (d, J=6.5 Hz, 3H) s, 1H), 7.33 (d, J=7.6 Hz, 2H), 4.77 (br s, 1H), 4.69-4.55 (m, 1H), 4.25-3.98 (m, 1H), 3.95-3.68 (m, 4H), 3.65 (s, 3H), 3.33 (br s, 2H), 3.12-3.02 (m, 1H), 2.97 (d, J=4.6 Hz, 3H), 2.91-2.78 (m, 1H), 2.74-2.59 (m, 2H), 2.55-2.39 (m, 2H), 2.07 (br d, J=11.5 Hz, 2H), 1.81-1.59 (m, 1H), 1.17 (d, J=6.5 Hz, 3H).

Example 36: Synthesis of methyl (S)-2-((7-chloro-2-(3,6-difluoro-2-methoxy-4-(methyl-carbamoyl)phenyl)imidazo[1,2-a]pyridin-3-yl)methyl)morpholine-4-carboxylate (A40)

A40

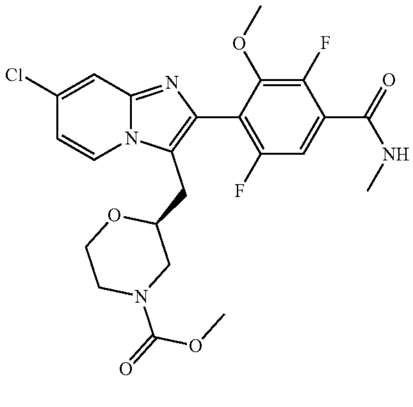

Compound A40 was prepared from 2,3,5-trifluorobromobenzene and 2-amino-4-(difluoromethyl)pyridine as described in Example 31. LCMS (ESI, m/z): 509.4 $[M+H]^+$. $^1H$ NMR (400 MHz, $CDCl_3$) 8.27 (br d, J=7.4 Hz, 1H), 7.67-7.59 (m, 2H), 6.83 (dd, J=1.7, 7.4 Hz, 1H), 6.74 (td, J=4.0, 7.7 Hz, 1H), 3.98-3.73 (m, 6H), 3.69 (s, 3H), 3.60-3.51 (m, 1H), 3.44-3.31 (m, 1H), 3.09 (d, J=4.6 Hz, 3H), 3.00-2.83 (m, 3H), 2.66-2.54 (m, 1H).

Example 37: Synthesis of methyl (S)-2-((2-(3,6-difluoro-2-methoxy-4-(methylcarbamoyl)-phenyl)-7-(difluoromethyl)imidazo[1,2-a]pyridin-3-yl)methyl)morpholine-4-carboxylate (A41)

A41

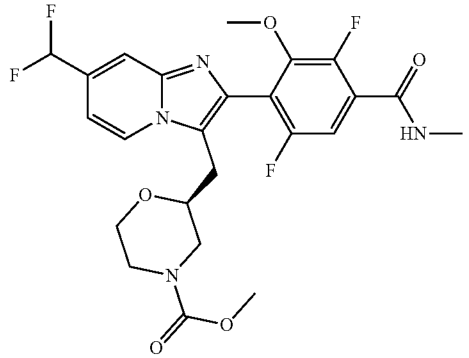

Compound A41 was prepared from 2-amino-4-(difluoromethyl)pyridine using the procedures described in Example 1, steps 1-5. LCMS (ESI, m/z): 525.3 $[M+H]^+$. $^1H$ NMR (400 MHz, $CDCl_3$) 8.41 (d, J=7.2 Hz, 1H), 7.75 (s, 1H), 7.64-7.60 (m, 1H), 6.99-6.97 (m, 1H), 6.76-6.75 (m, 1H), 6.83-6.55 (t, J=56 Hz, 1H), 3.78 (d, J=1.2 Hz, 6H), 3.67 (s, 3H), 3.62-3.51 (m, 1H), 3.43-3.28 (m, 1H), 3.08 (d, J=4.4 Hz, 3H), 3.03-2.79 (m, 3H), 2.63-2.61 (m, 1H).

Example 38: Synthesis of methyl (S)-2-((7-(difluoromethyl)-2-(2-fluoro-4-(methylcarbamoyl)phenyl)imidazo[1,2-a]pyridin-3-yl)methyl)morpholine-4-carboxylate (A42)

A42

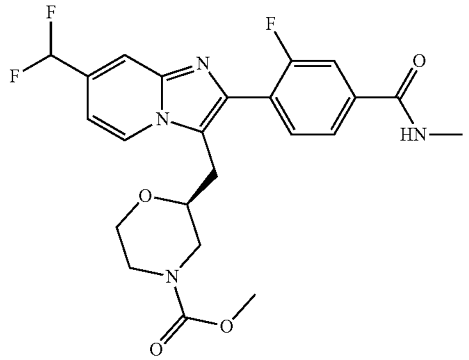

Compound A42 was prepared from 2-amino-4-difluoromethylpyridine, N-Boc-(S)-2-ethynylmorpholine and methyl 3-fluoro-4-formylbenzoate using the procedures described in Example 1, steps 1-5. LCMS (ESI, m/z): 477.3 $[M+H]^+$. $^1H$ NMR (400 MHz, $CDCl_3$) 8.45 (d, J=7.0 Hz, 1H), 7.82-7.72 (m, 2H), 7.70-7.55 (m, 2H), 6.98-6.95 (m, 1H), 6.87-6.53 (m, 1H), 6.35 (s, 1H), 4.09-3.75 (m, 3H), 3.74-3.57 (m, 4H), 3.38-3.37 (m, 1H), 3.16-2.99 (m, 5H), 2.98-2.86 (m, 1H), 2.66 (s, 1H).

Example 39: Synthesis of methyl (S)-2-((7-(difluoromethyl)-2-(2-methyl-4-(methylcarbamoyl)phenyl) imidazo[1,2-a]pyridin-3-yl)methyl)morpholine-4-carboxylate (A43)

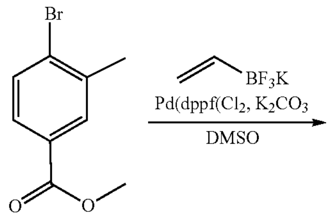

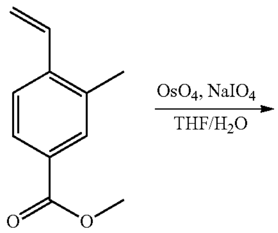

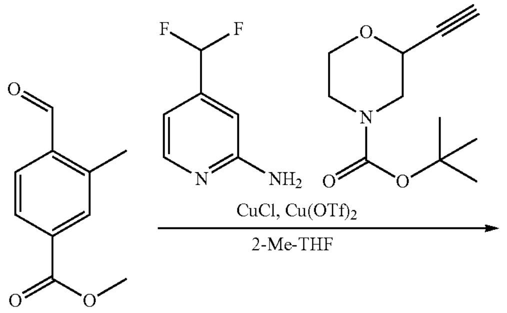

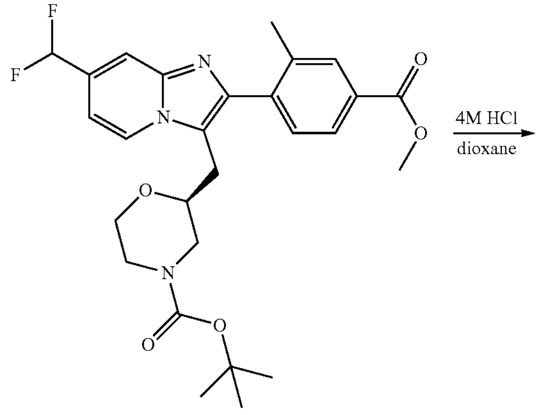

75

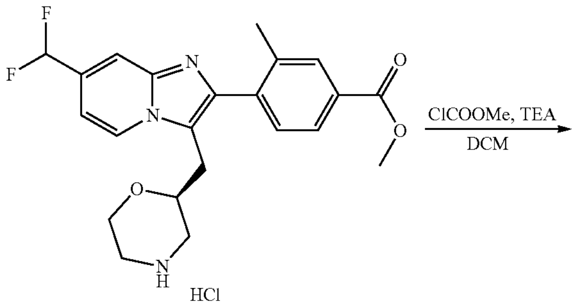

HCl
78

-continued

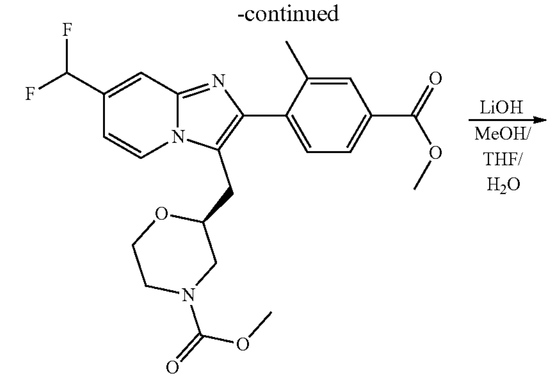

77

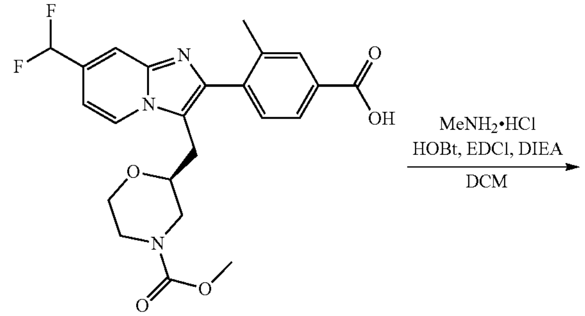

78

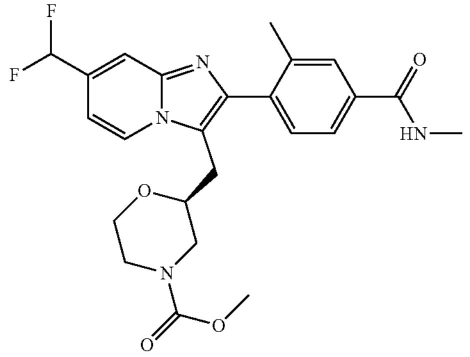

A43

Step 1: To a solution of methyl 4-bromo-3-methylbenzoate (2.00 g, 8.73 mmol) and potassium vinyl trifluoroborate (5.85 g, 43.7 mmol) in DMSO (10 mL) was added $K_2CO_3$ (3.62 g, 26 mmol). The mixture was degassed with $N_2$ and Pd(dppf)$Cl_2$ (319 mg, 0.44 mmol) was added. The mixture was stirred at 80° C. for 16 h under $N_2$, then washed with $H_2O$, extracted with EA (×3) and the combined extracts were dried over $Na_2SO_4$, filtered and concentrated. The residue was purified by silica gel chromatography to afford methyl 3-methyl-4-vinylbenzoate (1.00 g, 64%). LCMS (ESI, m/z): 177.2 $[M+H]^+$. $^1H$ NMR (400 MHz, $CDCl_3$) 7.83-7.82 (m, 2H), 7.52 (d, J=8.6 Hz, 1H), 6.97-6.90 (m, 1H), 5.75-5.71 (m, 1H), 5.41-5.38 (m, 1H), 3.90 (s, 3H), 2.38 (s, 3H).

Step 2: To a mixture of methyl 3-methyl-4-vinylbenzoate (1.00 g, 5.58 mmol) in THF (15 mL) and $H_2O$ (15 mL) was added a solution of $OsO_4$ [2.89 g, 2.5% wt in t-BuOH (prepared by 0.25 g $OsO_4$ dissolved in 9.75 g t-BuOH)]. The mixture was stirred at 25° C. for 0.5 h, then $NaIO_4$ (3.64 g, 17.0 mmol) was added and the mixture was stirred at 25° C. for 16 h. The mixture was added into sat. $Na_2S_2O_3$ solution (120 mL) and extracted with EA (50 mL×3). The combined extract was washed with brine, dried over $Na_2SO_4$, filtered and concentrated. The residue was purified by column chromatography to give methyl 3-methyl-4-formylbenzoate (0.70 g, 67%). LCMS (ESI, m/z): 179.0 $[M+H]^+$. $^1H$ NMR (400 MHz, $CDCl_3$) 10.33 (s, 1H), 7.98-7.96 (m, 1H), 7.92 (s, 1H), 7.85 (d, J=8.2 Hz, 1H), 3.93 (s, 3H), 2.70 (s, 3H).

Steps 3-7: Compound A43 was prepared from 2-amino-4-difluoromethylpyridine, N-Boc-(S)-2-ethynylmorpholine and methyl 3-fluoro-4-formylbenzoate using the procedures described in Example 1, steps 1-5. LCMS (ESI, m/z): 473.4 $[M+H]^+$. $^1H$ NMR (400 MHz, $CDCl_3$) 8.35 (br d, J=7.1 Hz, 1H), 7.73 (s, 2H), 7.63 (br d, J=7.6 Hz, 1H), 7.35 (d, J=7.9 Hz, 1H), 7.00 (d, J=7.5 Hz, 1H), 6.86-6.55 (t, J=56.0 Hz, 1H), 6.24 (br d, J=4.0 Hz, 1H), 3.97-3.74 (m, 3H), 3.68 (s, 3H), 3.52 (br d, J=1.8 Hz, 1H), 3.43-3.31 (m, 1H), 3.05 (d, J=4.9 Hz, 3H), 3.03-2.98 (m, 2H), 2.94-2.82 (m, 1H), 2.54 (br t, J=11.8 Hz, 1H), 2.31 (s, 3H).

Example 40: Synthesis of methyl (S)-2-((7-(difluoromethyl)-2-(5-fluoro-2-methyl-4-(meth-ylcarbamoyl)phenyl)imidazo[1,2-a]pyridin-3-yl)methyl)morpholine-4-carboxylate (A44)

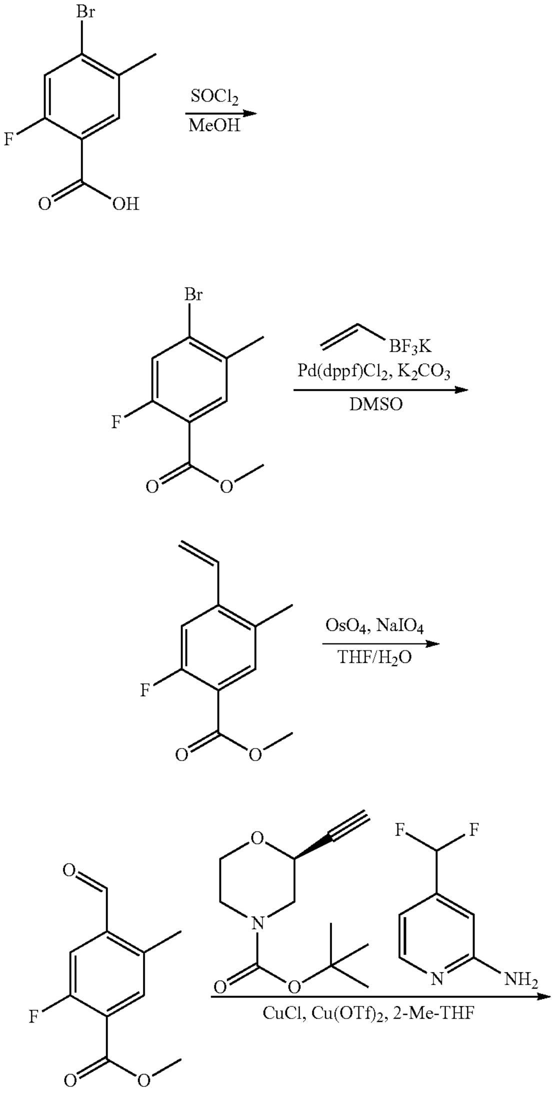

-continued

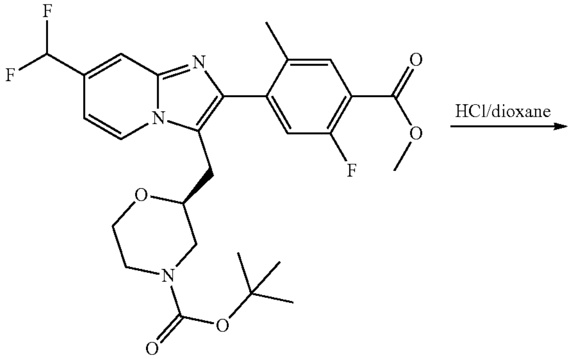

79

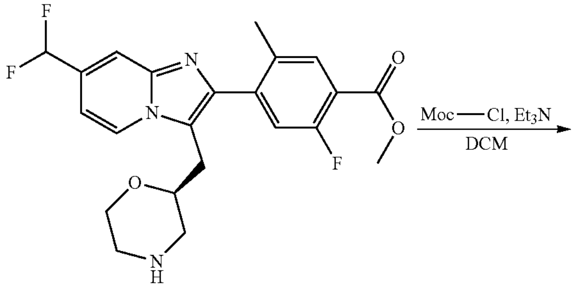

80

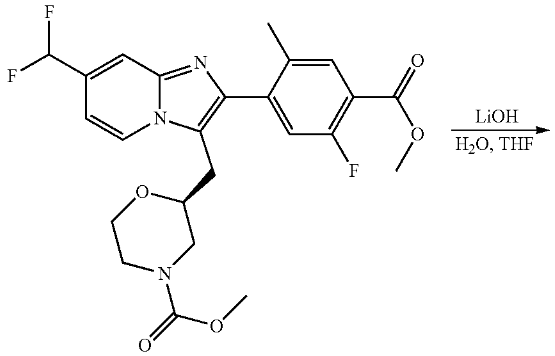

81

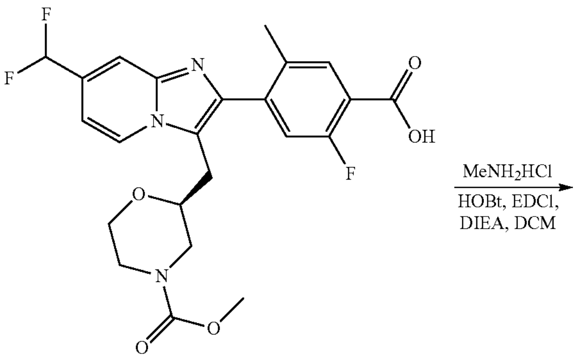

82

-continued

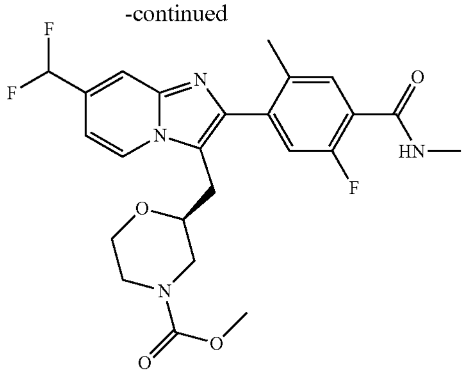

A44

Step 1: To a solution of 4-bromo-2-fluoro-5-methylbenzoic acid (2.00 g, 8.58 mmol) in MeOH (20 mL) was added $SOCl_2$ (43 mmol, 3.1 mL) dropwise at 0° C., and the mixture was stirred at 80° C. for 2 h. The mixture was concentrated, then dissolved with EA (10 mL), and added to $H_2O$ (30 mL) dropwise. The organic layer was separated, dried over $Na_2SO_4$, filtered and concentrated to afford methyl 4-bromo-2-fluoro-5-methylbenzoate (2.0 g, 940%), which was used into next step directly. LCMS (ESI, m/z): 246.9 $[M+H]^+$. $^1$H NMR (400 MHz, $CDCl_3$) 7.86-7.69 (m, 1H), 7.43-7.29 (m, 1H), 4.00-3.81 (m, 3H), 2.38 (d, J=2.8 Hz, 3H).

Step 2: To a solution of methyl 4-bromo-2-fluoro-5-methylbenzoate (2.00 g, 8.10 mmol) and potassium vinyl trifluoroborate (5.42 g, 40.5 mmol) in DMSO (10 mL) was added $K_2CO_3$ (3.36 g, 24.3 mmol). The mixture was purged/degassed with $N_2$ and Pd(dppf)$Cl_2$ (296 mg, 0.40 mmol) was added. The mixture was stirred at 80° C. for 16 h under $N_2$. The mixture was washed with $H_2O$ (100 mL) and extracted with EA (20 mL×3). The combined extracts were dried over $Na_2SO_4$, filtered and concentrated and the residue purified by silica gel chromatography to afford methyl 2-fluoro-5-methyl-4-vinylbenzoate (1.20 g, 76%). LCMS (ESI, m/z): 195.2 $[M+H]^+$. $^1$H NMR (400 MHz, $CDCl_3$) 7.71 (d, J=7.4 Hz, 1H), 7.21 (d, J=12.0 Hz, 1H), 6.89-6.82 (m, 1H), 5.73 (d, J=17.4 Hz, 1H), 5.45 (d, J=11.0 Hz, 1H), 3.91 (s, 3H), 2.32 (s, 3H).

Step 3: To a mixture of methyl 2-fluoro-5-methyl-4-vinylbenzoate (1.20 g, 6.15 mmol) in THE (15 mL) and $H_2O$ (15 mL) was added a solution of $OsO_4$ [3.14 g, 0.31 mmol, 0.05 eq., 2.5% wt in t-BuOH (prepared by 0.25 g $OsO_4$ dissolved in 9.75 g t-BuOH)]. The mixture was stirred at 25° C. for 0.5 h, then $NaIO_4$ (3.96 g, 18.5 mmol, 1.0 mL) was added and the mixture was stirred at 25° C. for 16 h. The mixture was added to sat. $Na_2S_2O_3$ (120 mL) and extracted with EA (30 mL×3). The combined organic layers were washed with brine, dried over $Na_2SO_4$, filtered and concentrated, and the residue was purified by silica gel chromatography to afford methyl 2-fluoro-4-formyl-5-methylbenzoate (1.00 g, 82%). LCMS (ESI, m/z): 197.2 $[M+H]^+$. $^1$H NMR (400 MHz, $CDCl_3$) 10.28 (d, J=1.6 Hz, 1H), 7.82 (d, J=6.6 Hz, 1H), 7.56 (d, J=10.4 Hz, 1H), 3.96 (s, 3H), 2.66 (s, 3H).

Steps 4-8: Compound A44 was prepared from 2-amino-4-difluoromethylpyridine, N-Boc-(S)-2-ethynylmorpholine and methyl 2-fluoro-4-formyl-5-methylbenzoate using the procedures described in Example 1, steps 1-5. LCMS (ESI, m/z): 491.3 $[M+H]^+$. $^1$H NMR (400 MHz, $CDCl_3$) 8.33 (br d, J=7.3 Hz, 1H), 8.05 (d, J=8.0 Hz, 1H), 7.74 (s, 1H), 7.12 (d, J=12.1 Hz, 1H), 7.01 (d, J=6.9 Hz, 1H), 6.83-6.73 (m, 1H), 6.72-6.55 (m, J=55.6 Hz, 1H), 4.00-3.76 (m, 3H), 3.69 (s, 3H), 3.59-3.47 (m, 1H), 3.45-3.31 (m, 1H), 3.08 (d, J=4.6 Hz, 3H), 3.05-2.99 (m, 2H), 2.95-2.84 (m, 1H), 2.57 (br t, J=11.9 Hz, 1H), 2.27 (s, 3H).

Example 41: Synthesis of methyl (S)-2-((7-ethyl-2-(2-fluoro-4-(methylcarbamoyl)phenyl)imidazo[1,2-a]pyridin-3-yl)methyl)morpholine-4-carboxylate (A45)

A45

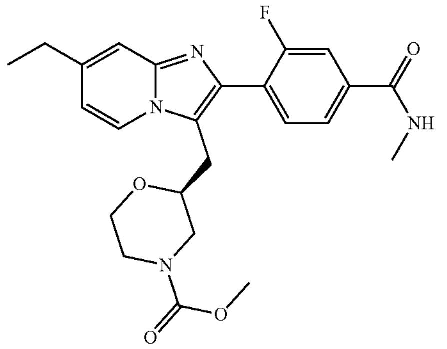

Compound A45 was prepared from methyl 3-fluoro-4-formylbenzoate, N-Boc-(S)-2-ethynylmorpholine, and 2-amino-4-ethylpyridine by the procedures described in Example 1, steps 1-5. LCMS (ESI, m/z): 455.2 $[M+H]^+$. $^1$H NMR (400 MHz, $CDCl_3$) 8.23 (br d, J=6.8 Hz, 1H), 7.77 (t, J=7.6 Hz, 1H), 7.69-7.57 (m, 2H), 7.43 (s, 1H), 6.73 (dd, J=1.4, 7.1 Hz, 1H), 6.51 (br d, J=3.9 Hz, 1H), 4.05-3.75 (m, 3H), 3.69 (s, 3H), 3.67-3.58 (m, 1H), 3.46-3.33 (m, 1H), 3.10-2.99 (m, 5H), 2.98-2.84 (m, 1H), 2.73 (q, J=7.5 Hz, 2H), 2.68-2.53 (m, 1H), 1.31 (t, J=7.6 Hz, 3H).

Example 42: Synthesis of methyl (2S)-2-((2-(2-fluoro-4-(methylcarbamoyl)phenyl)-7-(2,2,2-trifluoro-1-hydroxyethyl)imidazo[1,2-a]pyridin-3-yl)methyl)morpholine-4-carboxylate (A46)

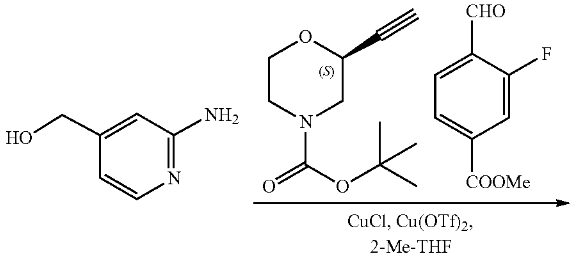

-continued
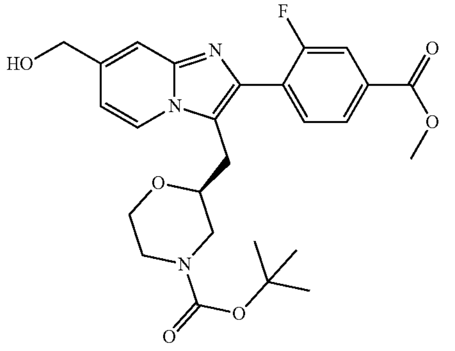
83
MnO2
CHCl3
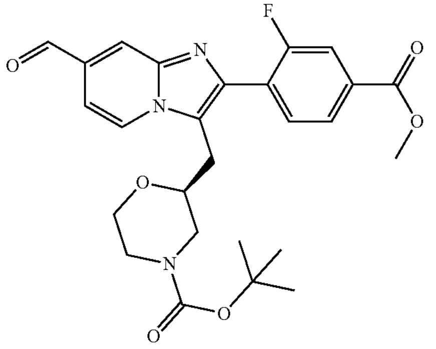
84
TMSCF3
K2CO3, DMF
HCl/dioxane
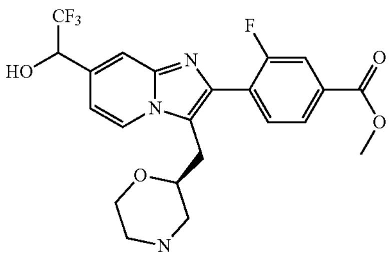
85
Moc—Cl, TEA
DCM
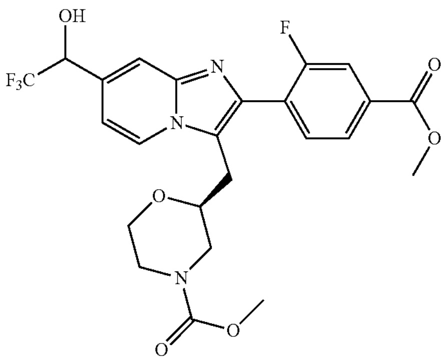
86
LiOH•H2O
H2O/THF
-continued
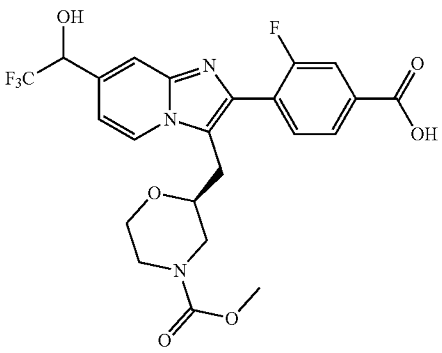
87
MeNH•HCl
EDCl, HOBt
DIEA, DCM
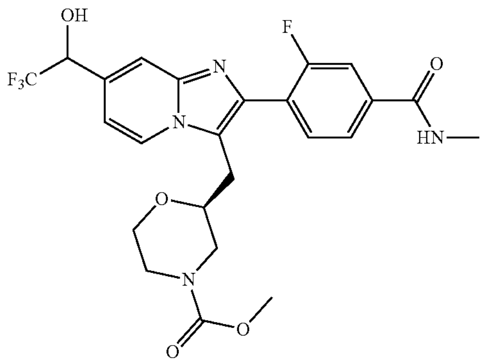
A46
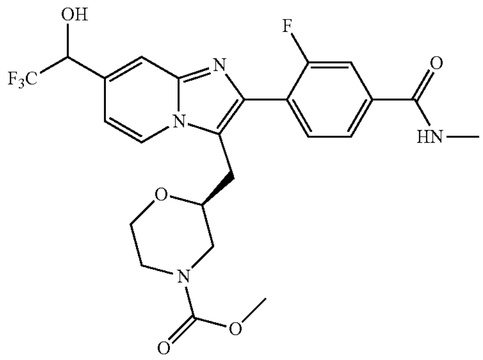
A46
SFC
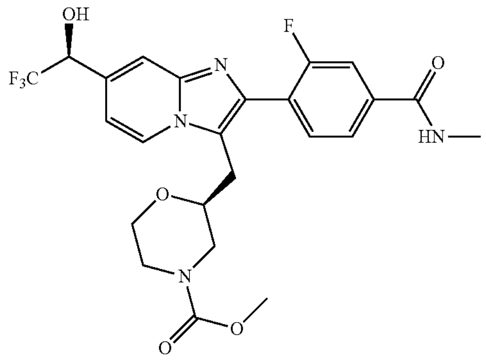
+

-continued

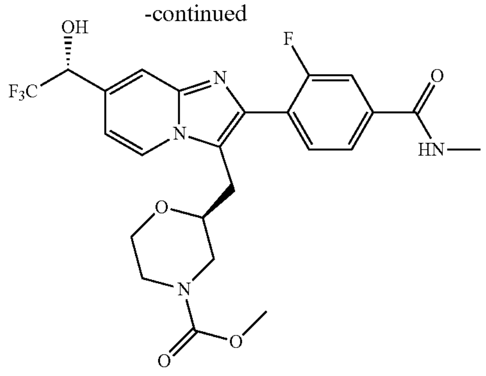

Step 1: 2-Amino-4-hydroxymethylpyridine, N-Boc-(S)-2-ethynylmorpholine and methyl 3-fluoro-4-formylbenzoate were reacted as described in Example 1, step 1, to afford compound 83 (300 mg, 28%) after preparative HPLC. LCMS (ESI, m/z): 500.5 $[M+H]^+$.

Step 2: A mixture of compound 83 (50 mg, 100 μmol) and $MnO_2$ (87 mg, 1.00 mmol) in $CHCl_3$ (1.0 mL) was stirred at 70° C. for 2 h. The mixture was filtered and the filter cake was washed with $CHCl_3$ (3 mL×3). The filtrate was concentrated to obtain compound 84 (200 mg) which was used directly in the next step without further purification. LCMS (ESI, m/z): 498.2 $[M+H]^+$. $^1H$ NMR (400 MHz, $CDCl_3$) 10.02 (s, 1H), 8.44 (br d, J=7.2 Hz, 1H), 8.11 (s, 1H), 7.97 (dd, J=1.5, 8.0 Hz, 1H), 7.91-7.78 (m, 2H), 7.35 (dd, J=1.5, 7.2 Hz, 1H), 3.97 (s, 3H), 3.88-3.73 (m, 2H), 3.66 (dt, J=3.7, 6.9 Hz, 1H), 3.37 (br t, J=11.2 Hz, 1H), 3.19-3.09 (m, 2H), 2.86 (br s, 1H), 2.60 (br t, J=11.1 Hz, 1H), 1.44 (s, 9H).

Step 3: To a solution of compound 84 (200 mg, 402 μmol) in DMF (2.0 mL) was added $K_2CO_3$ (0.5 mg, 4 μmol) and $TMSCF_3$ (171 mg, 1.21 mmol). The mixture was stirred at 25° C. for 3 h. The mixture was diluted with $H_2O$ (20 mL) and extracted with EA (5 mL×3). The combined extract was washed with brine, dried over $Na_2SO_4$, filtered and concentrated. The residue was dissolved in HCl/dioxane (2.0 mL) and the mixture was stirred at 25° C. for 16 h. The mixture was concentrated to obtain compound 85 (200 mg, 99%) as a yellow solid, which was used directly in the next step without further purification. LCMS (ESI, m/z): 468.2 $[M+H]^+$.

Steps 4-6: Compound 85 (200 mg, 397 μmol) was converted to A46 (13 mg) using the procedures described in Example 1, steps 3-5. LCMS (ESI, m/z): 525.2 $[M+H]^+$. $^1H$ NMR (400 MHz, $CDCl_3$) 8.31 (br s, 1H), 7.69-7.53 (m, 4H), 6.97 (br t, J=6.0 Hz, 1H), 6.86-6.75 (m, 1H), 6.50-5.89 (m, 1H), 5.09-4.95 (m, 1H), 4.01-3.75 (m, 3H), 3.61 (br s, 1H), 3.36 (dt, J=2.4, 11.8 Hz, 1H), 3.02 (br d, J=4.0 Hz, 2H), 2.98 (br d, J=4.6 Hz, 3H), 2.91 (br d, J=1.6 Hz, 1H), 2.73-2.57 (m, 1H).

Step 7: Compound A46 was separated into two stereoisomers by SFC (Column: Daicel Chiralcel OD (250×30 mm, 10 micron)), to afford the two products A46 (Peak 1) (4.34 mg) and A46 (Peak 2) (4.28 mg). The stereochemistry was not assigned to the peak order of elution. Individual A46 stereoisomers were isolated, but absolute stereochemistry was not determined.

A46 (Peak 1)

LCMS: 525.2 $[M+H]^+$.

1H NMR (400 MHz, $CDCl_3$) 8.31 (br d, J=5.4 Hz, 1H), 7.70-7.63 (m, 1H), 7.61-7.54 (m, 3H), 6.97 (br d, J=6.9 Hz, 1H), 6.77 (br d, J=1.4 Hz, 1H), 5.01 (q, J=6.7 Hz, 1H), 4.02-3.76 (m, 3H), 3.69 (s, 3H), 3.60 (dt, J=1.5, 2.3 Hz, 1H), 3.42-3.30 (m, 1H), 3.11-2.96 (m, 5H), 2.91 (br d, J=2.4 Hz, 1H), 2.73-2.56 (m, 1H).

A47 (Peak 2)

LCMS: 525.2 $[M+H]^+$.

1H NMR (400 MHz, $CDCl_3$) 8.32 (br dd, J=1.5, 3.8 Hz, 1H), 7.70-7.52 (m, 4H), 6.98 (br d, J=7.3 Hz, 1H), 6.78 (br d, J=1.0 Hz, 1H), 5.07-4.95 (m, 1H), 4.01-3.74 (m, 3H), 3.69 (s, 3H), 3.62 (br d, J=2.9 Hz, 1H), 3.37 (dt, J=2.6, 11.8 Hz, 1H), 3.09-2.96 (m, 5H), 2.95-2.84 (m, 1H), 2.73-2.56 (m, 1H).

Example 43: Synthesis of methyl (2S)-2-((2-(2-fluoro-4-(methylcarbamoyl)phenyl)-7-(methylsulfinyl)imidazo[1,2-a]pyridin-3-yl)methyl)morpholine-4-carboxylate (A47) and methyl (S)-2-((2-(2-fluoro-4-(methylcarbamoyl)phenyl)-7-(methylsulfonyl)imidazo[1,2-a]-pyridin-3-yl)methyl)morpholine-4-carboxylate (A48)

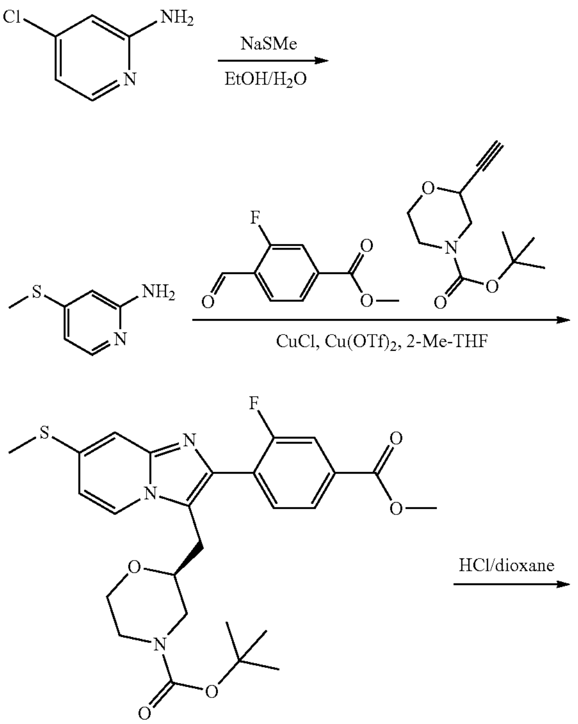

88

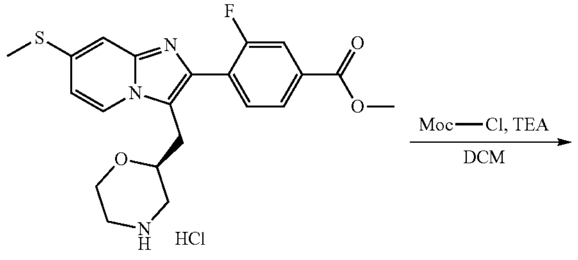

89

-continued

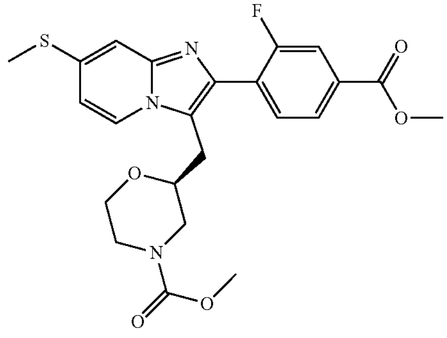

90

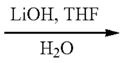

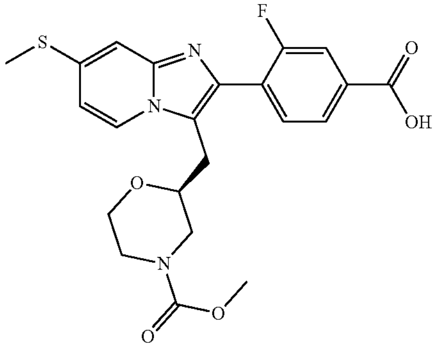

91

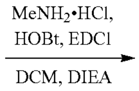

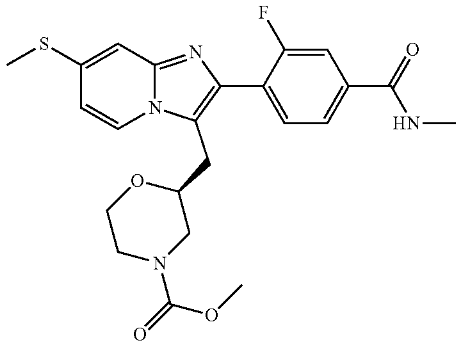

92

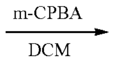

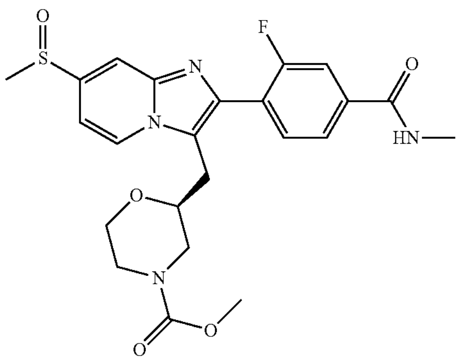

A47

+

-continued

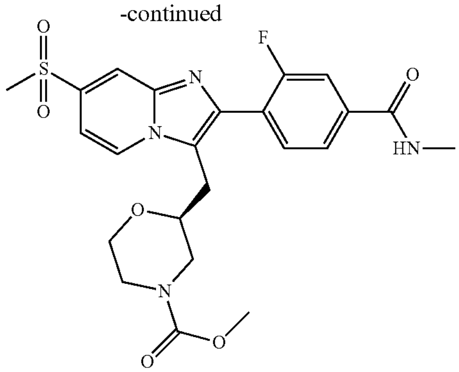

A48

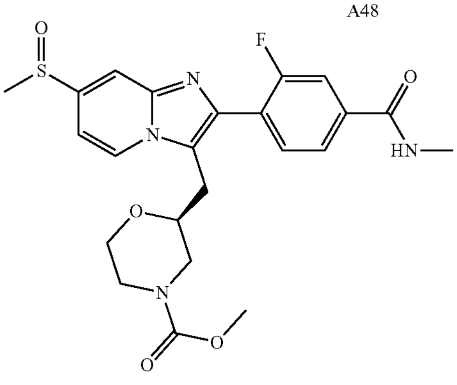

A47

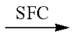

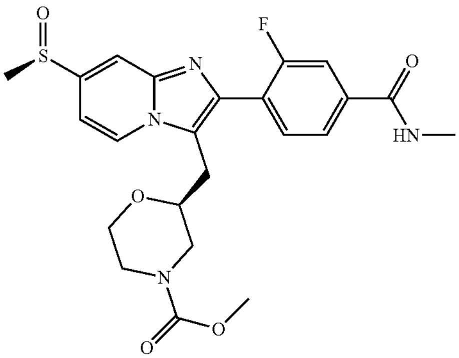

+

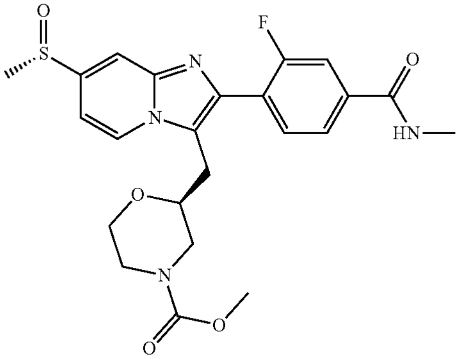

Step 1: A mixture of 4-chloro-2-aminopyridine (3.00 g, 23.3 mmol) and NaSMe (4.91 g, 70 mmol) in EtOH (37 mL) and $H_2d$ (9 mL) was stirred at 140° C. for 18 h in a sealed tube. The mixture was diluted with water (150 mL) and adjusted to pH=3 with aq. HCl (2 M). The mixture was extracted with DCM (30 mL) and the organic layer discarded. The aqueous layer was adjusted to pH=8 with sat. $NaHCO_3$. The mixture was extracted with DCM (50 mL×3). The organic layer was dried over $Na_2SO_4$, filtered and concentrated and the residue triturated with 5:1 PE/EA (20 mL) to reveal 4-(methylthio)-2-aminopyridine (2.8 g, 85%). LCMS (ESI, m/z): 141.3 $[M+H]^+$. $^1H$ NMR (400 MHz, $CDCl_3$) 7.88 (d, J=5.5 Hz, 1H), 6.50 (br d, J=4.5 Hz, 1H), 6.29 (s, 1H), 4.43 (br s, 2H), 2.43 (s, 3H).

Step 2: Methyl 3-fluoro-4-formylbenzoate (341 mg, 1.87 mmol), 4-(methylthio)-2-aminopyridine (250 mg, 1.78 mmol) and N-Boc-(S)-2-ethynylmorpholine (396 mg, 1.87 mmol) in 2-Me-THE (12 mL) were reacted as described in Example 1, step 1, to afford compound 88 (330 mg, 36%). LCMS (ESI, m/z): 516.1 $[M+H]^+$. $^1H$ NMR (400 MHz, $CDCl_3$) 8.21 (d, J=7.5 Hz, 1H), 7.94 (dd, J=1.5, 8.0 Hz, 1H), 7.88-7.78 (m, 2H), 7.30 (d, J=1.5 Hz, 1H), 6.69 (dd, J=1.8, 7.3 Hz, 1H), 3.97 (s, 3H), 3.91-3.74 (m, 3H), 3.68-3.57 (m, 1H), 3.45-3.33 (m, 1H), 3.13-2.98 (m, 2H), 2.94-2.77 (m, 1H), 2.63-2.53 (m, 4H), 1.44 (s, 9H).

Steps 3-6: Compound 92 (160 mg) was prepared from compound 88 using the procedures described in Example 1, steps 2-5. LCMS (ESI, m/z): 473.2 $[M+H]^+$. $^1H$ NMR (400 MHz, $CDCl_3$) 8.19 (br d, J=7.7 Hz, 1H), 7.79 (t, J=7.7 Hz, 1H), 7.70-7.57 (m, 2H), 7.29 (d, J=1.5 Hz, 1H), 6.69 (dd, J=1.8, 7.3 Hz, 1H), 6.31-6.24 (m, 1H), 4.02-3.77 (m, 3H), 3.70 (s, 3H), 3.64 (dt, J=4.2, 6.8 Hz, 1H), 3.46-3.34 (m, 1H), 3.06 (d, J=4.9 Hz, 4H), 2.98-2.84 (m, 1H), 2.71-2.59 (m, 1H), 2.55 (s, 3H), 2.41-2.33 (m, 2H), 2.25 (s, 5H).

Step 7: To a solution of compound 92 (110 mg, 233 μmol) in DCM (3.5 mL) was added a solution of m-CPBA (61.4 mg, 303 μmol, 85% purity) in DCM (0.5 mL) at 0° C. Then the reaction was stirred at 20° C. for 1 h. The mixture was quenched by sat. $NaHCO_3$ (30 mL) and extracted with EA (10 mL×3). The residue was purified by prep-HPLC and the eluted fractions lyophilized. Two products were isolated: product A47 (60 mg, 53%), and compound A48 (6.1 mg, 5%). Compound A47 was further separated into two diastereomers by preparative SFC to afford A47 (Peak 1) (22.4 mg, 37%) and A47 (Peak 2) (23.3 mg, 39%). Individual A47 diastereomers were isolated, but absolute stereochemistry was not determined.

A47 (Peak 1):

LCMS (ESI, m/z): 489.2 $[M+H]^+$.

$^1H$ NMR: (400 MHz, $CDCl_3$) 8.55 (br d, J=7.2 Hz, 1H), 7.92 (d, J=5.6 Hz, 1H), 7.77 (t, J=7.6 Hz, 1H), 7.71-7.60 (m, 2H), 7.15-7.07 (m, 1H), 6.37 (br d, J=4.6 Hz, 1H), 4.08-3.77 (m, 3H), 3.73-3.63 (m, 4H), 3.40 (br t, J=12.1 Hz, 1H), 3.17-3.08 (m, 2H), 3.06 (d, J=4.9 Hz, 3H), 3.00-2.87 (m, 1H), 2.82 (s, 3H), 2.76-2.61 (m, 1H).

A47 (Peak 2):

LCMS (ESI, m/z): 489.2 $[M+H]^+$.

$^1H$ NMR: (400 MHz, $CDCl_3$) 8.61-8.46 (m, 1H), 7.91 (s, 1H), 7.78 (t, J=7.6 Hz, 1H), 7.71-7.59 (m, 2H), 7.12 (dd, J=1.6, 7.3 Hz, 1H), 6.30 (br d, J=4.6 Hz, 1H), 4.07-3.76 (m, 3H), 3.71 (s, 3H), 3.69-3.64 (m, 1H), 3.46-3.35 (m, 1H), 3.10 (br d, J=8.1 Hz, 2H), 3.07 (d, J=4.9 Hz, 3H), 3.00-2.89 (m, 1H), 2.82 (s, 3H), 2.77-2.60 (m, 1H).

A48:

LCMS (ESI, m/z): 505.4 $[M+H]^+$.

$^1H$ NMR: (400 MHz, $CDCl_3$) 8.57 (br d, J=6.9 Hz, 1H), 8.29 (dd, J=0.8, 1.8 Hz, 1H), 7.79 (t, J=7.6 Hz, 1H), 7.73-7.60 (m, 2H), 7.29 (d, J=1.9 Hz, 1H), 6.26-6.18 (m, 1H), 4.10-3.77 (m, 3H), 3.75-3.65 (m, 4H), 3.46-3.34 (m, 1H), 3.19-3.10 (m, 5H), 3.07 (d, J=4.9 Hz, 3H), 3.01-2.88 (m, 1H), 2.80-2.58 (m, 1H).

Example 44: Synthesis of methyl (S)-2-((2-(2-fluoro-4-(methylcarbamoyl)phenyl)-7-(fluoromethyl)imidazo[1,2-a]pyridin-3-yl)methyl)morpholine-4-carboxylate (A49)

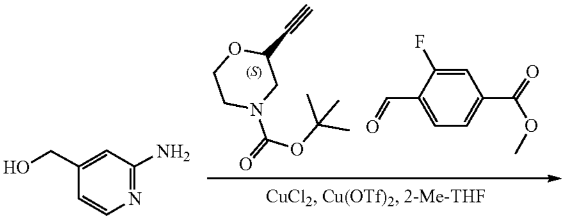

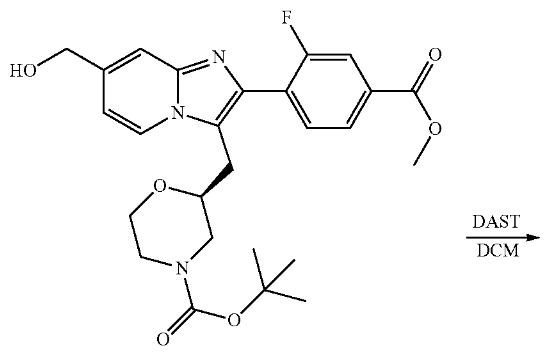

93

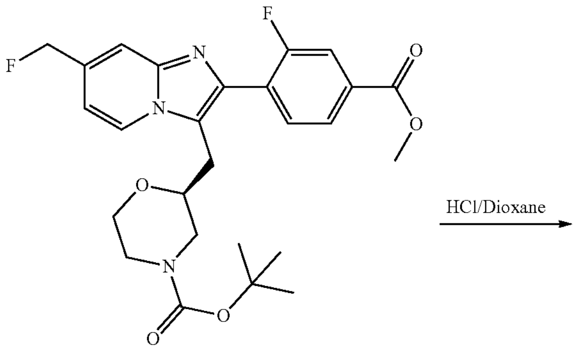

94

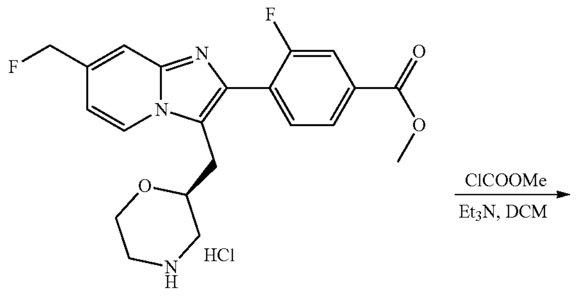

95

-continued

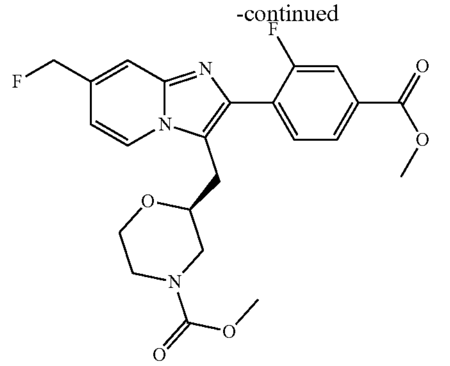

96

LiOH

THF, $H_2O$

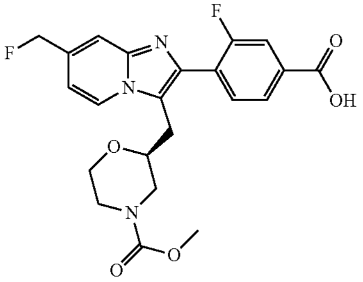

97

$MeNH_2$•HCl

EDCl, HOBT, DIPEA

DCM

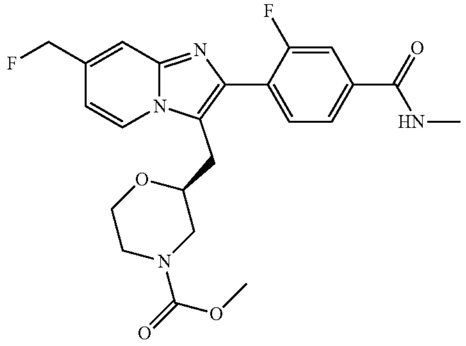

A49

Step 1: 4-Hydroxymethyl-2-aminopyridine (600 mg, 4.83 mmol), N-Boc-(S)-2-ethynylmorpholine (1.07 g, 5.07 mmol), and methyl 3-fluoro-4-formylbenzoate (924 mg, 5.07 mmol) were reacted as described in General Method 1 to afford compound 93 (720 mg, 25%). LCMS (ESI, m/z): 500.3 $[M+H]^+$.

Step 2: To a solution of compound 93 (300 mg, 0.60 mmol) in DCM (10 mL) was added DAST (145 mg, 0.90 mmol, 0.1 mL) at 0° C. and the mixture was stirred at 0° C. for 2 h. The mixture was poured into ice (20 g) and separated. The aqueous phase was extracted with DCM (10 mL×2). The combined organic layers were washed with brine, dried over $Na_2SO_4$, filtered and concentrated and the residue was purified by column chromatography to afford compound 94 (130 mg, 39%). LCMS (ESI, m/z): 502.1 $[M+H]^+$.

Steps 3-6: Compound A49 (32 mg) was prepared from compound 94 using the procedures described in Example 1, steps 2-5. LCMS (ESI, m/z): 459.4 $[M+H]^+$. $^1H$ NMR (400 MHz, $CDCl_3$) 8.36 (d, J=6.8 Hz, 1H), 7.74-7.71 (m, 1H), 7.67-7.50 (m, 3H), 6.85-6.83 (m, 1H), 6.66 (d, J=4.4 Hz, 1H), 5.49 (s, 1H), 5.37 (s, 1H), 4.07-3.73 (m, 3H), 3.72-3.55 (m, 4H), 3.37-3.36 (m, 1H), 3.12-2.99 (m, 5H), 2.92 (d, J=10.8 Hz, 1H), 2.64 (s, 1H).

Example 45: Synthesis of methyl (S)-2-((2-(2-fluoro-4-(methylcarbamoyl)phenyl)-7-(methyl-d3) imidazo[1,2-a]pyridin-3-yl)methyl)morpholine-4-carboxylate (A50)

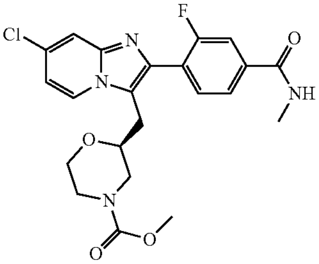

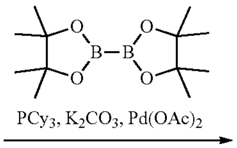

$PCy_3$, $K_2CO_3$, $Pd(OAc)_2$ dioxane

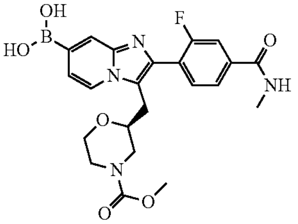

98

$CD_3I$ $Pd(dppf)Cl_2$•$CH_2Cl_2$, $K_3PO_4$

DMF

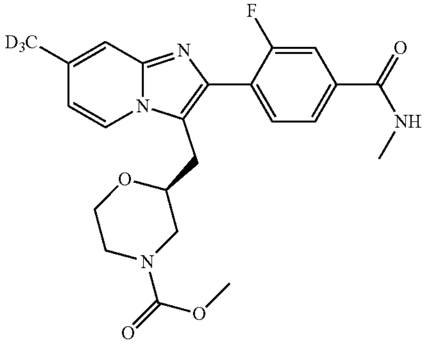

A50

Step 1: To a degassed ($N_2$ bubbling) solution of compound A11 (20 mg, 43 μmol) in dioxane (1.0 mL) was added bis-(pinacolato)diboron (55 mg, 217 μmol), $PCy_3$ (1 mg, 4 μmol), $K_2CO_3$ (18 mg, 130 μmol) and $Pd(OAc)_2$ (2 mg, 9 μmol) under $N_2$. The mixture was stirred at 110° C. for 12 h. The mixture was filtered, and the filter cake was washed with MeOH (2.0 mL×3). The combined filtrate was concentrated. The crude product compound 98 (20 mg) was used directly in the next step without further purification. LCMS (ESI, m/z): 471.4 $[M+H]^+$.

Step 2: To a mixture of compound 98 (20 mg) and trideuterio(iodo)methane (85 μmol, 5.3 uL) in DMF (1.0 mL) was added 2 M $K_3PO_4$ (85 μL) and Pd(dppf) $Cl_2$·$CH_2Cl_2$ (4 mg) under $N_2$. The mixture was stirred at 100° C. for 12 h under $N_2$. The mixture was diluted with $H_2O$ (10 mL) and extracted with EA (4.0 mL×3). The combined extracts were washed with brine, dried over $Na_2SO_4$, filtered and concentrated to obtain crude A50 (20 mg) as a dark oil. The product was purified by preparative HPLC to afford A50 (1.9 mg, 8%). LCMS (ESI, m/z): 444.1 $[M+H]^+$. $^1H$ NMR (400 MHz, $CDCl_3$) 8.26-8.14 (m, 1H), 7.82-7.75 (m, 1H), 7.68-7.57 (m, 2H), 7.41 (s, 1H), 6.69 (dd, J=1.4, 7.2 Hz, 1H), 6.36-6.19 (m, 1H), 3.96-3.78 (m, 3H), 3.71-3.68 (m, 3H), 3.66-3.59 (m, 1H), 3.47-3.36 (m, 1H), 3.10-3.03 (m, 5H), 3.00-2.85 (m, 1H), 2.71-2.61 (m, 1H).

Example 46: Synthesis of methyl (S)-2-((7-cyclopropyl-2-(2-fluoro-4-(methylcarbamoyl)-phenyl) imidazo[1,2-a]pyridin-3-yl)methyl)morpholine-4-carboxylate (A52)

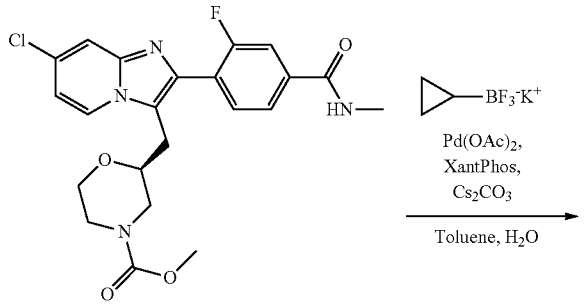

A11

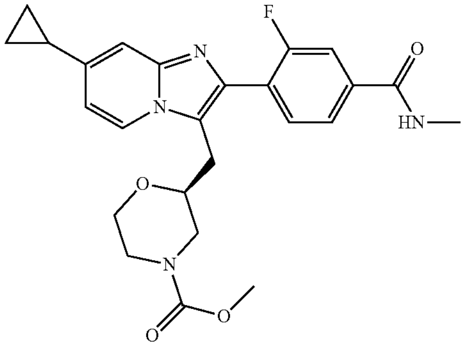

A52

In a Schlenk tube containing $Pd(OAc)_2$ (0.19 mg, 0.9 μmol), XantPhos (1.00 mg, 1.74 μmol), potassium cyclopropyltrifluoroborate (6.49 mg, 44 μmol) and $Cs_2CO_3$ (42.4 mg, 130 μmol) was added compound A11 (20 mg, 40 μmol) in toluene (0.9 mL) and $H_2O$ (0.1 mL). The mixture was stirred at 120° C. for 16 h under $N_2$. The mixture was filtered, and the filtrate was washed with $H_2O$ (5.0 mL), extracted with EA (2.0 mL×3). The combined organic layers were dried over $Na_2SO_4$, filtered and concentrated. The residue was purified by flash silica gel chromatography and further purified by preparative HPLC to afford A52 (4.87 mg, 23%). LCMS (ESI, m/z): 467.3 $[M+H]^+$. $^1H$ NMR (400 MHz, $CDCl_3$) 8.48-8.24 (m, 1H), 7.91-7.56 (m, 4H), 7.18-6.80 (m, 1H), 6.76 (d, J=7.2 Hz, 1H), 4.12-3.83 (m, 2H), 3.83-3.76 (m, 1H), 3.69 (s, 4H), 3.38-3.37 (m, 1H), 3.09-2.99 (m, 5H), 2.96-2.86 (m, 1H), 2.73-2.61 (m, 1H), 2.08-1.96 (m, 1H), 1.22-1.00 (m, 2H), 0.96-0.72 (m, 2H).

Example 47: Synthesis of methyl (2S)-2-((2-(2-fluoro-4-(methylsulfinyl)phenyl)-7-methyl-imidazo[1,2-a]pyridin-3-yl)methyl)morpholine-4-carboxylate (A58) and methyl (S)-2-((2-(2-fluoro-4-(methylsulfonyl)phenyl)-7-methylimidazo[1,2-a]pyridin-3-yl)methyl)morpholine-4-carboxylate (A61)

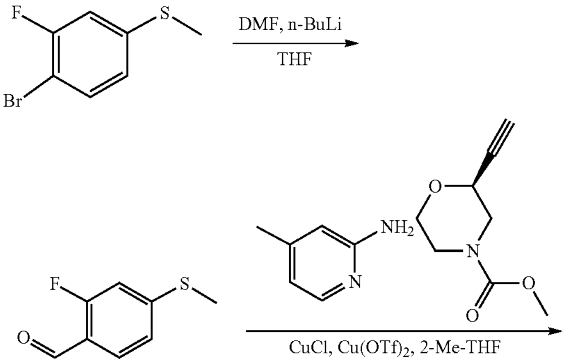

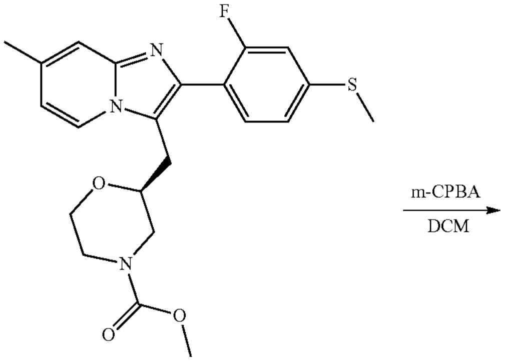

99

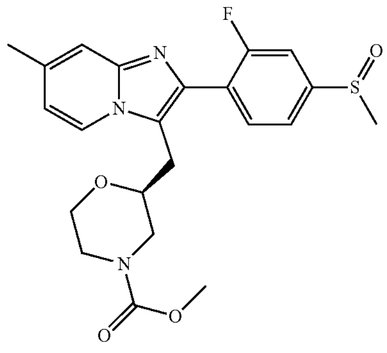

+

A58

-continued

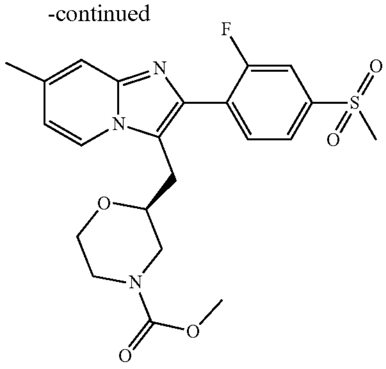

A61

Step 1: (4-Bromo-3-fluorophenyl)(methyl)sulfane (700 mg, 3.17 mmol) was reacted according to the procedure described in Example 6, step 1, to afford 2-fluoro-4-(methylthio)benzaldehyde (400 mg, 66%). LCMS (ESI, m/z): 171.2 $[M+H]^+$. $^1$H NMR (400 MHz, $CDCl_3$) 10.24 (s, 1H), 7.76-7.73 (m, 1H), 7.07-7.05 (m, 1H), 6.96-6.93 (m, 1H), 2.52 (s, 3H).

Step 2: N-Boc-(S)-2-ethynylmorpholine, 4-methyl-2-aminopyridine and 2-fluoro-4-(methylthio)benzaldehyde were reacted according to the procedure described in Example 1, step 1, to afford compound 99 (300 mg, 35%). LCMS (ESI, m/z): 430.2 $[M+H]^+$. $^1$H NMR (400 MHz, $CDCl_3$) 8.17 (d, J=7.2 Hz, 1H), 7.61-7.57 (m, 1H), 7.35 (s, 1H), 7.12-7.10 (m, 1H), 7.045-7.04 (m, 1H), 6.63-6.61 (m, 1H), 4.05-3.77 (m, 3H), 3.71-3.57 (m, 4H), 3.39-3.36 (m, 1H), 3.07-2.99 (m, 2H), 2.97-2.84 (m, 1H), 2.63-2.60 (m, 1H), 2.53 (s, 3H), 2.40 (s, 3H).

Step 3: To a solution of compound 99 (100 mg, 0.23 mmol) in DCM (3.5 mL) was added m-CPBA (37 mg, 0.18 mmol, 85% purity) in DCM (0.5 mL) at 0° C. The reaction mixture was stirred at 20° C. for 1 h. The mixture was washed with $H_2O$ (5 mL), extracted with DCM (3 mL×3). The combined organic layers were dried over $Na_2SO_4$, filtered and concentrated. The crude product was purified by preparative HPLC to afford compounds A58 (15.2 mg) and A61 (6.4 mg).

A58:

LCMS (ESI, m/z): 446.2 $[M+H]^+$.

$^1$H NMR: (400 MHz, $CDCl_3$) 8.62-8.42 (m, 1H), 8.16-7.99 (m, 2H), 7.80-7.63 (m, 1H), 7.61-7.48 (m, 1H), 7.08 (d, J=7.0 Hz, 1H), 4.11-3.76 (m, 3H), 3.75-3.62 (m, 4H), 3.50-3.32 (m, 1H), 3.08 (d, J=7.8 Hz, 2H), 3.01-2.87 (m, 1H), 2.83 (d, J=1.8 Hz, 3H), 2.78-2.65 (m, 1H), 2.56 (s, 3H).

A61:

LCMS (ESI, m/z): 462.2 $[M+H]^+$.

$^1$H NMR: (400 MHz, $CDCl_3$) 8.50 (s, 1H), 8.18-8.15 (m, 1H), 8.08 (s, 1H), 7.96 (d, J=8.2 Hz, 1H), 7.86-7.84 (m, 1H), 7.10 (d, J=6.8 Hz, 1H), 4.10-3.76 (m, 3H), 3.72 (s, 3H), 3.69-3.66 (m, 1H), 3.46-3.31 (m, 1H), 3.15 (s, 3H), 3.07 (d, J=4.4 Hz, 2H), 3.00-2.88 (m, 1H), 2.72 (d, J=9.2 Hz, 1H), 2.57 (s, 3H).

Example 48: Synthesis of methyl (2S)-2-((2-(2-fluoro-4-(S-methylsulfonimidoyl)phenyl)-7-methylimidazo[1,2-a]pyridin-3-yl)methyl)morpholine-4-carboxylate (A59)

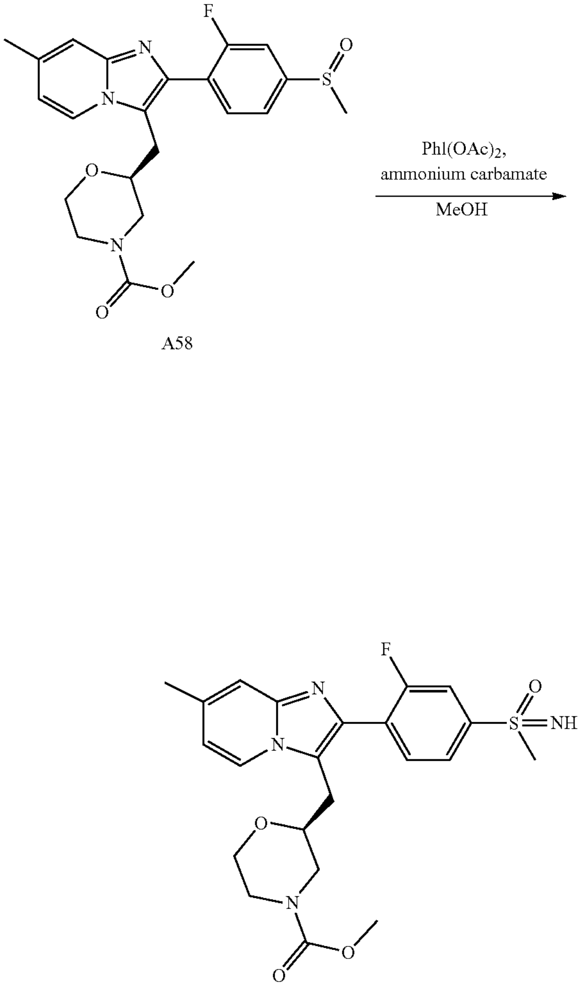

A58

A59

To a mixture of compound A58 (60 mg, 0.13 mmol), $PhI(OAc)_2$ (125 mg, 0.39 mmol) and ammonium carbamate (40 mg, 0.52 mmol) was added MeOH (0.3 mL). The mixture was stirred at 30° C. for 0.5 h. The reaction mixture was purified by preparative HPLC to afford A59 (31.0 mg). LCMS (ESI, m/z): 461.1 $[M+H]^+$. $^1$H NMR (400 MHz, $CDCl_3$) 8.24 (d, J=6.8 Hz, 1H), 8.00-7.94 (m, 1H), 7.93-7.87 (m, 1H), 7.85-7.83 (m, 1H), 7.46 (s, 1H), 6.73 (d, J=6.8 Hz, 1H), 4.05-3.76 (m, 3H), 3.69 (s, 3H), 3.66-3.57 (m, 1H), 3.39-3.38 (m, 1H), 3.17 (s, 3H), 3.06 (d, J=5.6 Hz, 2H), 3.00-2.85 (m, 1H), 2.82-2.59 (m, 2H), 2.44 (s, 3H).

Example 49: Synthesis of methyl (S)-2-((7-ethyl-2-(2-fluoro-4-(methylcarbamoyl)phenyl)imidazo[1,2-a]pyridin-3-yl)methyl)morpholine-4-carboxylate (A63)

A63

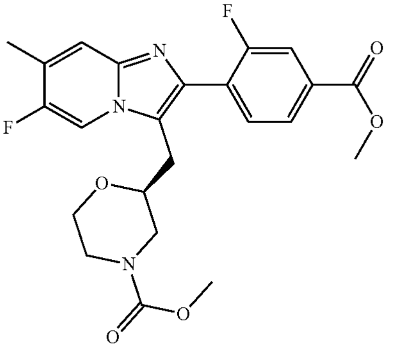

Compound A63 was prepared from methyl 3-fluoro-4-formylbenzoate, N-Boc-(S)-2-ethynylmorpholine and 2-amino-4-methyl-5-fluoropyridine by the procedures described in Example 1, steps 1, 4 and 5. LCMS (ESI, m/z): 459.3 $[M+H]^+$. $^1H$ NMR (400 MHz, $CDCl_3$) 8.28 (d, J=4.6 Hz, 1H), 7.77-7.73 (m, 1H), 7.67-7.55 (m, 2H), 7.41 (d, J=7.0 Hz, 1H), 6.31 (d, J=4.3 Hz, 1H), 4.02-3.76 (m, 3H), 3.69 (s, 3H), 3.65-3.64 (m, 1H), 3.55-3.34 (m, 1H), 3.09-2.90 (m, 6H), 2.65 (d, J=3.2 Hz, 1H), 2.39 (s, 3H).

Example 50: Synthesis of methyl (S)-2-((7-chloro-2-(4-(dimethylcarbamoyl)-2-fluoro-phenyl)imidazo[1,2-a]pyridin-3-yl)methyl)morpholine-4-carboxylate (A65)

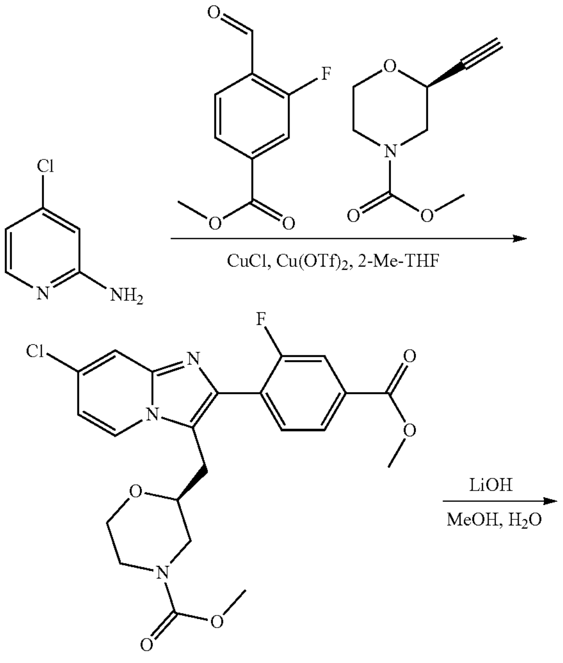

104

-continued

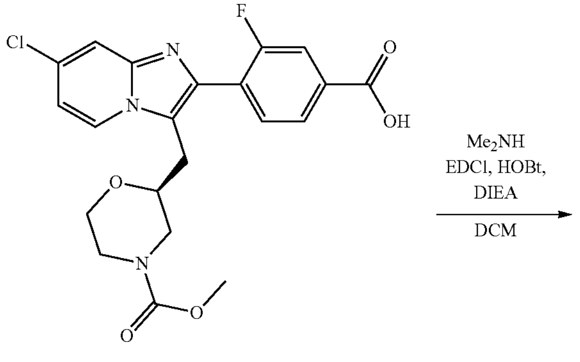

105

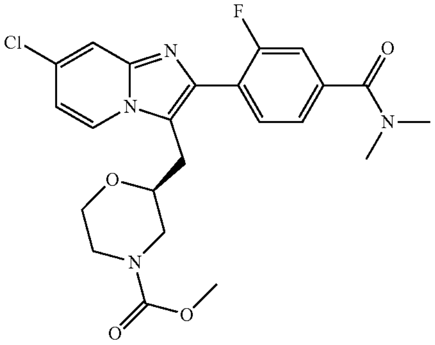

A65

Step 1: 4-Chloro-2-aminopyridine (1.10 g, 8.56 mmol), N-Moc-(S)-2-ethynylmorpholine (1.52 g, 8.98 mmol), and methyl 3-fluoro-4-formylbenzoate (1.64 g, 8.98 mmol) were reacted as described in Example 1 Step 1 to afford compound 104 (800 mg, 18%). LCMS (ESI, m/z): 462.4. $^1H$ NMR (400 MHz, $CDCl_3$) 8.31 (d, J=7.3 Hz, 1H), 7.95-7.92 (m, 1H), 7.86-7.84 (m, 1H), 7.79-7.78 (m, 1H), 7.63-7.59 (m, 1H), 6.82-6.79 (m, 1H), 3.96 (s, 3H), 3.86-3.76 (m, 2H), 3.72-3.60 (m, 5H), 3.41-3.39 (m, 1H), 3.11-2.98 (m, 2H), 2.97-2.84 (m, 1H), 2.73-2.58 (m, 1H).

Step 2 was performed as described in Example 1, Step 4 to afford compound 105. LCMS (ESI, m/z): 448.2. $^1H$ NMR (400 MHz, d6-DMSO) 14.05-12.72 (m, 1H), 8.75 (d, J=7.6 Hz, 1H), 7.92-7.89 (m, 2H), 7.88-7.79 (m, 2H), 7.30 (d, J=7.2 Hz, 1H), 3.87 (d, J=12.6 Hz, 1H), 3.80-3.74 (m, 1H), 3.71-3.63 (m, 2H), 3.58 (s, 4H), 3.31-3.10 (m, 3H), 2.95-2.70 (m, 1H).

Step 3: Compound A65 was prepared from 105 using the procedure described in Example 1, Step 5. LCMS (ESI, m/z): 475.3. $^1H$ NMR (400 MHz, $CDCl_3$) 8.33 (d, J=7.2 Hz, 1H), 7.73-7.71 (m, 1H), 7.64 (s, 1H), 7.36-7.26 (m, 2H), 6.83-6.81 (m, 1H), 4.02-3.77 (m, 3H), 3.70 (s, 3H), 3.65 (s, 1H), 3.39-3.36 (m, 1H), 3.14 (s, 3H), 3.06-2.82 (m, 6H), 2.69 (d, J=10.8 Hz, 1H).

Example 51: Synthesis of methyl (S)-2-((7-chloro-2-(4-(ethyl(methyl)carbamoyl)-2-fluoro-phenyl)imidazo[1,2-a]pyridin-3-yl)methyl)morpholine-4-carboxylate (A66)

A66

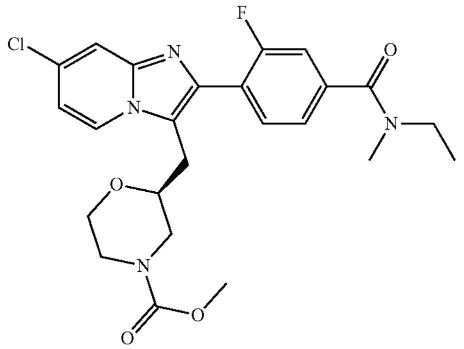

Compound A66 was prepared from compound 105 using the procedures described in Example 50. LCMS (ESI, m/z): 489.3. $^1$H NMR (400 MHz, $CDCl_3$) 8.31 (d, J=7.2 Hz, 1H), 7.73-7.69 (m, 1H), 7.59 (d, J=1.6 Hz, 1H), 7.29 (d, J=7.8 Hz, 1H), 7.23 (s, 1H), 6.81-6.79 (m, 1H), 4.12-3.77 (m, 3H), 3.70 (s, 3H), 3.68-3.53 (m, 2H), 3.45-3.29 (m, 2H), 3.15-2.86 (m, 6H), 2.75-2.61 (m, 1H), 1.30-1.13 (m, 3H).

Example 52: Synthesis of methyl (S)-2-((7-chloro-2-(2-fluoro-4-(pyrrolidine-1-carbonyl)-phenyl)imidazo[1,2-a]pyridin-3-yl)methyl)morpholine-4-carboxylate (A67)

A67

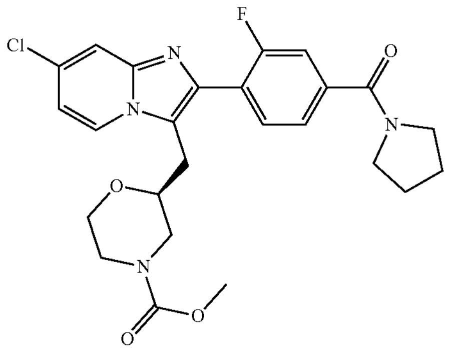

Compound A67 was prepared from compound 105 using the procedures described in Example 50. LCMS (ESI, m/z): 501.2. $^1$H NMR (400 MHz, $CDCl_3$) 8.31 (d, J=7.2 Hz, 1H), 7.73-7.71 (m, 1H), 7.60 (d, J=1.8 Hz, 1H), 7.45-7.34 (m, 2H), 6.81-6.78 (m, 1H), 4.11-3.76 (m, 3H), 3.70 (s, 3H), 3.69-3.65 (m, 3H), 3.49-3.46 (m, 2H), 3.44-3.35 (m, 1H), 3.12-2.84 (m, 3H), 2.75-2.60 (m, 1H), 2.02-1.90 (m, 4H).

Example 53: Synthesis of methyl (S)-2-((7-chloro-2-(2-fluoro-4-((S)-3-hydroxypyrrolidine-1-carbonyl)phenyl)imidazo[1,2-a]pyridin-3-yl)methyl)morpholine-4-carboxylate (A68)

A68

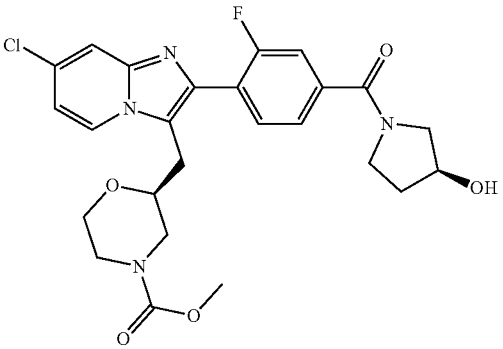

Compound A68 was prepared from compound 105 using the procedures described in Example 50. LCMS (ESI, m/z): 517.3. H NMR (400 MHz, $CDCl_3$) 8.41-8.17 (m, 1H), 7.73-7.69 (m, 1H), 7.60 (s, 1H), 7.48-7.35 (m, 2H), 6.81 (d, J=7.4 Hz, 1H), 4.67-4.43 (m, 1H), 3.99-3.74 (m, 5H), 3.72-3.60 (m, 5H), 3.54-3.33 (m, 2H), 3.17-2.97 (m, 2H), 2.96-2.81 (m, 1H), 2.78-2.57 (m, 1H), 2.43 (s, 1H), 2.13-1.99 (m, 2H).

Example 54: Synthesis of methyl (S)-2-((7-chloro-2-(2-fluoro-4-((R)-3-hydroxypyrrolidine-1-carbonyl)phenyl)imidazo[1,2-a]pyridin-3-yl)methyl)morpholine-4-carboxylate (A69)

A69

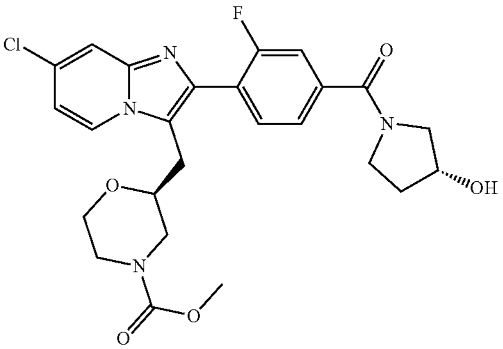

Compound A69 was prepared from compound 105 using the procedures described in Example 50. LCMS (ESI, m/z): 517.3. H NMR (400 MHz, $CDCl_3$) 8.34 (d, J=6.4 Hz, 1H), 7.75-7.69 (m, 1H), 7.65 (s, 1H), 7.51-7.34 (m, 2H), 6.83 (d, J=7.2 Hz, 1H), 4.67-4.45 (m, 1H), 3.92-3.75 (m, 5H), 3.71-3.68 (m, 3H), 3.67-3.58 (m, 2H), 3.57-3.47 (m, 1H), 3.43-3.32 (m, 1H), 3.16-3.00 (m, 2H), 2.95-2.81 (m, 2H), 2.77-2.60 (m, 1H), 2.16-2.05 (m, 1H), 2.01 (s, 1H).

Example 55: Synthesis of methyl (S)-2-((7-chloro-2-(2-fluoro-4-((2-methoxyethyl)carbamoyl)phenyl) imidazo[1,2-a]pyridin-3-yl)methyl)morpholine-4-carboxylate (A73)

A73

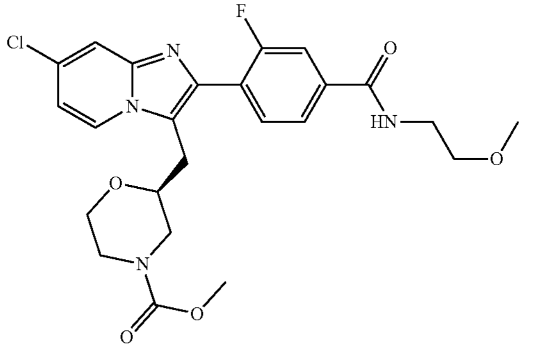

Compound A73 was prepared from compound 105 using the procedures described in Example 50. LCMS (ESI, m/z): 505.2. H NMR (400 MHz, $CDCl_3$) 8.30 (d, J=7.4 Hz, 1H), 7.78-7.74 (m, 1H), 7.70-7.59 (m, 3H), 6.81-6.79 (m, 1H), 6.61-6.60 (m, 1H), 4.06-3.76 (m, 3H), 3.72-3.62 (m, 6H), 3.61-3.57 (m, 2H), 3.42 (s, 4H), 3.12-2.85 (m, 3H), 2.65 (s, 1H).

Example 56: Synthesis of (S)-4-(3-((4-acetylmorpholin-2-yl)methyl)-7-chloroimidazo[1,2-a]pyridin-2-yl)-3-fluoro-N-methylbenzamide (A88)

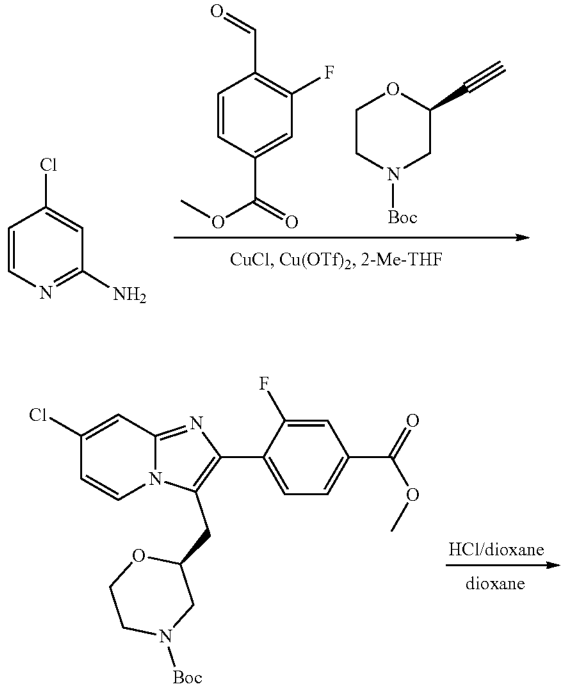

100

-continued

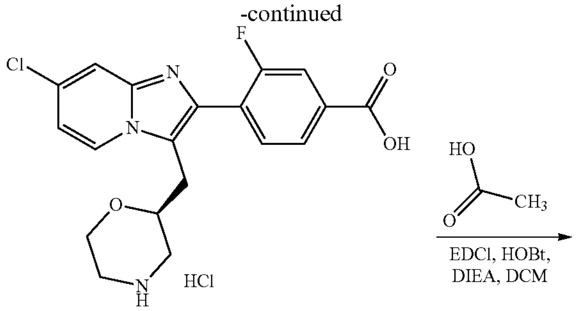

101

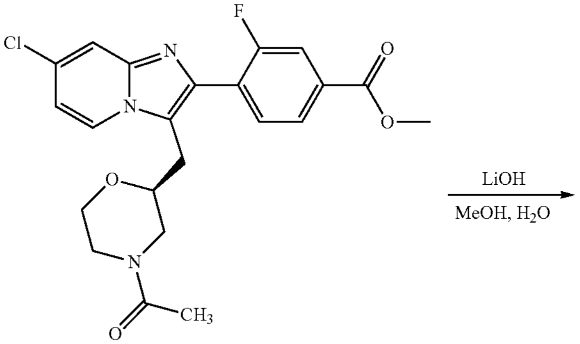

102

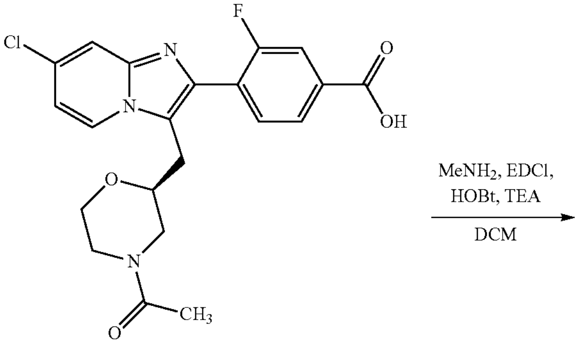

103

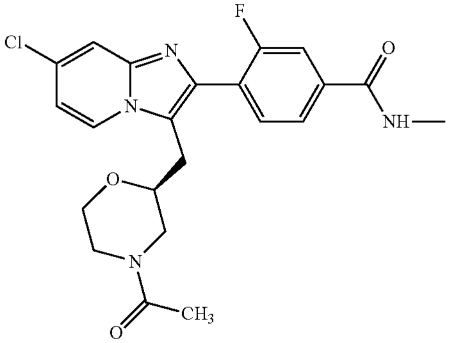

A88

Step 1: 4-Chloro-2-aminopyridine (2.30 g, 17.9 mmol), N-Boc-(S)-2-ethynylmorpholine (3.97 g, 18.8 mmol), and methyl 3-fluoro-4-formylbenzoate (3.42 g, 18.8 mmol) were reacted as described in Example 1 Step 1 to afford compound 100 (2.1 g, 22%). LCMS (ESI, m/z): 504.3 $[M+H]^+$. $^1H$ NMR (400 MHz, $CDCl_3$) 8.32 (d, J=7.2 Hz, 1H), 7.95-7.93 (m, 1H), 7.86-7.78 (m, 2H), 7.61 (d, J=1.8 Hz, 1H), 6.82-6.79 (m, 1H), 3.96 (s, 4H), 3.79 (d, J=9.2 Hz, 2H), 3.69-3.59 (m, 1H), 3.38-3.37 (m, 1H), 3.14-2.98 (m, 2H), 2.92-2.76 (m, 1H), 2.58-2.57 (m, 1H), 1.44 (s, 9H).

Step 2: Compound 100 was deprotected according to the method described in Example 1 Step 2 to afford compound 101, which was used directly in the next step without purification. LCMS (ESI, m/z): 404.3 $[M+H]^+$.

Step 3: To a solution of compound 101 (1.00 eq) in DCM (3 mL) was added EDCI (3.0 eq), HOBt (3.0 eq), acetic acid (3.0 eq) and DIEA (5.0 eq). The mixture was stirred at 30° C. for 16 h. The reaction mixture was concentrated and the residue was purified by flash silica gel chromatography to afford compound 102. LCMS (ESI, m/z): 446.2 $[M+H]^+$.

Steps 4 and 5: Compound A88 was prepared from compound 102 using the procedures described in Example 1, steps 4 and 5. LCMS (ESI, m/z): 445.2 $[M+H]^+$. $^1$H NMR (400 MHz, $CDCl_3$) 8.46-8.21 (m, 1H), 7.83-7.54 (m, 4H), 6.83-6.89 (m, 1H), 6.37 (s, 1H), 4.44-4.41 (m, 1H), 3.93-3.80 (m, 1H), 3.72-3.51 (m, 2H), 3.39-3.38 (m, 1H), 3.24-3.12 (m, 1H), 3.09-2.90 (m, 5H), 2.80-2.37 (m, 1H), 2.05 (d, J=7.0 Hz, 3H).

Example 57: Synthesis of (S)-4-(7-chloro-3-((4-propionylmorpholin-2-yl)methyl)imidazo-[1,2-a] pyridin-2-yl)-3-fluoro-N-methylbenzamide (A89)

A89

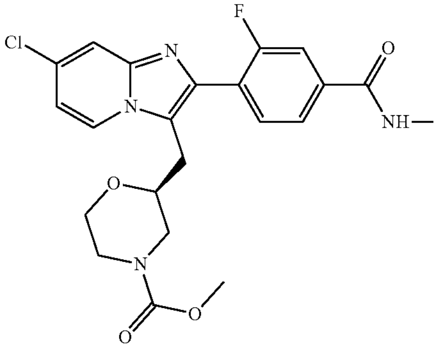

Compound A89 was prepared from compound 101 using the procedures described in Example 56. LCMS (ESI, m/z): 459.3 $[M+H]^+$. $^1$H NMR (400 MHz, $CDCl_3$) 8.42-8.22 (m, 1H), 7.82-7.54 (m, 4H), 6.86-6.76 (m, 1H), 6.58-6.57 (m, 1H), 4.44-4.38 (m, 1H), 3.94-3.78 (m, 1H), 3.73-3.53 (m, 2H), 3.46-3.32 (m, 1H), 3.15-3.34 (m, 1H), 3.09-2.88 (m, 5H), 2.76-2.39 (m, 1H), 2.37-2.17 (m, 2H), 1.13-1.09 (m, 3H).

Example 58: Synthesis of (S)-4-(7-chloro-3-((4-(2-methoxyacetyl)morpholin-2-yl)methyl)-imidazo[1,2-a]pyridin-2-yl)-3-fluoro-N-methylbenzamide (A90)

A90

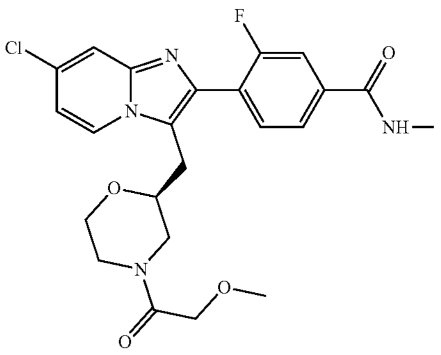

Compound A90 was prepared from compound 101 using the procedures described in Example 56. LCMS (ESI, m/z): 475.3 $[M+H]^+$. H NMR (400 MHz, $CDCl_3$) 8.40-8.20 (m, 1H), 7.77-7.73 (m, 1H), 7.69-7.53 (m, 3H), 6.83-6.80 (m, 1H), 6.43 (s, 1H), 4.39-4.36 (m, 1H), 4.15-3.97 (m, 2H), 3.92-3.60 (m, 3H), 3.46-3.33 (m, 4H), 3.19-2.88 (m, 6H), 2.83-2.41 (m, 1H).

Example 59: P2X3 Antagonist Assay

HEK293 were transiently or stably transfected with human ion channel cDNAs as indicated in section 1. Stable transfectants were selected by coexpression with the antibiotic-resistance gene(s) incorporated into the expression plasmid(s). Selection pressure was maintained by including selection antibiotics in the culture medium. HEK293 cells were cultured in Dulbecco's Modified Eagle Medium/Nutrient Mixture F-12 (D-MEM/F-12) supplemented with 10% fetal bovine serum, 100 U/mL penicillin G sodium, 100 J·Lg/mL streptomycin sulfate and appropriate selection antibiotics.

The effect of each test article to act as an antagonist was evaluated. Each test article was evaluated at eight (8) concentrations (0.001, 0.003, 0.01, 0.03, 0.1, 0.3, 1 and 3 μM, n=3) with 4 replicates for each concentration. Experiments were performed with the FLIPR calcium sensitive dye kit (Fluo-8 dye, AAT, Bioquest) according to the manufacturer's instructions.

Dye-loading: Growth media will be removed and add 20 μL of $Mg^{++}$-free HBPS containing Fluo-8 for 30 min at 37° C.

Preincubation (FLIPR step 1): Adding 5× (5 μL) test, vehicle, or control article solutions in $Mg^{+}$-free HBPS to each well for 20 minutes at room temperature, protected from light.

Stimulation (FLIPR step 2): After pre-incubation, cells will be stimulated with 6× (5 μL) αβ-meATP at final concentration of 3 μM prepared in $Mg^{++}$-free HBPS.

Non-Specific Calcium Influx (FLIPR step 3): 5 minutes after stimulation solution addition, non-specific calcium influx will be activated by adding 7×(5 μL) ionomycin at a final concentration of 5 μM. Fluorescence will be recorded continuously during FLIPR steps 2 and 3.

Positive Control Antagonist: PPADS (1 mM).

Data acquisition was performed via the FLIPRControl software that is supplied with the FLIPR System (MDS-AT) and data was analyzed using Microsoft Excel2003 (Microsoft Corp., Redmond, WA). $IC_{50}$ data for the test compounds are shown in the table below.

| Compound ID | P2X3 $IC_{50}$ |
|---|---|
| A1 | B |
| A2 | A |
| A3 | A |
| A4 | A |
| A5 | B |
| A6 | A |
| A7 | A |
| A8 | A |
| A9 | A |
| A10 | A |
| A11 | A |
| A12 | A |
| A13 | A |
| A14 (Peak 1) | 39% @ 1 μM |
| A14 (Peak 2) | A |
| A16 (Peak 1) | 29% @ 1 μM |
| A16 (Peak 2) | 23% @ 1 μM |
| A17 (Peak 1) | 30% @ 1 μM |
| A17 (Peak 2) | 21% @ 1 μM |
| A18 (Peak 1) | A |
| A18 (Peak 2) | B |
| (S)-A19 | A |
| (R)-A19 | A |
| A20 | A |
| cis-A21 | 20% @ 1 μM |
| trans-A21 | C |
| cis-A22 (Peak 1) | A |
| cis-A22 (Peak 2) | A |
| trans-A22 (Peak 1) | 22% @ 1 μM |
| trans-A22 (Peak 2) | 17% @ 1 μM |
| A23 | B |
| A24 | 10% @ 1 μM |
| A25 | C |
| A26 | C |
| A27 | 6% @ 1 μM |
| A28 | A |
| A29 | A |
| A30 | A |
| A31 | C |
| A32 | A |
| A33 | 5% @ 1 μM |
| A34 | B |
| A37 | B |
| A40 | A |
| A41 | B |
| A42 | A |
| A43 | A |
| A44 | A |
| A45 | A |
| A46 (Peak 1) | C |
| A46 (Peak 2) | C |
| A47 (Peak 1) | 5% @ 1 μM |
| A47 (Peak 2) | C |
| A48 | C |
| A49 | B |
| A50 | NT |
| A52 | 50% @ 1 μM |
| A53 | 16% @ 1 μM |
| A54 | 16% @ 1 μM |
| A55 | NT |
| A56 | NT |
| A58 | 16% @ 1 μM |
| A59 | NT |
| A60 | NT |
| A61 | B |
| A63 | A |
| A65 | B |
| A66 | A |
| A67 | B |

-continued

| Compound ID | P2X3 $IC_{50}$ |
|---|---|
| A68 | B |
| A69 | C |
| A73 | C |
| A88 | B |
| A89 | B |
| A90 | NT |

A: <100 nM; B: 100-1000 nM; C: >1000 nM; NT: not tested

We claim:

1. A compound of Formula (I), or a pharmaceutically acceptable salt or solvate thereof:

Formula (I)

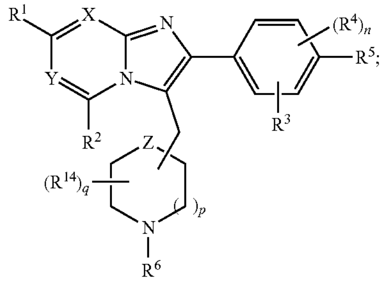

X is $C(R^2)$ or N;

Y is $C(R^2)$ or N;

Z is a bond, $CH_2$, or O;

$R^1$ is $C_1$-$C_6$haloalkyl;

each $R^2$ is independently selected from hydrogen, deuterium, halogen, —CN, $C_1$-$C_6$alkyl, $C_2$-$C_6$alkenyl, $C_2$-$C_6$alkynyl, $C_1$-$C_6$haloalkyl, $C_1$-$C_6$alkoxy, and $C_3$-$C_6$cycloalkyl;

$R^3$ is selected from hydrogen, deuterium, halogen, —CN, $C_1$-$C_6$alkyl, $C_2$-$C_6$alkenyl, $C_2$-$C_6$alkynyl, $C_1$-$C_6$haloalkyl, $C_3$-$C_6$cycloalkyl, —$OR^7$, —$N(R^7)_2$, —$C(=O)R^8$, —$C(=O)OR^7$, —$C(=O)N(R^7)_2$, —$NR^7C(=O)R^8$, —$NR^{10}S(=O)_2R^8$, —$S(=O)_2R^8$, and —$S(=O)_2N(R^7)_2$;

each $R^4$ is independently selected from deuterium, halogen, —CN, $C_1$-$C_6$alkyl, $C_2$-$C_6$alkenyl, $C_2$-$C_6$alkynyl, $C_1$-$C_6$haloalkyl, $C_1$-$C_6$alkoxy, and $C_3$-$C_6$cycloalkyl; or two $R^4$ are combined to form a bridged heterocycloalkyl ring;

$R^5$ is —$C(=O)N(R^9)(R^{10})$, —$C(=O)OR^9$, —$S(=O)R^{15}$, —$S(=O)_2R^{15}$, —$S(=O)(=NH)R^{15}$, —$C_2$-$C_9$heterocycloalkyl-$N(R^9)(R^{10})$, or —$C_1$-$C_6$haloalkyl-$N(R^9)(R^{10})$;

$R^6$ is selected from —$C(=O)OR^{11}$, —$C(=O)R^{11}$, and —$C(=O)N(R^{12})(R^{13})$;

each $R^7$ is independently selected from hydrogen, deuterium, $C_1$-$C_6$alkyl, and $C_1$-$C_6$haloalkyl;

each $R^8$ is independently selected from $C_1$-$C_6$alkyl;

$R^9$, $R^{10}$, $R^{12}$, and $R^{13}$ are independently selected from hydrogen, deuterium, and $C_1$-$C_6$alkyl;

$R^{11}$ is $C_1$-$C_6$alkyl or —$C_1$-$C_6$alkyl-O—$C_1$-$C_6$alkyl;

$R^{14}$ is $C_1$-$C_6$alkyl;

$R^{15}$ is $C_1$-$C_6$alkyl;

n is 0, 1, 2, or 3;

p is 1, 2, or 3; and q is 0, 1, 2, 3, or 4.

2. The compound of claim 1, or a pharmaceutically acceptable salt or solvate thereof, wherein $R^3$ is halogen or $C_1$-$C_6$alkyl.

3. The compound of claim 1, or a pharmaceutically acceptable salt or solvate thereof, wherein each $R^4$ is independently selected from halogen, $C_1$-$C_6$alkyl, and $C_1$-$C_6$alkoxy.

4. The compound of claim 1, or a pharmaceutically acceptable salt or solvate thereof, having the structure of Formula (Ia'):

Formula (Ia')

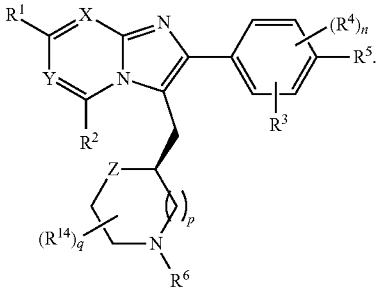

5. The compound of claim 1, or a pharmaceutically acceptable salt or solvate thereof, having the structure of Formula (Ia"):

Formula (Ia")

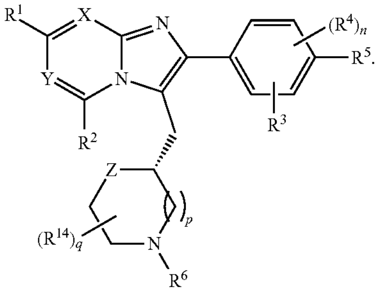

6. The compound of claim 1, or a pharmaceutically acceptable salt or solvate thereof, wherein Z is O and p is 1.

7. The compound of claim 6, or a pharmaceutically acceptable salt or solvate thereof, wherein X is $C(R^2)$ and Y is $C(R^2)$.

8. The compound of claim 7, or a pharmaceutically acceptable salt or solvate thereof, wherein each $R^2$ is hydrogen.

9. The compound of claim 8, or a pharmaceutically acceptable salt or solvate thereof, wherein n is 0 or 1.

10. The compound of claim 9, wherein q is 0.

11. The compound of claim 10, wherein $R^5$ is —C(O)N$(R^9)(R^{10})$.

12. The compound of claim 11, or a pharmaceutically acceptable salt or solvate thereof, wherein $R^{10}$ is hydrogen.

13. The compound of claim 11, or a pharmaceutically acceptable salt or solvate thereof, wherein $R^6$ is —C(O)$OR^{11}$.

14. The compound of claim 13, or a pharmaceutically acceptable salt or solvate thereof, wherein $R^{11}$ is $C_1$-$C_6$alkyl.

15. A compound selected from:

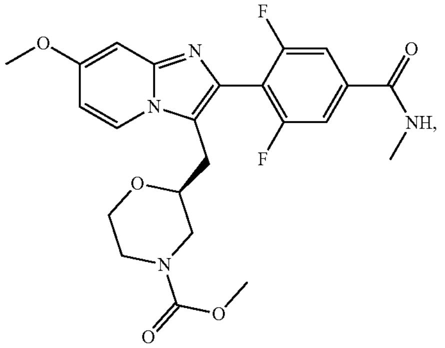

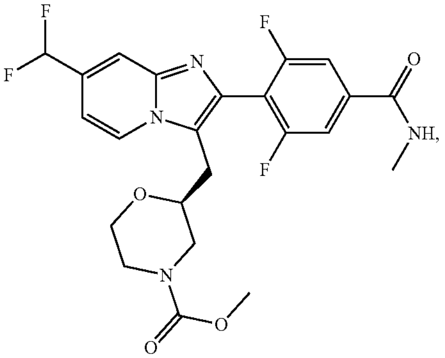

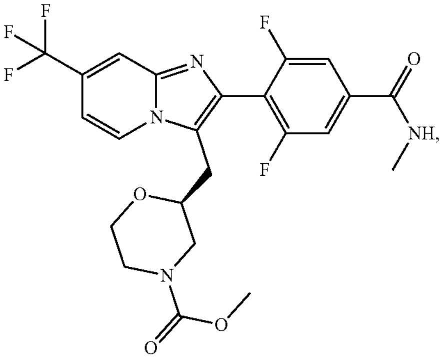

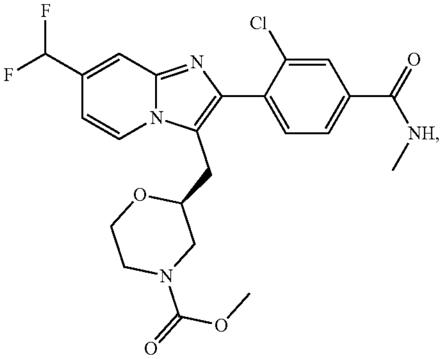

-continued

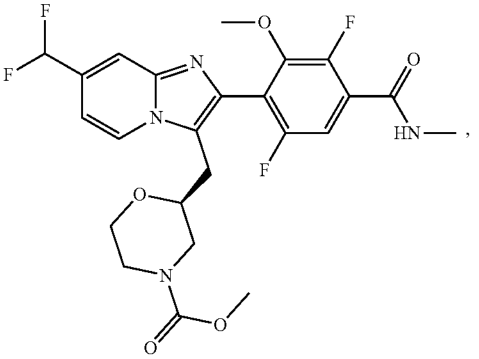

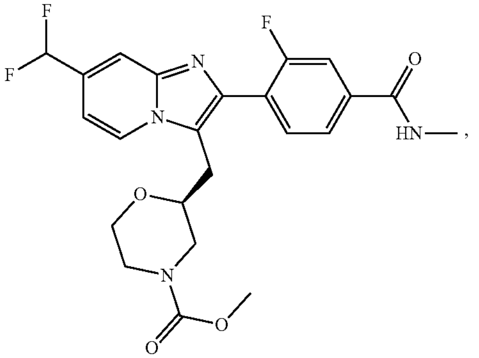

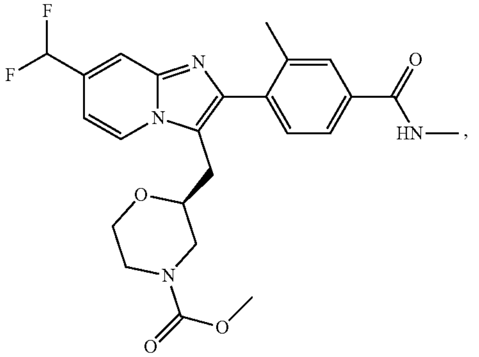

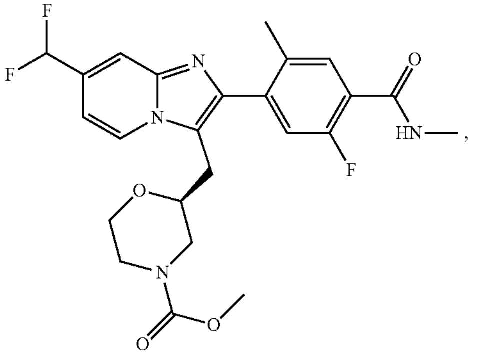

-continued

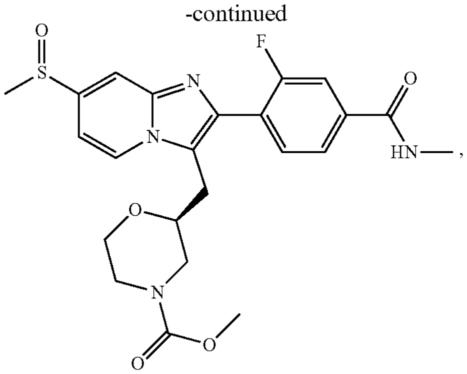

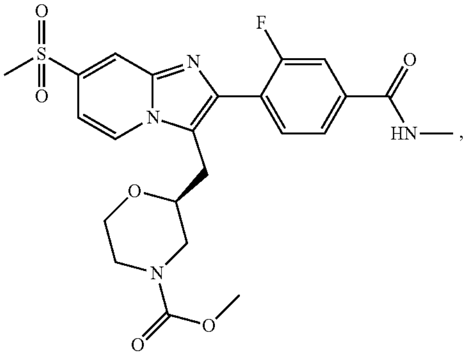

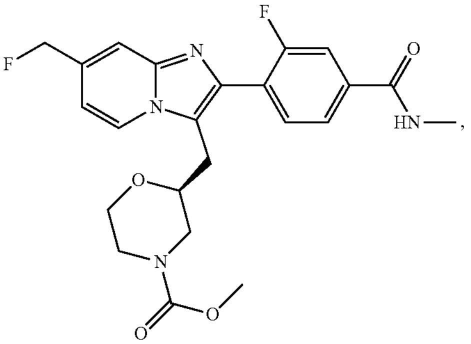

and

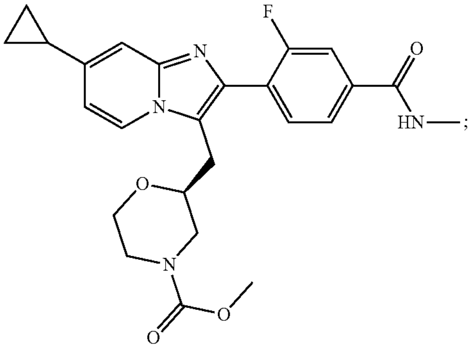

or a pharmaceutically acceptable salt or solvate thereof.

16. A pharmaceutical composition comprising a compound of claim 1, or a pharmaceutically acceptable salt or solvate thereof, and at least one inactive ingredient selected from pharmaceutically acceptable carriers, diluents, and excipients.

17. A method for treating a disorder associated with P2X3 activity in a mammal in need thereof, comprising administering to the mammal in need thereof a therapeutically effective amount of a compound of claim 1, or a pharmaceutically acceptable salt or solvate thereof.

18. A method for treating pain, a urinary tract disorder, cough, endometriosis, endometriosis-associated pain, and endometriosis-associated symptoms in a mammal in need thereof, comprising administering to the mammal in need thereof a therapeutically effective amount of a compound of claim 1, or a pharmaceutically acceptable salt or solvate thereof.

19. The method of claim 17, further comprising the administration of a second therapeutic agent.

20. The method of claim 18, further comprising the administration of a second therapeutic agent.

* * * * *